United States Patent
Yousef et al.

(10) Patent No.: US 12,329,801 B2
(45) Date of Patent: Jun. 17, 2025

(54) REGENERATIVE POLYPEPTIDES AND USES THEREOF

(71) Applicant: JUVENA THERAPEUTICS, INC., Redwood City, CA (US)

(72) Inventors: Hanadie Yousef, Palo Alto, CA (US); Jeremy O'Connell, Palo Alto, CA (US); Thach Mai, South San Francisco, CA (US); Zhihua Li, San Jose, CA (US)

(73) Assignee: JUVENA THERAPEUTICS, INC., Redwood City, CA (US)

( * ) Notice: Subject to any disclaimer, the term of this patent is extended or adjusted under 35 U.S.C. 154(b) by 0 days.

(21) Appl. No.: 18/662,443

(22) Filed: May 13, 2024

(65) Prior Publication Data
US 2024/0294597 A1    Sep. 5, 2024

Related U.S. Application Data

(63) Continuation of application No. 18/572,740, filed as application No. PCT/US2022/033059 on Jun. 10, 2022.

(60) Provisional application No. 63/259,088, filed on Jun. 21, 2021.

(51) Int. Cl.
| A61K 38/17 | (2006.01) |
| A61K 9/00 | (2006.01) |
| A61K 38/30 | (2006.01) |
| A61P 21/00 | (2006.01) |
| C07K 14/65 | (2006.01) |
| C07K 14/765 | (2006.01) |

(52) U.S. Cl.
CPC ........ *A61K 38/1709* (2013.01); *A61K 9/0019* (2013.01); *A61K 38/30* (2013.01); *A61P 21/00* (2018.01); *C07K 14/65* (2013.01); *C07K 14/765* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 5,061,620 A | 10/1991 | Tsukamoto et al. | |
| 5,155,038 A | 10/1992 | Eyal et al. | |
| 5,525,593 A | 6/1996 | Lake et al. | |
| 5,622,932 A | 4/1997 | DiMarchi et al. | |
| 5,843,780 A | 12/1998 | Thomson | |
| 6,200,806 B1 | 3/2001 | Thomson | |
| 6,686,179 B2 | 2/2004 | Fleer et al. | |
| 6,994,857 B2* | 2/2006 | Rosen ................... | A61P 7/00 435/7.1 |
| 7,029,913 B2 | 4/2006 | Thomson | |
| 7,355,018 B2 | 4/2008 | Glass | |
| 7,396,918 B2 | 7/2008 | Glass et al. | |
| 7,521,211 B2 | 4/2009 | Glass | |
| 7,632,503 B2 | 12/2009 | Stitt et al. | |
| 7,781,404 B2 | 8/2010 | Glass | |
| 7,837,993 B2 | 11/2010 | Conboy et al. | |
| 7,837,999 B2 | 11/2010 | Glass et al. | |
| 7,981,864 B2 | 7/2011 | LeBowitz | |
| 8,158,581 B2 | 4/2012 | Glass et al. | |
| 8,334,365 B2* | 12/2012 | Rosen ................... | A61P 43/00 530/350 |
| 8,445,434 B2 | 5/2013 | Glass et al. | |
| 8,563,691 B2 | 10/2013 | LeBowitz et al. | |
| 8,603,973 B2 | 12/2013 | Fu et al. | |
| 9,114,094 B2 | 8/2015 | Fu et al. | |
| 9,376,480 B2 | 6/2016 | Aoyagi-Scharber et al. | |
| 9,469,683 B2 | 10/2016 | LeBowitz et al. | |
| 9,758,763 B2 | 9/2017 | Conboy et al. | |
| 9,771,408 B2 | 9/2017 | Aoyagi-Scharber et al. | |
| 9,834,587 B2 | 12/2017 | Aoyagi-Scharber et al. | |
| 9,834,588 B2 | 12/2017 | Aoyagi-Scharber et al. | |
| 9,845,346 B2 | 12/2017 | Aoyagi-Scharber et al. | |
| 10,040,840 B2 | 8/2018 | Antipov et al. | |
| 10,265,372 B2 | 4/2019 | Conboy et al. | |
| 10,301,369 B2 | 5/2019 | Aoyagi-Scharber et al. | |
| 10,472,404 B2 | 11/2019 | Qin et al. | |
| 10,571,467 B2 | 2/2020 | Singh et al. | |

(Continued)

FOREIGN PATENT DOCUMENTS

| CN | 110036024 A | 7/2019 |
| CN | 110229238 A | 9/2019 |

(Continued)

OTHER PUBLICATIONS

Athens Research & Technology, product information for human thrombospondin. Product No. 16-20-201319 (2 pages) printed Mar. 17, 2020.
Barghorn et al.: Globular amyloid beta.-peptide 1-42 oligomer—a homogenous and stable neuropathological protein in Alzheimer's disease. Journal of Neurochemistry 95(3):834-847 (2005).
Bella et al.: Blockade of IGF2R improves muscle regeneration and ameliorates Duchenne muscular dystrophy. EMBO Mol Med. 12(1):e11019 pp. 1-18 (2020).
Bergman, Daniel, et al., Insulin-Like Growth Factor 2 in Development and Disease: A Mini-Review. Gerontology 59:240-249 (2013).
Bischoff: Cell cycle commitment of rat muscle satellite cells. The Journal of Cell Biology 111(1):201-207 (1990).
Bischoff: Proliferation of muscle satellite cells on intact myofibers in culture. Developmental Biology 115 (1):129-139 (1986).

(Continued)

*Primary Examiner* — Hope A Robinson
(74) *Attorney, Agent, or Firm* — Wilson Sonsini Goodrich & Rosati

(57) ABSTRACT

Described herein are polypeptides with an IGF2 amino acid sequence and an amino acid sequence from a heterologous polypeptide for treatment of soft-tissue and muscle diseases, disorders, and injuries. Mutations within the IGF2 amino acid sequence improved stability by reducing backbone cleavage. Synergistic combinations of an Insulin-like Growth Factor 1 Receptor (IGF1R) agonist and a short chain fatty acid are also described. Methods of treating muscle and soft-tissue diseases comprising administering the polypeptides and/or synergistic compositions are provided herein.

12 Claims, 30 Drawing Sheets

Specification includes a Sequence Listing.

(56) References Cited

U.S. PATENT DOCUMENTS

| | | | |
|---|---|---|---|
| 10,633,425 | B2 | 4/2020 | Antipov et al. |
| 10,654,912 | B2 | 5/2020 | Takahashi et al. |
| 10,821,155 | B2 | 11/2020 | Yousef et al. |
| 10,874,750 | B2 | 12/2020 | Do et al. |
| 11,046,751 | B2 | 6/2021 | Takahashi et al. |
| 11,155,593 | B2 | 10/2021 | Antipov et al. |
| 11,208,451 | B2 | 12/2021 | Qin et al. |
| 11,254,725 | B2 | 2/2022 | Aoyagi-Scharber et al. |
| 11,299,554 | B2* | 4/2022 | Moore .................. C07K 16/22 |
| 11,351,231 | B2 | 6/2022 | LeBowitz et al. |
| 11,401,348 | B2* | 8/2022 | Lazar .................. C07K 16/283 |
| 11,466,066 | B2 | 10/2022 | Pancook et al. |
| 11,491,243 | B2 | 11/2022 | Do et al. |
| 11,634,474 | B2 | 4/2023 | Takahashi et al. |
| 2003/0008821 | A1 | 1/2003 | Detmar et al. |
| 2003/0072761 | A1 | 4/2003 | LeBowitz |
| 2006/0121018 | A1 | 6/2006 | LeBowitz |
| 2006/0166328 | A1 | 7/2006 | Glass et al. |
| 2006/0223753 | A1 | 10/2006 | Glass |
| 2008/0241118 | A1 | 10/2008 | LeBowitz |
| 2009/0018061 | A1 | 1/2009 | Williams et al. |
| 2009/0029914 | A1 | 1/2009 | Rosen et al. |
| 2014/0038892 | A1 | 2/2014 | Yayon et al. |
| 2015/0329614 | A1 | 11/2015 | Fornaro et al. |
| 2016/0024580 | A1 | 1/2016 | Masli |
| 2016/0271265 | A1 | 9/2016 | Fischbeck et al. |
| 2017/0233447 | A1 | 8/2017 | Qin |
| 2017/0239320 | A1 | 8/2017 | Conboy et al. |
| 2017/0315117 | A1 | 11/2017 | Singh et al. |
| 2017/0355744 | A1 | 12/2017 | Aoyagi-Scharber et al. |
| 2017/0368173 | A1 | 12/2017 | Kipps et al. |
| 2018/0085438 | A1 | 3/2018 | Concino et al. |
| 2018/0251770 | A1 | 9/2018 | Friedland et al. |
| 2019/0240156 | A1 | 8/2019 | Lim |
| 2020/0000882 | A1 | 1/2020 | Yousef et al. |
| 2020/0002397 | A1 | 1/2020 | Qin et al. |
| 2021/0038693 | A1 | 2/2021 | Yousef et al. |
| 2021/0380654 | A1 | 12/2021 | Dong et al. |
| 2022/0009991 | A1 | 1/2022 | Antipov et al. |
| 2022/0031812 | A1 | 2/2022 | Pfaff et al. |
| 2022/0127326 | A1 | 4/2022 | Aoyagi-Scharber et al. |
| 2022/0162283 | A1 | 5/2022 | Antipov et al. |
| 2022/0354934 | A1 | 11/2022 | LeBowitz et al. |
| 2022/0409696 | A1 | 12/2022 | Yousef et al. |
| 2023/0060624 | A1 | 3/2023 | Fecteau et al. |
| 2023/0233711 | A1 | 7/2023 | Do et al. |
| 2023/0241187 | A1 | 8/2023 | LeBowitz et al. |
| 2023/0312663 | A1 | 10/2023 | Yousef et al. |
| 2023/0398187 | A1 | 12/2023 | Yousef et al. |
| 2023/0405089 | A1 | 12/2023 | Yousef et al. |
| 2024/0024423 | A1 | 1/2024 | Yousef et al. |
| 2024/0043484 | A1 | 2/2024 | Yousef et al. |
| 2024/0189397 | A1 | 6/2024 | Yousef et al. |

FOREIGN PATENT DOCUMENTS

| | | |
|---|---|---|
| CN | 115379850 A | 11/2022 |
| EP | 0394827 A1 | 10/1990 |
| EP | 1833847 B1 | 7/2011 |
| EP | 2241575 B1 | 6/2015 |
| EP | 3348635 B1 | 2/2021 |
| EP | 3813861 A1 | 5/2021 |
| EP | 4081235 A1 | 11/2022 |
| KR | 20100119437 A | 11/2010 |
| TW | 202019458 A | 6/2020 |
| WO | WO-8500831 A1 | 2/1985 |
| WO | WO-9114438 A1 | 10/1991 |
| WO | WO-9222311 A1 | 12/1992 |
| WO | WO-9303152 A1 | 2/1993 |
| WO | WO-9404030 A1 | 3/1994 |
| WO | WO-9740072 A2 | 10/1997 |
| WO | WO-0179258 A1 | 10/2001 |
| WO | WO-0179444 A2 | 10/2001 |
| WO | WO-2005033134 A2 | 4/2005 |
| WO | WO-2006074390 A2 | 7/2006 |
| WO | WO-2006081190 A2 | 8/2006 |
| WO | WO-2009048540 A1 | 4/2009 |
| WO | WO-2009137721 A2 | 11/2009 |
| WO | WO-2012037687 A1 | 3/2012 |
| WO | WO-2013166156 A2 | 11/2013 |
| WO | WO-2013170636 A1 | 11/2013 |
| WO | WO-2014082080 A2 | 5/2014 |
| WO | WO-2018100483 A1 | 6/2018 |
| WO | WO-2018189661 A2 | 10/2018 |
| WO | WO-2018200322 A1 | 11/2018 |
| WO | WO-2019213180 A1 | 11/2019 |
| WO | WO-2020006273 A1 | 1/2020 |
| WO | WO-2020132100 A1 | 6/2020 |
| WO | WO-2021072372 A1 | 4/2021 |
| WO | WO-2021133822 A1 | 7/2021 |
| WO | WO-2021133858 A1 | 7/2021 |
| WO | WO-2021263061 A2 | 12/2021 |
| WO | WO-2022271466 A1 | 12/2022 |
| WO | WO-2022271981 A2 | 12/2022 |

OTHER PUBLICATIONS

Buchli et al.: Inhibition of Nogo: a key strategy to increase regeneration, plasticity and functional recovery of the lesioned central nervous system. Annals of Medicine 37(8):556-567 (2005).
Capila et al.: Heparin-protein interactions. Angew Chem Int Ed Engl.; 41(3):391-412 (2002).
Carlson et al.: Loss of stem cell regenerative capacity within aged niches. Aging Cell 6: 371-382 (2007).
Chen: AB063. Development of a fusion protein combined alpha-galactosidase A and insulin-like growth factor 2 for treatment of Fabry disease. Annals of Translational Medicine 5. Suppl 2 p. 84 (2017).
Chichili, Reddy Vishnu Priyanka et al. Linkers in the Structural Biology of Protein-Protein Interactions. Protein Science vol. 22,2: pp. 153-167 (2013).
Chriett et al.: The histone deacetylase inhibitor sodium butyrate improves insulin signalling in palmitate-induced insulin resistance in L6 rat muscle cells through epigenetically-mediated up-regulation of Irs1. Molecular and Cellular Endocrinology. 439:224-232 (2017).
Chung et al.: Human Embryonic Stem Cell Lines Generated without Embryo Destruction. Cell Stem Cell 2 (2):113-117 (2008).
Conboy et al.: Aging, stem cells and tissue regeneration: lessons from muscle. Cell Cycle 4(3):407-410 (2005).
Conboy et al.: Embryonic anti-aging niche. Aging 3(5):555-563 (2011).
Conboy et al.: Heterochronic parabiosis for the study of the effects of aging on stem cells and their niches. Cell Cycle 11(12):2260-2267 (2012).
Conboy et al.: Immuno-analysis and FACS sorting of adult muscle fiber-associated stem/precursor cells. Methods Mol Biol 621:165-173 (2010).
Conboy et al.: Notch-Mediated Restoration of Regenerative Potential to Aged Muscle. Science 302:1575-1577 (2003).
Conboy et al.: Preparation of adult muscle fiber-associated stem/precursor cells. Methods Mol Biol 621:149-163 (2010).
Conboy et al.: The Regulation of Notch Signaling Controls Satellite Cell Activation and Cell Fate Determination in Postnatal Myogenesis. Dev Cell 3:397-409 (2002).
Co-pending U.S. Appl. No. 17/843,676, filed Jun. 17, 2022.
Co-pending U.S. Appl. No. 18/572,740, filed Dec. 20, 2023.
Database: WPI Week 201082. Clarivate Analytics. Thomson Scientific, London, GB AN 2010-P24302XP002805690 (2017).
Duguay et al.: Post-translational processing of the insulin-like growth factor-2 precursor: analysis of O-glycosylation and endoproteolysis. Journal of Biological Chemistry. 273(29):18443-18451 (1998).
EP20904271.2 European Search Report dated Jan. 8, 2024.
EP20906531.7 European Search Report dated Jan. 8, 2024.
Frazier et al., Age-dependent regulation of skeletal muscle mitochondria by the thrombospondin-1 receptor CD47. Matrix Biol. 30(2):154-161 (2011).

(56) References Cited

OTHER PUBLICATIONS

Grounds: Age-associated Changes in the Response of Skeletal Muscle Cells to Exercise and Regeneration. Ann NY Acad Sci 854:78-91 (1998).
Hayashi, Shinichiro, et al., Sequence of IGF-I, IGF-II, and HGF Expression in Regenerating Skeletal Muscle. Histochem Cell Biol122:427-434 (2004).
Ho et al.: PEDF-derived peptide promotes skeletal muscle regeneration through its mitogenic effect on muscle progenitor cells. Am J Physiol Cell Physiol. 309(3):C159-168 (2015).
Jensen et al.: Quantification of Alzheimer amyloid beta peptides ending at residues 40 and 42 by novel ELISA systems. Mol Med 6(4):291-302 (2000).
Kan et al.: Insulin-like growth factor II peptide fusion enables uptake and lysosomal delivery of α-N-acetylglucosaminidase to mucopolysaccharidosis type IIIB fibroblasts. Biochem J. 458(2):281-289 (2014).
Kirk et al., Insulin-like growth factor-II delays early but enhances late regeneration of skeletal muscle. Journal of Histochemistry & Cytochemistry 51(12):1611-1620 (2003).
Kuo et al.: Microfracture and bone morphogenetic protein 7 (BMP-7) synergistically stimulate articular cartilage repair. Osteoarthritis and Cartilage. Elsevier. Amsterdam, NL. 14(11):1126-1135 (2006).
Kuo et al.: Water-soluble Abeta (N-40, N-42) oligomers in normal and Alzheimer disease brains. J Biol Chem 271(8):4077-4081 (1996).
Ludwig et al.: Feeder-independent culture of human embryonic stem cells. Nat Methods 3(8):637-646 (2006).
Malinowska, Marcelina et al. Genistein Improves Neuropathology and Corrects Behaviour in a Mouse Model of Neurodegenerative Metabolic Disease. PLoS One vol. 5, 12: e14192, pp. 1-9 (2010).
Malito, E et al. Amyloid Beta-Degrading Cryptidases: Insulin Degrading Enzyme, Presequence Peptidase, and Neprilysin. Cellular and Molecular Life Sciences vol. 65, 16: pp. 2574-2585 (2008).
Mateos-Aierdi et al.: Muscle wasting in myotonic dystrophies: a model of premature aging. Front Aging Neurosci. 7:125 pp. 1-16 (2015).
McCarthy et al.: Effective fiber hypertrophy in satellite cell-depleted skeletal muscle. Development. 138(17):3657-66 (2011).
Morrison et al.: Prospective Identification, Isolation by Flow Cytometry, and In Vivo Self-Renewal of Multipotent Mammalian Neural Crest Stem Cells. Cell 96:737-749 (1999).
Morrison et al.: Regulatory Mechanisms in Stem Cell Biology. Cell 88(3):287-298 (1997).
Motohashi et al.: Muscle satellite cell heterogeneity and self-renewal. Front Cell Dev Biol. 2:1. doi: 10.3389/fcell.2014.00001 (2014).
Nguyen et al.: Surface plasmon resonance: a versatile technique for biosensor applications. Sensors (Basel). 15(5):10481-510 (2015).
PCT/US2019/039567 International Search Report and Written Opinion dated Nov. 6, 2019.
PCT/US2020/066658 International Search Report and Written Opinion dated May 13, 2021.
PCT/US2020/066739 International Search Report and Written Opinion dated Jun. 3, 2021.
PCT/US2022/033059 International Search Report and Written Opinion dated Sep. 19, 2022.
Piantino et al.: An injectable, biodegradable hydrogel for trophic factor delivery enhances axonal rewiring and improves performance after spinal cord injury. Experimental Neurology 201(2):359-367 (2006).
Ramilowski, Jordan A. A Draft Network of Ligand-Receptor-Mediated Multicellular Signalling in Human. Nature Communications vol. 6: pp. 7866 (2015).
Ranke et al.: Insulin-like growth factor binding-protein-3 (IGFBP—3). Best Practice & Research Clinical Endocrinology & Metabolism 29:701-711 (2015).
Rinderknecht et al.: Primary structure of human insulin-like growth factor II. FEBS Letters 89.2:283-286 (1978).
Shin et al.: Functional Properties of Antibody Insulin-like Growth Factor Fusion Proteins. Journal of Biological Chemistry. 269(7):4979-4985 (1994).
Smith et al.: IGF-II ameliorates the dystrophic phenotype and coordinately down-regulates programmed cell death. Cell death and Differentiation. 7:1109-1118 (2000).
Song et al.: MBNL1 reverses the proliferation defect of skeletal muscle satellite cells in myotonic dystrophy type 1 by inhibiting autophagy via the mTOR pathway. Cell Death Dis. 11(7):545 pp. 1-16 (2020) doi: 10.1038/s41419-020-02756-8.
Steinmetz et al.: Insulin-like growth factor 2 rescues aging-related memory loss in rats. Neurobiol Aging. 44:9-21 (2016).
Strohl, William R et al. Fusion Proteins for Half-Life Extension of Biologics as a Strategy to Make Biobetters. BioDrugs vol. 29,4: pp. 215-239 (2015).
Subramanian et al.: Thrombospondin-4 controls matrix assembly during development and repair of myotendinous junctions. Elife. 3:e02372 (2014).
Thornell et al.: Satellite cell dysfunction contributes to the progressive muscle atrophy in myotonic dystrophy type 1. Neuropathol Appl Neurobiol. 35(6):603-613 (2009).
Uchimura et al.: Insulin-Like Growth Factor II (IGF-II) Inhibits IL-1 [beta]-Induced Cartilage Matrix Loss and Promotes Cartilage Integrity in Experimental Osteoarthritis: OA. Journal of Cellular Biochemistry. 116(12):2858-1869(2015).
Ueda, Keisuke et al.: Albumin Fusion at the N-terminus or C-terminus of Human Lactoferrin Leads to Improved Pharmacokinetics and Anti-proliferative Effects on Cancer Cell Lines. European Journal of Pharmaceutical Sciences vol. 155: 105551 (2020).
U.S. Appl. No. 16/455,445 First Action Interview dated Mar. 23, 2020.
U.S. Appl. No. 16/455,445 Restriction Requirement dated Sep. 20, 2019.
U.S. Appl. No. 17/072,636 Office Action dated Apr. 27, 2023.
U.S. Appl. No. 17/072,636 Office Action dated Dec. 9, 2022.
U.S. Appl. No. 18/448,054 Office Action dated Nov. 3, 2023.
U.S. Appl. No. 18/471,220 Office Action dated Jan. 23, 2024.
U.S. Appl. No. 17/072,636 Office Action dated Mar. 11, 2024.
U.S. Appl. No. 17/843,748 Office Action dated Apr. 3, 2024.
U.S. Appl. No. 18/471,220 Office Action dated May 9, 2024.
Vanhoutte et al.: Thrombospondin expression in myofibers stabilizes muscle membranes. Elife. 5:e17589 pp. 1-33 (2016).
Ward et al.: Disproportionate growth in mice with Igf-2 transgenes. Proc Natl Acad Sci U S A. 91(22):10365-10369 (1994).
Xie et al.: IGF-IR determines the fates of BCR/ABL leukemia. Journal of Hematology & Oncology. 8(3):1-9 (2015).
Yousef et al.: hESC-secreted proteins can be enriched for multiple regenerative therapies by heparin-binding. Aging; vol. 5, No. 5: 357-372 (2013).
Yousef et al.: Mechanisms of action of hESC-secreted proteins that enhance human and mouse myogenesis. Aging; vol. 6, No. 8: 602-620 (2014).
Zanou, Nadège, et al., Skeletal Muscle Hypertrophy and Regeneration: Interplay Between the Myogenic Regulatory Factors (MRFs) and Insulin-like Growth Factors (IGFs) Pathways. Cell Mol Life Sci 70(21):4117-4130 (2013).
Chang et al.: Advances and challenges in developing cytokine fusion proteins as improved therapeutics. Expert Opinion. Drug Discov 4(2):181-194 (2009).
Charge et al.: Cellular and Molecular Regulation of Muscle Regeneration. Physiological Reviews. American Physiological Society. US. 84:209-238 (2004).
EP20904271.2 Supplementary European Search Report dated Jun. 25, 2024.
Fountoulakis, Michael et al. Interferon Gamma Receptor Extracellular Domain Expressed as IgG Fusion Protein in Chinese Hamster Ovary Cells. Purification, biochemical characterization, and stoichiometry of binding. Journal of Biological Chemistry 270(8):3958-3964 (1995).
Kamachi et al.: Induction of differentiation of muscle cells by introducing IGFII gene into ES cells—Transplantation therapy into

(56) References Cited

OTHER PUBLICATIONS muscle injury and muscle disease model mice—Translation of Inflammation and Regeneration. 25(4):301-302 (2005) Machine English Translation.

Kamochi et al.: Transplantation of Myocyte Precursors Derived from Embryonic Stem Cells Transfected with IGFII Gene in a Mouse Model of Muscle Injury. Experimental Transplantation. 82(4):516-526 (2006).

Osborn, Blaire L. et al. Pharmacokinetic and pharmacodynamic studies of a human serum albumin-interferon-alpha fusion protein in cynomolgus monkeys. Journal of Pharmacology and Experimental Therapeutics 303(2):540-548 (2002).

PCT/US2024/045683 International Search Report and Written Opinion dated Dec. 17, 2024.

PCT/US2024/045683 Invitation to Pay Additional Fees dated Oct. 17, 2024.

Sung, Cynthia et al. An IFN-Beta-albumin fusion protein that displays improved pharmacokinetic and pharmacodynamic properties in nonhuman primates. Journal of interferon & cytokine research 23(1):25-36 (2003).

Traunecker, Andre et al. Soluble CD4 molecules neutralize human immunodeficiency virus type 1. Nature 331(6151): 84-86 (1988).

U.S. Appl. No. 17/843,748 Office Action dated Jul. 18, 2024.

Yao, Zhengsheng et al. Effect of albumin fusion on the biodistribution of interleukin-2. Cancer Immunology, Immunotherapy 53(5):404-410 (2004). Published Online Nov. 18, 2003.

\* cited by examiner

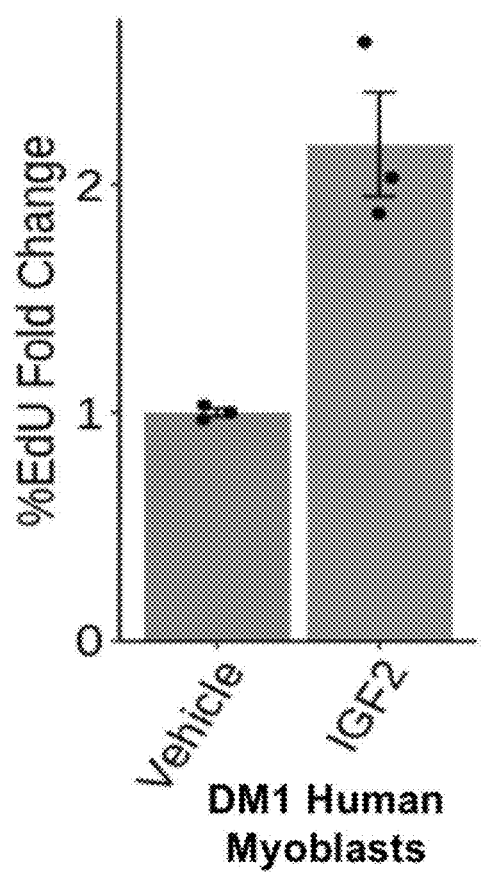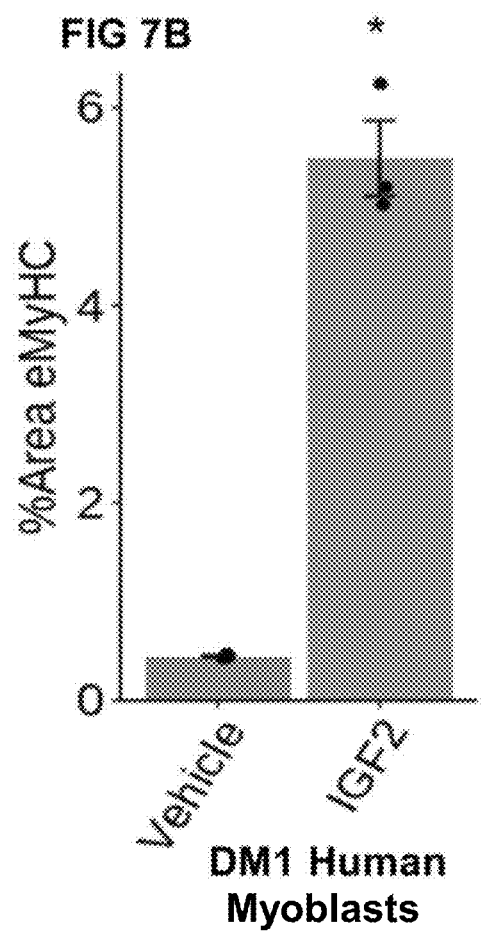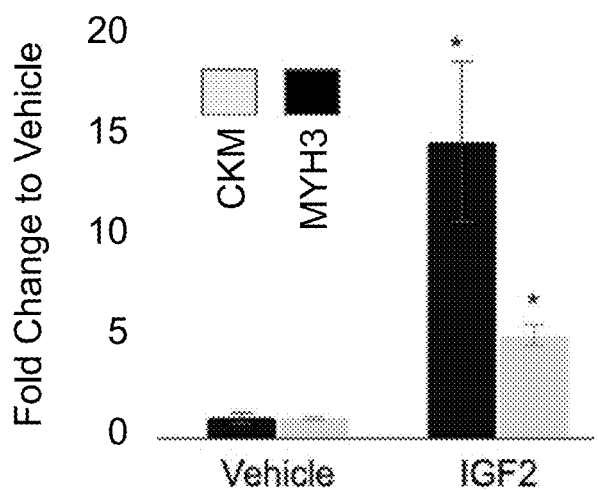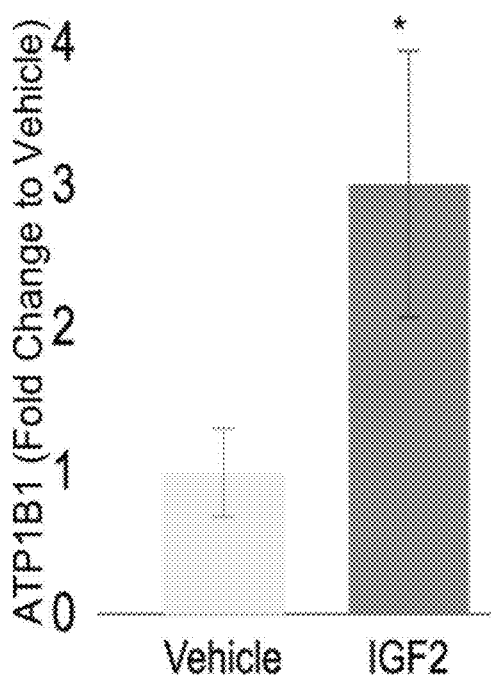

FIG 10A

● Vehicle, SC or
◐ IGF2/NaB, SC

Sarcopenia experiment old 21M
Vehicle (N=6): Vehicle
IGF2/NaB (N=6): IGF2 (150ug/kg) + Sodium butyrate (1.2 g/kg)

Safety/ toxicity

Daily injection of Vehicle or IGF2 or IGF2/NaBut

Days: 1  14

FIG 10B 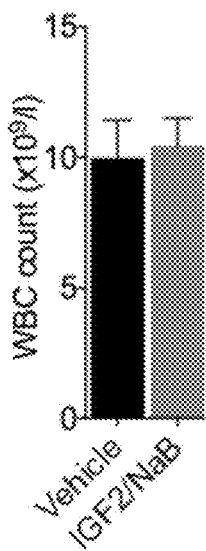

FIG 10C 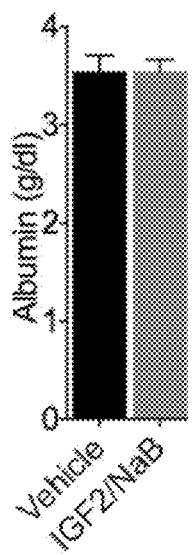

FIG 10D 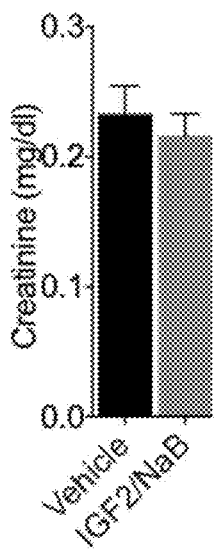

FIG 10E 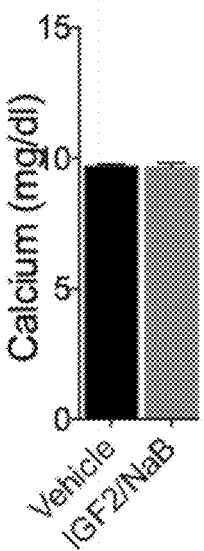

FIG 11A

▤ Dexamethasone 25mg/kg
● Vehicle, SC or
◐ IGF2/NaBut, SC

Muscle Function & histology

Daily injection of Dexa with Vehicle or IGF2/NaB

Days:1  14

Atrophy experiment overview: 3M old mice
Vehicle (N=14): Dexamethasone + Vehicle
IGF2/NaB (N=13): Dexamethasone + IGF2 (150ug/kg) + Sodium butyrate (1.2g/kg)

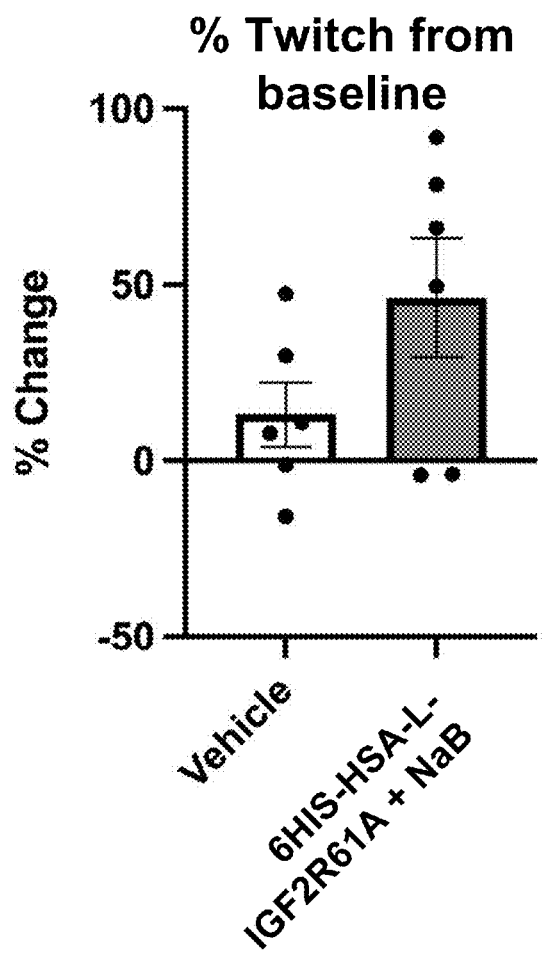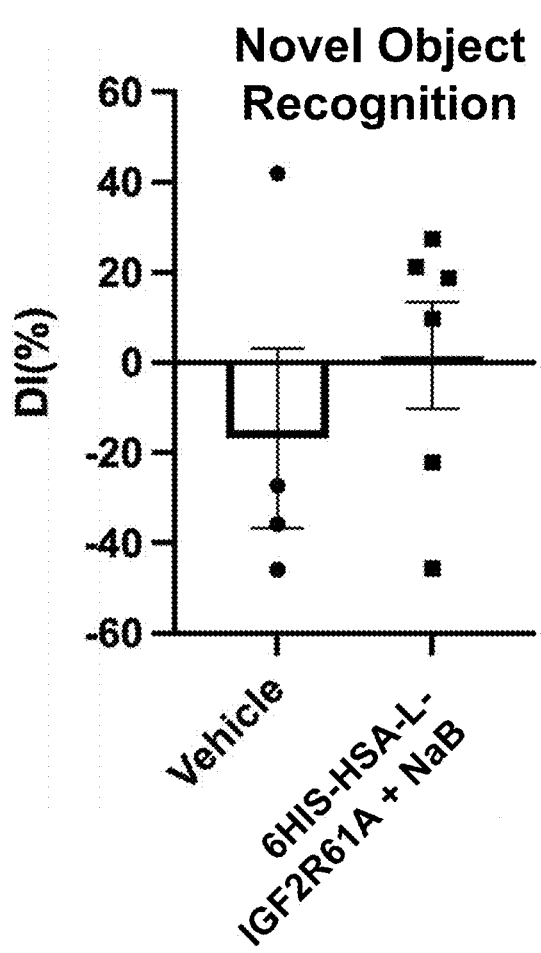

REGENERATIVE POLYPEPTIDES AND USES THEREOF

CROSS-REFERENCE TO RELATED APPLICATIONS

This application is a continuation of U.S. patent application Ser. No. 18/572,740, a 371 National Phase entry of International Application No. PCT/US2022/033059 filed Jun. 10, 2022, which claims the benefit of U.S. Provisional Application Ser. No. 63/259,088 filed Jun. 21, 2021, all of which are incorporated by reference herein in their entireties.

INCORPORATION BY REFERENCE OF SEQUENCE LISTING

The instant application is being filed along with a Sequence Listing in electronic format. The Sequence Listing is provided as a file entitled 54275-708_301_SL.xml, created on May 8, 2024, which is 104,781 bytes in size. The information in the electronic format of the Sequence Listing is incorporated by reference in its entirety.

BACKGROUND

As the average life span increases, increasing emphasis is placed upon "healthy aging." Individuals would like to live more active lifestyles as they age, and as a result, many aging disorders can have a significant impact on the quality of life of aging individuals. Treatments directed to regenerative ends have utility for treating aging diseases. Additionally, many treatments for aging disorders can be applicable to younger individuals who have suffered illness, injury, or who possess genetic or developmental defects leading to premature tissue loss, wasting, or weakening.

SUMMARY

As individuals age, tissue progenitor cells lose their regenerative potential.

Described herein are polypeptides comprising an IGF2 amino acid sequence and an amino acid sequence from a heterologous polypeptide useful for the treatment of soft-tissue and muscle diseases, disorders, and injuries. Also described herein mutations within the IGF2 amino acid sequence improved the stability of the molecule by reducing backbone cleavage. Also described herein are mutations within IGF2 sequences that block cleavage of its peptide backbone. Also described are methods of treating muscle and soft-tissue diseases comprising administering the polypeptides and/or synergistic compositions.

BRIEF DESCRIPTION OF THE DRAWINGS

FIG. 7A depicts IGF2 treatment promoted proliferation in DM1 human myoblast (32 year old caucasian female) cells FIG. 7B depicts IGF2 treatment promoted fusion in DM1 human myoblast (32 year old caucasian female) cells FIG. 8A depicts depicts IGF2 enhanced MYH3 and CKM expression in DM1 human myoblast (32 year old caucasian female) cells FIG. 8B depicts depicts IGF2 enhanced ATP1B1 expression in DM1 human myoblast (32 year old caucasian female) cells FIG. 10A depicts experimental overview for demonstrating chronic, systemic administration of IGF2/sodium butyrate was safe for liver, kidney and pancreas function FIG. 10B depicts systemic administration of IGF2/sodium butyrate had no adverse effects on white blood cell count, Albumin concentration (FIG. 10C), Creatinine concentration (FIG. 10D) and Calcium concentration (FIG. 10E)

FIG. 11A depicts an experimental overview of systemic administration of IGF2 and sodium butyrate protecting against Dexamethasone induced muscle atrophy.

FIG. 21F shows the muscle mass of mice receiving 6HIS-HSA-IGF2R61A compared mice receiving control (vehicle).

FIG. 22A shows blood glucose normalized to a baseline level for mice receiving 6 mg/kg 6HIS-HSA-IGF2R61A and 0.3 g/kg of sodium butyrate (NaB) or mice receiving control (vehicle). FIG. 22B shows force generation measured by both limb grip strength (normalized for body weight) for mice receiving 6 mg/kg 6HIS-HSA-IGF2R61A and 0.3 g/kg of sodium butyrate (NaB) or mice receiving control (vehicle). FIG. 22C shows force generation measured by forelimb grip strength (normalized for body weight) for mice receiving 6 mg/kg 6HIS-HSA-IGF2R61A and 0.3 g/kg of sodium butyrate (NaB) or mice receiving control (vehicle). FIG. 22D shows recovery of muscle force production for mice receiving 6 mg/kg 6HIS-HSA-IGF2R61A and 0.3 g/kg of sodium butyrate (NaB) or mice receiving control (vehicle). FIG. 22E shows force frequency, normalized for body weight, for mice receiving 6 mg/kg 6HIS-HSA-IGF2R61A and 0.3 g/kg of sodium butyrate (NaB) or mice receiving control (vehicle).

FIG. 23A shows fiber type distribution for mice receiving 6 mg/kg 6HIS-HSA-IGF2R61A and 0.3 g/kg of sodium butyrate (NaB) or mice receiving control (vehicle). FIG. 23B shows cross sectional areas (CSA) for mice receiving 6 mg/kg 6HIS-HSA-IGF2R61A and 0.3 g/kg of sodium butyrate (NaB) or mice receiving control (vehicle).

FIG. 24A-FIG. 24D shows results from a muscle dystrophy (DM1) mouse model. FIG. 24A shows muscle fiber distribution for mice receiving 6 mg/kg 6HIS-HSA-IGF2R61A and 0.3 g/kg of sodium butyrate (NaB) or mice receiving control (vehicle). FIG. 24B shows cross sectional areas (CSA) for mice receiving 6 mg/kg 6HIS-HSA-IGF2R61A and 0.3 g/kg of sodium butyrate (NaB) or mice receiving control (vehicle). FIG. 24C shows change in twitch from baseline for mice receiving 6 mg/kg 6HIS-HSA-IGF2R61A and 0.3 g/kg of sodium butyrate (NaB) or mice receiving control (vehicle). FIG. 24D shows change in novel object recognition for mice receiving 6 mg/kg 6HIS-HSA-IGF2R61A and 0.3 g/kg of sodium butyrate (NaB) or mice receiving control (vehicle).

DETAILED DESCRIPTION

Figure 1A:
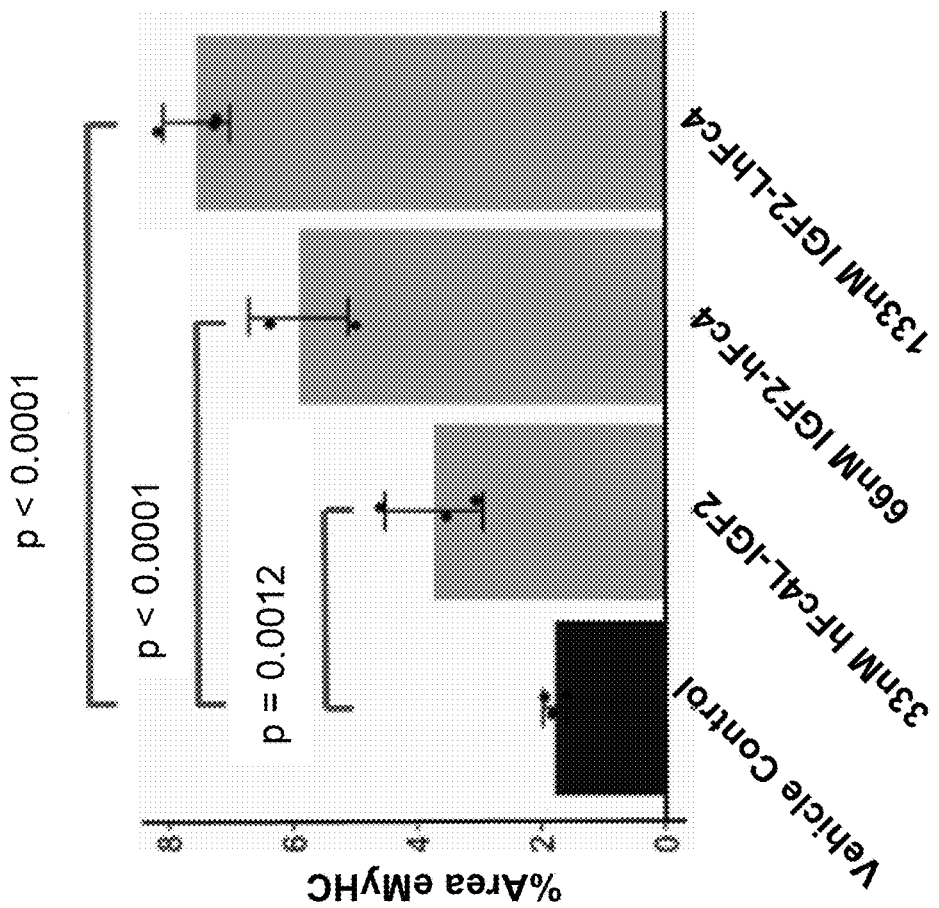
FIG. 1A depicts purified IGF2-hFcm promoted differentiation of human myoblast cells

In certain aspects disclosed herein is a therapeutically active protein or polypeptide sequence or derivative or fragment thereof that enhances progenitor cell growth or regeneration or function through activation of a cell surface receptor, and one or more of: a secretion signal a multimerizing component, or a stabilizing component. We modify and combined the sequences of certain polypeptides to create secreted, therapeutically active proteins with applications to muscle and soft tissue regeneration useful to treat acute and chronic muscle wasting diseases or conditions, such as sarcopenia, cachexia, muscular dystrophies, and muscle injury. In certain aspects, disclosed herein is a method of treating individuals with acute and chronic muscle wasting diseases or conditions, such as sarcopenia, cachexia, muscular dystrophies, and muscle injury.

In certain aspects, disclosed herein is a polypeptide comprising an IGF2 amino acid sequence and a heterologous polypeptide amino acid sequence, wherein the heterologous polypeptide amino acid sequence increases the stability or biological function of the IGF2 amino acid sequence. In certain aspects, disclosed herein is a composition comprising an IGF1R agonist and a short fatty acid chain.

The secretion signal sequence can either be one naturally occurring with a therapeutically active protein or polypeptide sequence or a different one selected, modified, or created to optimize expression yield through secretion efficiency, processing kinetics, or cell line specific processing Further examples and SEQ IDs are found in the Table of Sequences at the end of this disclosure. In certain aspects, the polypeptide may comprise a secretory signal peptide. In certain embodiments, the secretory signal peptide is SEQ ID NO: 10, SEQ ID NO: 11, SEQ ID NO: 12, SEQ ID NO: 13, SEQ ID NO: 14, SEQ ID NO: 15, or SEQ ID NO: 16. Production of the fusion polypeptides herein in heterologous production systems (e.g., bacteria or yeast) may result in imprecise cleavage of the signal sequence of the fusion polypeptide or non-specific early truncation at the C-terminal end of the fusion polypeptide. Processing of the secretory sequence or N- or C-terminal processing may result in loss of amino acids from either the N- or the C-terminus of the polypeptide.

There are several polypeptide sequences that can induce a regenerative effect through membrane receptors. Examples from the stem cell secretome selected for their ability to improve muscle and soft tissue regeneration listed in Table of Sequences, including IGF2, and variants thereof. Multimerizing components join two or more other protein components. A multimerizing component can take the form of a linker sequence of amino acids that joins other components tandemly into a single consecutive amino acid sequence. Or multimerizing components can take the form of proteins or protein domains that dimerize, resulting in covalent disulfide linking or non-covalent associations driving dimerization. Examples are disclosed in the Table of Sequences at the end of this disclosure.

Stabilizing components can reduce degradation rate, increase translational or post-translation folding, reduce unfolding rates, or increase circulating half-life. Examples can include abundant, circulating proteins or fragments thereof such as albumin or the fragment crystallizable (Fc) region from a human antibody. Further examples are disclosed in the Table of Sequences at the end of this disclosure.

Certain Definitions

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

As used herein the term "about" refers to an amount that is near the stated amount by 10%.

As used herein the terms "individual," "patient," or "subject" are used interchangeably and refer to individuals diagnosed with, suspected of being afflicted with, or at-risk of developing at least one disease for which the described compositions and method are useful for treating. In certain embodiments the individual is a mammal. In certain embodiments, the mammal is a mouse, rat, rabbit, dog, cat, horse, cow, sheep, pig, goat, llama, alpaca, or yak. In certain embodiments, the individual is a human.

As used herein the term "treat" or "treating" refers to interventions to a physiological or disease state of an individual designed or intended to ameliorate at least one sign or symptom associated with said physiological or disease state. The skilled artisan will recognize that given a heterogeneous population of individuals afflicted with a disease, not all individuals will respond equally, or at all, to a given treatment.

As used herein, the term "heterologous" refers to a nucleotide or amino acid sequence that is from a different source (e.g., gene, polypeptide, or organism) compared to the amino acid or nucleotide sequence to which it refers to as being heterologous. Heterologous includes biological sequences derived from different organisms or to sequences derived from different sources (e.g., genes or proteins) of the same organism. Heterologous sequences include recombinant DNA molecules comprising nucleotide sequences from different sources, fusion proteins comprising amino acid sequences from different sources, and epitope or purification tags of natural or synthetic origin.

As used herein, the term "muscle" refers to skeletal muscle, and does not refer to smooth muscle or cardiac muscle.

As used herein, the term "soft tissue" refers to connective tissues, including without limitations, tendons, ligaments, and cartilage.

As used herein, the term "mitogenic activity" refers to an activity that induces cell division or proliferation.

As used herein, the term "fusion promoting activity" refers to activity that promotes the fusion of cells into multinucleated cells, such as the fusion of myocytes into multinucleated myofibers, or advances the differentiation of a terminal differentiating stem or progenitor cells toward a committed cell lineage type, such as the progression of myoblasts into myocytes or the increase in cell size of expanding myofibers.

The terms "polypeptide" and "protein" are used interchangeably to refer to a polymer of amino acid residues, and are not limited to a minimum length. Polypeptides, including the provided antibodies and antibody chains and other peptides, e.g., linkers and binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The polypeptides described herein can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In the expression vectors regulatory elements such as promoters, enhancers, polyadenylation signals for use in controlling transcription can be derived from mammalian, microbial, viral or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements.

IGF2 Fusion Proteins

Insulin-like growth factor (IGF) ligands IGF1 and IGF2 are involved in many cell signaling and developmental processes. IGF2 is one of the major embryonic growth factors in humans, with minimal expression in adults, transient bursts are localized to skeletal muscle cells transitioning through cell states. Further complexity in its regulation stems from its genomic imprinting, with IGF2 being one of the few proteins that are expressed only from the paternal copy. Its effects are differentially mediated by binding cell surface receptors: insulin receptor, insulin-like growth factor receptor 1 (IGF1R) and insulin-like growth factor receptor 2 (IGF2R). IGF1R activates many signaling including pathways involved in cell proliferation, cell differentiation, and cell survival. IGF2R is involved in attenuating the signaling response. Described herein are certain therapeutically useful IGF2 polypeptides, including IGF2 fusion polypeptides that promote in vivo stability and function of the IGF2 comprising polypeptides, or combinations of IGF2 or IGF2 fusion proteins with IGF binding proteins (IGFBP) such as IGFBP1, IGFBP2, IGFBP3, IGFBP4, IGFBP5, or IGFBP6.

In certain aspects described herein are IGF receptor ligand polypeptides. In certain aspects, described herein, are IGF2 polypeptides, that comprise an IGF2 amino acid sequence. In certain embodiments, the IGF2 amino acid sequence is that of a human IGF2 polypeptide. In certain embodiments, the human IGF2 polypeptide comprises amino acids 25 to 91 of SEQ ID NO: 32 (i.e. SEQ ID NO: 29). In certain embodiments, the IGF2 amino acid sequence is at least about 90%, 95%, 97%, 98%, 99%, or 100% identical to SEQ ID NO: 29. In certain embodiments, the IGF2 amino acid sequence is 100% identical to SEQ ID NO: 29. In certain embodiments, the IGF2 amino acid sequence comprises an amino acid sequence at least about 90%, 95%, 97%, 98%, 99%, or 100% identical to SEQ ID NO: 29, but with 1, 2, 3, 4, 5, 6, 7, 8, 9, 10 or more amino acids deleted from the N- or C-terminus.

In certain embodiments, the IGF2 amino acid sequence is at least about 90%, 95%, 97%, 98%, 99% or 100% identical to SEQ ID NO: 29 and 1, 2, 3, 4, 5, 6, 7, 8, 9, or 10 amino acids are deleted from the N- or C-terminus of the polypeptide. In certain embodiments, the IGF2 fusion polypeptide amino acid sequence is at least about 90%, 95%, 97%, 98%, 99% or 100% identical to SEQ ID NO: 32 and 1, 2, 3, 4, 5, 6, 7, 8, 9, or 10 amino acids are deleted from the N- or C-terminus of the polypeptide. In certain embodiments, the IGF2 fusion polypeptide amino acid sequence is at least about 90%, 95%, 97%, 98%, 99% or 100% identical to SEQ ID NO: 34 and 1, 2, 3, 4, 5, 6, 7, 8, 9, or 10 amino acids are deleted from the N- or C-terminus of the polypeptide. In certain embodiments, the IGF2 amino acid sequence is at least about 90%, 95%, 97%, 98%, 99% or 100% identical to SEQ ID NO: 39 and 1, 2, 3, 4, 5, 6, 7, 8, 9, or 10 amino acids are deleted from the N- or C-terminus of the polypeptide.

In certain IGF2 polypeptides described herein are fusion proteins or polypeptides that may comprise additional heterologous (non-IGF2) amino acid sequences that enhance the expression, stability or function of the IGF2 polypeptide compared to a polypeptide not comprising the heterologous amino acid sequence. These heterologous amino acid sequences may increase the expression of the IGF2 fusion polypeptide from a cell system (e.g., CHO cells or other suitable cell system for bulk production) by 10%, 20%, 25%, 30%, 40%, 50%, 75%, 100%, 150%, 200%, 200%, 400%, 500%, 1,000% or more compared to a polypeptide not comprising the heterologous amino acid sequence. These heterologous amino acid sequences may increase the bioavailability (e.g., increasing the $T_{1/2}$) of the IGF2 polypeptide in vivo by 10%, 20%, 25%, 30%, 40%, 50%, 75%, 100%, 150%, 200%, 200%, 400%, 500%, 1,000% or more compared to a polypeptide not comprising the heterologous amino acid sequence. These heterologous amino acid sequences may increase the function (e.g., signaling through an IGF receptor) of the IGF2 polypeptide in vivo by 10%, 20%, 25%, 30%, 40%, 50%, 75%, 100%, 150%, 200%, 200%, 400%, 500%, 1,000% or more compared to a polypeptide not comprising the heterologous amino acid sequence.

Also described herein are IGF receptor ligand fusion polypeptides or polypeptides that comprise an amino acid sequence heterologous to IGF2. In certain embodiments, the IGF receptor ligand fusion is to a heterologous amino acid sequence that promotes the stability or function of the IGF receptor ligand. In certain embodiments, the IGF2 amino acid sequence of the IGF2-heterologous polypeptide fusion protein is at least about 90%, 95%, 97%, 98%, 99%, or 100% identical to SEQ ID NO: 29. In certain embodiments, the IGF2 amino acid sequence of the fusion protein is 100% identical to SEQ ID NO: 29. In certain embodiments, the IGF2 amino acid sequence of the fusion protein is at least about 90%, 95%, 97%, 98%, 99%, or 100% identical to SEQ ID NO: 33. In certain embodiments, the IGF2 amino acid sequence of the fusion protein is 100% identical to SEQ ID NO: 33. In certain embodiments, the IGF2 amino acid sequence of the fusion protein is at least about 90%, 95%, 97%, 98%, 99%, or 100% identical to SEQ ID NO: 41. In certain embodiments, the IGF2 amino acid sequence of the fusion protein is 100% identical to SEQ ID NO: 41. Additional representative sequences can be found in the Table of Sequences at the end of this disclosure.

Secretory Signal Peptides

In certain aspects, the fusion polypeptide may comprise a secretory signal peptide. In certain embodiments, the secretory signal peptide is any well known mammalian secretory signal peptide. Production of the fusion polypeptides herein in heterologous production systems (e.g., bacteria or yeast) may result in imprecise cleavage of the signal sequence of the fusion polypeptide or non-specific early truncation at the C-terminal end of the fusion polypeptide. Processing of the secretory sequence or N- or C-terminal processing may result in loss of amino acids from either the N or the C terminus of the polypeptide.

Multimerizing components join two or more other protein components. A multimerizing component may comprise a linker sequence of amino acids that joins other components that are identical or different into a single consecutive amino acid sequence. Suitable linkers include polypeptide linkers such as a Gly-Ser linker or spacer described herein. A multimerizing component can take the form of proteins or protein domains that multimerize or dimerize, resulting in covalent disulfide linking (e.g., through the addition of one or more de novo cysteine residues) or non-covalent associations driving dimerization (e.g., a leucine zipper). In certain embodiments, the multimerizing components may link or multimerize a plurality of IGF2 amino acid sequences. In certain embodiments, the multimerizing components may link or multimerize two IGF2 amino acid sequences. The two IGF2 amino acid sequences may be the same, or different, and selected from any of the IGF2 sequences described herein. In certain embodiments, the multimerizing components may link or multimerize two, three, four, five or more IGF2 amino acid sequences. In certain embodiments, the multimerizing components may link or multimerize an IGF2 amino acid sequence with another polypeptide that provides fusion promoting or proliferation promoting function or increased plasma half-life.

In some embodiments, the IGF2 amino acid sequence may comprise functional fragments, mutated sequences, or modified polypeptides thereof. The Table of Sequences lists some exemplary fragments, polypeptides and modified polypeptides. In some embodiments, the IGF2 sequence is N-, C-, or O-linked glycosylated. In some embodiments, the IGF2 sequence is glycosylated at one amino acid. In some embodiments, the IGF2 sequence is glycosylated at a site corresponding to Thr96, Thr99, or Thr163.

IGF family proteins are substrates for a number of proteases for processing during maturation and degrading intracellularly and extracellularly. The M16A family zinc metalloprotease, known as Insulin Degrading Enzyme (IDE) have a high affinity (~100 nM) for IGF2 as a substrate, rapidly degrading it (Malito et al. Cell Mol Life Sci. 2008; 65:2574-85). Described herein are mutations within IGF2 that reduce protease mediated cleavage of the IGF2 peptide backbone. In some embodiments, these mutations are within the C-domain, SEQ ID NO: 42. In some embodiments, mutations are specific to altering positively charged amino acids, such as arginine or lysine, to other amino acids. In some embodiments the mutations are the arginine 61 or arginine 64, as SEQ ID NO: 35 or SEQ ID NO: 37. In some embodiments, the mutations alter the positively charged amino acids to other amino acids with lower molecular weights. In some embodiments the mutations mutate the amino acid sequence into one or more alanines, as SEQ ID NO: 34 or SEQ ID NO: 36.

The IGF2 receptor ligand polypeptides and receptor ligand fusion polypeptides described herein may be encoded by nucleic acids to facilitate production of the receptor ligand polypeptide or fusion polypeptide. These nucleic acids can be compatible with bacterial, yeast, insect, or mammalian expression systems. They may comprise promoters/enhancers (either constructive or inducible), polyadenylation signals, selectable markers (such as antibiotic resistance), origins of replication or other accessory nucleic acid sequences. IGF2 sequences can be used from many organisms. In certain embodiments, the IGF2 sequence comprises a human IGF2 amino acid sequence. In certain embodiments, the IGF2 sequence comprises a cat, dog or a horse IGF2 sequence. In certain embodiments, the IGF2 sequence comprises a mouse, rat, rabbit, dog, cat, horse, cow, sheep, pig, goat, llama, alpaca, yak, or monkey sequence.

IGF2 Nucleic Acid Sequences

In certain embodiments, the IGF2 nucleic acid sequence is at least about 90%, 95%, 97%, 98%, 99%, or 100% identical to SEQ ID NO: 17. In certain embodiments, the IGF2 nucleic acid sequence is 100% identical to SEQ ID NO: 17. In certain embodiments, the IGF2 nucleic acid sequence is at least about 90%, 95%, 97%, 98%, 99%, or 100% identical to SEQ ID NO: 21. In certain embodiments, the IGF2 nucleic acid sequence is 100% identical to SEQ ID NO: 21. In certain embodiments, the IGF2 nucleic acid sequence is at least about 90%, 95%, 97%, 98%, 99%, or 100% identical to SEQ ID NO: 23. In certain embodiments, the IGF2 nucleic acid sequence is 100% identical to SEQ ID NO: 23. In certain embodiments, the IGF2 amino acid sequence is at least about 90%, 95%, 97%, 98%, 99%, or 100% identical to SEQ ID NO: 32. In certain embodiments, the IGF2 amino acid sequence is 100% identical to SEQ ID NO: 32.

Heterologous Peptides

The heterologous polypeptide that comprises part of the fusion proteins described herein may comprise, consist, or consist essentially of a fragment of an immunoglobulin molecule, an albumin molecule, a transferrin molecule, an XTEN sequence, a proline-alanine-serine polymer, a homo-amino acid polymer, a glycine-rich sequence, a gelatin-like polymer, an elastin-like peptide, a carboxy-terminal peptide, or combinations thereof.

In one aspect described herein the therapeutic polypeptide is IGF receptor ligand polypeptide or an IGF2 polypeptide.

In one aspect described herein the therapeutic polypeptide fused to a heterologous polypeptide amino acid sequence, either directly or through a linker, wherein the heterologous amino acid sequence imparts increased function or stability to the therapeutic polypeptide.

In one aspect of this invention, the heterologous peptide increases the stability or biological function of the therapeutic amino acid sequence. In certain embodiments, the heterologous sequence may be fused to the therapeutic amino acid sequence at the C-terminus or at the N-terminus of the therapeutic amino acid sequence. In certain aspects, the therapeutic amino acid sequence is fused to a heterologous sequence at the N-terminus. In certain embodiments, the therapeutic amino acid sequence is fused to a heterologous sequence at the C-terminus. In certain embodiments, a flexible linker is used between the therapeutic amino acid sequence and the heterologous sequence at the N terminus. In certain embodiments, a flexible linker is used between the therapeutic amino acid sequence and the heterologous sequence at the C terminus. In certain embodiments, a spacer is used between the therapeutic amino acid sequence and the heterologous sequence at the N terminus. In certain embodiments, a spacer is used between the therapeutic amino acid sequence and the heterologous sequence at the C terminus.

Heterologous peptides may be used to increase the stability or the biological function of the IGF2 amino acid sequence. Fusion proteins can be used to improve the pharmacokinetics of the biologically active molecules, such as by prolonging the half-life, as discussed in Strohl, "Fusion Proteins for Half-Life Extension of Biologics as a Strategy to Make Biobetters," *BioDrugs* (2015) 29:215-239. Fusing a polypeptide to a molecule or a fragment of a molecule with a long half-life, such as an immunoglobulin, an albumin, or a transferrin increases the half-life of the polypeptide. An XTEN sequence is a repeating amino acid polymer containing the amino acid residues A, E, G, P, S, and T which when fused to a peptide is capable of extending the half-lives of the peptides, while being otherwise inert. Fusing small repeating sequences such as proline-alanine-serine polymers (repeats of proline, alanine and serine), a homo-amino acid polymer sequence such as glycine-rich sequences (G-G-G-S), gelatin-like proteins, and elastin-like sequences (V-P-G-x-G, where x is any amino acid except proline) can also extend the half-life of a polypeptide. Fusing a polypeptide to a carboxy-terminal peptide (CTP) can increase the half-life of the polypeptide in the serum due to the strong negative change of CTP. In certain embodiments, the heterologous polypeptide comprises a fragment of an immunoglobulin molecule, an albumin molecule, a transferrin molecule, an XTEN sequence, a proline-alanine-serine polymer, a homo-amino acid polymer, a glycine-rich sequence, a gelatin-like polymer, an elastin-like peptide, a carboxy-terminal peptide, or combinations thereof. In certain embodiments the heterologous peptides improving the pharmacokinetics of the biologically active molecule are genetically encoded to produce a fusion protein. In certain embodiments the heterologous peptides improving the pharmacokinetics of the biologically active molecule are covalently or non-covalently associated with the biologically active molecule post translationally. In certain embodiments, that non-covalent association may be driven by a genetically or covalent modified portion of the biologically active molecule.

Immunoglobulins are large effector molecules produced by the immune system. IgG immunoglobulins possess a plasma half-life of approximately 21 days. When an immunoglobulin fragment is fused to a second polypeptide, this can increase the half-life of the second polypeptide. In some embodiments, the fragment of the immunoglobulin molecule comprises the hinge domain of an IgG, the CH2 domain of an IgG, the CH3 domain of an IgG, or any combination thereof. In some embodiments, the fragment of the immunoglobulin molecule comprises the hinge domain of IgG1, the CH2 domain of IgG1, the CH3 domain of IgG1, or any combination thereof. In some embodiments, the fragment of the immunoglobulin molecule comprises the hinge domain of IgG4, the CH2 domain of IgG4, the CH3 domain of IgG4, or any combination thereof.

In some circumstances, mutations of the immunoglobulin molecule or fragment may increase the half-life or stability of the immunoglobulin molecule or fragment. In some embodiments, the fragment of the immunoglobulin molecule comprises the hinge domain of IgG1, the CH2 domain of IgG1, the CH3 domain of IgG1, or any combination thereof with one or more of the following amino acid mutations in the immunoglobulin molecule: P329G, L234A and L235A. In some embodiments, the fragment of the immunoglobulin molecule comprises an IgG4 molecule. In some embodiments, the fragment of the immunoglobulin molecule comprises an IgG4 molecule with at least one of the following amino acid mutations in the immunoglobulin molecule: N434A, N434H, T307A/E380A/N434A, M252Y/S254T/T256E, 433K/434F/436H, T250Q, T250F, M428L, M428F, T250Q/M428L, N434S, V308W, V308Y, V308F, M252Y/M428L, D259I/V308F, M428L/V308F, Q311V/ N434S, T307Q/N434A, E258F/V427T, S228P, L235E, S228P/L235E/R409K, S228P/L235E, K370Q, K370E, deletion of G446, deletion of K447, and combinations thereof of IgG4 according to the EU numbering system.

Secretory signal sequences are sequence motifs that target proteins to the secretory pathway in the cell. Secretory sequences may be cleaved from the protein to produce the mature, secreted protein. In some embodiments, the polypeptide comprises a secretory signal sequence. In some embodiments, the polypeptide comprises human IGF2 secretory sequence (SEQ ID NO 9, SEQ ID NO 11, SEQ ID NO 12). In some embodiments, the polypeptide comprises a secretory signal that is SEQ ID NO: 10, SEQ ID. NO. 13, SEQ ID NO: 14, SEQ ID NO: 15, or SEQ ID NO: 16.

Linkers and Spacers

Linkers or spacers are short amino acid sequences that separate different domains in a single protein, or domains between fusion proteins. As used herein, the term "linker" and spacer" are interchangeable. Linkers can either be rigid or flexible. Rigid linkers may prevent unwanted interactions between different domains. Proline-rich linkers tend to be more rigid, while glycine rich linkers tend to be more flexible. Flexible linkers may allow domains within a single protein to interact. Another use for flexible linkers is to covalently bond protein complexes and binding partners to generate stable protein complexes. Flexible linkers may also be used to promote dimerization. Linkers and spacers are reviewed in Chichili et al, Linkers in the Structural biology of protein-protein interactions, Protein Sci. February 2013. 22(2): 153-167.

The fusion polypeptides described herein may further comprise a linker or a spacer amino acid sequence that separate the therapeutics polypeptide and the heterologous polypeptide. In certain embodiments, the linker or spacer is a peptide linker or spacer. In certain embodiments, the linker or spacer is a flexible linker or spacer. In certain embodiments, the linker is three alanines (AAA). In certain embodiments, the peptide linker is a glycine-serine linker. In certain embodiments, the linker is (in one-letter amino acid code): GGGGS (4GS) or multimers of the 4GS linker, such as repeats of 2, 3, 4, or 5 4GS linkers. In certain embodiments, the glycine-serine linker comprises the amino acid sequence set forth in SEQ ID NO: 43 or 44, or 2, 3, 4, 5, or repeats of SEQ ID NO: 43 or 44. In certain embodiments, the linker comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 amino acids derived from neither the polypeptide sequences in the Table of Sequences nor the heterologous polypeptide amino acid sequences of Table of Sequences.

The linker or spacers can be a single amino acid residue or greater in length. In certain embodiments, the peptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 amino acids in length. In certain embodiments, the peptide linker has at least one amino acid residue but is no more than 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, or 2 amino acid residues in length.

Combinations of an IGF1R Agonist and a Short Fatty Acid Chain

In certain aspects, disclosed herein is a composition comprising an IGF1R agonist and a short fatty acid chain. IGF1R signaling activates downstream pathways including pathways involved in cell proliferation, cell differentiation, and cell survival. The two IGF ligands, IGF1 and IGF2, activate IGF1R signaling. Additional peptides that activate IGF1R signaling are INS. Other agonists of IGF1R include, without limitations, demethylasterriquinone B1, Ginsenoside Rg5, and the human antimicrobial peptide LL-37. In some embodiments, the IGF1R agonist comprises an IGF1R agonistic antibody, an IGF polypeptide or a functional fragment thereof, IGF2 or a functional fragment thereof, insulin, demethylasterriquinone B1, Ginsenoside Rg5, LL-37, or combinations thereof. These compositions comprise an unexpected synergistic effect and are useful for treating the muscle and/or soft-tissue conditions or disorders. This synergistic effect may also be promoted by methods comprising separate administration of an IGF1R agonist and a short fatty acid chain.

In certain embodiments, the IGF2R agonist is an IGF ligand. In certain embodiments, the IGF1R agonist is IGF2. In certain embodiments, the IGF2 polypeptide is at least about 90%, 95%, 97%, 98%, 99%, or 100% identical to SEQ ID NO: 29. In certain embodiments, the IGF2 polypeptide is 100% identical to SEQ ID NO: 29. In certain embodiments, the IGF2 polypeptide is at least about 90%, 95%, 97%, 98%, 99%, or 100% identical to SEQ ID NO: 33. In certain embodiments, the IGF2 polypeptide is 100% identical to SEQ ID NO: 33. In certain embodiments, the IGF2 polypeptide is at least about 90%, 95%, 97%, 98%, 99%, or 100% identical to SEQ ID NO: 34. In certain embodiments, the IGF2 polypeptide is 100% identical to SEQ ID NO: 34.

In some embodiments, the composition comprises an IGF1R agonist and a short fatty acid chain. Short fatty acid chains include, without limitations, butyrates, a phenylbutyrate, valproic acid, propionic acid, methanoic acid, ethanoic acid, 2-methylpropanoic acid, 3-methylbutanoic acid, pentanoic acid, and a multimerized version thereof such as tributyrin. Butyrates include, without limitations, butyric acids, sodium butyrate, methyl butyrate, ethyl butyrate, butyl butyrate, pentyl butyrate, or sodium butyrate. In some embodiments, the short chain fatty acid is a butyrate. In some embodiments, the butyrate is butyric acid. In some embodiments, the butyrate is sodium butyrate. In some embodiment, that short chain fatty acid is a phenylbutyrate, valproic acid, propionic acid, methanoic acid, ethanoic acid, 2-methylpropanoic acid, 3-methylbutanoic acid, pentanoic acid, or a multimerized version thereof such as tributyrin.

Also described herein are methods comprising administering an IGF1R agonist and a short fatty acid chain. The administration can be in the same composition, separate formulations. When separate formulations are administered, they can be administered effectively simultaneously (e.g., during the same treatment) or separately with an interval of at least 1 hour, 12 hours, 24 hours, 2 days, 3 days, 4 days, 5 days, 6 days, 7 days, or more.

Therapeutic Indications

In certain aspects, the fusion polypeptides comprising an IGF ligand amino acid sequence and a heterologous polypeptide, compositions comprising an IGF1R agonist and a short fatty acid chain, and the methods described herein, are useful for treating diseases and disorders that involve soft-tissue injury, degradation, or destruction, or for use in treating an individual with an aging disorder, a muscle wasting disorder, a muscle injury, an injury to a connective tissue, or an injury to a non-muscle soft-tissue, or any combination thereof.

Aging disorders that result in the deterioration and loss of muscle tissue are such disorders. Sarcopenia, for example, is the degenerative loss of skeletal muscle mass quality, and strength and can be associated with aging. Injuries that result in acute muscle damage are other muscle disorders, which are treatable by the polypeptides, compositions and methods described herein. The disorders include muscle ruptures, strains, and contusions. A rupture is a separating of the muscle tissues. Muscle strains are contraction-induced injuries in which muscle fibers tear due to extensive mechanical stress, and can be classified as a grade I, II, or III. Muscle contusions are muscle hematomas. Muscle injury can also be caused by non-mechanical stresses such as cachexia. Cachexia may be caused by malnutrition, cancer, AIDS, coeliac disease, chronic obstructive pulmonary disease, multiple sclerosis, rheumatoid arthritis, congestive heart failure, tuberculosis, familial amyloid polyneuropathy, mercury poisoning (acrodynia), Crohn's disease, untreated/severe type 1 diabetes mellitus, anorexia nervosa, chemotherapy, muscular dystrophy or other genetic diseases which cause immobility, and hormonal deficiencies. Certain disorders that are weaknesses of specific muscles such as dysphagia or facioscapulohumeral muscular dystrophy may also be treated by the polypeptides described herein. Additional soft-tissues disorders that may be treated using the polypeptides comprising an IGF ligand amino acid sequence and compositions comprising an IGF1R agonist and a short fatty acid chain described herein are those that inflict injury to the tendons, ligaments or cartilage.

In certain embodiments, the muscle wasting disease is a muscular dystrophy. In certain embodiments, the muscular dystrophy comprises a myotonic muscular dystrophy, Duchenne muscular dystrophy, Becker muscular dystrophy, Limb-girdle muscular dystrophy, facioscapulohumeral muscular dystrophy, congenital, muscular dystrophy, oculopharyngeal muscular dystrophy, or distal muscular dystrophy. In certain embodiments, the muscular dystrophy is myotonic dystrophy.

In certain embodiments, the aging disorder is sarcopenia. In certain embodiments, the muscle wasting disorder is cachexia. In certain embodiments, the cachexia is a result of a cancer, AIDS, end stage kidney disease, or cardiovascular disease. In certain embodiments, the injury is a muscle injury. In certain embodiments, the muscle wasting is atrophy due to limb immobilization or disuse. In certain embodiments, the muscle injury is a strain or a tear. In certain embodiments, the muscle injury is a Grade III strain. In certain embodiments, sarcopenia contributes to the incidence of the muscle injury. In certain embodiments, the injury is ligament damage. In certain embodiments, the ligament damage is a rupture or a tear. In certain embodiments, the injury is tendon damage. In certain embodiments, the tendon damage is a rupture or a tear. In certain embodiments, the injury is cartilage damage.

In certain embodiments, the compositions described herein, are for use in a method of treating myositis. In certain embodiments, the myositis comprises dermatomyositis, polymyositis, necrotizing myopathy (also called necrotizing autoimmune myopathy or immune-mediated necrotizing myopathy), juvenile myositis, or sporadic inclusion-body myositis.

In certain embodiments, the compositions described herein are for use in a method of treating cartilage related-disorders. In certain embodiments, the cartilage related disorder may be due to tears, injuries, or wear. In certain embodiments, the cartilage-associated disease may be osteoarthritis, osteochondritis dissecans, achondroplasia, or degenerative cartilage lesions.

In certain embodiments, the compositions described herein are for use in a method of increasing proliferation or promoting survival of a cell associated with soft-tissue damage. In certain embodiments, the polypeptides comprising an IGF ligand amino acid sequence and compositions comprising an IGF1R agonist and a short fatty acid chain described herein are useful in a method of increasing proliferation or promoting survival of any one or more of a muscle cell, a muscle precursor cell, a tenocyte, a tenocyte precursor cell, a chondrocyte, a chondrocyte precursor cell, a mesenchymal stem cell, or a fibroblast.

Muscle fibrosis is an excessive accumulation of extracellular matrix components, including collagen. Muscle fibrosis impairs muscle function, negatively affects muscle regeneration after injury, and increases muscle susceptibility to re-injury. In certain embodiments, the compositions described herein are for use in a method of reducing muscle fibrosis. In certain embodiments, the fibrosis is associated with aging, muscular dystrophy, or an injury. In certain embodiments, the IGF ligand is IGF2.

In order to differentiate into mature muscle cells, myoblasts must fuse and form multinucleated cells. In certain embodiments, the fusion polypeptides comprising an IGF ligand amino acid sequence and a heterologous polypeptide, compositions comprising an IGF1R agonist and a short fatty acid chain, and the methods described herein are for use in a method of increasing myoblast fusion. In certain embodiments, the IGF ligand is IGF2.

In certain embodiments, the fusion polypeptides comprising an IGF ligand amino acid sequence and a heterologous polypeptide, compositions comprising an IGF1R agonist and a short fatty acid chain, and the methods described herein are for use in a method of increasing muscle mass. In certain embodiments, muscle mass is increased by at least about 1%, 2.5%, 5%, 10%, 20%, 30%, 40%, 50% or more than 50%. In certain embodiments, the IGF ligand is IGF2.

In certain embodiments, the fusion polypeptides comprising an IGF ligand amino acid sequence and a heterologous polypeptide, compositions comprising an IGF1R agonist and a short fatty acid chain, and the methods described herein are for use in a method of increasing grip strength. In certain embodiments, grip strength is increased by at least about 1%, 2.5%, 5%, 10%, 20%, 30%, 40%, 50% or more than 50%. In certain embodiments, the IGF ligand is IGF2.

In certain embodiments the fusion polypeptides comprising an IGF ligand amino acid sequence and a heterologous polypeptide, compositions comprising an IGF1R agonist and a short fatty acid chain, and the methods described herein are for use in a method of increasing muscle endurance. In certain embodiments, muscle endurance is increased by at least about 1%, 2.5%, 5%, 10%, 20%, 30%, 40%, 50% or more than 50%. In certain embodiments the IGF ligand is IGF2.

Methods of Treatment

In certain aspects, disclosed herein is a method of treating an individual with a disorder comprising administering an IGF1R agonist and a short fatty acid chain to the individual. In some embodiments, the IGF1R agonist and the short fatty acid chain are administered in separate formulations. In some embodiments, the IGF1R agonist and the short fatty acid chain are administered simultaneously. In some embodiments, the IGF1R agonist and the short fatty acid chain are administered at different times.

In certain aspects, disclosed herein is a method of treating an individual with a disorder comprising administering a polypeptide comprising an IGF ligand amino acid sequence and a butyrate to the individual the disorder. In some embodiments, the polypeptide comprising the IGF ligand amino acid sequence and the butyrate are administered in separate formulations. In some embodiments, the polypeptide comprising the IGF ligand amino acid sequence and the butyrate are administered simultaneously. In some embodiments, the polypeptide comprising the IGF ligand amino acid sequence and the butyrate are administered at different times.

In certain aspects, disclosed herein is a method of treating an individual with a disorder comprising administering a polypeptide comprising an IGF2 amino acid sequence and a short fatty acid chain to the individual the disorder. In some embodiments, the polypeptide comprising the IGF ligand amino acid sequence and the short fatty acid chain are administered in separate formulations. In some embodiments, the polypeptide comprising the IGF2 amino acid sequence and the short fatty acid chain are administered simultaneously. In some embodiments, the polypeptide comprising the IGF2 amino acid sequence and the short fatty acid chain are administered at different times.

In certain aspects, disclosed herein is a method of treating an individual with a disorder comprising administering a polypeptide comprising an IGF2 amino acid sequence and a butyrate to the individual the disorder. In some embodiments, the polypeptide comprising the IGF2 amino acid sequence and the butyrate are administered in separate formulations. In some embodiments, the polypeptide comprising the IGF2 amino acid sequence and the butyrate are administered simultaneously. In some embodiments, the polypeptide comprising the IGF2 amino acid sequence and the butyrate are administered at different times.

In certain embodiments, the treatment can be administered by any suitable route such as, for example, subcutaneous, intravenous, or intramuscular. In certain embodiments, the treatment is administered on a suitable dosage schedule, for example, weekly, twice weekly, monthly, twice monthly, once every three weeks, or once every four weeks. The treatment can be administered in any therapeutically effective amount. In certain embodiments, the therapeutically effective amount is about 0.001 mg/kg to about 1 mg/kg. In certain embodiments, the therapeutically effective amount is about 0.001 mg/kg to about 0.002 mg/kg, about 0.001 mg/kg to about 0.005 mg/kg, about 0.001 mg/kg to about 0.01 mg/kg, about 0.001 mg/kg to about 0.02 mg/kg, about 0.001 mg/kg to about 0.05 mg/kg, about 0.001 mg/kg to about 0.1 mg/kg, about 0.001 mg/kg to about 0.2 mg/kg, about 0.001 mg/kg to about 0.5 mg/kg, about 0.001 mg/kg to about 1 mg/kg, about 0.002 mg/kg to about 0.005 mg/kg, about 0.002 mg/kg to about 0.01 mg/kg, about 0.002 mg/kg to about 0.02 mg/kg, about 0.002 mg/kg to about 0.05 mg/kg, about 0.002 mg/kg to about 0.1 mg/kg, about 0.002 mg/kg to about 0.2 mg/kg, about 0.002 mg/kg to about 0.5 mg/kg, about 0.002 mg/kg to about 1 mg/kg, about 0.005 mg/kg to about 0.01 mg/kg, about 0.005 mg/kg to about 0.02 mg/kg, about 0.005 mg/kg to about 0.05 mg/kg, about 0.005 mg/kg to about 0.1 mg/kg, about 0.005 mg/kg to about 0.2 mg/kg, about 0.005 mg/kg to about 0.5 mg/kg, about 0.005 mg/kg to about 1 mg/kg, about 0.01 mg/kg to about 0.02 mg/kg, about 0.01 mg/kg to about 0.05 mg/kg, about 0.01 mg/kg to about 0.1 mg/kg, about 0.01 mg/kg to about 0.2 mg/kg, about 0.01 mg/kg to about 0.5 mg/kg, about 0.01 mg/kg to about 1 mg/kg, about 0.02 mg/kg to about 0.05 mg/kg, about 0.02 mg/kg to about 0.1 mg/kg, about 0.02 mg/kg to about 0.2 mg/kg, about 0.02 mg/kg to about 0.5 mg/kg, about 0.02 mg/kg to about 1 mg/kg, about 0.05 mg/kg to about 0.1 mg/kg, about 0.05 mg/kg to about 0.2 mg/kg, about 0.05 mg/kg to about 0.5 mg/kg, about 0.05 mg/kg to about 1 mg/kg, about 0.1 mg/kg to about 0.2 mg/kg, about 0.1 mg/kg to about 0.5 mg/kg, about 0.1 mg/kg to about 1 mg/kg, about 0.2 mg/kg to about 0.5 mg/kg, about 0.2 mg/kg to about 1 mg/kg, or about 0.5 mg/kg to about 1 mg/kg. In certain embodiments, the therapeutically effective amount is about 0.001 mg/kg, about 0.002 mg/kg, about 0.005 mg/kg, about 0.01 mg/kg, about 0.02 mg/kg, about 0.05 mg/kg, about 0.1 mg/kg, about 0.2 mg/kg, about 0.5 mg/kg, or about 1 mg/kg. In certain embodiments, the therapeutically effective amount is at least about 0.001 mg/kg, about 0.002 mg/kg, about 0.005 mg/kg, about 0.01 mg/kg, about 0.02 mg/kg, about 0.05 mg/kg, about 0.1 mg/kg, about 0.2 mg/kg, or about 0.5 mg/kg. In certain embodiments, the therapeutically effective amount is at most about 0.002 mg/kg, about 0.005 mg/kg, about 0.01 mg/kg, about 0.02 mg/kg, about 0.05 mg/kg, about 0.1 mg/kg, about 0.2 mg/kg, about 0.5 mg/kg, or about 1 mg/kg. In certain embodiments, the therapeutically effective amount is about 0.1 mg/kg to about 50 mg/kg. In certain embodiments, the therapeutically effective amount is about 0.1 mg/kg to about 0.2 mg/kg, about 0.1 mg/kg to about 0.5 mg/kg, about 0.1 mg/kg to about 1 mg/kg, about 0.1 mg/kg to about 2 mg/kg, about 0.1 mg/kg to about 5 mg/kg, about 0.1 mg/kg to about 10 mg/kg, about 0.1 mg/kg to about 20 mg/kg, about 0.1 mg/kg to about 50 mg/kg, about 0.2 mg/kg to about 0.5 mg/kg, about 0.2 mg/kg to about 1 mg/kg, about 0.2 mg/kg to about 2 mg/kg, about 0.2 mg/kg to about 5 mg/kg, about 0.2 mg/kg to about 10 mg/kg, about 0.2 mg/kg to about 20 mg/kg, about 0.2 mg/kg to about 50 mg/kg, about 0.5 mg/kg to about 1 mg/kg, about 0.5 mg/kg to about 2 mg/kg, about 0.5 mg/kg to about 5 mg/kg, about 0.5 mg/kg to about 10 mg/kg, about 0.5 mg/kg to about 20 mg/kg, about 0.5 mg/kg to about 50 mg/kg, about 1 mg/kg to about 2 mg/kg, about 1 mg/kg to about 5 mg/kg, about 1 mg/kg to about 10 mg/kg, about 1 mg/kg to about 20 mg/kg, about 1 mg/kg to about 50 mg/kg, about 2 mg/kg to about 5 mg/kg, about 2 mg/kg to about 10 mg/kg, about 2 mg/kg to about 20 mg/kg, about 2 mg/kg to about 50 mg/kg, about 5 mg/kg to about 10 mg/kg, about 5 mg/kg to about 20 mg/kg, about 5 mg/kg to about 50 mg/kg, about 10 mg/kg to about 20 mg/kg, about 10 mg/kg to about 50 mg/kg, or about 20 mg/kg to about 50 mg/kg. In certain embodiments, the therapeutically effective amount is about 0.1 mg/kg, about 0.2 mg/kg, about 0.5 mg/kg, about 1 mg/kg, about 2 mg/kg, about 5 mg/kg, about 10 mg/kg, about 20 mg/kg, or about 50 mg/kg. In certain embodiments, the therapeutically effective amount is at least about 0.1 mg/kg, about 0.2 mg/kg, about 0.5 mg/kg, about 1 mg/kg, about 2 mg/kg, about 5 mg/kg, about 10 mg/kg, or about 20 mg/kg. In certain embodiments, the therapeutically effective amount is at most about 0.2 mg/kg, about 0.5 mg/kg, about 1 mg/kg, about 2 mg/kg, about 5 mg/kg, about 10 mg/kg, about 20 mg/kg, or about 50 mg/kg.

In certain embodiments, the individual treated is a mammal. In certain embodiments, the mammal is a mouse, rat, rabbit, dog, cat, horse, cow, sheep, pig, goat, llama, alpaca, or yak. In certain embodiments, the individual is a dog, cat, or a horse. In certain embodiments, the individual to be treated is a human.

Methods of Production

Ther polypeptide comprising an IGF2 ligand amino acid sequence can be purified or synthesized in any suitable manner. A nucleic acid encoding the polypeptide can be cloned into a suitable vector and expressed in a suitable cellular system. In certain embodiments, the cellular system is a prokaryotic cell system. In certain embodiments, the cellular system is a eukaryotic cell system. In certain embodiments, the cellular system is a mammalian cell system. In certain embodiments, the polypeptide may be expressed from *Eschericia coli*. In certain embodiments, the polypeptide may be expressed from a yeast cell, including without limitations, *Saccharomyces cerevisiae, Pichia pastoris, Kluyveromyces lactis, Hansenula polymorpha*, or *Yar-*

*rowia lipolytica*. In certain embodiments, the polypeptide may be expressed from a mouse myeloma cell, including without limitations, NSO, Sp2/0, and FO. In certain embodiments, the polypeptide may be expressed from a chinese hamster ovary (CHO) cell. In certain embodiments, the polypeptide may be expressed by a mammalian cell, including without limitations, a COS cell, a Vero cell, or a BHK cell. In certain embodiments, the polypeptide may be expressed from a human cell, including without limitations a HeLa cell, a HEK-293 cell, a CAP cell, a CAP-T cell, a PER.C6® cell The supernatants from such an expression system can be subjected to one or more purification steps involving centrifugation, ultracentrifugation, filtration, diafiltration, tangential-flow filtration, dialysis, chromatography (e.g., cation exchange, ion exchange, hydrophobic interaction, reverse phase, affinity, or size exclusion). The polypeptides can be purified to an extent suitable for human administration. Additionally, polypeptides can be synthesized for inclusion in a formulation to be administered to a human individual. In certain embodiments, the polypeptides can be produced by a suitable peptide synthesis method, such as solid-phase synthesis.

In certain embodiments, the mammalian expression vector pmax Cloning is used to make C- In certain embodiments, the mammalian expression vector pmax Cloning is used to make C-terminally 6×His-tagged, StrepII-tagged, and human IgG1 Fc-tagged vectors. The DNA fragments encoding the secreted myogenic factors are amplified by PCR from human open reading frame (ORF) clones, and subsequently inserted into the tagged vectors by In-Fusion cloning technology (Takara Bio Inc.). The expression vectors carrying the secreted myogenic factors are transiently transfected into ExpiCHO-S cells at a density of 6×10$^6$ per ml by using ExpiFectamine CHO transfection kit (Thermo Scientific).

The expressed myogenic factors with different tags in the culture supernatants are affinity-purified by using different purification media. In some embodiments, the polypeptide comprises an Fc region. For these polypeptides a matrix or resin comprising Protein A, Protein G, protein L or any combination thereof can be used. The matrix or resin may suitably be loaded onto a column for ease in batch purification.

Purification of Immunoglobulin Fusion Proteins

In certain embodiments, the heterologous sequence may comprise an immunoglobulin or a fragment thereof. When the polypeptide comprises an immunoglobulin or a fragment thereof, the polypeptide may be purified by means of protein A, G, or L affinity. Protein A and G are cell surface proteins found in *Staphylococcus aureus*. They have the property of binding the Fc region of a mammalian antibody, in particular of IgG class antibodies. For use in protein A or G affinity chromatography, protein A or G is coupled to a solid matrix such as crosslinked, uncharged agarose (Sepharose, freed from charged fraction of natural agarose), trisacryl, crosslinked dextran or silica-based materials. Methods for such are commonly known in the art, e.g. coupling via primary amino functions of the protein to a CNBr-activated matrix. Protein A binds with high affinity and high specificity to the Fc portion of IgG, that is the Cγ2-Cγ3 interface region of IgG as described in Langone et al., 1982, supra. In particular, it binds strongly to the human allotypes or subclasses IgG1, IgG2, IgG3 and the mouse allotypes or subclasses IgG2a, IgG2b, IgG3.

After purification by Protein A, G, or L the bound fraction can be eluted and passed over or through an additional resin or matrix comprising one or more ion exchange columns. The first ion exchanger is generally an anion exchanger resin. The pH of buffer used for loading and running the first ion exchanger is set as to put opposing total change on the Fc comprising fusion polypeptide and the protein A to be separated by means of the ion exchanger in a flow-through mode according to the present invention, taking the pI's of the Fc comprising fusion polypeptide and protein A into account. The mode of operation of a first anion exchanger according to the present invention requires buffer exchange of the acidic or neutralized eluate from the protein A affinity chromatography step with the equilibrium buffer of the first anion exchanger. After the first anion exchanger, the Fc comprising fusion polypeptide is ready for use in applications or may be deemed to require further polishing by customary purification methods. In a further preferred embodiment, the first ion exchange step is followed by a second ion exchange step in which second step the antibody is loaded and bound by the second ion exchange medium and is eluted with a buffer other than the loading buffer, by means of increased salt and/or pH, as an essentially monomeric, non-aggregated antibody.

In certain embodiments, in the method according to the present invention at least 70%, 80%, or 90% of the Fc comprising fusion polypeptide loaded onto the first ion exchanger can be recovered in the flow-through of the ion-exchanger. In certain embodiments, disregarding glycoforms and eventual processing variants of the same Fc comprising fusion polypeptide, there is only one type of species of Fc comprising fusion polypeptide present in the mixture.

Master Cell Bank and Transgenic Cells

In a certain embodiment, described herein is a master cell bank comprising a cell that comprises a nucleic acid encoding one or more IGF ligand or IGF2 fusion polypeptides integrated into its genome creating a transgenic cell-line. In some embodiments, the master cell bank comprises a plurality of cells that each comprise a nucleic acid encoding an IGF ligand or IGF2 fusion polypeptide. In certain embodiments, the nucleic acid is maintained extrachromosomally on a plasmid or yeast artificial chromosome. In certain embodiments, the nucleic acid is integrated into a chromosomal location. In certain embodiments, the cell is a yeast cell. In certain embodiments, the yeast is *Pichia pastoris* or *Saccharomyces cerevisiae*. In certain embodiments, the cell is a mammalian cell. In certain embodiments, the mammalian cell is a 293T cell or derivative thereof (e.g., 293T-Rex). In certain embodiments, the cell is a bacterial cell.

In certain embodiments, the transgenic mammalian, yeast, or bacterial cell is a master cell bank that comprises a cryopreservative suitable for freezing to at least about −80° or below. In certain embodiments, the master cell bank comprises glycerol or DMSO at between about 10 and about 30%, and is suitable for long-term storage at about −80° or below. In certain embodiments, the master cell bank can preserve a transgenic mammalian, yeast, or bacterial strain for at least 1, 2, 3, 4, 5, 6, 7, 8, 9, 10, or more years.

Pharmaceutically Acceptable Excipients, Carriers, and Diluents

The polypeptides comprising an IGF2 amino acid sequence and an amino acid sequence from a heterologous polypeptide described herein can be administered in a pharmaceutical composition that comprises one or more pharmaceutically acceptable excipients, carriers, or diluents. The exact components can differ based upon the preferred route of administration. The excipients used in a pharmaceutical composition can provide additional function to the polypeptide by making the polypeptide suitable for a particular route of administration (e.g., intravenous, topical, subcutaneous, or intramuscular), increasing polypeptide stability, increasing penetration of a desired tissue (e.g., muscle or skin), increasing residence time at particular site, increasing solubility, enhancing the efficacy of the polypeptide, and/or reducing inflammatory reactions coincident with administration.

In certain embodiments, the compositions are included in a pharmaceutical composition with a solubilizing emulsifying, or dispersing agent. In certain embodiments, the solubilizing agent can allow high-concentration solutions of fusion polypeptides that exceed at least about 2 mg/mL, 5 mg/mL, 10 mg/mL, 15 mg/mL, or 20 mg/mL. Carbomers in an aqueous pharmaceutical composition serve as emulsifying agents and viscosity modifying agents. In certain embodiments, the pharmaceutically acceptable excipient comprises or consists of a carbomer. In certain embodiments, the carbomer comprises or consists of carbomer 910, carbomer 934, carbomer 934P, carbomer 940, carbomer 941, carbomer 1342, or combinations thereof. Cyclodextrins in an aqueous pharmaceutical composition serve as solubilizing and stabilizing agents. In certain embodiments, the pharmaceutically acceptable excipient comprises or consists of a cyclodextrin. In certain embodiments, the cyclodextrin comprises or consists of alpha cyclodextrin, beta cyclodextrin, gamma cyclodextrin, or combinations thereof. Lecithin in a pharmaceutical composition may serve as a solubilizing agent. In certain embodiments, the solubilizing agent comprises or consists of lecithin. Poloxamers in a pharmaceutical composition serve as emulsifying agents, solubilizing agents, and dispersing agents. In certain embodiments, the pharmaceutically acceptable excipient comprises or consists of a poloxamer. In certain embodiments, the poloxamer comprises or consists of poloxamer 124, poloxamer 188, poloxamer 237, poloxamer 338, poloxamer 407, or combinations thereof. Polyoxyethylene sorbitan fatty acid esters in a pharmaceutical composition serve as emulsifying agents, solubilizing agents, surfactants, and dispersing agents. In certain embodiments, the pharmaceutically acceptable excipient comprises or consists of a polyoxyethylene sorbitan fatty acid ester. In certain embodiments, the polyoxyethylene sorbitan fatty acid ester comprises or consists of polysorbate 20, polysorbate 21, polysorbate 40, polysorbate 60, polysorbate 61, polysorbate 65, polysorbate 80, polysorbate 81, polysorbate 85, polysorbate 120, or combinations thereof. Polyoxyethylene stearates in a pharmaceutical composition serve as emulsifying agents, solubilizing agents, surfactants, and dispersing agents. In certain embodiments, the pharmaceutically acceptable excipient comprises or consists of a polyoxyethylene stearate. In certain embodiments, the polyoxyethylene stearate comprises or consists of polyoxyl 2 stearate, polyoxyl 4 stearate, polyoxyl 6 stearate, polyoxyl 8 stearate, polyoxyl 12 stearate, polyoxyl 20 stearate, polyoxyl 30 stearate, polyoxyl 40 stearate, polyoxyl 50 stearate, polyoxyl 100 stearate, polyoxyl 150 stearate, polyoxyl 4 distearate, polyoxyl 8 distearate, polyoxyl 12 distearate, polyoxyl 32 distearate, polyoxyl 150 distearate, or combinations thereof. Sorbitan esters in a pharmaceutical composition serve as emulsifying agents, solubilizing agents, and non-ionic surfactants, and dispersing agents. In certain embodiments, the pharmaceutically acceptable excipient comprises or consists of a sorbitan ester. In certain embodiments, the sorbitan ester comprises or consists of sorbitan laurate, sorbitan oleate, sorbitan palmitate, sorbitan stearate, sorbitan trioleate, sorbitan sesquioleate, or combinations thereof. In certain embodiments, solubility can be achieved with a protein carrier. In certain embodiments the protein carrier comprises recombinant human albumin.

In certain embodiments, the polypeptides comprising an IGF2 amino acid sequence and an amino acid sequence from a heterologous polypeptide described herein are formulated to increase stability. Polypeptides in aqueous formulations may require stabilization to prevent degradation. In certain embodiments, the stabilizer comprises pH buffers, salts, amino acids, polyols/disaccharides/polysaccharides, liposomes, surfactants, antioxidants, reducing agents, or chelating agents. In certain embodiments, the stabilizer comprises or consists of a polyol/non-reducing sugar. In certain embodiments, the non-reducing sugar comprises or consists of sucrose, mannitol, trehalose, raffinose, stachyose, xylitol, starch, verbascose, or combinations thereof. Polypeptides can be encapsulated in liposomes to increase stability. In certain embodiments, the stabilizer comprises or consists of liposomes. In certain embodiments, the liposomes comprise or consists of ipalmitoylphosphatidylcholine (DPPC) liposomes, phosphatidylcholine: cholesterol (PC:Chol) (70:30) liposomes, or dipalmitoylphosphatidylcholine: dipalmitoylphosphatidylserine (DPPC:DPPS) liposomes (70:30). Non-ionic surfactants can increase the stability of a polypeptide. In certain embodiments, the stabilizer comprises or consists of a non-ionic surfactant. In certain embodiments, the non-ionic surfactant comprises or consists of polysorbates (e.g., poly sorbate 80, poly sorbate 20), alkylsaccharides alkyl ethers and alkyl glyceryl ethers, polyoxyethelene (4) lauryl ether; polyoxyethylene cetyl ethers, polyoxyethylene stearyl ethers, sorbitan fatty acid esters, polyoxyethylene fatty acid esters, or combinations thereof. In certain embodiments, the polypeptide is formulated with a protein surfactant, such as recombinant human serum albumin as a stabilizer. Antioxidants or reducing agents can increase the stability of a polypeptide. In certain embodiments, the stabilizer comprises or consists of an antioxidant or reducing agent. In certain embodiments, the reducing agent comprises or consists of dithiothreitol, ethylenediaminetetraacetic acid, 2-Mercaptoethanol, Tris(2-carboxyethyl) phosphine hydrochloride, Tris(hydroxypropyl)phosphine, or combinations thereof. In certain embodiments, the antioxidant comprises or consists of methionine, ascorbic acid, citric acid, alpha tocopherol, sodium bisulfite, ascorbyl palmitate, erythorbic acid, or combinations thereof. Chelating agents can stabilize polypeptides by reducing the activity of proteases. In certain embodiments, the stabilizer comprises or consists of a chelating agent. In certain embodiments, the chelating agent comprises or consists of ethylenediaminetetraacetic acid (EDTA), ethylene glycol-bis(β-aminoethyl ether)-N,N,N', N'-tetraacetic acid (EGTA), metal complexes (e.g. Zn-protein complexes), or combinations thereof. Buffer agents can stabilize polypeptides by reducing the acid hydrolysis of polypeptides. In certain embodiments, the stabilizer comprises or consists of a buffer agent. In certain embodiments, the buffer agent comprises or consists sucrose octa-sulfate, ammonium carbonate, ammonium phosphate, boric acid, sodium citrate, potassium citrate, lactic acid, 3-(N-morpholino) propanesulfonic acid (MOPS), 2-(N-morpholino) ethanesulfonic acid (MES), hydroxymethylaminomethane (Tris), calcium carbonate, calcium phosphate or combinations thereof.

The polypeptides comprising an IGF2 amino acid sequence and an amino acid sequence from a heterologous polypeptide described herein also may be entrapped in or associated with microcapsules prepared, for example, by coacervation techniques or by interfacial polymerization (for example, hydroxymethylcellulose or gelatin-microcapsules and poly-(methylmethacylate) microcapsules, respectively), in colloidal delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980).

The polypeptides comprising an IGF2 amino acid sequence and an amino acid sequence from a heterologous polypeptide described herein may be formulated or delivered with an anti-inflammatory agent. In certain embodiments, the anti-inflammatory agent comprises or consists of a corticosteroid. In certain embodiments, the corticosteroid comprises or consists of hydrocortisone, cortisone, ethamethasoneb (Celestone), prednisone (Prednisone Intensol), prednisolone (Orapred, Prelone), triamcinolone (Aristospan Intra-Articular, Aristospan Intralesional, Kenalog), methylprednisolone (Medrol, Depo-Medrol, Solu-Medrol), or dexamethasone (Dexamethasone Intensol). In certain embodiments, the anti-inflammatory comprises or consists of a non-steroidal anti-inflammatory (NSAID). In certain embodiments, the NSAID comprises or consists of aspirin, celecoxib, diclofenac, diflunisal, etodolac, ibuprofen, indomethacin, ketoprofen, ketorolac, nabumetone, naproxen, oxaprozin, piroxicam, salsalate, sulindac, or tolmetin.

In certain embodiments, the polypeptides comprising an IGF2 amino acid sequence and an amino acid sequence from a heterologous polypeptide described herein are included in a pharmaceutical composition suitable for intravenous administration comprising one or more pharmaceutically acceptable excipients, carriers, and diluents. In certain embodiments, the polypeptides of the current disclosure are administered suspended in a sterile solution. In certain embodiments, the solution is one commonly used for administration of biological formulations, and comprises, for example, about 0.9% NaCl or about 5% dextrose. In certain embodiments, the solution further comprises one or more of: buffers, for example, acetate, citrate, histidine, succinate, phosphate, potassium phosphate, bicarbonate and hydroxymethylaminomethane (Tris); surfactants, for example, polysorbate 80 (Tween 80), polysorbate 20 (Tween 20), and poloxamer 188; polyol/disaccharide/polysaccharides, for example, glucose, dextrose, mannose, mannitol, sorbitol, sucrose, trehalose, and dextran 40; amino acids, for example, glycine, histidine, leucine, or arginine; antioxidants, for example, ascorbic acid, methionine; or chelating agents, for example, EDTA, or EGTA.

In certain embodiments, the polypeptides comprising an IGF2 amino acid sequence and an amino acid sequence from a heterologous polypeptide described herein are included in a pharmaceutical composition suitable for intramuscular or subcutaneous administration comprising one or more pharmaceutically acceptable excipients, carriers, and diluents. Formulations suitable for intramuscular or subcutaneous injection can include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include ethanol, polyols (inositol, propyleneglycol, polyethylene-glycol, glycerol, cremophor and the like) and suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

In certain embodiments, the polypeptides comprising an IGF2 amino acid sequence and an amino acid sequence from a heterologous polypeptide described herein are formulated for topical administration as a cream, gel, paste, ointment, or emulsion. Excipients in a cream, gel, paste, ointment, or emulsion can comprise gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecyl sulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars, and starches.

The excipient used with the polypeptides comprising an IGF2 amino acid sequence and an amino acid sequence from a heterologous polypeptide described herein will allow for storage, formulation, or administration of highly concentrated formulations. In certain embodiments, a highly concentrated fusion polypeptide(s) comprises at least about 1, 2, 3, 4, 5, 6, 7, 8, 9, 10, 15, 20, 25, 20, 25, 40, 45, 50 or more milligrams per milliliter.

In certain embodiments, the polypeptides and/or compositions of the current disclosure are shipped/stored lyophilized and reconstituted before administration. In certain embodiments, lyophilized ligand fusion polypeptide formulations comprise a bulking agent such as, mannitol, sorbitol, sucrose, trehalose, and dextran 40. The lyophilized formulation can be contained in a vial comprised of glass. The fusion polypeptides when formulated, whether reconstituted or not, can be buffered at a certain pH, generally less than 7.0. In certain embodiments, the pH can be between 4.5 and 6.5, 4.5 and 6.0, 4.5 and 5.5, 4.5 and 5.0, or 5.0 and 6.0.

Kits

Also described herein are kits comprising one or more of the polypeptides comprising an IGF2 amino acid sequence and an amino acid sequence from a heterologous polypeptide described herein in a suitable container and one or more additional components selected from: instructions for use; a diluent, an excipient, a carrier, and a device for administration.

In certain embodiments, described herein is a method of preparing a soft tissue or muscle disease or disorder treatment comprising admixing one or more pharmaceutically acceptable excipients, carriers, or diluents and polypeptides comprising an IGF2 amino acid sequence and an amino acid sequence from a heterologous polypeptide described herein. In certain embodiments, described herein is a method of preparing a soft tissue or muscle disease or disorder treatment for storage or shipping comprising lyophilizing one or more antibodies of the current disclosure.

EXAMPLES

Example 1—Expression and Purification of Recombinant Proteins

Mammalian expression plasmids carrying genes with different tags were transiently transfected into CHO cells.

The genes were expressed to produce proteins that were subsequently secreted into the culture medium. The proteins in the culture medium were visualized on polyacrylamide gels and their activities were measured by in vitro functional assays. Then the recombinant proteins in the culture medium were affinity purified. The purified proteins were visualized on polyacrylamide gels to evaluate the purity and assayed by in vitro functional assays to determine their biological activities.

Expression vector engineering: Mammalian expression vector pmax Cloning was used to make C-terminally 6×His-tagged, StrepII-tagged, and human IgG1 and IgG4 Fc-tagged vectors. The DNA fragments encoding the secreted myogenic factors were amplified by PCR from human open reading frame (ORF) clones, and subsequently inserted into the tagged vectors by In-Fusion cloning technology (Takara Bio Inc.).

Expressing secreted myogenic polypeptides: The expression vectors carrying the secreted myogenic factors were transiently transfected into ExpiCHO-S cells at a density of $6 \times 10^6$ per ml by using ExpiFectamine CHO transfection kit (Thermo Scientific). After 18-22 hours, CHO feed and enhancer were added into the transfected culture. Then the expressed proteins were monitored by SDS-PAGE every 24 hours to achieve maximal expression level. In most of the cases, cell culture was collected at day 4, and cells were spun down. The supernatant was spun down again to get rid of cellular debris. The clarified culture supernatant containing the secreted myogenic factors was stored at $-80°$ C. or immediately processed for use.

Measuring expression level of secreted myogenic polypeptides: To measure the improved expression level of the secreted myogenic factors, three protein analytical techniques were applied: sodium dodecyl sulfate polyacrylamide gel electrophoresis (SDS-PAGE), Western blotting, and enzyme-linked immunosorbent assay (ELISA). Western Blots were performed to identify the myogenic factors. ELISAs were used to measure the absolute amount of myogenic factors in the culture supernatant.

Isolation of engineered myogenic polypeptides: The expressed myogenic factors with different tags in the culture supernatants were affinity-purified by using different purification media. For Fc-fusion factors, either Protein A magnetic beads (GenScript) or Protein A membrane column (Takara Bio Inc.) were used to specifically bind to the Fc-fusion factors. For 6×His-tagged factors, NTA-magnetics beads (NEB) were used to isolate the factor.

Example 2—Purified IGF2-hFcm Promoted Differentiation of Human Myoblast Cells FIG. 1A: The suspension CHO cells were transiently transfected with the IGF2-hFcm encoding plasmid. IGF2-hFcm was affinity-purified by Protein A membrane column. The purified IGF2-hFcm was added into the culture of human myoblast cells for 96 hours. Myosin heavy chain (MyHC) was immunostained and imaged by a fluorescence microscope. The percentage area of MyHC of human myoblasts treated with the purified IGF2-hFcm is significantly higher than the percentage area of MyHC of human myoblasts treated with the vehicle control (One-Way ANOVA Tukey Honest Significant Difference, n=2-6).

| Condition | % MyHC | SD | p-value |
|---|---|---|---|
| Vehicle control | 1.787 | 0.186 | |
| 33 nM IGF2-hFcm | 3.734 | 0.790 | 0.012 |
| 66 nM IGF2-hFcm | 5.922 | 0.795 | 3.20E−05 |
| 133 nM IGF2-hFcm | 7.568 | 0.538 | 1.46E−06 |

Example 3 IGF2—LhFc4 Promoted Differentiation of Human Myoblast Cells

Figure 1B:
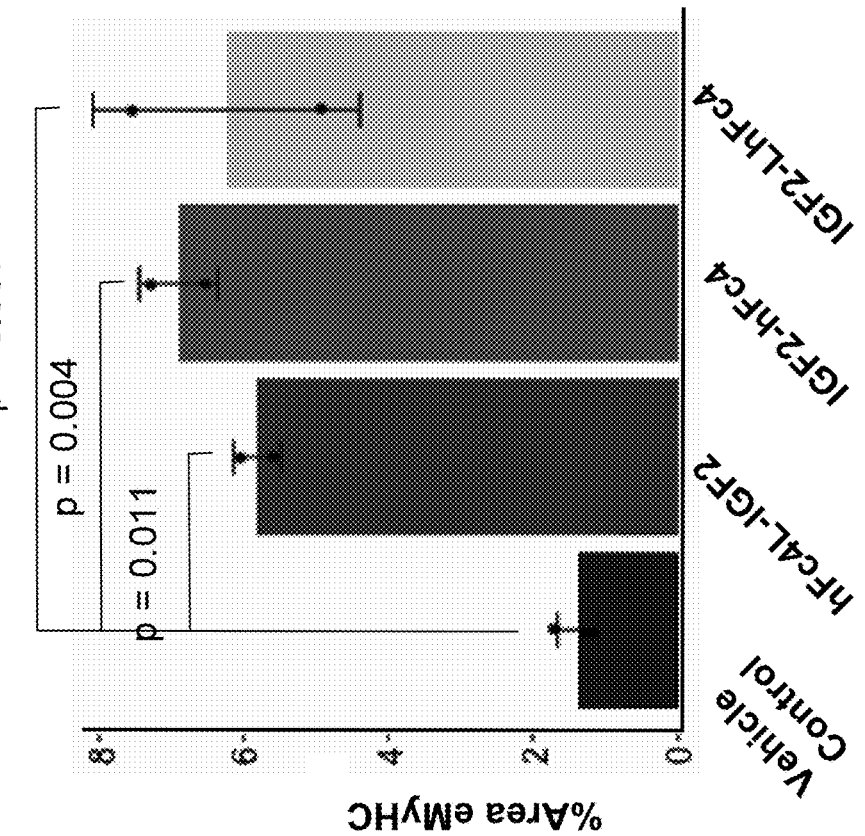
FIG. 1B depicts purified IGF2-LhFc4 promoted differentiation of human myoblast cells FIG. 2A purified HSA-L-IGF2R61A promoted differentiation of human myoblast cells.

FIG. 1B: The suspension CHO cells were transiently transfected with the IGF2-LhFc4 encoding plasmid. IGF2-LhFc4 was affinity-purified by Protein A membrane column. The purified IGF2-LhFc4 was added into the culture of human myoblast cells for 96 hours with daily media change. Myosin heavy chain (MyHC) was immunostained and imaged by a fluorescence microscope. The percentage area of MyHC of human myoblasts treated with the purified IGF2-LhFc4 is significantly higher than the percentage area of MyHC of human myoblasts treated with the vehicle control (One-Way ANOVA Tukey Honest Significant Difference, n=2-6).

| Condition | % MyHC | SD | p-value |
|---|---|---|---|
| Vehicle control | 1.384 | 0.285 | |
| hFc4L-IGF2 | 5.820 | 0.319 | 0.011 |
| IGF2-hFc4 | 6.901 | 0.537 | 0.004 |
| IGF2-LhFc4 | 6.237 | 1.848 | 0.007 |

Example 4—Purified HSA-L-IGF2R61A Differentiation of Human Myoblast Cells

Figure 2A:
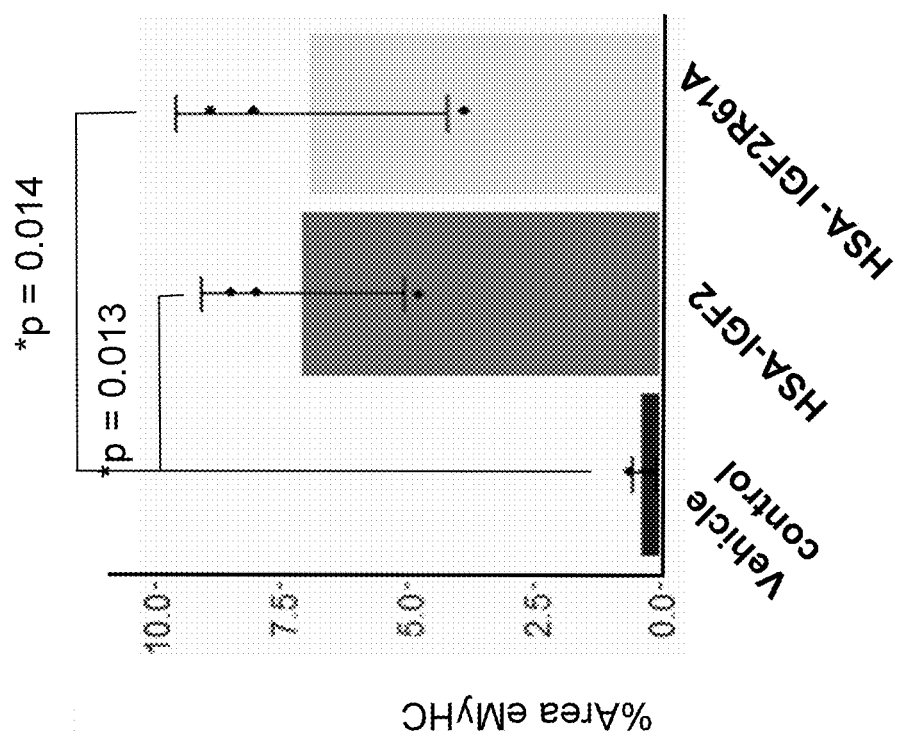
FIG. 2B depicts IGF2 and IGF2 receptors were expressed in human myoblast
FIG. 2C depicts IGF2 and IGF2 receptors were expressed in human myoblast

FIG. 2A: The suspension CHO cells were transiently transfected with the HSA-L-IGF2R61A encoding plasmid. HSA-L-IGF2R61A was affinity-purified by Protein A membrane column. The purified HSA-L-IGF2R61A was added into the culture of human myoblast cells for 96 hours with daily media change. Myosin heavy chain (MyHC) was immunostained and imaged by a fluorescence microscope. The percentage area of MyHC of human myoblasts treated with the purified HSA-L-IGF2R61A is significantly higher than the percentage area of MyHC of human myoblasts treated with the vehicle control (One-Way ANOVA Tukey Honest Significant Difference, n=2-6).

| Condition | % MyHC | SD | p-value |
|---|---|---|---|
| Vehicle control | 0.34 | 0.221 | |
| HSA-IGF2 | 7.079 | 2.009 | 0.013 |
| HSA-IGF2R61A | 6.914 | 2.691 | 0.014 |

Example 5 IGF2 and IGF2 Receptors are Expressed in Human Myoblast

Figure 2B:
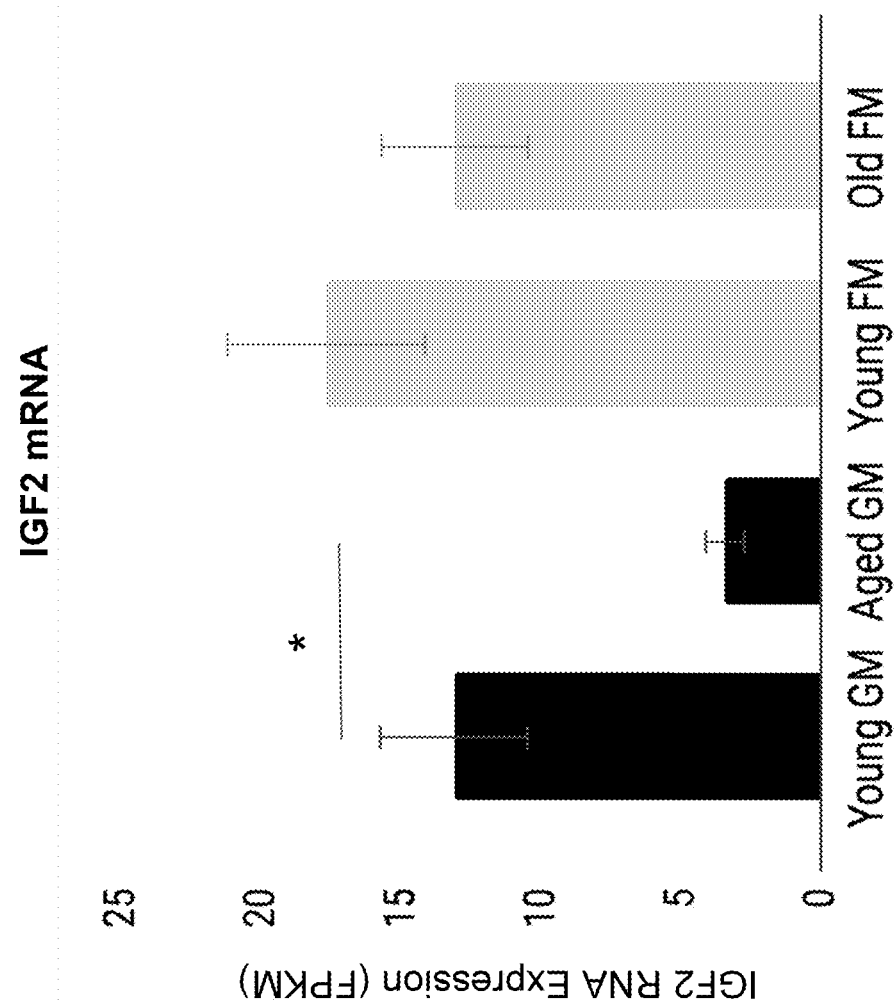
Figure 2C:
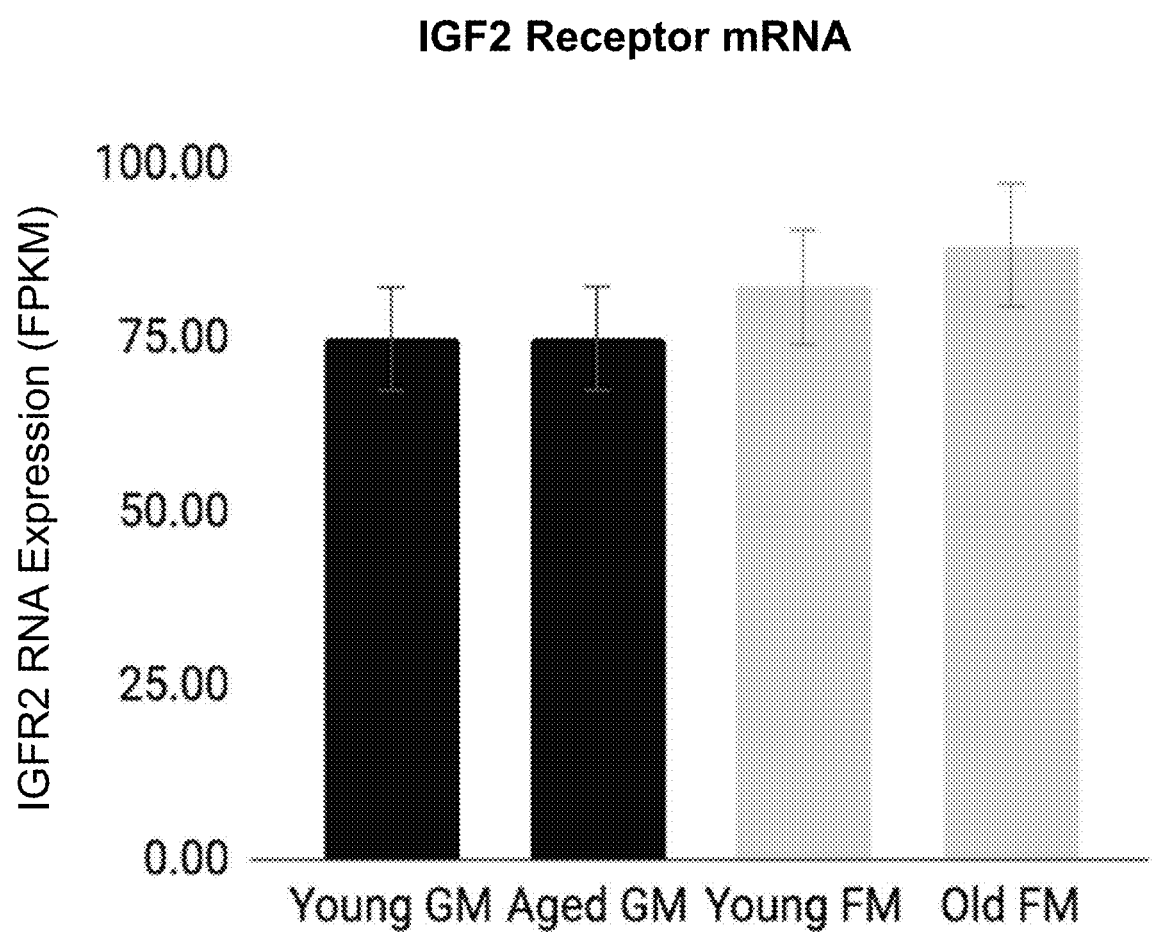

Bar graph and quantitation table of IGF2 (FIG. 2B) and IGF2 receptor (FIG. 2C) RNASeq expression in young (17-21 year old caucasian males) and aged human myoblast (68-69 year old caucasian males) cell lines. Myoblast were cultured growth media (GM) or 96 h in fusion media (FM). Fresh media was added every 24 h. Mean±SEM. n=6. Expression are expressed as FPKM. Significant p-values (Young GM~Aged GM: 3.54E-04).

FIG. 2B

| n = 6 | IGF2 (FPKM) | SEM | p-val (n = 6) |
|---|---|---|---|
| Young GM | 13.11 | 3.275 | — |
| Aged GM | 3.413 | 1.12 | 3.54E−04 |
| Young FM | 17.68 | 6.42 | — |
| Aged FM | 13.08 | 3.67 | n.s. |

FIG. 2C

| n = 6 | IGF2R (FPKM) | SEM | P-val (n = 6) |
|---|---|---|---|
| Young GM | 74.93 | 9.45 | — |
| Aged GM | 75.01 | 6.89 | n.s. |
| Young FM | 82.35 | 3.43 | — |
| Aged FM | 88.44 | 9.86 | n.s. |

Example 6 Sodium Butyrate Enhances Muscle Fusion

Figure 3A:
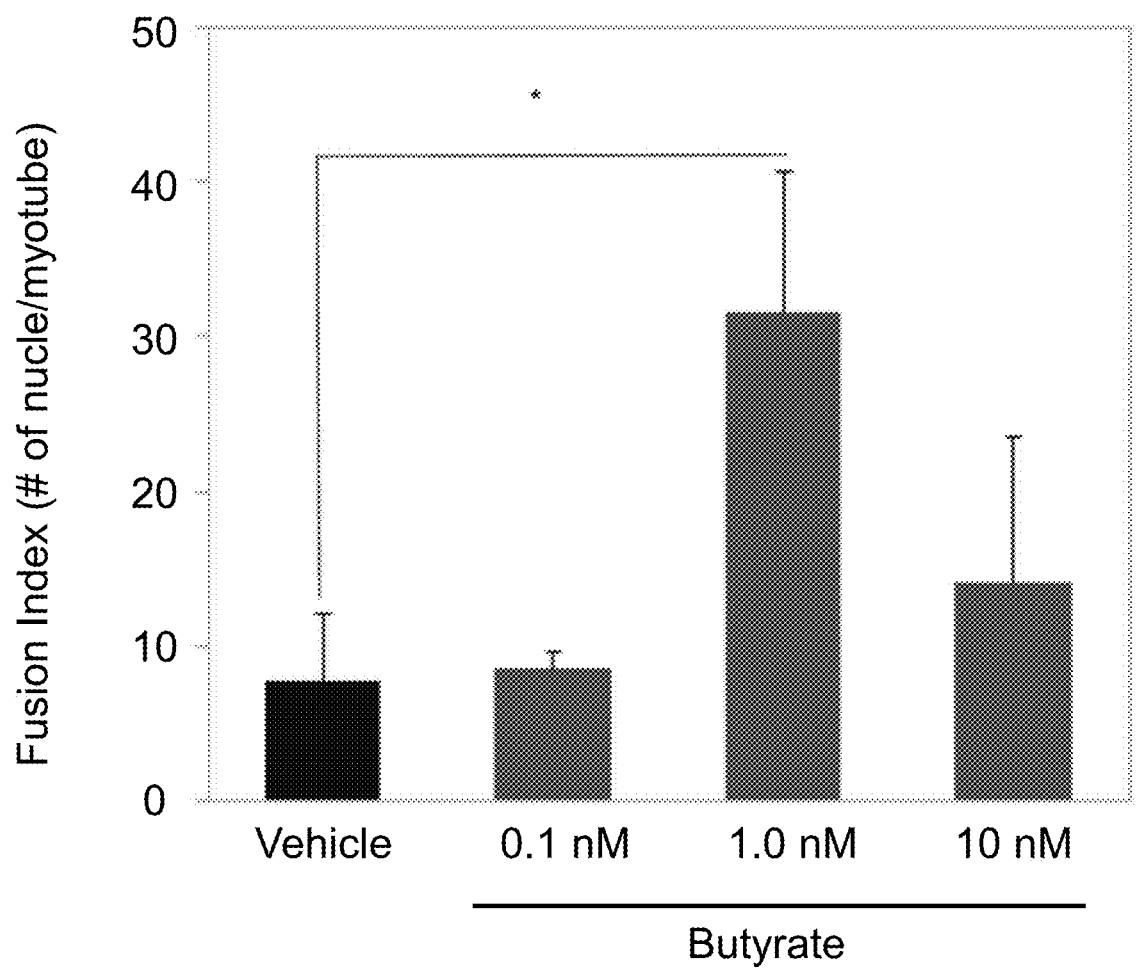
FIG. 3A depicts sodium butyrate enhanced muscle fusion

Mouse myoblasts were treated with PBS or sodium butyrate at concentrations 0.1 nM, 1 nM, and 10 nM. Myoblasts were cultured for 48 hours, with fresh media added every 24 hours. Cells were pulsed for 2-5 hours with EdU (30 uM), ethanol fixed, stained with Hoescht 3342, immunostained for proliferation—as measured by the percent of cells staining positive for EdU (% EdU)-, and immunostained for differentiation—as measured by the increase in cellular area staining positive for embryonic myosin heavy chain (% eMyHC) relative to the negative controls, which received media and vehicle only. When compared to untreated myoblasts, the cells treated with 1 nM of sodium butyrate had increased rates of fusion, as depicted in FIG. 3A. Significance was determined by a p-value less than 0.05 by the one-way ANOVA Tukey Honest Significant Difference test.

FIG. 3A: Bar graph of fusion index in response to sodium butyrate (NaBut) compared to vehicle. Myoblast were cultured 48 h in the presence of NaBut at indicated dose. Fresh media and NaBut were added every 24 h. Mean∓S.D. Table with quantitation of fusion index and p-values also shown. (*p<0.05 by Student's Two-tailed T-test, n=3-5)

| Condition | Fusion Index (nuclei/myotube) | p-value |
|---|---|---|
| vehicle | 7.56 | — |
| NaBut 0.1 nM | 8.44 | n.s. |
| NaBut 1 nM | 31.60 | 2.02E−3 |
| NaBut 10 nM | 14.00 | n.s. |

Example 7 Sodium Butyrate Enhances IGF2 Activity

Human myoblast cells were treated with either PBS (vehicle), IGF2 (15 ng/ml), sodium butyrate, or IGF2 and sodium butyrate. Fresh media was added every 24 hours. After 96 hours, cells were pulsed for 2-5 hours with EdU (30 uM), ethanol fixed, stained with Hoescht 3342, immunostained for proliferation—as measured by the percent of cells staining positive for EdU (% EdU)-, and immunostained for differentiation—as measured by the increase in cellular area staining positive for embryonic myosin heavy chain (% eMyHC) relative to the negative controls, which received media and vehicle only. The total area of eMyHc positive cells was analyzed, and treated cells were compared to cells treated with the vehicle alone. Cells that had been treated with IGF alone and two conditions in which cells had been treated with IGF2 and sodium butyrate produced a significant increase in the amount of differentiation. There was a significant increase in the total area of eMyHC cells in the cells treated with 1 nM and 100 nM of sodium butyrate and IGF2, compared to the cells treated with IGF2 alone. Significance was determined by a p-value less than 0.05 by the one-way ANOVA Tukey Honest Significant Difference test.

Figure 3B:
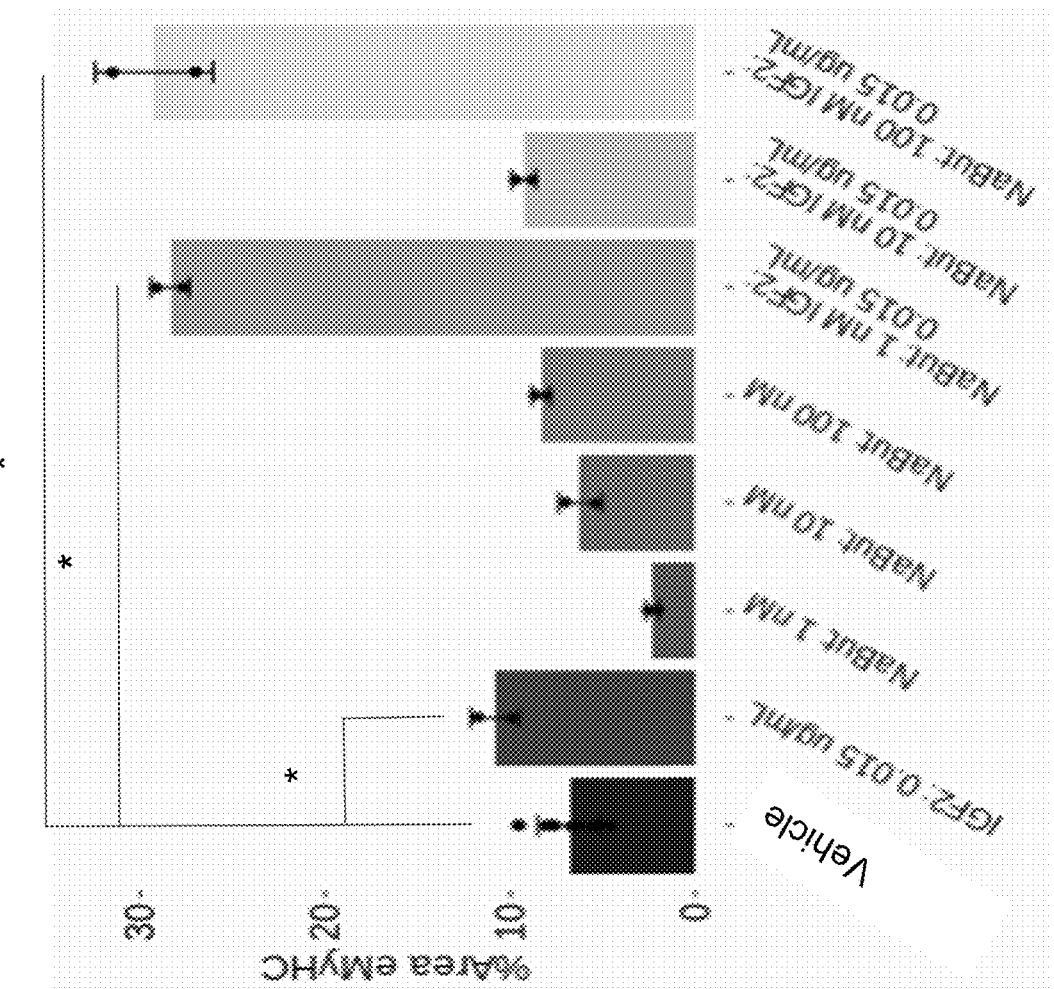
FIG. 3B depicts sodium butyrate enhanced IGF2 activity

FIG. 3B: Bar graph of fusion index of mouse myoblast in response to sodium butyrate (NaBut) compared to vehicle. Mouse myoblast were cultured 48 h in the presence of NaBut at indicated dose. Fresh media and NaBut were added every 24 h. Mean∓S.D. Table with quantitation of fusion index and p-values shown. (*p<0.05 by Student's Two-tailed T-test, n=3-5). Significant p-values (Vehicle~IGF2: 0.015 ug/mL: 6.33E-06, Vehicle~NaBut: 1 nM IGF2: 0.015 ug/mL: 1.79E-11, Vehicle~NaBut: 100 nM IGF2: 0.015 ug/mL: 1.79E-11)

Table of data for FIG. 3B

| Condition | % eMyHC | SD | p-value |
|---|---|---|---|
| Vehicle | 6.813 | 1.695 | — |
| IGF2: 0.015 ug/mL | 10.843 | 1.308 | |
| NaBut: 1 nM | 2.321 | 0.374 | |
| NaBut: 10 nM | 6.199 | 1.174 | |
| NaBut: 100 nM | 8.341 | 0.477 | |
| NaBut: 1 nM IGF2: 0.015 ug/mL | 28.387 | 1.036 | 1.79E−11 |
| NaBut: 10 nM IGF2: 0.015 ug/mL | 9.274 | 0.654 | |
| NaBut: 100 nM IGF2: 0.015 ug/mL | 29.239 | 3.185 | 1.79E−11 |

Figure 3C:
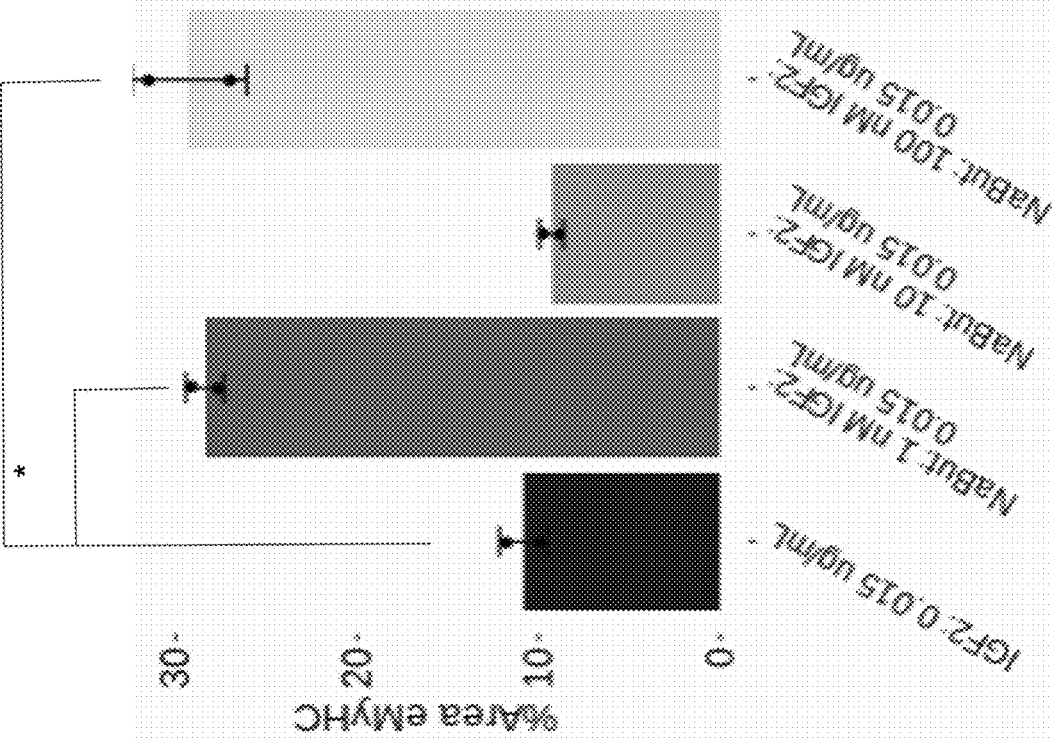
FIG. 3C depicts sodium butyrate enhanced IGF2 activity

FIG. 3C Bar graph quantitation of % Area eMyHC+ human myoblast in response to indicated treatment compared to IGF2 (15 ng/mL). Myoblast were cultured 96 h in the presence of IGF2 at indicated dose. Fresh media and IGF2 was added every 24 h. Mean∓S.D. (*p<0.05 by One-Way Anova Tukey Honest Significant Difference, n=2-12)

Table of data for FIG. 3C

| Condition | % eMyHC | SD | p-value |
|---|---|---|---|
| IGF2: 0.015 ug/mL | 10.843 | 1.308 | |
| NaBut: 1 nM IGF2: 0.015 ug/mL | 28.387 | 1.036 | 6.18E−8 |
| NaBut: 10 nM IGF2: 0.015 ug/mL | 9.274 | 0.654 | |
| NaBut: 100 nM IGF2: 0.015 ug/mL | 29.239 | 3.185 | 3.50E−3 |

Example 8 Sodium Butyrate Enhances IGF2 Activity

Human myoblast cells were treated with either PBS (vehicle), IGF2 (15 ng/ml), sodium butyrate, or IGF2 and sodium butyrate. Fresh media was added every 24 hours.

Figure 4A:
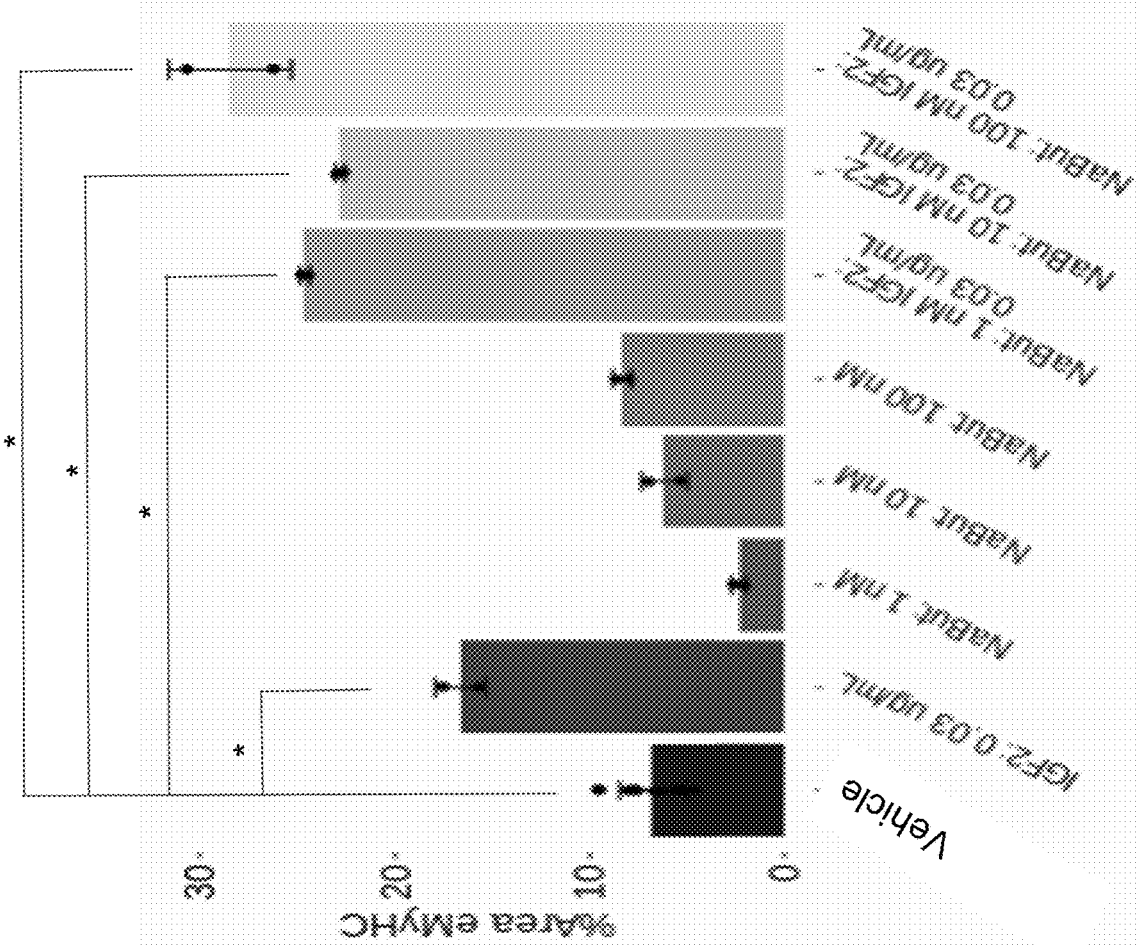
FIG. 4A depicts the change in percent area of eMyHC positive cells treated with additional doses of vehicle, IGF2, sodium butyrate, or IGF2 and sodium butyrate FIG. 4B depict the change in percent area of eMyHC positive cells treated with additional doses of vehicle, IGF2, sodium butyrate, or IGF2 and sodium butyrate

After 48 hours, cells were pulsed for 2-5 hours with EdU (30 uM), ethanol fixed, stained with Hoescht 3342, immunostained for proliferation—as measured by the percent of cells staining positive for EdU (% EdU)-, and immunostained for differentiation—as measured by the increase in cellular area staining positive for embryonic myosin heavy chain (% eMyHC) relative to the negative controls, which received media and vehicle only. The total area of eMyHc positive cells was analyzed, and treated cells were compared to cells treated with the vehicle alone, as seen in FIG. 4A. Myoblasts that had been treated with either 0.03 ug/mL of IGF2 or with IGF2 in combination with sodium butyrate showed a significant increase in the eMyHC+ area when compared to cells cultured with the vehicle alone.

Table of data for FIG. 4A

| Condition | % eMyHC | SD | p-value |
| --- | --- | --- | --- |
| Vehicle | 6.813 | 1.695 | — |
| IGF2: 0.03 ug/mL | 16.620 | 1.301 | 1.42E−08 |
| NaBut: 1 nM | 2.321 | 0.374 | n.s. |
| NaBut: 10 nM | 6.199 | 1.174 | n.s. |
| NaBut: 100 nM | 8.341 | 0.477 | n.s. |
| NaBut: 1 nM IGF2: 0.03 ug/mL | 24.615 | 0.258 | 1.79E−11 |
| NaBut: 10 nM IGF2: 0.03 ug/mL | 22.821 | 0.234 | 1.80E−11 |
| NaBut: 100 nM IGF2: 0.03 ug/mL | 28.427 | 3.136 | 1.79E−11 |

Figure 4B:
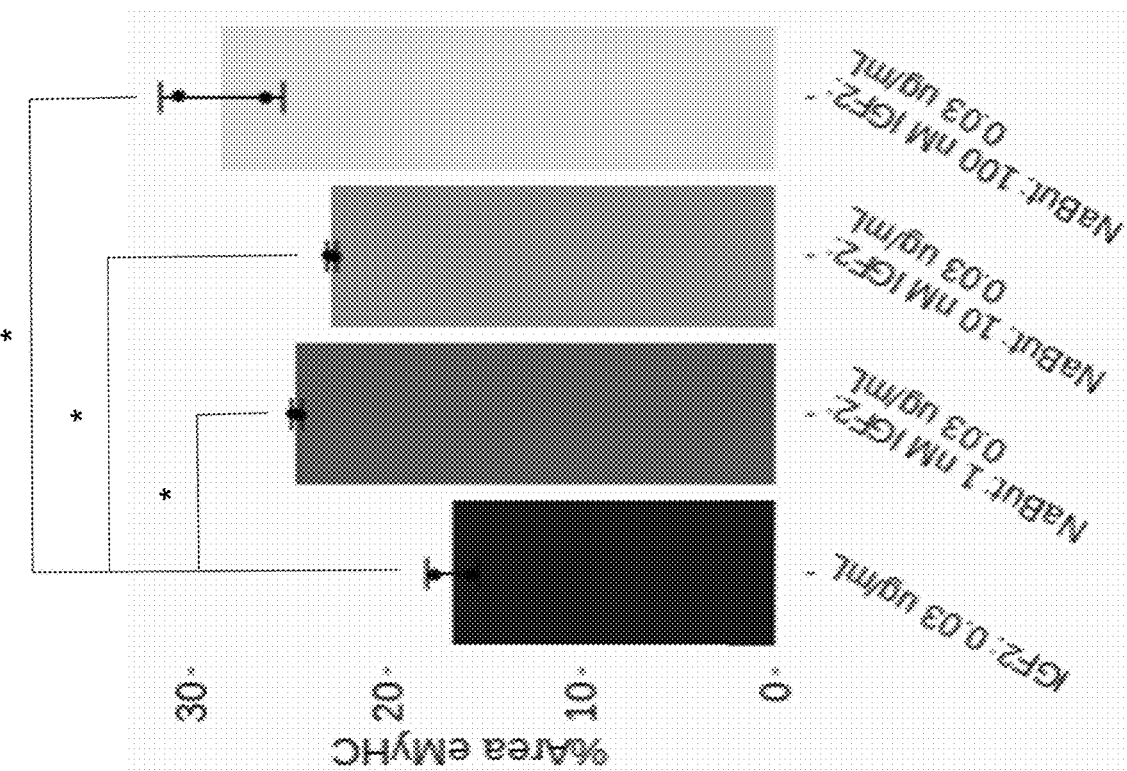

The myoblasts that had been treated with a combination of IGF2 and sodium butyrate were compared to the cells treated with IGF2 alone. There was a significant increase in all cells treated with the combination compared to cells treated with IGF2 alone, as depicted in FIG. 4B and Table. Significance was determined by a p-value less than 0.05 by the one-way ANOVA Tukey Honest Significant Difference test.

Table of data for FIG. 4B

| Condition | % eMyHC | SD | p-value |
| --- | --- | --- | --- |
| IGF2: 0.03 ug/mL | 16.620 | 1.301 | — |
| NaBut: 1 nM IGF2: 0.03 ug/mL | 24.615 | 0.258 | 1.88E−3 |
| NaBut: 10 nM IGF2: 0.03 ug/mL | 22.821 | 0.234 | 4.80E−3 |
| NaBut: 100 nM IGF2: 0.03 ug/mL | 28.427 | 3.136 | 1.87E−3 |

Example 9 IGF2 Enhances MYOG Expression in DM1 Human Myoblast Cells

Figure 5:
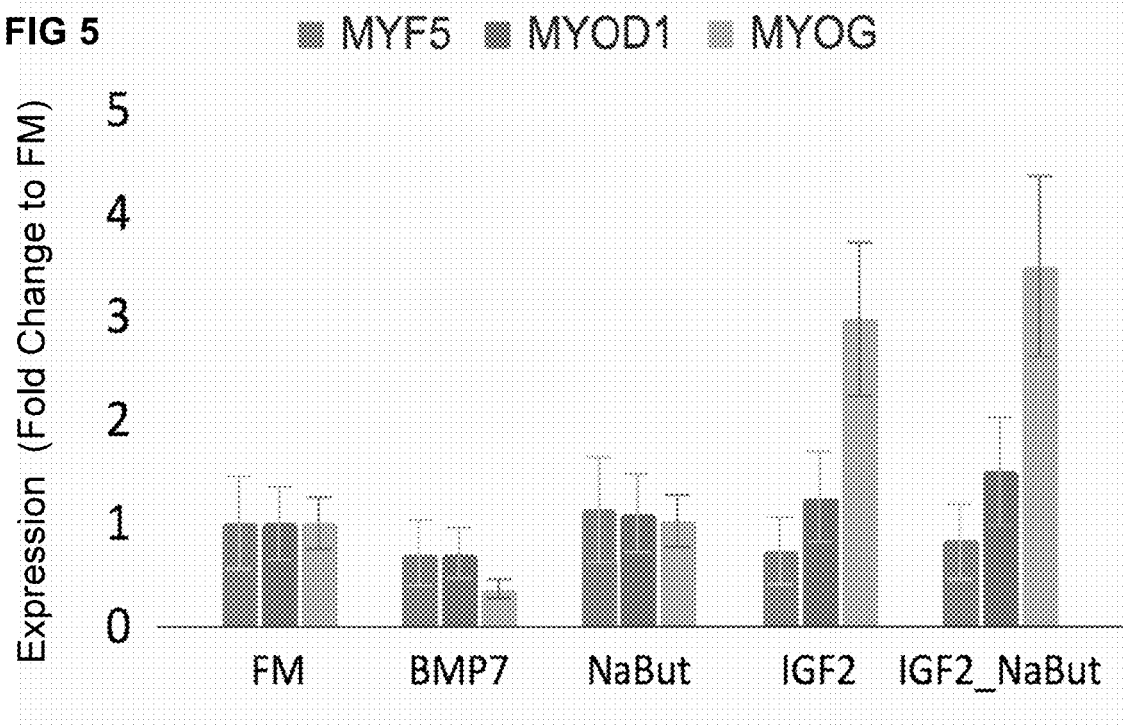
FIG. 5 depicts IGF2 enhances MYOG expression in DM1 human myoblast cells.

FIG. 5 Bar graph of myogenic gene expression fold change in DM1 human myoblast in response to indicated treatment compared to FM (vehicle). Myoblasts were cultured 48 h in the presence of factors (BMP7 50 ng/mL, Butyrate 100 nM, IGF2 200 ng/mL). Mea∓S.D. Significant p-values (FM~IGF2: 4.94E-04, FM~ IGF2_NaBut: 6.53E-03) (*p<0.01) Table of mean and p-value of MYF5, MYOD1, and MYOG (n=3).

Table of data for FIG. 5

| Condition | MYF5 | MYF5 p-value | MYOD1 | MYOD1 p-value | MYOG | MYOG p-value |
| --- | --- | --- | --- | --- | --- | --- |
| FM | 1.000 | | 1.000 | | 1.000 | |
| BMP7 | 0.709 | n.s. | 0.709 | n.s. | 0.361 | n.s. |
| NaBut | 1.128 | n.s. | 1.095 | n.s. | 1.020 | n.s. |
| IGF2 | 0.730 | n.s. | 1.252 | n.s. | 2.972 | 4.94E−04 |
| IGF2 NaBut | 0.820 | n.s. | 1.500 | n.s. | 3.483 | 6.53E−03 |

Example 10 IGF2 Receptor is Expressed on Chondrocyte and Osteocytes

Figure 6:
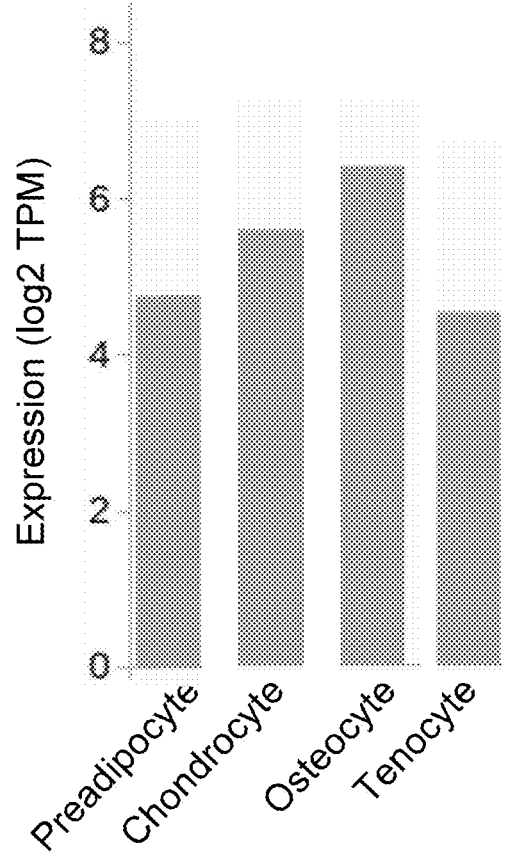
FIG. 6 depicts IGF2 Receptor was expressed on chondrocyte and osteocytes

FIG. 6: Bar graph showing IGF2 receptors are expressed on cartilage-associated cells. Data is derived from Ramilowsky et al., Nature 2015.

Table of data for FIG. 6 RNA Expression (TPM)

| Cell Type | IGF2R |
| --- | --- |
| Preadipocyte (Subcutaneous) | 27.083 |
| Chondrocyte | 47.63 |
| Osteocyte | 83.96 |
| Tenocyte | 23.12 |

Example 11 IGF2 Treatment Promotes Proliferation and Fusion in DM1 Human Myoblast (32 Year Old Caucasian Female) Cells FIG. 7A Bar graph of % EdU+ human myoblast (32 year old caucasian female) and FIG. 7B % area MyHC in response to IGF2. Myoblast were cultured 72 h for proliferation and 96 h for fusion in the presence of indicated factor. Mean∓S.D. Mean∓SD. Significant p-values (EdU: Vehicle~IGF2: 6.8E-3, % eMyHC Area: Vehicle~IGF2: 1.9E-4) (*p<0.05 by Students Two-Tailed T-test, n=3-6).

Table of data for FIG. 7A

| n = 3-6 | EdU FC | s.d. | p-val |
| --- | --- | --- | --- |
| Vehicle | 1.0 | 0.02 | |
| IGF2 | 2.18 | 0.32 | 6.8E−3 |

Table of data for FIG. 7B

| n = 3 | % eMyHC area | s.d. | p-val |
| --- | --- | --- | --- |
| Vehicle | 0.45 | 0.02 | |
| IGF2 | 5.49 | 0.54 | 1.9E−4 |

Example 12 IGF2 Enhances MYH3, CKM, and ATP1B1 Expression in DM1 Human Myoblast (32 Year Old Caucasian Female) Cells FIG. 8A Bar graph of MYH3 and CKM expression fold change in DM1 human myoblast (32 year old caucasian female) in response to indicated treatment compared to vehicle. Myoblasts were cultured 96 h in the presence of factors (IGF2 200 ng/ml). Mean∓S.D. Significant p-values (MYH3: Vehicle~IGF2: 1.13E-03, CKM: Vehicle~IGF2: 7.67E-03) FIG. 8B Bar graph of ATP1B1 expression fold change in DM1 human myoblast (32 year old caucasian female) in response to indicated treatment compared to FM (vehicle). Myoblasts were cultured 48 h in the presence of factors (IGF2 200 ng/mL). Mean∓S.D. Significant p-values (Vehicle~IGF2: 3.11E-05) (*p<0.05 by Students Two-Tailed T-test, n=3).

| Table of data for FIG. 8A | | | | |
|---|---|---|---|---|
| | MYH3 | p-val | CKM | p-val |
| Vehicle | 1 | | 1 | |
| IGF2 | 14.833 | 1.13E−03 | 5.165 | 7.67E−03 |

| Table of data for FIG. 8B | | |
|---|---|---|
| n = 3 | ATP1B1 | p-val |
| Vehicle | 1 | |
| IGF2 | 3.01789 | 3.11E−05 |

Figure 9A:
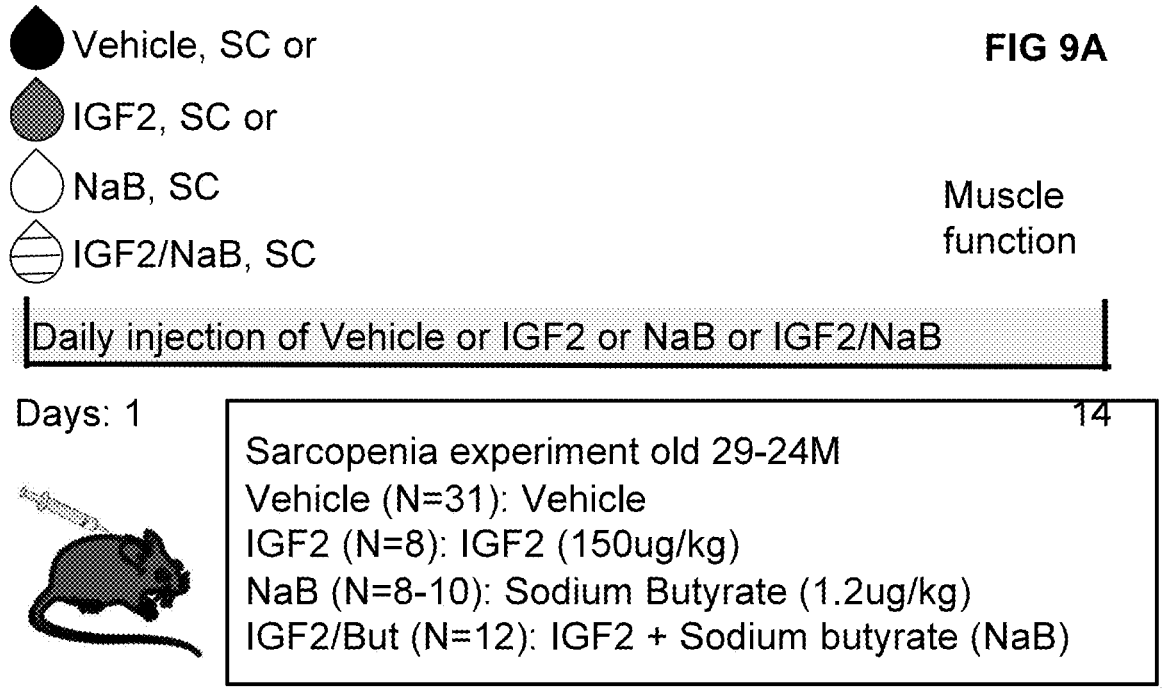
FIG. 9A depicts systemic administration of IGF2/sodium butyrate protected against aging induced muscle dysfunction
Figure 9B:
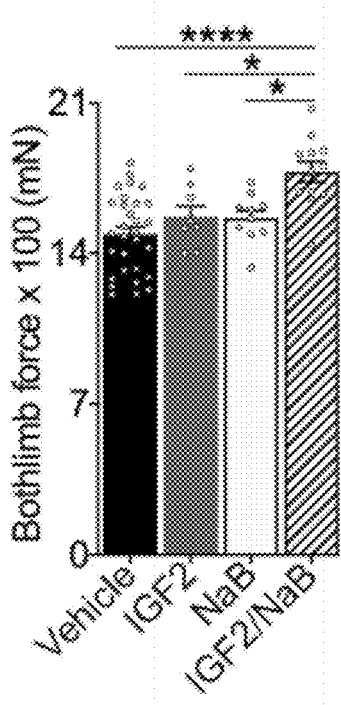
FIG. 9B depicts an experimental overview of systemic administration of IGF2/NaB protected against aging induced muscle dysfunction as measured by grip strength force
Figure 9C:
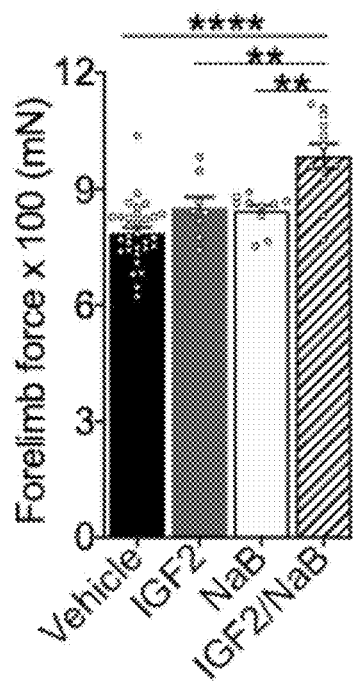
FIG. 9C depicts systemic administration of IGF2/sodium butyrate protected against aging induced muscle dysfunction as measured by both limb grip strength force
Figure 9D:
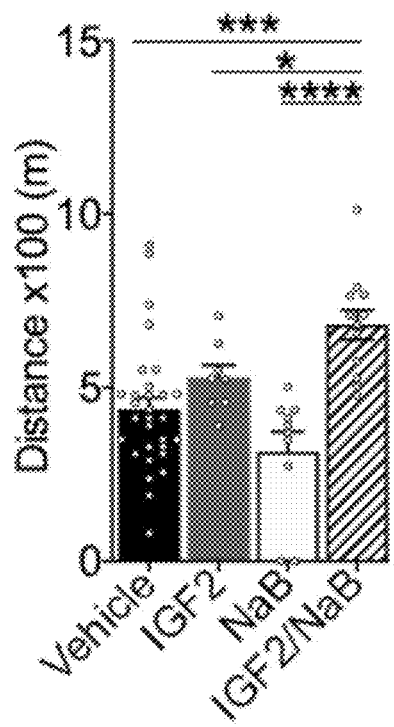
FIG. 9D depicts systemic administration of IGF2/sodium butyrate protected against aging induced muscle dysfunction as measured by forelimb force
Figure 9E:
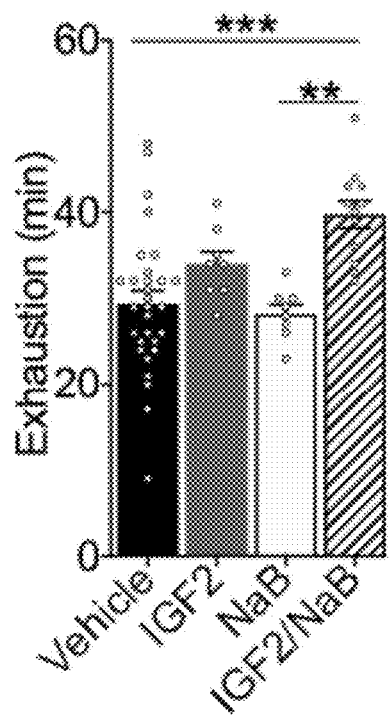
FIG. 9E depicts systemic administration of IGF2/sodium butyrate protected against aging induced muscle dysfunction as measured by treadmill performance
Figure 9F:
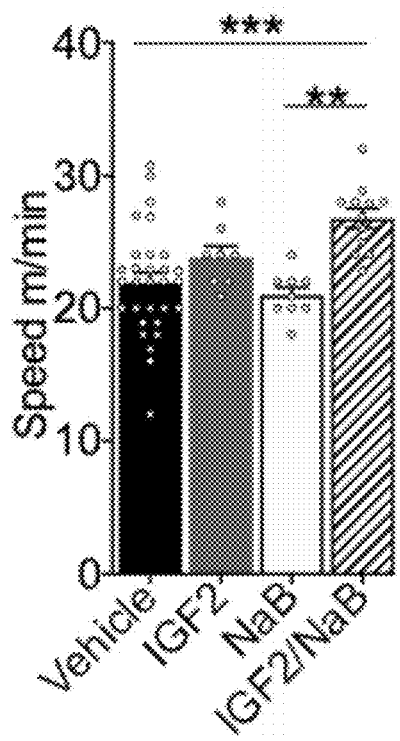
FIG. 9F depicts systemic administration of IGF2/sodium butyrate protected against aging induced muscle dysfunction as measured by running time to exhaustion
Figure 9G:
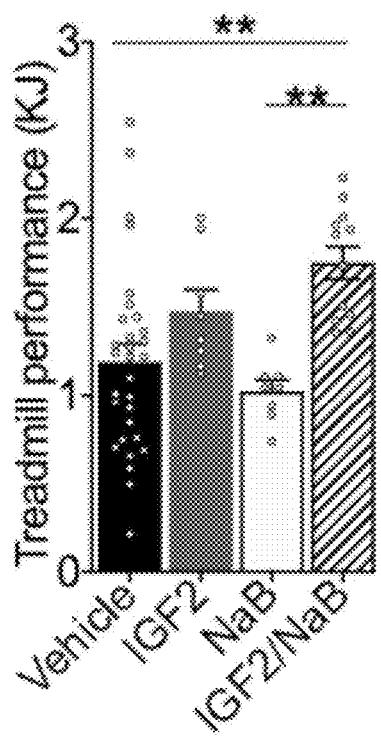
FIG. 9G depicts systemic administration of IGF2/sodium butyrate protected against aging induced muscle dysfunction as measured by maximum running speed

Example 13 Systemic Administration of IGF2/NaB Protects Against Aging Induced Muscle Dysfunction FIG. 9A: Subcutaneous injection of IGF2 (50 ug/kg) or NaB (1.2 g/kg), IGF2/NaB (150 ug/kg; 1.2 g/kg) or vehicle (PBS) were administered to 21-24M old mice for 14 days. Muscle function was assessed at days 13 and 14. (FIG. 9B) Grip strength force assessed at day 13. The first graph FIG. 9B shows Bothlimb grip strength force, **p<0.0001, p=0.0043, p=0.001 (One-way ANOVA, multiple comparisons). FIG. 9C) Forelimb force, **p<0.0001, *p=0.0368, *p=0.0187 (One-way ANOVA, multiple comparisons). FIG. 9D) Treadmill performance measured at day 14 using an induced treadmill running model set to progressively increase speed 2 m/min every subsequent 2 min. Distance ran shown. ***p=0.0005, *p=0.0459, **p<0.0001 (One-way ANOVA, multiple comparisons) FIG. 9E) Time to exhaustion *p=0.0002, p=0.0024 (One-way ANOVA, multiple comparisons) FIG. 9F) Maximum speed *p=0.0004, p=0.0013 FIG. 9G) Work in kj p=0.0026, **p=0.0035 (One-way ANOVA, multiple comparisons).

Example 14 Systemic Administration of IGF2/NaB is Safe

FIG. 10A) Subcutaneous injection of vehicle or IGF2/NaB were administered to 21M old mice for 14 days, blood and serum were collected to assess complete blood count and a metabolic panel for liver, kidney and pancreas function. FIG. 10B-E) 4 representative graphs out of 37 readouts measured showing the white blood cell count (Unpaired t-test, p=0.8020), Albumin concentration (Unpaired t-test, p>0.9999), Creatinine concentration (Unpaired t-test, p=0.5490) and Calcium concentration (Unpaired t-test, p=0.811).

Figure 11B:
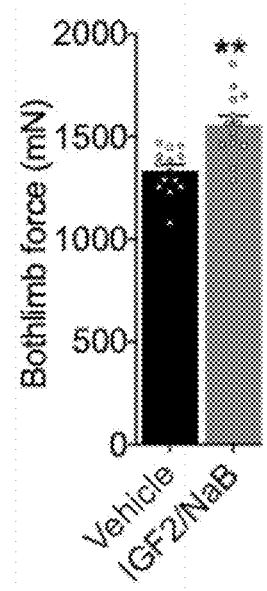
FIG. 11B depicts systemic administration of IGF2 and sodium butyrate protected against Dexamethasone induced muscle atrophy as measured by bothlimb force
Figure 11C:
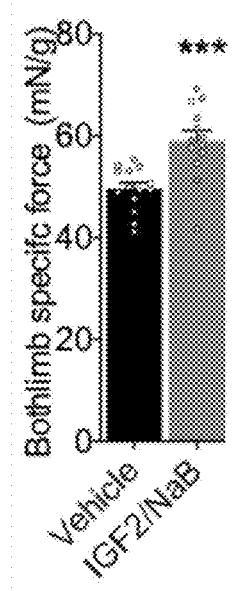
FIG. 11C depicts systemic administration of IGF2 and sodium butyrate protected against Dexamethasone induced muscle atrophy as measured by specific bothlimb force
Figure 11D:
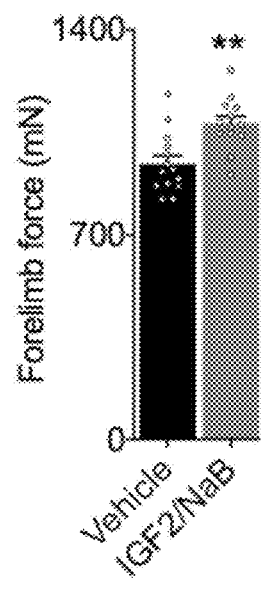
FIG. 11D depicts systemic administration of IGF2 and sodium Butyrate protected against Dexamethasone induced muscle atrophy as measured by forelimb force
Figure 11E:
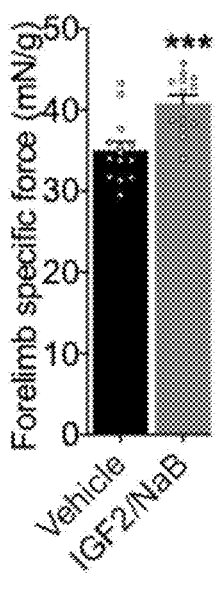
FIG. 11E depicts systemic administration of IGF2 and sodium Butyrate protected against Dexamethasone induced muscle atrophy as measured by specific bothlimb force calculated as the ratio of bothlimb force in mN over the weight
Figure 11F:
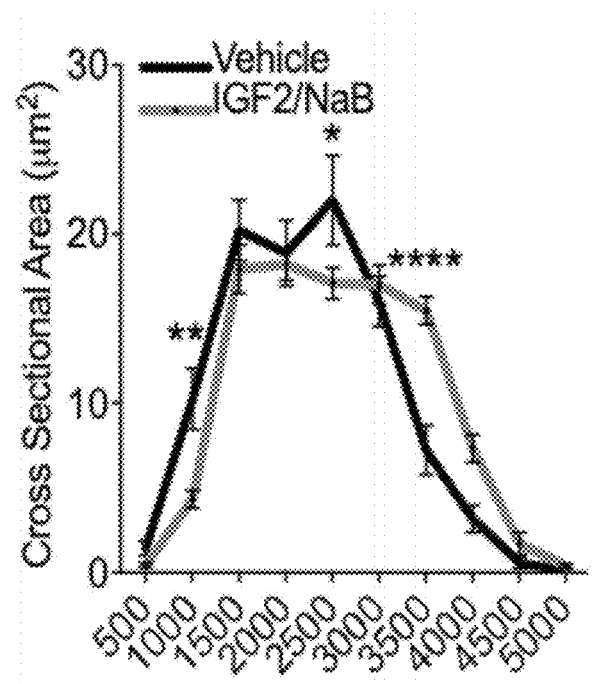
FIG. 11F depicts systemic administration of IGF2 and sodium butyrate protected against Dexamethasone induced muscle atrophy as measured by muscle fiber cross sectional area

Example 15 Systemic Administration of IGF2/but Protects Against Dexamethasone Induced Muscle Atrophy FIG. 11A) Dexamethasone (25 mg/kg i.p.) was administered to 12 weeks old mice for 14 days simultaneously with a subcutaneous injection of IGF2/NaB (150 ug/kg; 1.2 g/kg) or vehicle (PBS). Muscle function was assessed at day 13-14. Grip strength force assessed at day 13, graphs showing FIG. 11B) bothlimb force and FIG. 11C) specific bothlimb force measured on Day 13. Specific bothlimb force calculated as the ratio of bothlimb force in mN over the weight in g, *p=0.0003, *p=0.0004 (Unpaired t-test). FIG. 11D) Grip strength force assessed at day 13, graphs showing FIG. 11D) forelimb force and FIG. 11E) forelimb specific force measured on Day 13. Specific forelimb force calculated as the ratio of forelimb force in mN over the weight in g, p=0.0012, *p=0.0005 (Unpaired t-test). FIG. 11F) At day 15, mice were euthanized and TAs were collected for histological analysis, graphs showing muscle fiber size distribution assessed using SMASH software. **p=0.054, *p=0.037, and **** p<0.0001 (2-way ANOVA, multiple comparisons).

Example 16 Myogenic Activity Measurement Assay In Vitro

Myoblast Proliferation Assay

Reduced regeneration from an individual's tissue progenitor cells is a hallmark of age or disease related dysfunction, therefore assays that measure mitogenic capacity in tissue progenitor cells serve as a read-out for potential success of a treatment. Measuring the increased proliferation rate, degree of differentiation, and cellular survival of treated mouse or human muscle progenitor cells will provide good basis for potentially therapeutic regenerative factors for treating individuals who have suffered illness, injury, or who possess genetic or developmental defects leading to premature tissue loss, wasting, or weakening.

Mouse muscle progenitor cells (early passage myoblasts) were cultured and expanded in mouse growth medium: Ham's F-10 (Gibco), 20% Bovine Growth Serum (Hyclone), 5 ng/mL FGF2 and 1% penicillin-streptomycin on Matrigel coated plates (1:300 matrigel: PBS), at 37° C. and 5% CO2. For experimental conditions, cells were plated at 40,000 cells/well on Matrigel coated 8-well chamber slides in 250-500 µL medium per well (1:100 matrigel: PBS) in mouse fusion medium: DMEM (Gibco)+2% horse serum (Hyclone). One hour after plating, mouse myoblasts were treated with 50% respective media: Mouse myoblasts were cultured for 24 hours in the above conditions, at 37° C. in 10% $CO_2$ incubator. BrdU (300 uM) in DMSO was added for 2 hours prior to fixation with cold 70% ethanol and stored at 4° C. until staining.

Human muscle progenitor cells (early passage myoblasts) were cultured and expanded in growth medium: Ham's F-10 (Gibco), 20% Bovine Growth Serum (Hyclone), 5 ng/mL FGF2 and 1% penicillin-streptomycin on Matrigel coated plates (1:300 matrigel: PBS), at 37° C. and 5% CO2. For experimental conditions, cells were plated at 40,000 cells/well on Matrigel coated 8-well chamber slides in 250-500 µL medium per well (1:100 matrigel: PBS) in human fusion medium: DMEM (Gibco)+2% horse serum (Hyclone). One hour after plating, human myoblasts were treated with 50% respective media: Mouse myoblasts were cultured for 24 hours in the above conditions, at 37° C. in 10% $CO_2$ incubator. BrdU (300 uM) in DMSO was added for 2 hours prior to fixation with cold 70% ethanol and stored at 4° C. until staining.

Figure 17A:
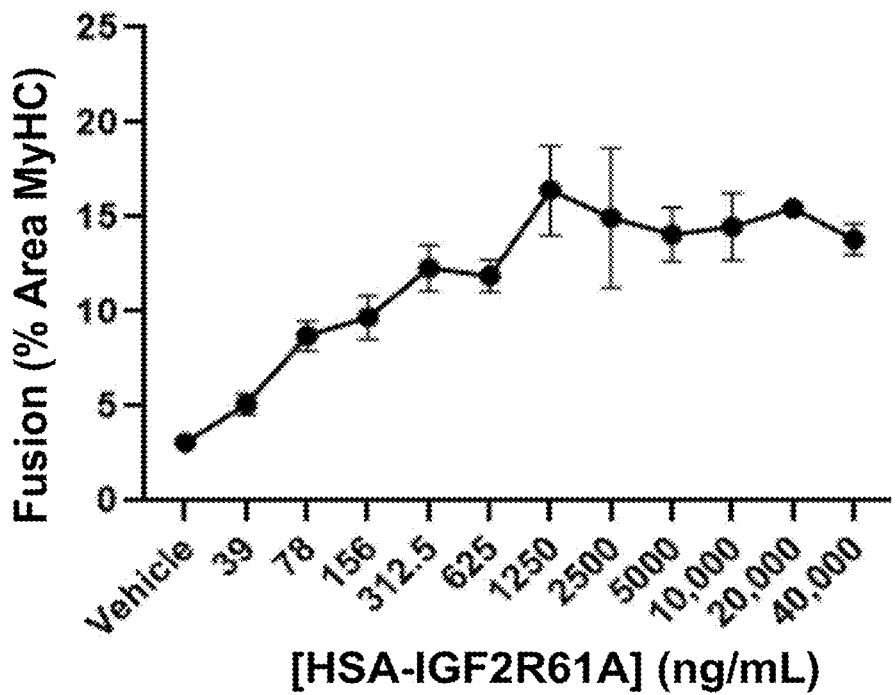
FIG. 17A depicts in vitro myogenesis assay results demonstrates HSA-IGF2R61A mutant sequences retain equal activity relative to IGF2 in healthy human muscle precursors from 32-year-old female
Figure 17B:
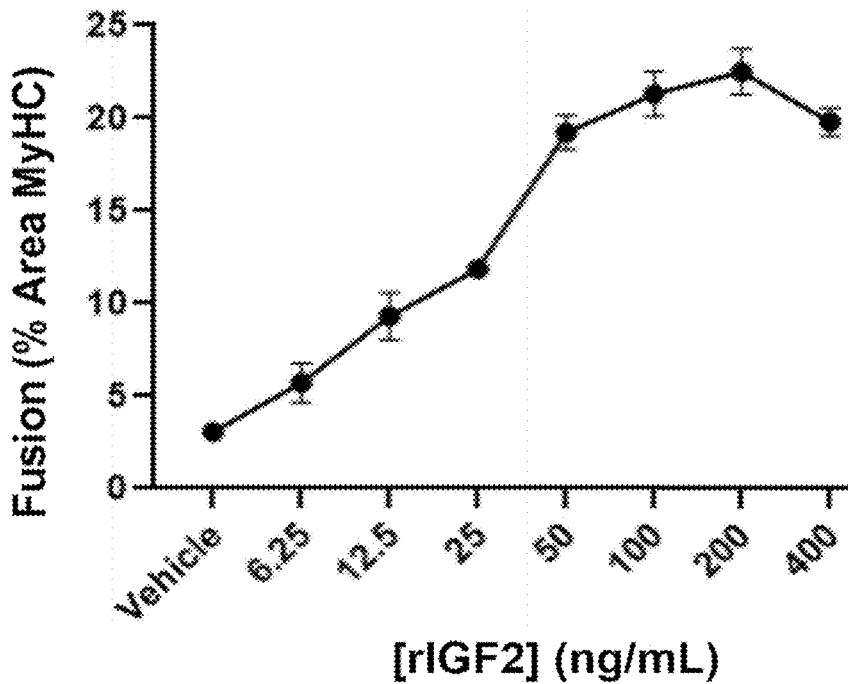
FIG. 17B depicts in vitro myogenesis assay results demonstrates IGF2 displays equal activity relative to an equimolar amount of HSA-IGF2R61A in healthy human muscle precursors from 32-year-old female

Testing in the in vitro myogenesis assay described above using healthy human muscle precursors from 32-year-old female demonstrated HSA-IGF2R61A (FIG. 17A) mutant sequences retain equal activity relative to IGF2 (FIG. 17B) at equimolar concentrations across a range of test article concentrations.

Figure 20:
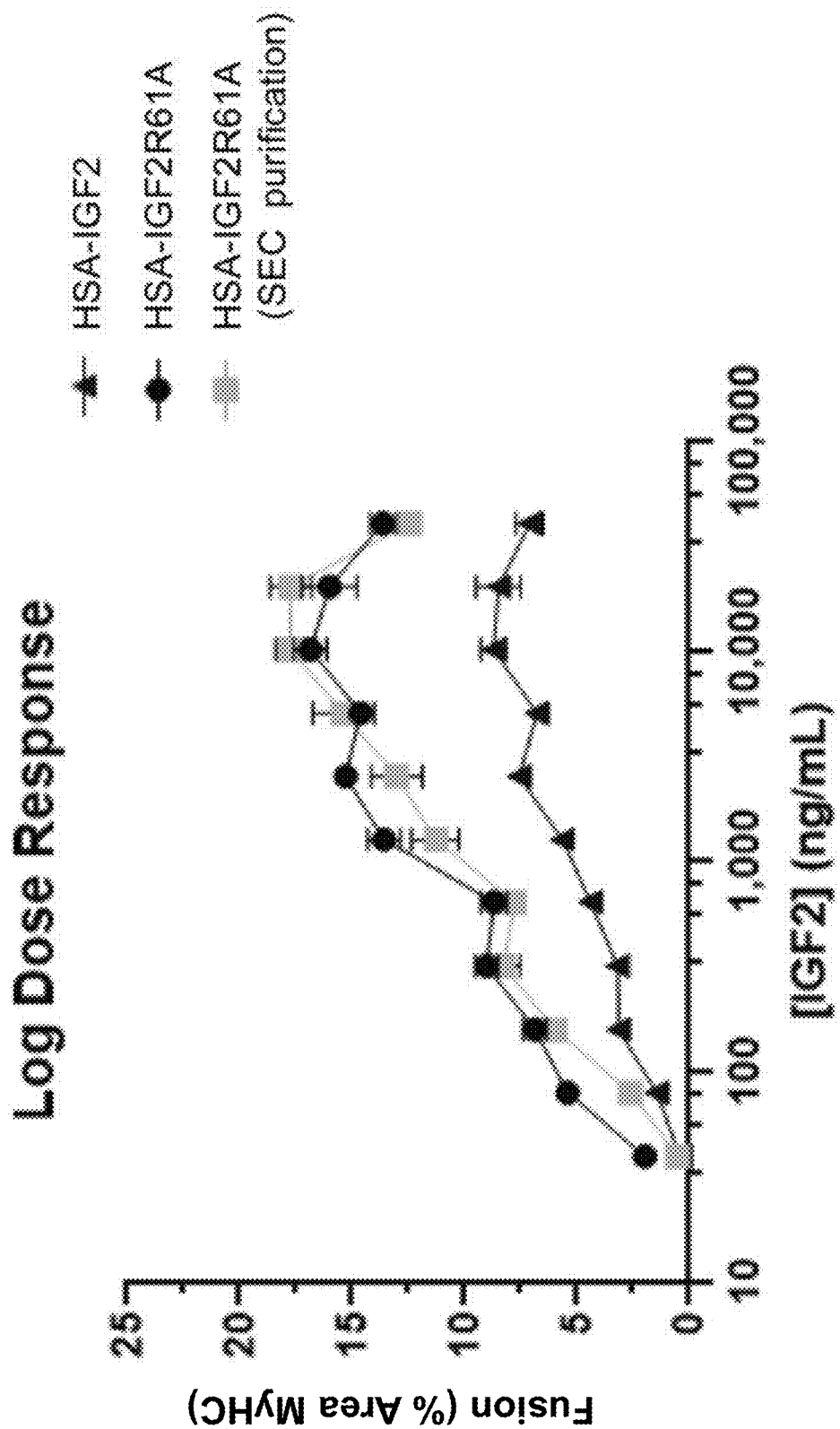
FIG. 20 depicts a mutant sequence HSA-IGF2R61A retains equal or increased activity to HSA-IGF2 at equimolar concentrations FIG. 21A

Testing in the in vitro myogenesis assay described above using healthy human muscle precursors from 32-year-old female demonstrated mutant sequence HSA-IGF2R61A retains equal or increased activity to HSA-IGF2 at equimolar concentrations before or after size exclusion purification via HPLC FIG. 20.

Quantifying Regenerative Index

Following permeabilization in PBS+0.25% t-Octylphenoxypolyethoxyethanol (Triton™ X-100), antigen retrieval was performed. Primary staining was performed with primary antibodies including: a species-specific monoclonal antibody for mouse anti-embryonic Myosin Heavy Chain (eMyHC, hybridoma clone 1.652, Developmental Studies Hybridoma Bank) and Rat-anti-BrdU (Abcam Inc. ab6326). Secondary staining with fluorophore-conjugated, species-specific antibodies (Donkey anti-Rat-488, #712-485-150; Donkey anti-Mouse-488, #715-485-150. Nuclei are visualized by Hoechst staining. Using the Hoechst stain to tally cell numbers, the percent of cells positive for BrdU and eMyHC were tabulated and reported.

Testing in Myotonic Dystrophy Muscle Precursor Cells

Figure 16A:
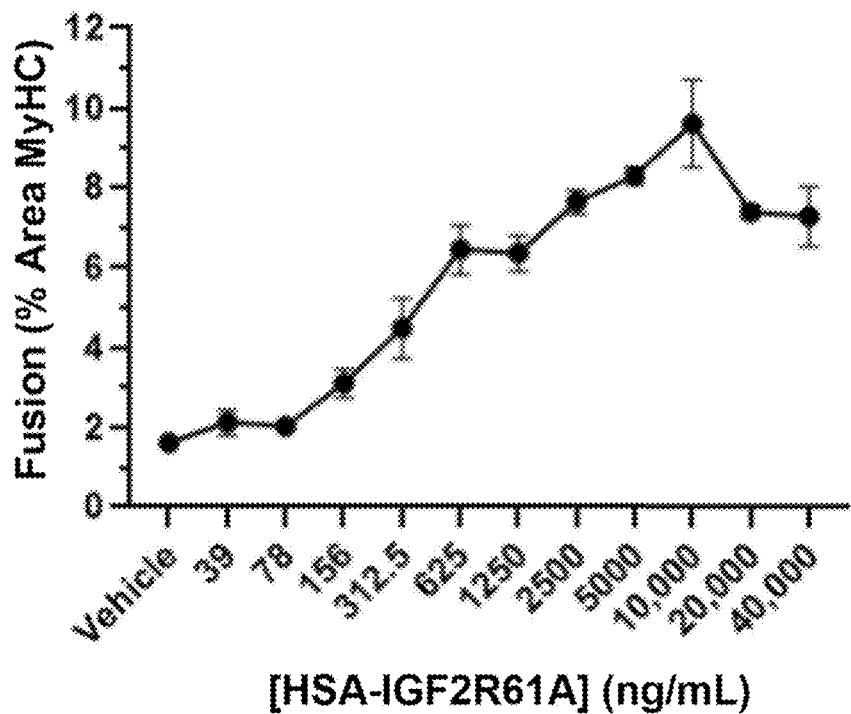
FIG. 16A depicts in vitro myogenesis assay results demonstrates HSA-IGF2R61A mutant sequences retain equal activity relative to IGF2 in human DM1 muscle precursors from 32-year-old female
Figure 16B:
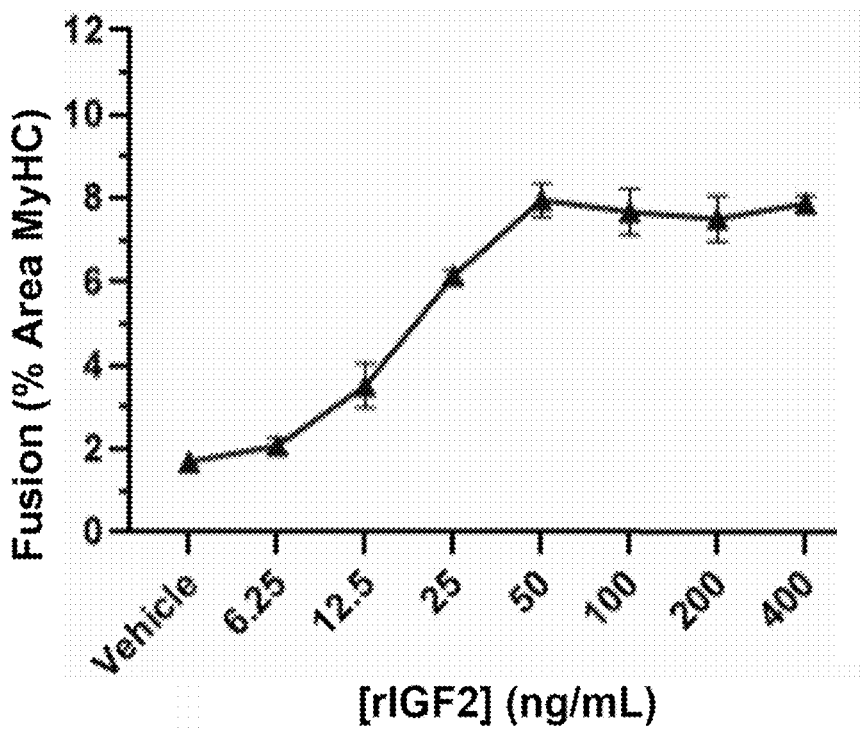
FIG. 16B depicts in vitro myogenesis assay results demonstrates IGF2 displays equal activity relative to HSA-IGF2R61A in human DM1 muscle precursors from 32-year-old female

Testing in the in vitro myogenesis assay described above using human DM1 muscle precursors from 32-year-old female demonstrated HSA-IGF2R61A (FIG. 16A) mutant sequences retain equal activity relative to IGF2 (FIG. 16B) at equimolar concentrations across a range of test article concentrations.

Example 17 Myogenic Gene Profiling for Pro-Regenerative Factors

Expression of myogenic factors Pax7, Myf5, Myod1, and Myog are key indicators of the functional status of muscle progenitor cells. Factors upregulating of Pax7 and Myf5 indicate rejuvenation of proliferative progenitor cells whereas upregulation of Myod1 and Myog are indicative of muscle myofiber regeneration. A read-out of these gene expressions will provide potential success for any given polypeptide comprising an IGF2 amino acid sequence and an amino acid sequence from a heterologous polypeptide or combinations of an Insulin-like Growth Factor 1 Receptor (IGF1R) agonist and a short chain fatty acid described herein. Measuring myogenic genes in mouse or human muscle progenitor cells treated with factors will provide a good characterization of the therapeutic effect for treating individuals who have suffered injury, or who possess genetic or developmental defects leading to premature tissue loss, wasting, or weakening. As a control, the assay will also be performed on proteins purified from differentiated cells, which result in no in myoblast proliferation, cultured in medium conditioned by differentiated cells, or purified heparin-associated fractions.

RNA was isolated from each well (RNeasy Mini Kit, Qiagen) and cDNA was obtained by reverse-transcription (High Capacity Reverse Transcription Kit, Thermo Fisher Scientific). Real-time quantitative PCR was performed using QuantStudio3 (Thermo Fisher).

Aged human myoblasts were cultured in well plates. Culturing the cells with the different medias resulted in differential induction of myogenic gene expression. All factors resulted in changes in at least one myogenic receptor gene at 48 hours and 72 hours when compared to cells cultured in fusion media, as depicted in the Table below. Cells that had been cultured with IGF2 had increases in levels of MYOG at 48 hours and levels of MYOD at 72 hours.

TABLE

| | Myogenic transcription factor fold change increase in myoblasts cultured with IGF2 | | | | | |
|---|---|---|---|---|---|---|
| Condition | MYF5 −48 h | MYOD1 −48 h | MYOG −48 h | MYF5 −72 h | MYOD1 −72 h | MYOG −72 h |
| FM | 1.04 | 1.001 | 1.013 | 1.023 | 1.055 | 1.092 |
| IGF2 | 0.409 | 0.519 | 5.756 | 0.708 | 5.723 | 0.018 |

Myogenic Gene Profiling in Human or Mouse Progenitor Cells

Human or mouse muscle progenitor cells will be plated and cultured as described above for myogenic activity testing. One hour after plating, myoblasts will be treated with respective factors. Myoblasts are analyzed for expression of Pax7, Myf5, Myod1, and Myog to characterize the regenerative effect of treatment with polypeptides comprising an IGF2 amino acid sequence and will be tested to characterize the effects an amino acid sequence from a heterologous polypeptide or combinations of an Insulin-like Growth Factor 1 Receptor (IGF1R) agonist and a short chain fatty acid.

Example 18 In Vivo Testing of Stem Cell Secreted Factors

Multiple in vivo models of muscle degeneration will be tested. Given that polypeptides comprising an IGF2 amino acid sequence and an amino acid sequence from a heterologous polypeptide or combinations of an Insulin-like Growth Factor 1 Receptor (IGF1R) agonist and a short chain fatty acid described herein have regenerative properties in in vitro models, these in vivo models will show that similar regenerative and proliferative effects in the context of intact organ systems.

Acute Injury Model

The experimental groups will be: C57BL/6J male mice, N=18; Young: 12-13 week old (3-month-old) mice, n=6; Aged: 77-78 week old (18-month-old) mice, n=12. This design will be used to test any single factor identified and validated in in vitro assays or polypeptides comprising an IGF2 amino acid sequence and an amino acid sequence from a heterologous polypeptide or combinations of an Insulin-like Growth Factor 1 Receptor (IGF1R) agonist and a short chain fatty acid.

On Day 0, mice will be weighed and undergo muscle injury with focal injection of barium chloride ($BaCl_2$, 10 μL, 1.2% w/v in saline, Sigma-Aldrich) in the Tibialis anterior (TA; Day 0) of both the right and left hindlegs. Injections of vehicle or factor A (0.1 mg/kg) will be co-administered intramuscularly (i.m) following the $BaCl_2$ into the TA injured hindleg sites, and again 48 hours later on day 2 (i.m.) into the TA injured hindleg sites. Also on day 2, $BaCl_2$ (Ctx; 10 µL, 1.2% w/v in saline, Sigma-Aldrich) was injected into the Gastrocnemius (GA, Day 2, i.m.) muscles of both right and left hind legs. Injections of vehicle or a factor will be sequentially administered (i.m.) following the BaCl2 into the TA hindleg sites post-injury, and again 48 hours later on day 4 (i.m.) into the GA injured hind leg sites. Bromodeoxyuridine (BrdU) will be administered (100 mg/kg, i.p.) once daily for 3 days, day 2-4, before sacrifice to label proliferating cells.

On day 5, animals will be sacrificed, and animal weight recorded followed by collecting 0.5 ml of terminal blood via cardiac puncture which was processed to plasma and stored at 80° C. We then perfuse the animal with 1×PBS, carefully dissect the skin from the GA/TA muscles of each hind leg and took photos (prior to excision). After excision of exclusively the GA or TA muscle, excised tissue is photographed, weighed, then placed into 25% sucrose in PBS at 4° C. for 4 hr rinsed in 1×PBS, immersed in Tissue-TEK OCT and rapidly frozen before storing the muscles tissues frozen at 80° C. Cryosectioning and H&E will be performed to ensure muscle injury site was appropriately visualized. Muscle tissue composition from new skeletal muscle fibers, fibrotic tissue, and adipose (fat), will be measured. Muscle regeneration, as defined as the number of new myofibers with centrally located nuclei per millimeter, fibrosis as defined as the area of fibrotic scarring, size of the fibers, as defined as the width and area, adipose tissue, as defined by the amount of fat surrounding the muscle, will be measured to assess level of regeneration.

Sarcopenia/Chronic Administration Model

The experimental design is C57BL/6J male mice, N=18; Young: 12-13 week old (3-month-old) mice, n=6; Aged: 77-78 week old (18-month-old) mice, n=12. This design can be used to test any single factor identified and validated in in vitro assays or complex mixtures of 2 or more factors or synergistic small molecules.

On Day 0, mice will have the following in vivo healthspan measurements will be performed over 1 day as a baseline for age-based parameters: Weight, running wheel performance, grip strength, and horizontal bar. Each assay should be run for 4 trials per assay per animal. These healthspan assays will be repeated on day-1. After one day of rest on day-9, mice will begin 1× daily injections (0.1 mg/kg) of vehicle or factor A for the remainder of the experiment until sacrifice (days-8 to +5, 13 days of dosing). On day-4, 6 days after dosing begins, mice will undergo a repeat of the healthspan assays. On day 0, 5 days prior to sacrifice, mice will undergo muscle injury with focal injection of cardiotoxin (Ctx; 10 ug, Sigma-Aldrich) in the Tibialis anterior (TA; day 0) of the right hindleg only. On day 2, the Gastrocnemius (GA; day 2) muscle of the right hind leg will then receive cardiotoxin (Ctx; 10 ug, Sigma-Aldrich). BrdU will be administered (100 mg/kg, i.p.) once daily for 3 days, day 2-4, before sacrifice. On day +5, prior to take-down, the animals will have an in vivo incapacitance assay run. On day +5, animals will be sacrificed, and animal weight recorded. We will Collect 0.5 ml of blood via cardiac puncture, process to plasma and store plasma samples at 80° C. The animals will then be perfused with 1×PBS. Carefully dissect the skin from the GA/TA muscles of each hind leg and take photos (prior to excision). After excision of exclusively the GA or TA muscle, we will weigh the muscles, then place muscles into 25% sucrose in PBS at 4° C. for 4 hours, then rinse the muscles in 1×PBS, adding Tissue-TEK OCT and storing the muscles tissues frozen at 80° C. Perform cryosectioning and H&E, ensuring muscle injury site is appropriately visualized. Carefully excising the inguinal white adipose tissue (WAT) will be weighed.

Muscle tissue composition, from new skeletal muscle fibers, fibrotic tissue, and adipose (fat), will be measured. Muscle regeneration, as defined as the number of number of new myofibers with centrally located nuclei per millimeter, fibrosis, as defined as the area of fibrotic scarring, size of the fibers, as defined as the width and area, adipose tissue, as defined by the amount of fat surrounding the muscle, will be measured to assess level of regeneration. Weights of the animals during the duration of treatment, as well as healthspan assays including performance on a running wheel (speed, distance, duration), grip strength, and performance on a horizontal bar will take into account the phenotypic outcomes of treatment of the aged animals systemically with the polypeptides comprising an IGF2 amino acid sequence and an amino acid sequence from a heterologous polypeptide or combinations of an Insulin-like Growth Factor 1 Receptor (IGF1R) agonist and a short chain fatty acid.

The horizontal bar test will be performed as described previously (Malinowska et al. 2010) at 8 months (n=6 WT, n=7 MPS IIIB) and 10 months (n=3 WT, n=4 MPS IIIB) of age. In brief, a 300-mm metal wire, 2 mm in diameter, was secured between two posts 320 mm above a padded surface. The mouse will be allowed to grip the center of the wire and the time to fall or reach the side was recorded, and after 2 minutes the test was stopped. Crossing the bar in x seconds will be scored as 240-x, remaining on the bar will be scored as 120, and falling off the bar after y seconds will be recorded as the value of y. The test will be repeated three times as a practice run followed by a 10-min rest prior to three tests where the score was recorded.

Animals will also have better healthspan outcomes: reduced weight, fat composition, scar tissue around muscles, increased running speed, duration, and distance, increased grip strength, and enhanced performance on the horizontal bar test.

Genetically Obese Muscle Dystrophy Model

Genetically obese (ob/ob) mice will be injected with $BaCl_2$ on day 0 in the TA muscle. 3 mice will be treated with vehicle only, 3 mice will be injected with the hPSC factors and 3 mice will be treated with FGF19 (positive control) on day 0 and day 2. On day 5, the mice will be euthanized, the TA muscles perfused with PBS, and dissected. Muscles will be then analyzed for regenerative index and fibrotic index.

Methods of Testing Muscle Strength, Endurance and Function

Forelimb and Both limb grip strength test: After 30 min acclimation, the mice are introduced to the grip strength meter. For forelimb grip strength, the mice held by the tail are allowed to grasp the grip bar with only its forelimbs. For both limb measurements the mice are placed on the grid and allowed to grasp the grid with both limbs. The force generated by each mouse is calculated as the average of 5-6 measurements.

Limb endurance test: Mice are allowed to discover and acclimate the rodent treadmill environment through 2 training sessions of 10 minutes each at 10 m/min on separate days prior to the endurance test. For the endurance test, mice are placed in the individual lanes of the rodent treadmill. The speed is gradually increased at 2 m/min until exhaustion is reached. Exhaustion is defined as a mouse staying on a grill electrified to deliver a shock of 2 Hz, intensity 5 for 3-5 seconds.

In vivo tetanic force measurement: Mice are under anesthesia using regulated delivery of isoflurane during the whole process. Following anesthetization, the animal is placed onto a heated chamber with the foot secured on the foot pedal of an Aurora force transducer. The 2 electrodes are placed specifically to stimulate the sciatic nerve. The force generated by the ankle torsion of the animal's hind limb, as opposed to direct force is measured in response to a series of stimulation that includes 50, 100, 150 and 200 Hz.

In situ tetanic force measurement: This experiment is performed using Aurora force measurement. Mice are under anesthesia during the whole process. A small incision in the skin around the Anterior Tibialis exposes the Achilles tendon which is connected via surgical suture to the Aurora force transducer through a hook. The force generated by the muscle in response to a series of stimulation that includes 50, 100, 150 and 200 Hz by 2 electrodes placed on the anterior tibialis is recorded.

Example 19-Mitogenic Polypeptide Stability In Vivo Assayed by Bioavailability and Pharmacokinetics Bioavailability in Tissues The bioavailability of the therapeutic polypeptides will be assessed in the target tissues in young mice (10-12 weeks old) and old mice (78 weeks old). For this experiment, 1 cohort of young mice (10-12 weeks old; N=24) and 1 cohort of old mice (78 weeks old; N=24) will receive 1 subcutaneous (SC) injection of a therapeutic composition. 4 young mice (10-12 weeks old; N=6) and 4 old mice (78 weeks old; N=6) will receive 1 SC injection of Vehicle and used as control. 4 mice from each cohort will be euthanized after 30 minutes, 1 hour, 1.5 hours, 2 hours, or 4 hours. At each time point blood will be collected by heart puncture followed by harvesting select tissues, such as the tibialis anterior, gastrocnemius, quadriceps, heart and diaphragm. The detection and quantitation of the administered therapeutic polypeptides will be detected by enzyme-linked immunosorbent assay (ELISA). The level of therapeutic polypeptides will be compared to the samples collected from mice injected with vehicle to determine tissue level bioavailability.

Pharmacokinetics of Engineered Mitogenic Polypeptides

Figure 18A:
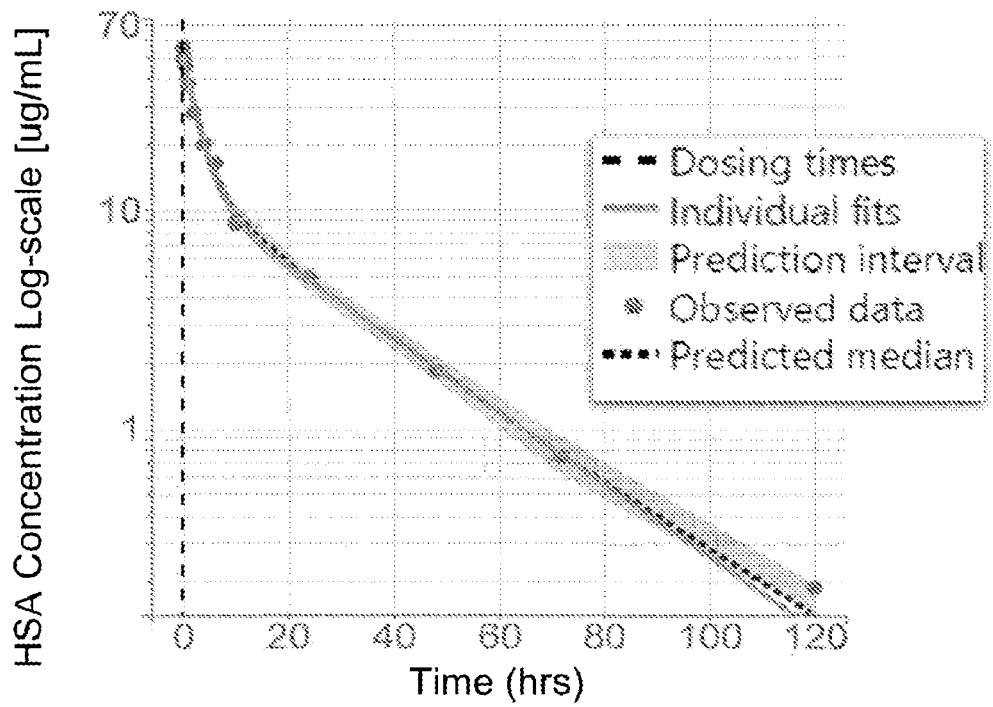
FIG. 18A depicts Non-Compartment Analysis fit of pharmacodynamics data for intravenous administration of the HSA-IGF2R61 in mice which demonstrates significantly improved serum half-life compared to the natural sequence of IGF2
Figure 18B:
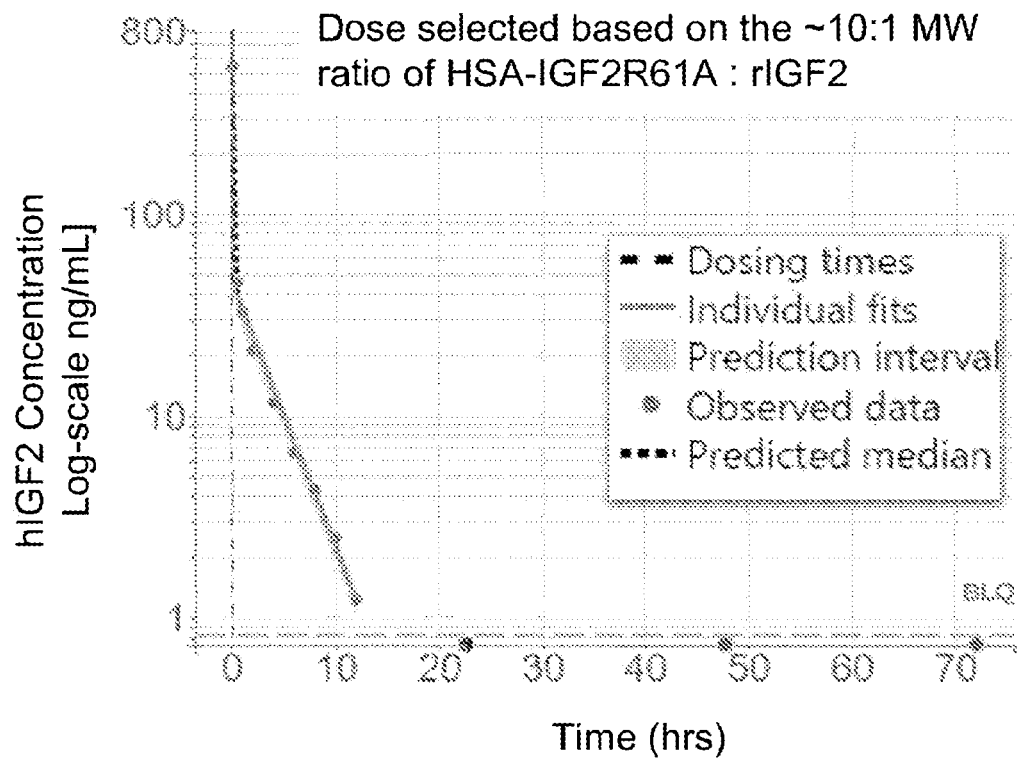
FIG. 18B depicts Non-Compartment Analysis fit of pharmacodynamics data for intravenous administration of the IGF2 in mice which demonstrates significantly improved serum half-life compared to the natural sequence of HSA-IGF2R61

Murine pharmacokinetics (PK) represents the absorption, distribution, metabolism, and elimination of drugs from the body. The pharmacokinetic profile of the therapeutic polypeptides were determined in mice (10-12 weeks old). Mice were fed ad libitum and housed under controlled conditions of lighting (12-hour light/12-hour dark) and temperature (22-24° C.). Mice were allowed to acclimate for 3 days prior to the initiation of the experiment. Intravenous (IV) injection in 10-12 weeks old mice. Engineered mitogenic polypeptides concentrations in the samples were measured by ELISA. Various pharmacokinetics will be calculated as well as the absorption/elimination dynamics following different routes of administration. Non-Compartment Analysis fit of pharmacodynamics data for intravenous administration of the HSA-IGF2R6 (Seq. ID 81) FIG. 18A in mice which demonstrates significantly improved serum half-life compared to the natural sequence of IGF2 (Seq. ID 76) FIG. 18B.

| Table of data for FIG. 18. HSA-IGF2R61A demonstrated increased stability compared to IGF2 | | |
|---|---|---|
| Molecule | Half-life | Dose |
| HSA-IGF2R61A | 20.81 hr | 10 mg/kg |
| IGF2 | 2.85 hr | 600 ug/kg |

Example 20—the Purified IGF2-hFcm Promoted Differentiation of Myoblast Cells

Suspension CHO cells were transiently transfected with the IGF2-hFcm encoding plasmid. After four days, the culture supernatants were collected and IGF2-hFcm was affinity-purified by Protein A membrane column. The purified IGF2-hFcm was added into the culture of human myoblast cells. Myosin heavy chain (MyHC) was immunostained and imaged by a fluorescent microscope. After quantification of the stained MyHC, the percentage area of MyHC was calculated as the percent of pixels within the field that are illuminated above background in the stained channel. The percentage of EdU of mouse myoblasts treated with the purified IGF2-hFcm is significantly higher than the percentage of EdU of mouse myoblasts treated with the culture supernatant of CHO cells expressing the empty control vector. Significance was determined by a p-value less than 0.05 by the one-way ANOVA Tukey Honest Significant Difference test.

TABLE

| IGF2 promoted differentiation of myoblast cells | | | |
|---|---|---|---|
| Condition | % MyHC | SD | p_value |
| Vehicle control | 1.787 | 0.186 | |
| 33 nM IGF2-hFcm | 3.734 | 0.790 | 0.012 |
| 66 nM IGF2-hFcm | 5.922 | 0.795 | 3.20E−05 |
| 133 nM IGF2-hFcm | 7.568 | 0.538 | 1.46E−06 |

This example found that the IGF2-fusion protein was able to induce cell proliferation. The IGF2-fusion protein shares in vitro properties with the HAPs, which is suggestive of shared in vivo properties.

Example 21—Modelling Treatment of a Muscular Dystrophy with an IGF2 Composition In Vitro Muscular dystrophies (MD) encompass a variety of muscular degeneration diseases typically due to genetic mutations in genes encoding proteins responsible for forming and stabilizing skeletal muscle. The phenotypic consequence of these genetic mutations is the progressive loss of muscle mass and strength over time, similar to sarcopenia but with different underlying causes. As HAPs provided phenotypic improvements on sarcopenic muscle, we tested for similar improvements in a model for MD.

IGF2 was tested individually for its ability to promote proliferation and/or fusion of human muscle progenitor cells from an individual with myotonic dystrophy type 1 (hMD)—a muscular dystrophy caused by mutations in the DMPK1 gene. The effect of IGF2 on myogenic activity was assayed in biological triplicate across a range of concentrations centered around expected physiological levels by adding each factor to hMD myoblasts for 72 hours with daily media changes (DMEM +2% horse serum) and a second pulse of factors at the first media change. After 72 or 96 hours, cells were pulsed for 2-5 hours with EdU (30 uM), ethanol fixed, stained with Hoescht 3342, immunostained for proliferation—as measured by the percent of cells staining positive for EdU (% EdU)-, and immunostained for differentiation—as measured by the increase in cellular area staining positive for embryonic myosin heavy chain (% eMyHC) relative to the negative controls, which received media and vehicle only. Wells were imaged on a Keyence BZ-100 at 4×, the images quantified in Cell Profiler, and the statistics were computed in R. Additionally, RNA was extracted from myoblast and select transcript abundances quantified by qPCR. FIGS. 7A and 7B depicts IGF2 treatment promoted proliferation and differentiation respectively in DM1 human myoblast (32 year old caucasian female) cells. FIGS. 8A and 8B depict IGF2 enhanced MYH3, CKM, and ATP1B1 expression in DM1 human myoblast (32 year old caucasian female) cells.

Example 22-Systemic Administration of Therapeutic Polypeptides Reverses Sarcopenia and Protects from Muscle Injury A daily subcutaneous injection of therapeutic polypeptides or vehicle only is administered to 78 week old mice for 14 days. IGF2 is injected at a concentration of 100-1000 μg/kg. In some experiments, treatment groups receive a single therapeutic factor while in other experiments, treatment groups receive a combination of factors. At 7 days, muscle function is assessed using forelimb grip strength and both grip strength. On day 12, 13 and 14, groups 1 and 2 are injected with BrdU intraperitoneally. On days 13-15, all mice are assessed for grip strength and an endurance test to determine max distance and max speed and tetanic force.

At 15 days, mice in groups 1 and 2 are euthanized and the muscles are analyzed for markers of proliferation and fibrosis. At 15 days, an intramuscular injection of 1.2% of $BaCl_2$ (7 ul/TA) is used to generate chemical injury in the TAs of group 3 and group 4. Mice from groups 3 and 4 continue to receive a therapeutic polypeptide injected subcutaneously on days 15-21. They also receive BrdU injections intraperitoneally on days 19, 20, and 21. On day 21, the TA muscles are tested for in situ tetanic force. The TA muscles are dissected and assessed for signs of proliferation and fibrosis.

Example 23—Systemic Administration of Fusion Polypeptides Reversed Induced Muscle Atrophy 12-week-old mice are divided into 3 treatment groups: group 1 which receives injections only of the vehicle, group 2 which receives injections of dexamethasone, and group 3 which receives injections of dexamethasone and IGF2 fusion polypeptide. Dexamethasone (25 mg/kg i.p.) is administered for 14 days simultaneously with a subcutaneous injection of IGF2 fusion polypeptide.

At 7 days, mice are assessed for forelimb and both limb grip strength. At days 13-15, mice are assessed for grip strength, in vivo tetanic force, and undergo a treadmill endurance test to determine max speed and max distance.

Example 24—Systemic Administration of IGF2 Fusion Polypeptide Predicted to Improve Muscle Atrophy in Genetically Obese Mice Thirteen-week old genetically obese mice (ob/ob) will be injected subcutaneously with an IGF2 fusion polypeptide for 14 days. At day 7, forelimb and both grip strength will be measured. BrdU is injected on days 12, 13 and 14. On days 13, 14 and 15, forelimb and both limb grip strength and in vivo tetanic force will be tested, and an endurance test to determine max distance and max speed is performed. At 14 days, the mice will be euthanized, and the TA muscles dissected. Muscle weight and proliferation will be analyzed.

Example 25—Systemic Administration of IGF2 Fusion Polypeptide Predicted to Reverse of Slow Down Dystrophic Features in 70 Weeks Old Mdx Mice Another class of human myopathies in need of treatment are the genetic abnormality induced muscular dystrophies, among which Duchenne muscular dystrophy is a rare but fatal case. Old genetically dystrophic (mdx) mice (>15 month old) show similar features to the human Duchenne muscular dystrophy (DMD), notably, a decrease in muscle regeneration leading to muscle wasting. Treatment with IGF2 fusion polypeptide can reverse the dystrophic features of old mdx mice. During the acclimation period, the weight, Forelimb and both limb grip strength as well as in vivo tetanic force will be assessed to determine the baseline strength of each mouse. 70 week dystrophic mice (mdx) are injected with the IGF2 fusion polypeptide subcutaneously for 14 days. At day 7, forelimb and both grip strength are measured. BrdU is injected on days 12, 13 and 14. On days 13, 14, and 15, forelimb and both limb grip strength and in vivo tetanic force are tested, and an endurance test to determine max distance and max speed is performed. The right tibialis anterior and gastrocnemius will be collected, immersed in Tissue-TEK OCT and then flash frozen in chilled isopentane bath precooled in liquid nitrogen and stored at −80° C. Tissue will be sectioned and stained for Laminin to determine the cross sectional area (CSA) of muscle fibers, for eMyHC to measure new fiber formation and for BrdU to assess the proliferation rate. The left anterior tibialis and gastrocnemius will be collected and flash frozen in liquid nitrogen for molecular analysis that include qPCR and western blot.

IGF2 is predicted to be effective at a concentration of 10-200 ug/kg.

Example 26-Systemic Administration of IGF2 Fusion Polypeptide Improved Dystrophic Features in 10 Week Old Mice Between 3-6 weeks old, the skeletal muscle of mdx mice undergoes severe necrosis followed by an increase in the activation of satellite cells to promote muscle regeneration. Treatment with IGF2 fusion polypeptide described herein can improve the regeneration process and therefore muscle health. Mice were fed ad libitum and housed under controlled conditions of lighting (12-hour light/12-hour dark) and temperature (22-24° C.). Mice were allowed to acclimate for 3 days prior to the initiation of the experiment. During the acclimation period, the weight, forelimb and both limb grip strength as well as in vivo tetanic force were assessed to determine the baseline strength of each mouse. 10 week old dystrophic mice (mdx) were injected with the IGF2 fusion polypeptide with sodium butyrate subcutaneously for 14 days. At day 7, forelimb and both grip strength are measured as described in Example 4. BrdU was injected on days 12, 13 and 14. On days 13, 14 and 15, forelimb and both limb grip strength and in vivo tetanic force were tested, and an endurance test to determine max distance and max speed was performed using methods described in Example 4.

Mice were euthanized. The right tibialis anterior and gastrocnemius were collected, immersed in Tissue-TEK OCT and then flash frozen in a chilled isopentane bath precooled in liquid nitrogen and stored at −80° C. Tissue was sectioned and stained for Laminin to determine the cross sectional area (CSA) of muscle fibers, for eMyHC to measure new fiber formation and for BrdU to assess the proliferation rate. The left anterior tibialis and gastrocnemius were collected and flash frozen in liquid nitrogen for molecular analysis that include qPCR and western blot.

Figure 12A:
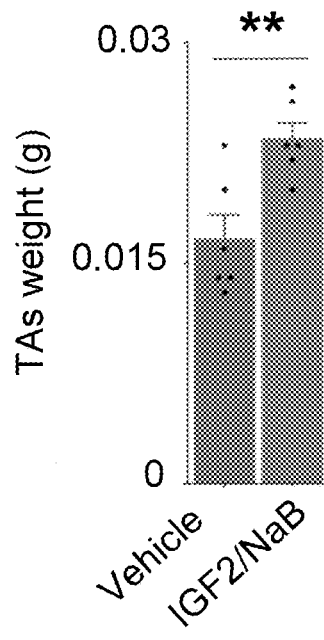
FIG. 12A depicts systemic administration of IGF2 and sodium butyrate regenerates and enhances muscle health in the D2-mdx model Duchenne's muscular dystrophy model improving tibialis anterior muscle weight relative to vehicle treatment
Figure 12B:
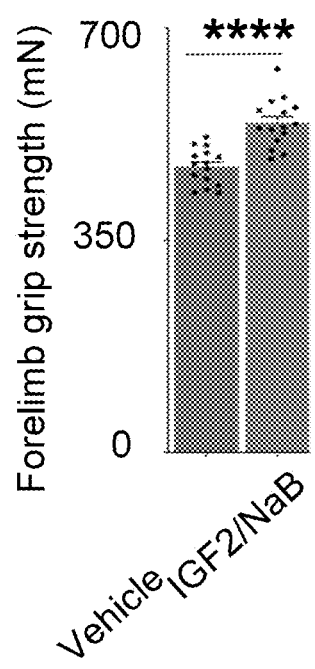
FIG. 12B depicts systemic administration of IGF2 and sodium butyrate regenerates and enhances muscle function in the D2-mdx model Duchenne's muscular dystrophy model improving forelimb grip strength relative to vehicle treatment
Figure 12C:
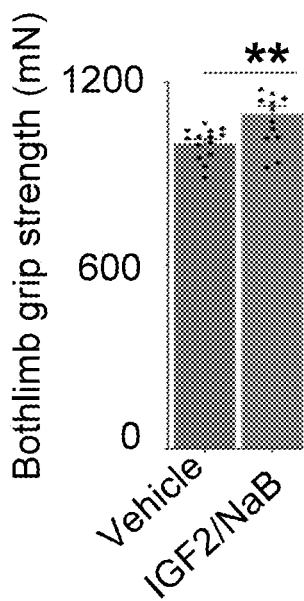
FIG. 12C depicts systemic administration of IGF2 and sodium butyrate protected against regenerates and enhances muscle function in the D2-mdx model Duchenne's muscular dystrophy model improving both limb grip strength relative to vehicle treatment
Figure 12D:
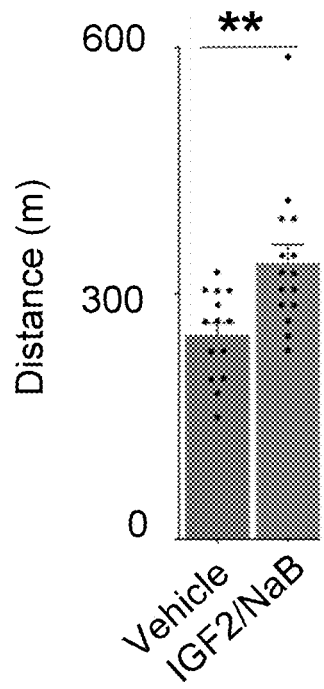
FIG. 12D depicts systemic administration of IGF2 and sodium butyrate regenerates and enhances muscle function in the D2-mdx model Duchenne's muscular dystrophy model improving distance run on a treadmill relative to vehicle treatment
Figure 12E:
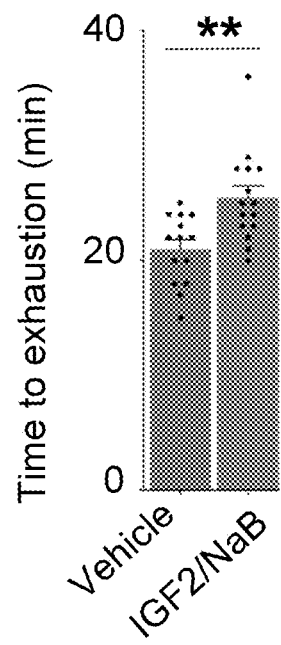
FIG. 12E depicts systemic administration of IGF2 and sodium butyrate regenerates and enhances muscle function in the D2-mdx model Duchenne's muscular dystrophy model improving distance run on a treadmill relative to vehicle treatment
Figure 12F:
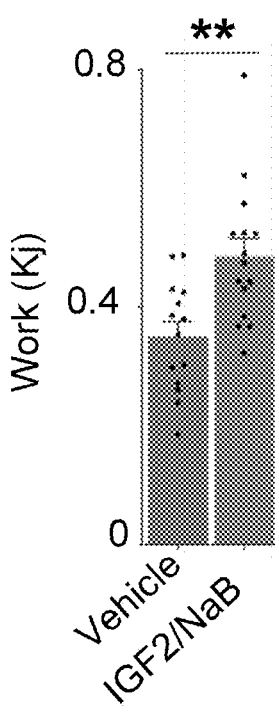
FIG. 12F depicts systemic administration of IGF2 and sodium butyrate regenerates and enhances muscle function in the D2-mdx model Duchenne's muscular dystrophy model improving distance run on a treadmill relative to vehicle treatment

IGF2 was effective at improving muscle weight (Unpaired t-test, p=0.0055) FIG. 12A, bothlimb grip strength (Unpaired t-test, p=0.0011) 12B, forelimb grip strength (Unpaired t-test, p<0.001) 12C, treadmill running distance (Unpaired t-test, p=0.0035) 12D, and treadmill running time to exhaustion (Unpaired t-test, p=0 . . . 0023) 12E, and total work (Unpaired t-test, p=0.0022) 12F at a concentration of 150 µg/kg with 1.2 g/kg sodium butyrate administered subcutaneously every 24 hours.

Example 27-Engineering the Sequence of IGF2 to Reduce Backbone Cleavage

Figure 13A:
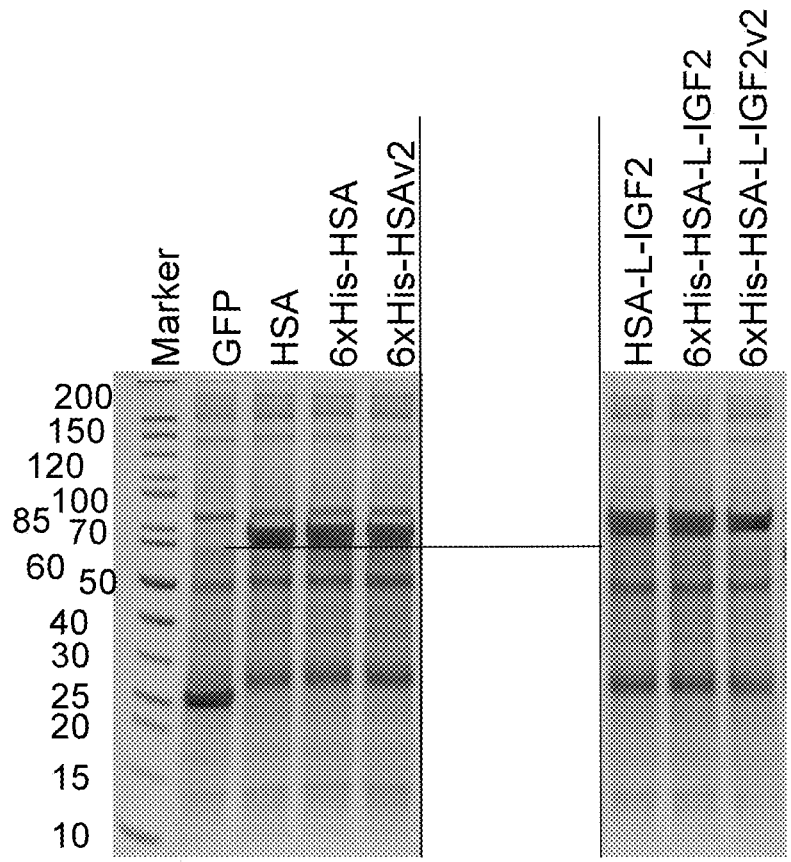
FIG. 13A depicts HSA-L-IGF2 is cleaved when expressed from CHO cells as visualized on a reducing SDS-PAGE
Figure 13B:
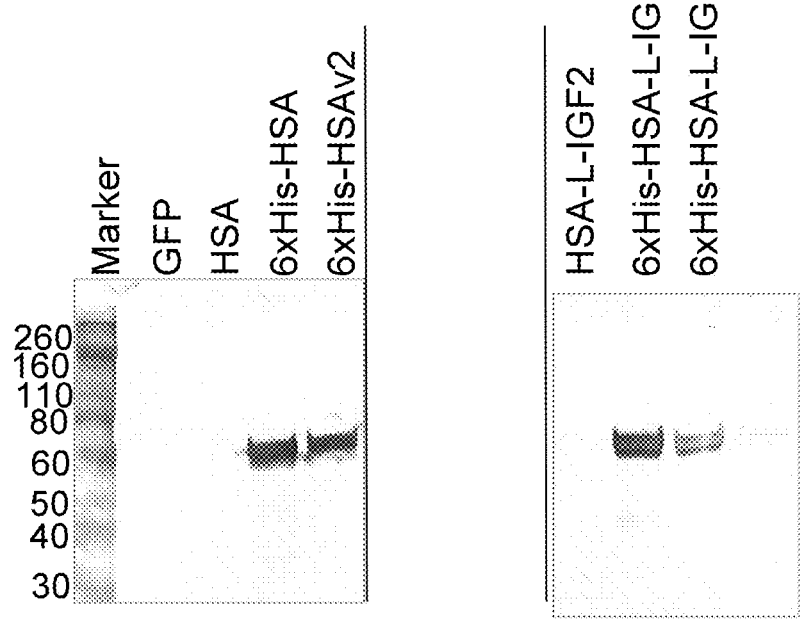
FIG. 13B depicts that HSA-L-IGF2 is cleaved when expressed from CHO cells as visualized on a reducing SDS-PAGE followed by Western blotting to detect 6×HIS tag, and depicts cleavage of IGF2 as confirmed by double tagged IGF2 as visualized on a reducing SDS-PAGE followed by Western blotting to detect 6×HIS tag and the antibody constant region, hFc4, tag

The amino acid backbone of IGF2 is cleaved when expressed from Chinese Hamster Ovary (CHO) cells (FIG. 13A) as visualized on a reducing SDS-PAGE and Western blot (FIG. 13B). The CHO cells were grown in a 37° C. incubator with a humidified atmosphere of 8% CO2 on an orbital shaker platform with a shaking speed 125 rpm to reach 4E6 cells/mL, followed by transferring the calculated volume of cells to fresh, pre-warmed ExpiCHO™ Expression Medium in a shake flask. Incubated flasks in a 37° C. incubator with a humidified atmosphere of 8% CO2 shook on an orbital shaker platform until cultures reached a density of 4×106–6×106 viable cells/mL.

Figure 14:
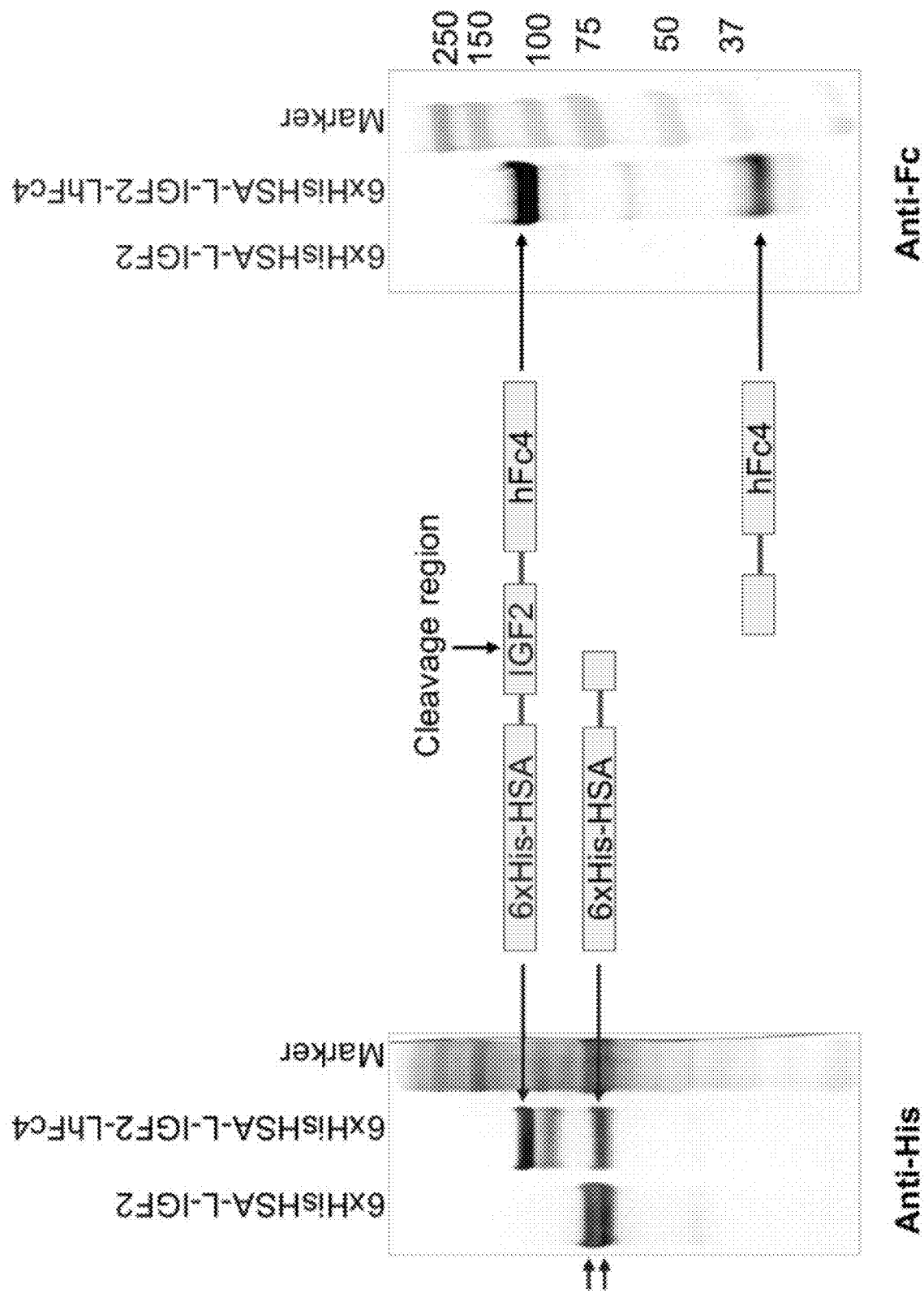
FIG. 14 depicts IGF2 cleavage with the amino acid sequence tagged on each end (HSA and hFc4) as visualized on a reducing SDS-PAGE followed by Western blotting to detect 6×HIS tag and the hFc4 tag
Figure 15A:
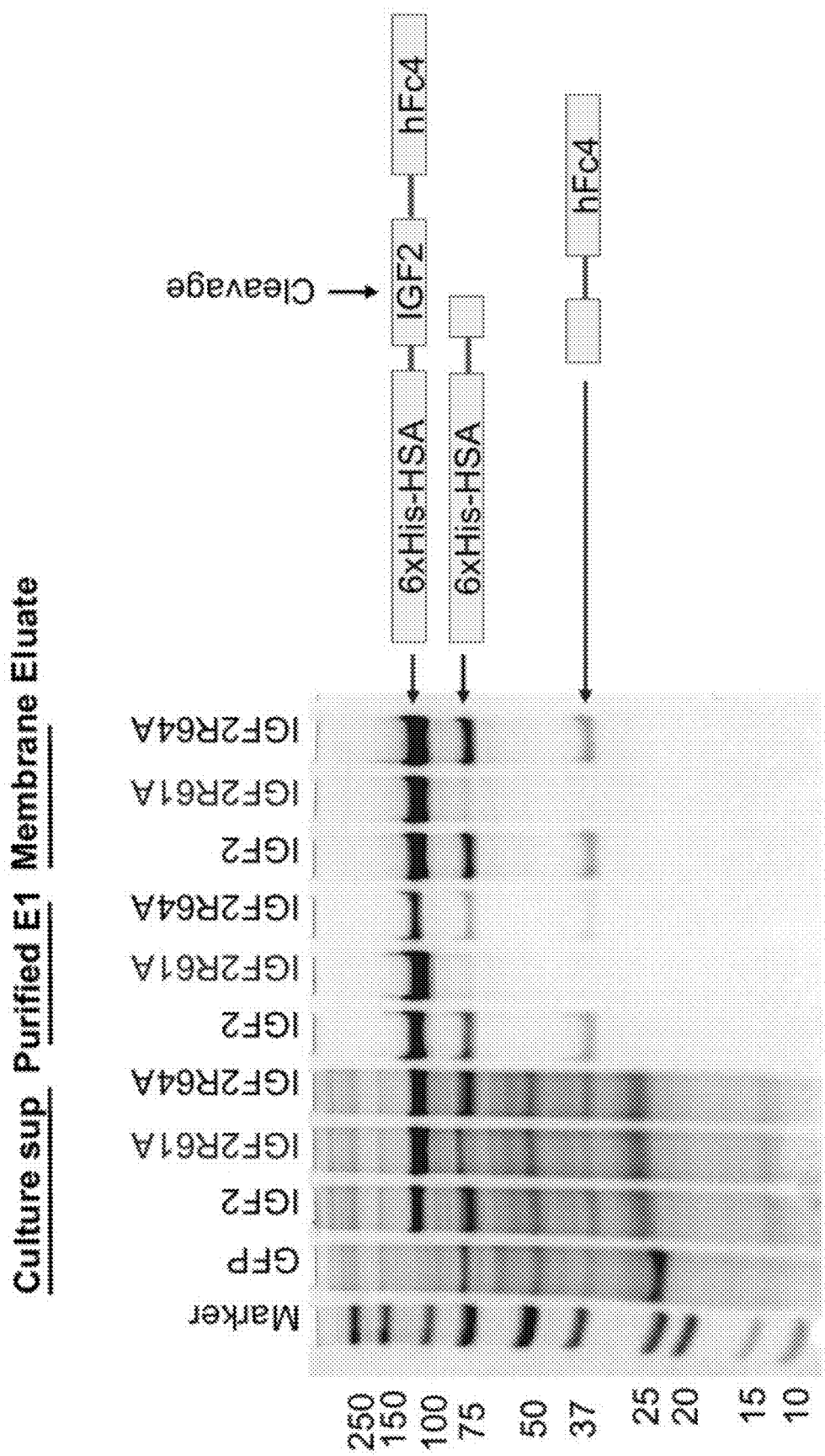
FIG. 15A depicts double tagged (HSA and hFc4) IGF2 cleavage was blocked by mutations as visualized on a reducing SDS-PAGE FIG. 15B epicts double tagged (HSA and hFc4) IGF2 cleavage was blocked by mutations as visualized on a reducing SDS-PAGE followed by Western blotting to detect 6×HIS tag and hFc4 tags
Figure 15B:
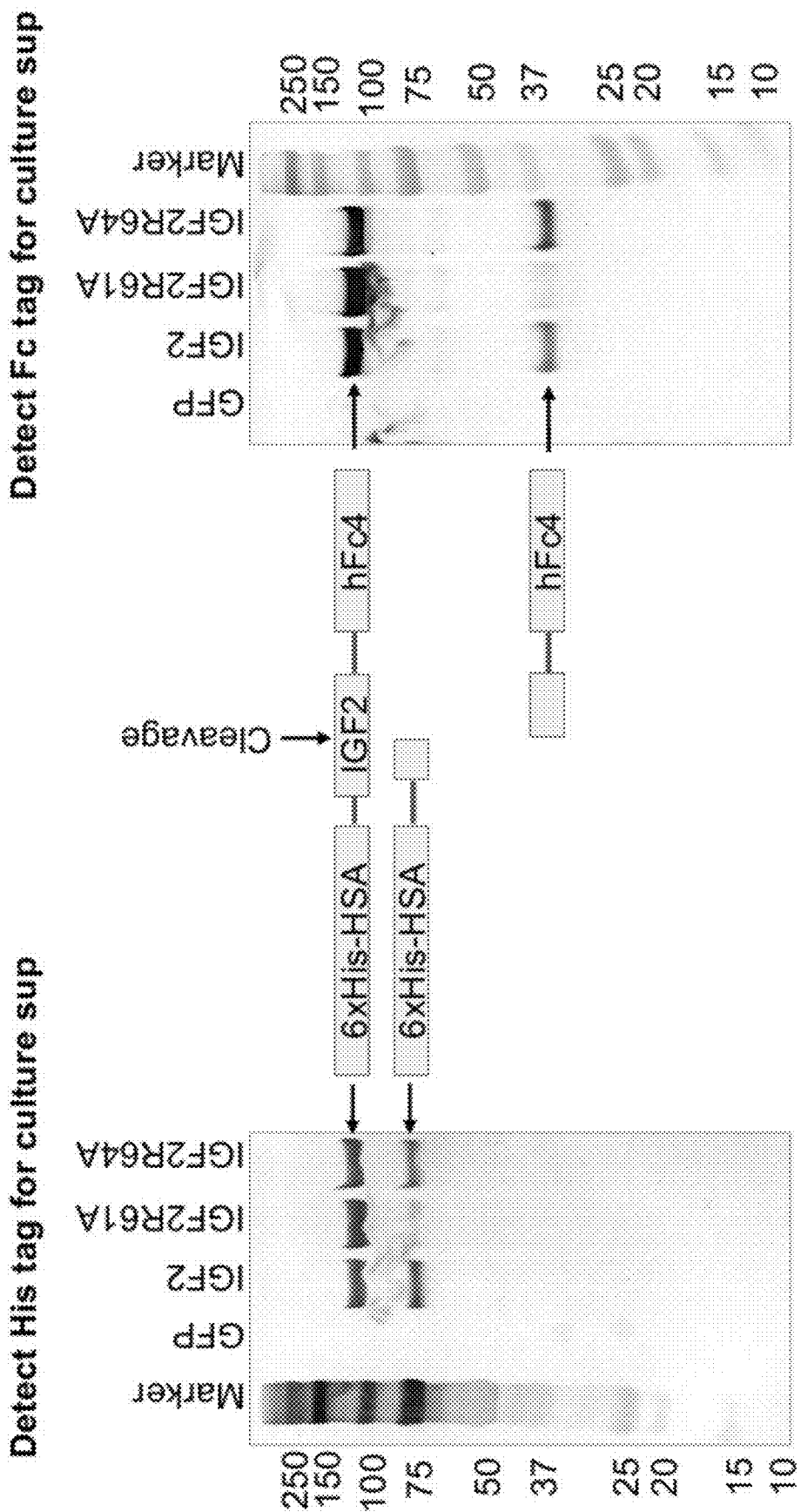

After mixing each plasmid with 100 ul SFM in a microtube; ExpiFectamine (8 ul ×10.5=84 ul) with OptiPro medium (92 ul×10.5=966 ul) in a microtube; adding 100 ul into the plasmid tube and mix by pipetting; After 5 min, add 200 ul into each well and swirl to mix. mix enhancer (15×10.2=153 ul) with feed (600×10.2-6.12 ml), add 615 ul into each well. Culture supernatant collected at intervals was spun down at low speed and high speed, then frozen at −80 deg. Aliquots were analyzed for protein concentration by nanodrop, and then an equivalent amount loaded onto 4-12% SDS-PAGE gels for molecular weight distribution analysis. The cleavage of IGF2 was confirmed by expression of a construct a of double tagged IGF2, n-terminus tagged with human serum albumin, HSA, and c-terminus tagged with human immunoglobulin heavy chain 4, hFc4, FIG. 14. The sequence of IGF2 was engineered to prevent cleavage by mutation one or more arginines as confirmed by visualization on a reducing SDS-PAGE followed by Western blotting to detect 6×HIS tag FIG. 15B in and in following purification with mini Protein A columns as visualized on a reducing SDS-PAGE FIG. 15A.

Example 28—Clinical Testing of IGF2 Fusion Polypeptides

Figure 19:
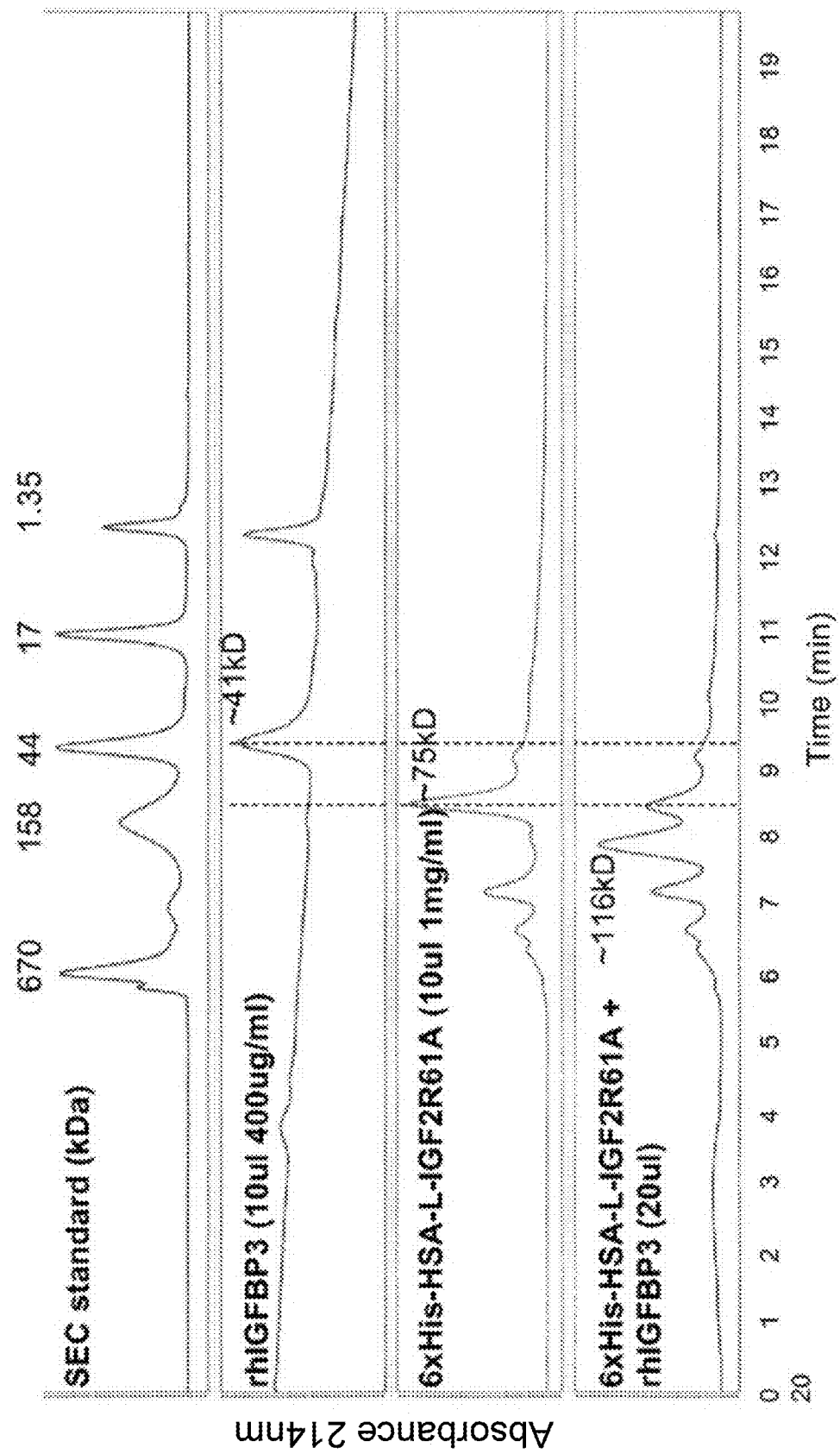
FIG. 19 depicts HSA-IGF2R61A interacts with rhIGFBP3 as demonstrated by mass shifts in size exclusion chromatography by HPLC

In physiological conditions IGF2 will bind IGF binding proteins (IGFBPs). The purpose of this study was to determine if mutant sequences of IGF2 interact with IGFBPs. Retention time across a size exclusions chromatography column is proportional to the size of the molecule. Thus molecular interactions can be ascertained by a corresponding change in retention time on a size exclusions chromatography column. Measuring the retention of HSA-IGF2R61A and rhIGFBP3 separately and as a 1:1 stoichiometric mixture demonstrated evidence of preserved affinity as demonstrated by mass shifts in size exclusion chromatography by HPLC (FIG. 19).

Example 29—Clinical Testing of IGF2 Fusion Polypeptides

The purpose of this study is to determine the safety, tolerability, and pharmacokinetics of repeat dosing with multiple dose levels of polypeptides comprising an IGF2 amino acid sequence and an amino acid sequence from a heterologous polypeptide in healthy individuals or individuals diagnosed with sarcopenia, a muscular dystrophy, or recovery from surgery. In certain embodiments, the muscular dystrophy is myotonic dystrophy. In addition, this study will generate data on the physical function, skeletal muscle mass and strength resulting from treatment with IGF2 fusion polypeptides in such individuals. Individuals will be administered placebo or IGF2 fusion polypeptide compositions and monitored for 25 weeks of study. The following primary and secondary outcome measures will be assessed:
Primary Outcome Measures:
Safety and tolerability as assessed by various measures such as percent of adverse events per study arm.
Secondary Outcome Measures:
Plasma Pharmacokinetics (Cmax, Tmax, AUC) [Plasma at 0.5, 1, 1.5, 2, 4, 6, 8, 12 and 24 hrs after dosing.]
Short Physical Performance Battery (SPPB). Change from baseline to week 25.
10-meter walk test. Change from baseline to week 25.
Change in total lean body mass and appendicular skeletal muscle index measured by Dual-energy X-ray Absorptiometry (DEXA) or MRI from baseline to week 25.
Inclusion Criteria:
Diagnosis of sarcopenia, a muscular dystrophy, or recovery from surgery; Low muscle mass as confirmed by DXA; Low gait speed; SPPB score less than or equal to 9; Weigh at least 35 kg; with adequate dietary intake as determined by patient interview. Independently ambulatory to 10 meters.
Protocol
Patients will be i.v.-administered placebo (5% dextrose solution) or treatment article (in 5% dextrose). Starting on day 1, week 1 and repeated every week (day one of weeks 1 through 25). At the end of week 13 and 25 patients will be assessed by the above methods for improvement. Doses will be selected from a traditional 3+3 design, and selected as the top two-doses that lack dose-limiting toxicity.

Example 30-Administration of 6HIS-HSA-L-IGF2R61A Enhances Myogenic Activation, Fusion and Maturation in an Acute Injury Model The acute injury model of Example 18 was used. Brown female C57/BL6 (NIA) mice (20 months of age) were injected intramuscularly (IM) in each tibialis anterior with cardiotoxin at day one (10 ug/20 µL) and from day two the mice were given IM injections every other day with 0.4 ug/20 µL of 6HIS-HSA-IGF2R61A (SEQ ID NO: 34) or vehicle (0.4 ug/20 µL of HSA).

Figure 21A:
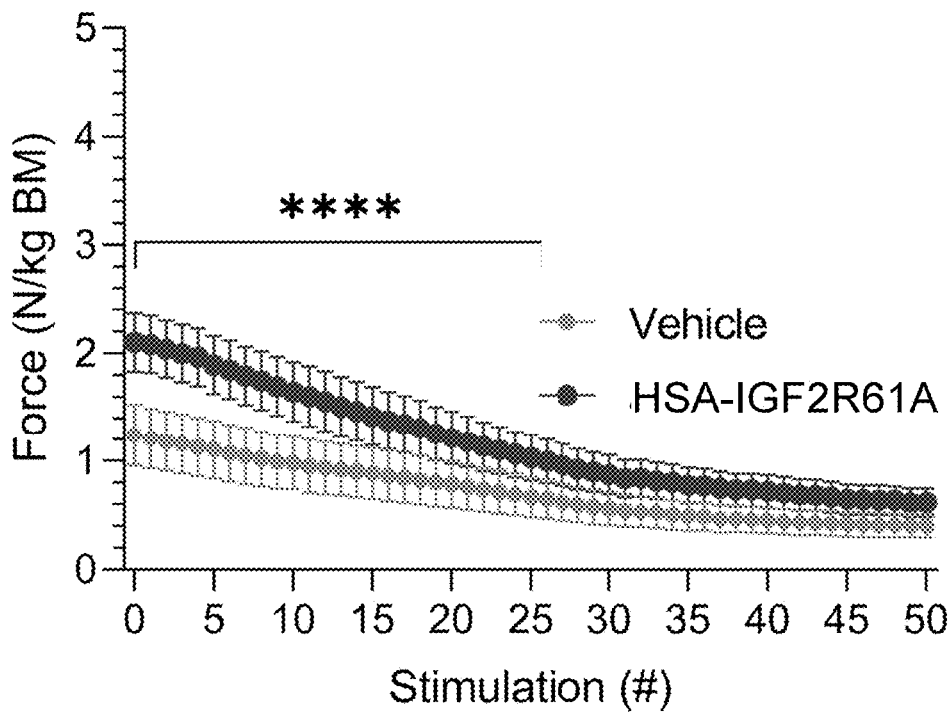
FIG. 21A shows the fatigue index for mice receiving 6HIS-HSA-IGF2R61A or mice receiving control (vehicle).
Figure 21B:
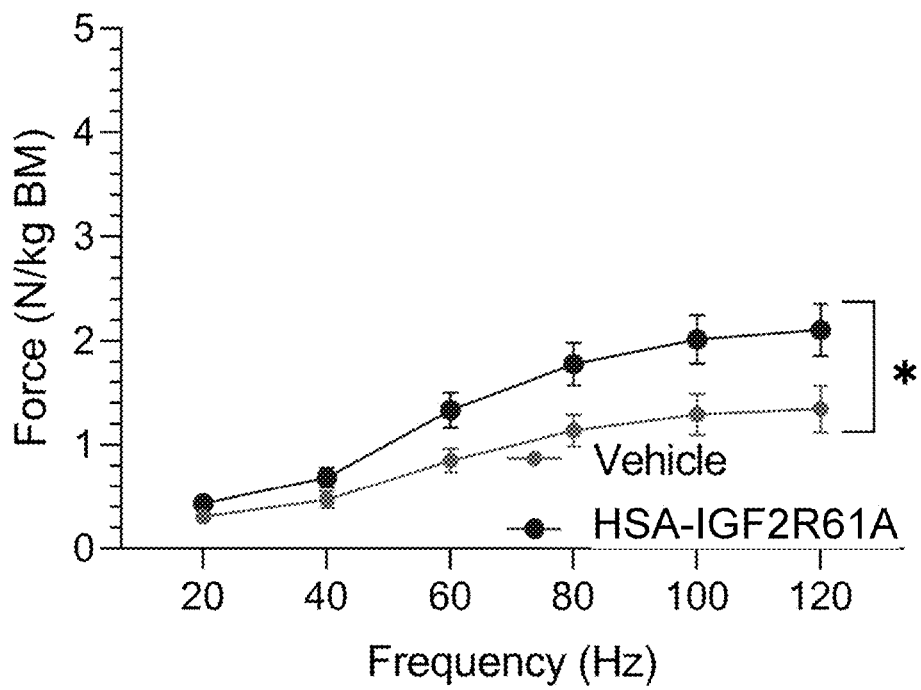
FIG. 21B shows the force production as measured by specific force frequency for mice receiving 6HIS-HSA-IGF2R61A or mice receiving control (vehicle).
Figure 21C:
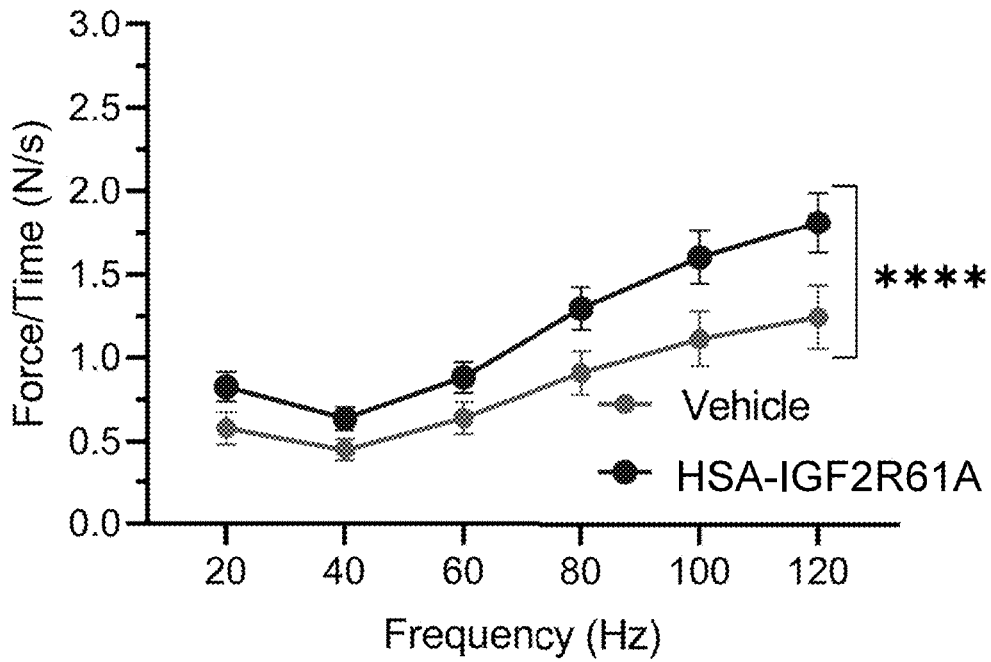
FIG. 21C shows the force production as measured by max contraction rate for mice receiving 6HIS-HSA-IGF2R61A or mice receiving control (vehicle).
Figure 21D:
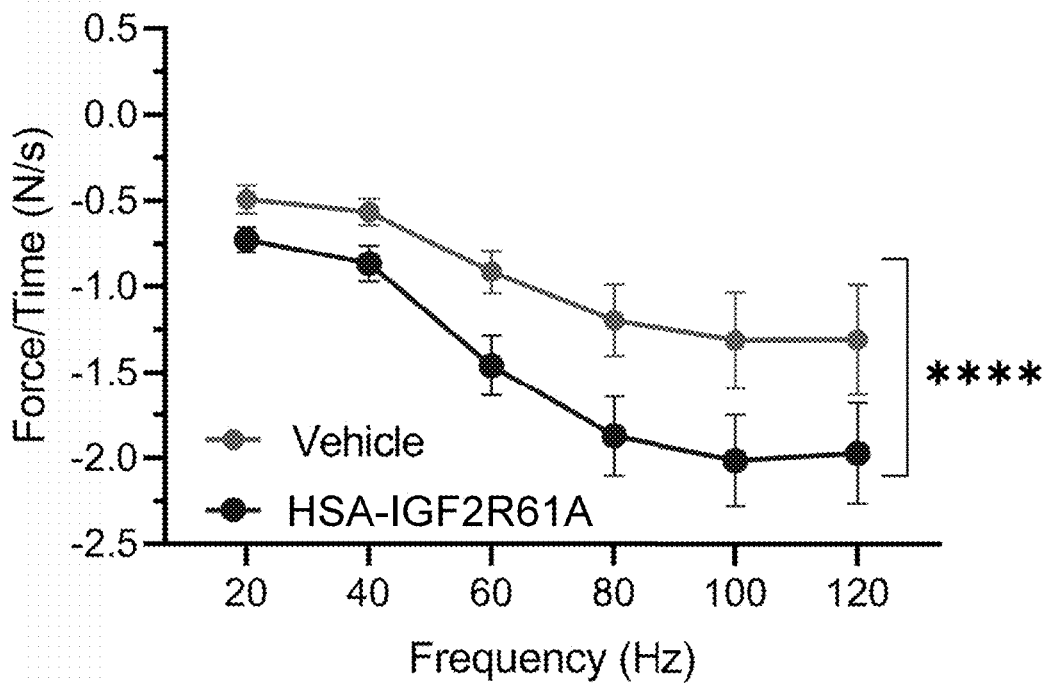
FIG. 21D shows the relation rates of mice receiving 6HIS-HSA-IGF2R61A compared mice receiving control (vehicle).
Figure 21E:
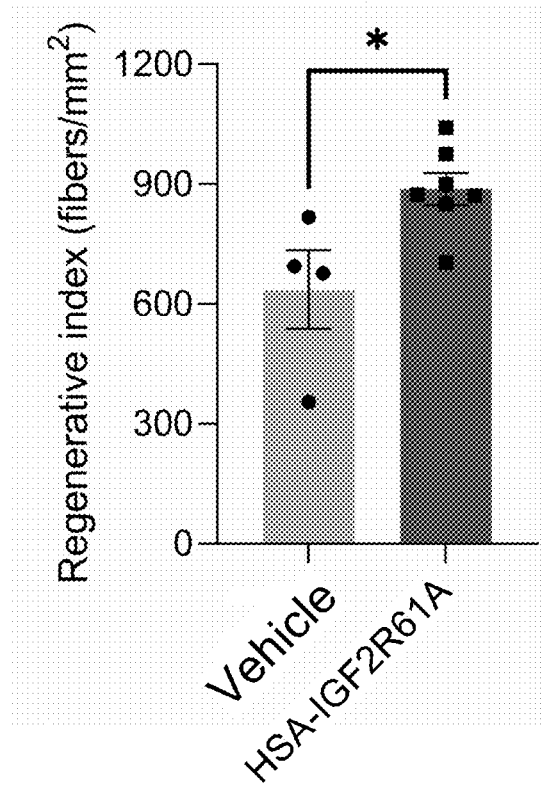
FIG. 21E shows the regenerative index measured as the number of new muscle fibers per square millimeter for mice receiving 6HIS-HSA-IGF2R61A or mice receiving control (vehicle).
Figure 21F:
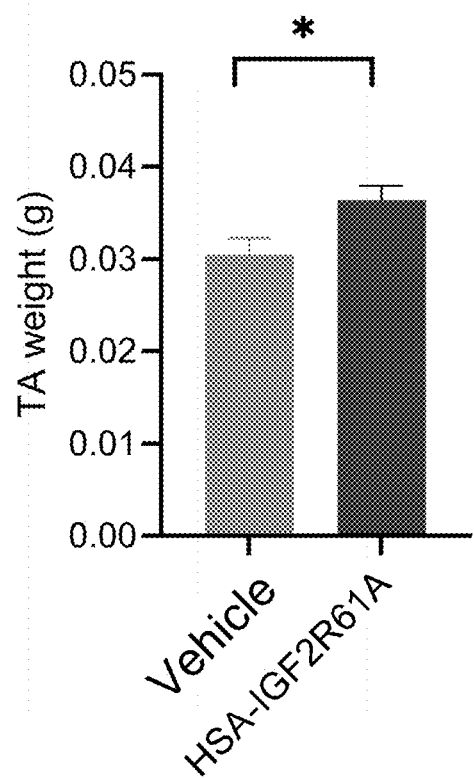
-FIG. 21F shows results from an acute injury mouse model.

Mice receiving 6HIS-HSA-IGF2R61A showed reduced muscle fatigue compared to control treatment (vehicle) as measured by specific fatigue index. These results are shown in FIG. 21A. Mice receiving the 6HIS-HSA-IGF2R61A showed increased force production relative to control treatment (vehicle) as measured by specific force-frequency. These results are shown in FIG. 21B. Mice receiving 6HIS-HSA-IGF2R61A showed increased force production comparted to control treatment (vehicle) as measured by max contraction rate index. These results are shown in FIG. 21C. Mice receiving 6HIS-HSA-IGF2R61A showed improved relation rates relative to control treatment (vehicle) index. These results are shown in FIG. 21D. Mice receiving 6HIS-HSA-IGF2R61A showed increased regenerative index compared to control treatment (vehicle) as measured by number of new fibers per square millimeter. These results are shown in FIG. 21E. Mice receiving 6HIS-HSA-IGF2R61A showed increased muscle mass relative to control treated (vehicle) mice. These results are shown in FIG. 21F.

Example 31—Administration of 6HIS-HSA-L-IGF2R61A and Sodium Butyrate Preserved Muscle Function and Fiber Size in a Sarcopenia Model The sarcopenia model of Example 18 was used. Brown male C57/BL6 (NIA) mice (83-86 weeks of age) were injected every other day with 6 mg/kg of 6HIS-HSA-IGF2R61A (SEQ ID NO: 34) and 0.3 g/kg of sodium butyrate (NaB), or vehicle for 4 weeks to measure muscle regeneration and functional changes.

Figure 22C:
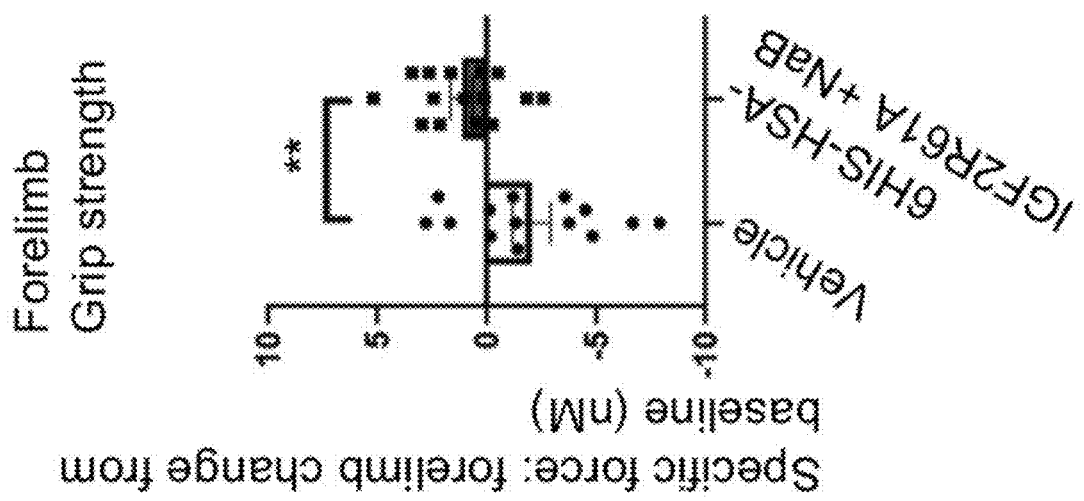
FIG. 22A-FIG. 22E shows results from a sarcopenia mouse model.
Figure 22B:
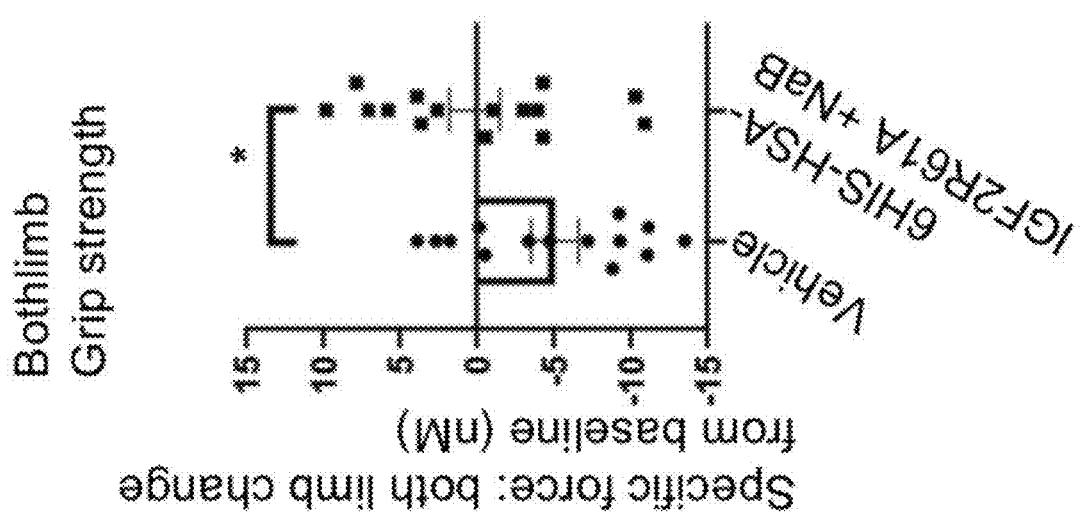
Figure 22A:
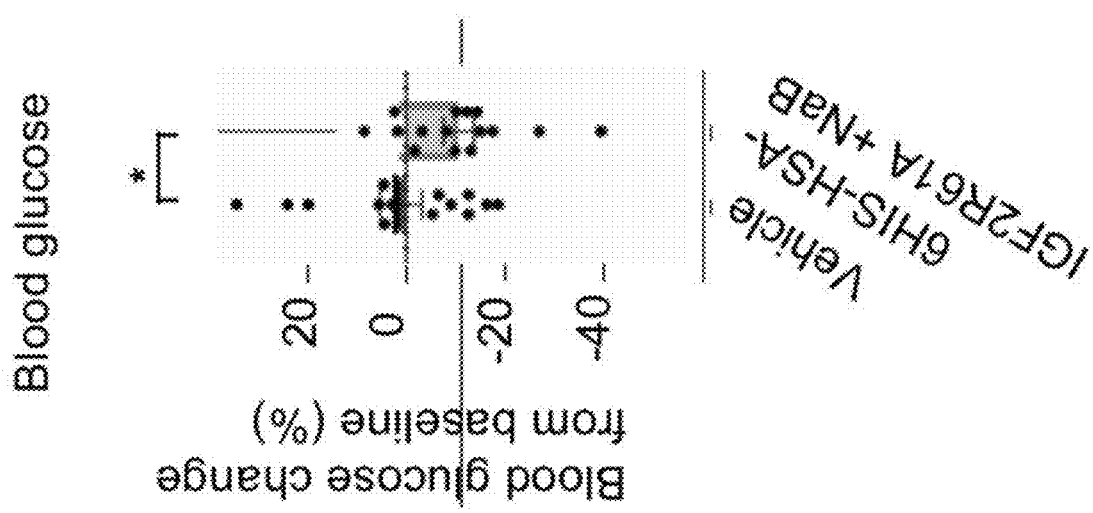

Blood glucose was measured in both groups and normalized to the baseline level within each mouse. Treatment with 6HIS-HSA-IGF2R61A and NaB decreased blood glucose relative to control (vehicle) treated mice. These results are shown in FIG. 22A.

Figure 22E:
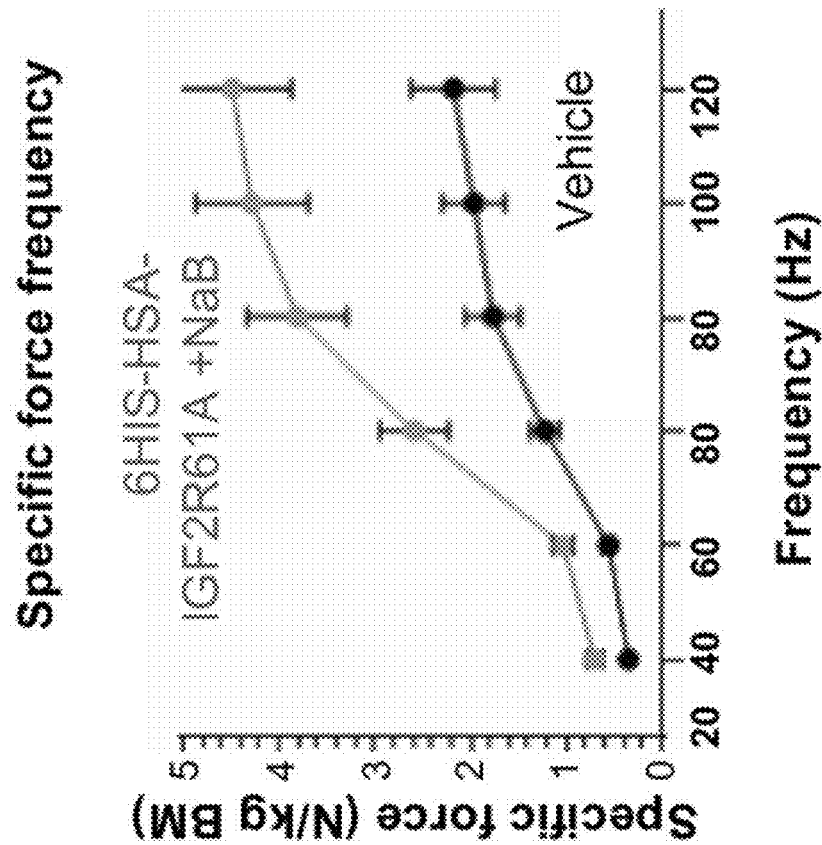
Figure 22D:
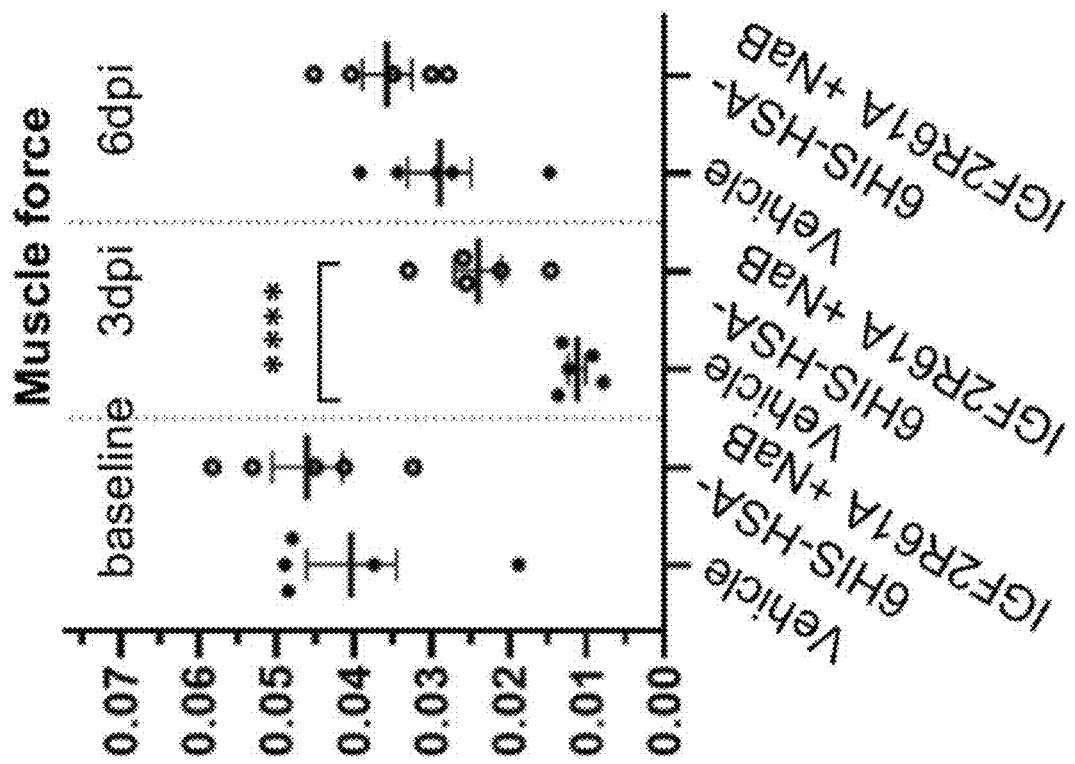

Limb Grip strength was measured in both groups and normalized by body weight within each mouse to determine specific force generation. Treatment with 6HIS-HSA-IGF2R61A and NaB increased specific force generation relative to mice treated with control (vehicle). These results are shown in FIG. 22B. Forelimb Grip strength was measured in both groups and normalized by body weight within each mouse to determine specific force generation. Treatment with 6HIS-HSA-IGF2R61A and NaB increased specific force generation relative to mice treated with control (vehicle). These results are shown in FIG. 22C. Recovery of muscle force production was measured in both groups. Treatment with 6HIS-HSA-IGF2R61A and NaB increased force generation relative to mice treated with control (vehicle) as measured by twitch force. These results are shown in FIG. 22D. Force-frequency was measured in both groups and normalized by body weight within each mouse to determine specific force frequency. Treatment with 6HIS-HSA-IGF2R61A and NaB increased specific force generation relative to mice treated with control (vehicle). These results are shown in FIG. 22E.

Example 32-Administration of 6HIS-HSA-L-IGF2R61A and Sodium Butyrate Preserved Muscle Function and Fiber Size in a Sarcopenia Model The sarcopenia model of Example 18 was used. Brown male C57/BL6 (NIA) mice (23 months of age) were injected daily with 6 mg/kg of HSA-IGF2R61A (SEQ ID NO: 34) and 0.3 g/kg of sodium butyrate (NaB), or vehicle for 2 weeks to measure muscle regeneration and functional changes.

Figure 23A:
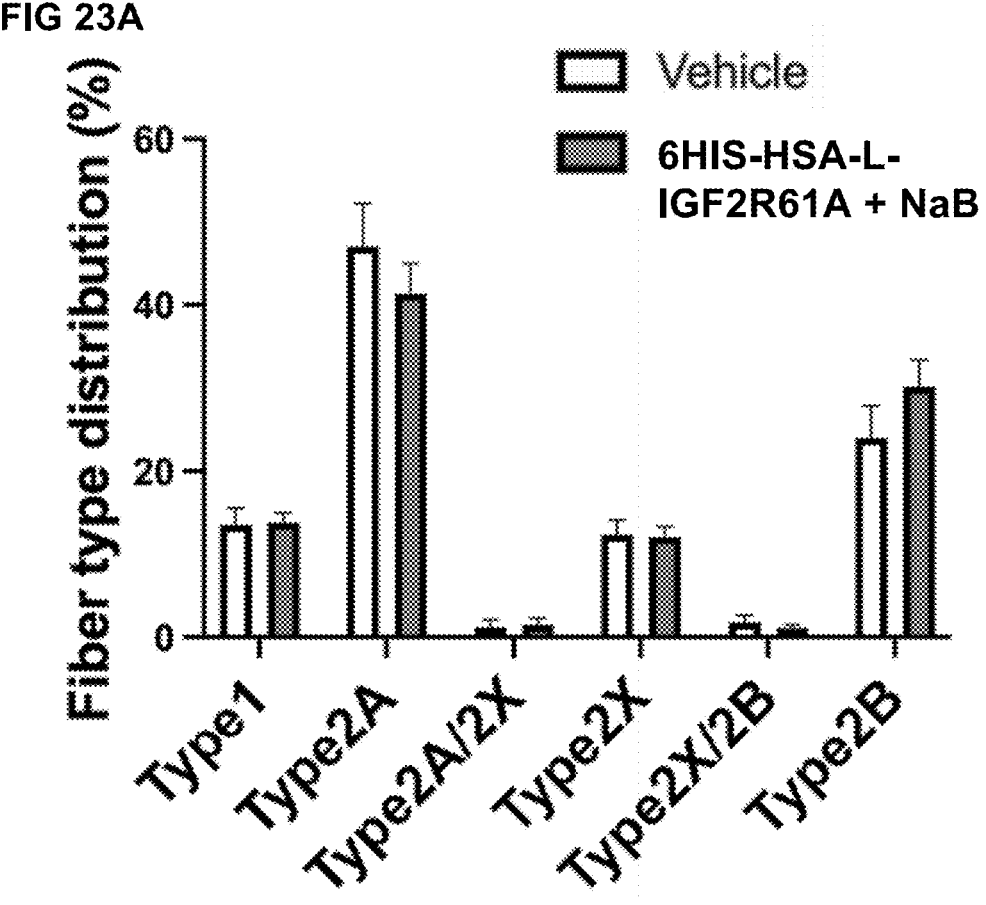
FIG. 23A-FIG. 23B shows results from a sarcopenia mouse model.
Figure 23B:
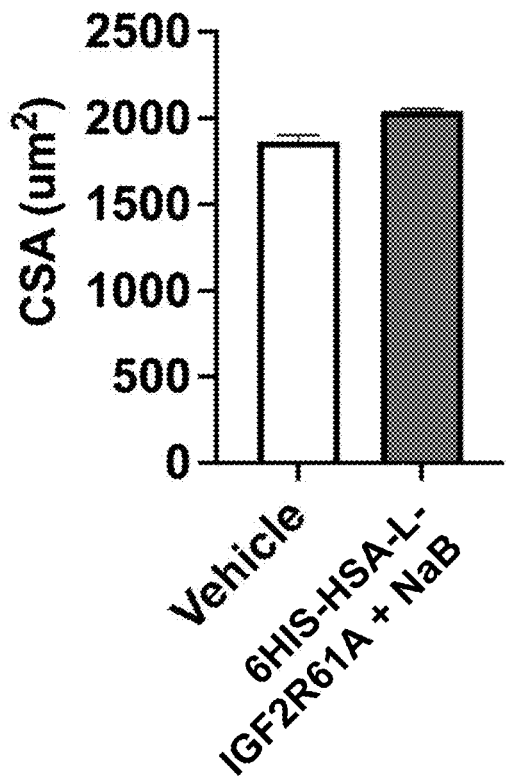

The fiber type distribution was measured in both groups. The fiber type 2A was lower and type 2B higher in the 6HIS-HSA-IGF2R61A and NaB treated mice compared to the mice treated with control (vehicle). These results are shown in FIG. 23A. The cross-sectional areas (CSA) were measured and plotted by group. The mice treated with 6HIS-HSA-IGF2R61A and NaB showed an increase in muscle tissue with larger CSA values compared to mice treated with control (vehicle). These results are shown in FIG. 23B.

Example 33-Administration of 6HIS-HSA-L-IGF2R61A and Sodium Butyrate Restored Muscle Function, Fiber Size, and Fiber Composition in a Myotonic Dystrophy (DM1) Mouse Model Brown male TRED960I(+/+)/M2rtTA(+/−) mice were fed doxycycline chow from birth, and muscle wasting phenotype was observed by weeks 12-14. Mice were injected daily with 6 mg/kg of 6HIS-HSA-IGF2R61A (SEQ ID NO: 34) and 0.3 g/kg of sodium butyrate (NaB) or vehicle for 2 weeks to measure muscle regeneration and functional changes, and post-mortem histology analysis.

Figure 24A:
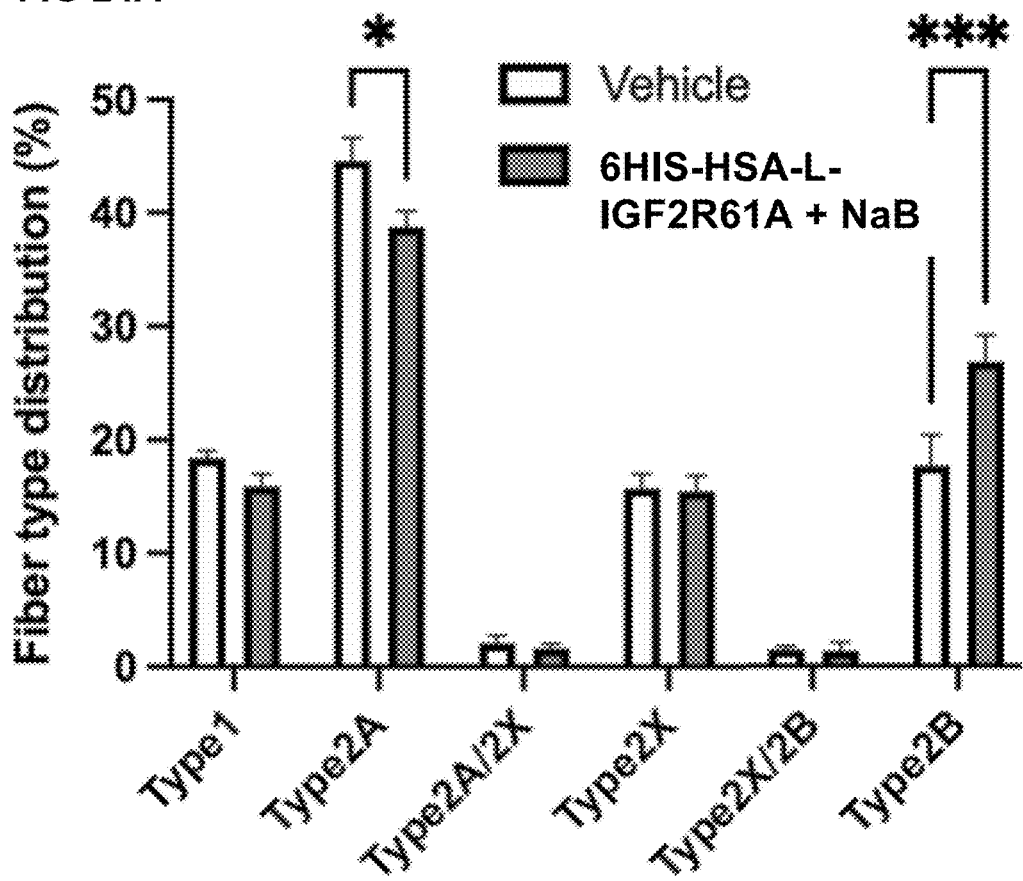
Figure 24B:
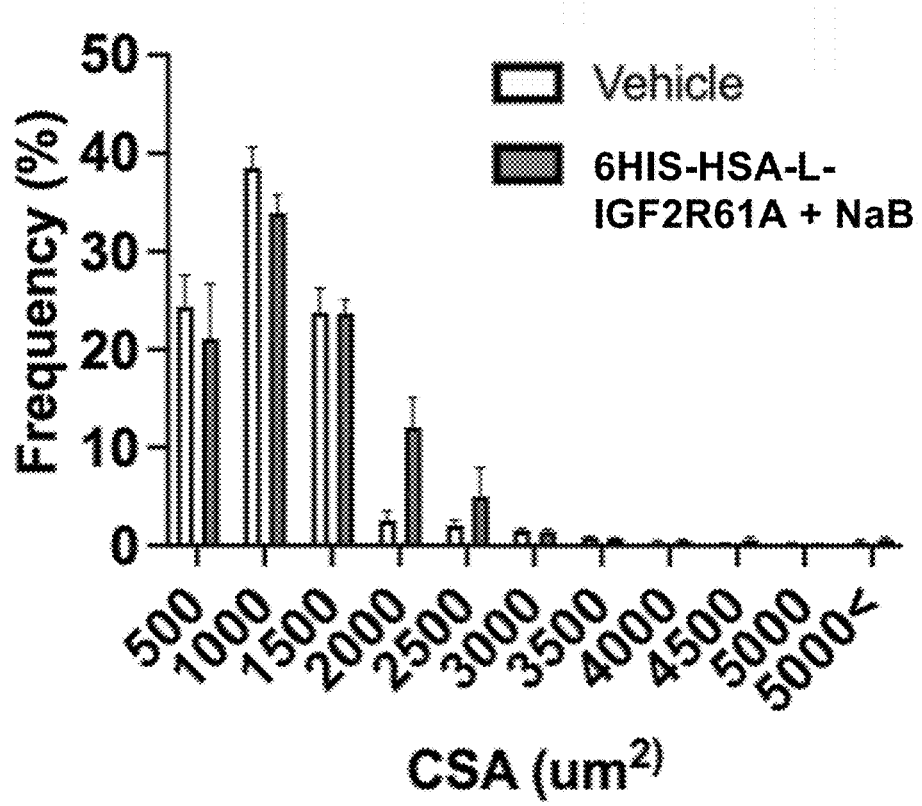

The fiber type distribution was measured in both groups. The fiber types 2A and 2B were significantly different (P-value<0.05) in the two groups with 2A being decreased and 2B increased in mice treated with 6HIS-HSA-IGF2R61A and NaB compared to mice treated with control (vehicle). These results are shown in FIG. 24A. The cross-sectional areas (CSA) were measured and plotted by group. The mice treated with 6HIS-HSA-IGF2R61A and NaB showed an increase in muscle tissue with larger CSA values compared to mice treated with control (vehicle). These results are shown in FIG. 24B.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

TABLE OF SEQUENCES

| Seq ID No | Sequence Name | Description | Sequence |
|---|---|---|---|
| 1 | spFGF-17 | Human FGF-17 secretory signal peptide nucleotide sequence | ATGGGAGCCGCCCGCCTGCTGCCCAACCTCACTCTGTGCTTA CAGCTGCTGATTCTCTGCTGTCAA |

TABLE OF SEQUENCES-continued

| Seq ID No | Sequence Name | Description | Sequence |
|---|---|---|---|
| 2 | spTHBS1 | Human THBS1 secretory signal peptide nucleotide sequence | ATGGGGCTGGCCTGGGGACTAGGCGTCCTGTTCCTGATGCAT GTGTGTGGCACC |
| 3 | spIGF-2 | Human IGF-2 secretory signal peptide nucleotide sequence | ATGGGAATCCCAATGGGGAAGTCGATGCTGGTGCTTCTCACC TTCTTGGCCTTCGCCTCGTGCTGCATTGCT |
| 4 | spBMP-7 | Human BMP-7 secretory signal peptide nucleotide sequence | ATGCACGTGCGCTCACTGCGAGCTGCGGCGCCGCACAGCTTC GTGGCGCTCTGGGCACCCCTGTTCCTGCTGCGCTCCGCCCTG GCC |
| 5 | spALB | Human Albumin secretory signal peptide nucleotide sequence | ATGAAGTGGGTAACCTTTATTTCCCTTCTTTTTCTCTTTAGC TCGGCTTATTCC |
| 6 | spAZU1 | Human Azurocidin secretory signal peptide nucleotide sequence | ATGACCCGGCTGACAGTCCTGGCCCTGCTGGCTGGTCTGCTG GCGTCCTCGAGGGCC |
| 7 | spBM40 | Human osteonectin secretory signal peptide nucleotide sequence | ATGAGGGCCTGGATCTTCTTTCTCCTTTGCCTGGCCGGGAGG GCTCTGGCAGCA |
| 8 | spGAU | Gaussia luciferase secretory signal peptide nucleotide sequence | ATGGGAGTCAAAGTTCTGTTTGCCCTGATCTGCATCGCTGTG GCCGAGGCC |
| 9 | spFGF-17 | Human FGF-17 secretory signal peptide amino acid sequence | MGAARLLPNLTLCLQLLILCCQ |
| 10 | spTHBS1 | Human THBS1 secretory signal peptide amino acid sequence | MGLAWGLGVLFLMHVCGT |
| 11 | spIGF-2 | Human IGF-2 secretory signal peptide amino acid sequence | MGIPMGKSMLVLLTFLAFASCCIA |
| 12 | spBMP-7 | Human BMP-7 secretory signal peptide amino acid sequence | MHVRSLRAAAPHSFVALWAPLFLLRSALA |
| 13 | spALB | Human Albumin secretory signal peptide amino acid sequence | MKWVTFISLLFLFSSAYS |
| 14 | spAZU1 | Human Azurocidin secretory signal peptide amino acid sequence | MTRLTVLALLAGLLASSRA |

TABLE OF SEQUENCES-continued

| Seq ID No | Sequence Name | Description | Sequence |
|---|---|---|---|
| 15 | spBM40 | Human osteonectin secretory signal peptide amino acid sequence | MRAWIFFLLCLAGRALAA |
| 16 | spGAU | Gaussia luciferase secretory signal peptide amino acid sequence | MGVKVLFALICIAVAEA |
| 17 | IGF2 | Human IGF2 nucleotide sequence | GCTTACCGCCCCAGTGAGACCCTGTGCGGCGGGGAGCTGGTG<br>GACACCCTCCAGTTCGTCTGTGGGACCGCGGCTTCTACTTC<br>AGCAGGCCCGCAAGCCGTGTGAGCCGTCGCAGCCGTGGCATC<br>GTTGAGGAGTGCTGTTTCCGCAGCTGTGACCTGGCCCTCCTG<br>GAGACGTACTGTGCTACCCCCGCCAAGTCCGAG |
| 18 | IGF2-linker1-hFcm | Human IGF2-linker1-hFcm nucleotide | GCTTACCGCCCCAGTGAGACCCTGTGCGGCGGGGAGCTGGTG<br>GACACCCTCCAGTTCGTCTGTGGGACCGCGGCTTCTACTTC<br>AGCAGGCCCGCAAGCCGTGTGAGCCGTCGCAGCCGTGGCATC<br>GTTGAGGAGTGCTGTTTCCGCAGCTGTGACCTGGCCCTCCTG<br>GAGACGTACTGTGCTACCCCCGCCAAGTCCGAGGGATCGGGA<br>TCGGACAAAACTCACACATGCCCACCGTGCCCAGCACCTGAA<br>GCTGCCGGGGACCGTCAGTCTTCCTCTTCCCCCCAAAACCC<br>AAGGACACCCTCATGATCTCCCGGACCCCTGAGGTCACATGC<br>GTGGTGGTGGACGTGAGCCACGAAGACCCTGAGGTCAAGTTC<br>AACTGGTACGTGGACGGCGTGGAGGTGCATAATGCCAAGACA<br>AAGCCGCGGGAGGAGCAGTACAACAGCACGTACCGTGTGGTC<br>AGCGTCCTCACCGTCCTGCACCAGGACTGGCTGAATGGCAAG<br>GAGTACAAGTGCAAGGTCTCCAACAAAGCCCTCGGCGCCCCC<br>ATCGAGAAAACCATCTCCAAAGCCAAAGGGCAGCCCCGAGAA<br>CCACAGGTGTACACCCTGCCCCCATCCCGGGATGAGCTGACC<br>AAGAACCAGGTCAGCCTGACCTGCCTGGTCAAAGGCTTCTAT<br>CCCAGCGACATCGCCGTGGAGTGGGAGAGCAATGGGCAGCCG<br>GAGAACAACTACAAGACCACGCCTCCCGTGCTGGACTCCGAC<br>GGCTCCTTCTTCCTCTACAGCAAGCTCACCGTGGACAAGAGC<br>AGGTGGCAGCAGGGGAACGTCTTCTCATGCTCCGTGATGCAT<br>GAGGCTCTGCACAACCACTACACGCAGAAaAGCCTCTCCCTG<br>TCTCCGGGTAAA |
| 19 | IGF2-linker2-hFcm | nucleotide sequence | GCTTACCGCCCCAGTGAGACCCTGTGCGGCGGGGAGCTGGTG<br>GACACCCTCCAGTTCGTCTGTGGGACCGCGGCTTCTACTTC<br>AGCAGGCCCGCAAGCCGTGTGAGCCGTCGCAGCCGTGGCATC<br>GTTGAGGAGTGCTGTTTCCGCAGCTGTGACCTGGCCCTCCTG<br>GAGACGTACTGTGCTACCCCCGCCAAGTCCGAGGGATCTGGG<br>AGCGCTGACAAAACTCACACATGCCCACCGTGCCCAGCACCT<br>GAAGCTGCCGGGGACCGTCAGTCTTCCTCTTCCCCCCAAAA<br>CCCAAGGACACCCTCATGATCTCCCGGACCCCTGAGGTCACA<br>TGCGTGGTGGTGGACGTGAGCCACGAAGACCCTGAGGTCAAG<br>TTCAACTGGTACGTGGACGGCGTGGAGGTGCATAATGCCAAG<br>ACAAAGCCGCGGGAGGAGCAGTACAACAGCACGTACCGTGTG<br>GTCAGCGTCCTCACCGTCCTGCACCAGGACTGGCTGAATGGC<br>AAGGAGTACAAGTGCAAGGTCTCCAACAAAGCCCTCGGCGCC<br>CCCATCGAGAAAACCATCTCCAAAGCCAAAGGGCAGCCCCGA<br>GAACCACAGGTGTACACCCTGCCCCCATCCCGGGATGAGCTG<br>ACCAAGAACCAGGTCAGCCTGACCTGCCTGGTCAAAGGCTTC<br>TATCCCAGCGACATCGCCGTGGAGTGGGAGAGCAATGGGCAG<br>CCGGAGAACAACTACAAGACCACGCCTCCCGTGCTGGACTCC<br>GACGGCTCCTTCTTCCTCTACAGCAAGCTCACCGTGGACAAG<br>AGCAGGTGGCAGCAGGGGAACGTCTTCTCATGCTCCGTGATG<br>CATGAGGCTCTGCACAACCACTACACGCAGAAaAGCCTCTCC<br>CTGTCTCCGGGTAAA |
| 20 | 6xHis-HSA-linker3-IGF2 | His tagged HSA fusion IGF2 with a long linker nucleotide sequence | CACCATCACCATCACCATAGCGGCGATGCACACAAGAGTGAG<br>GTTGCTCATCGGTTTAAAGATTTGGGAGAAGAAAATTTCAAA<br>GCCTTGGTGTTGATTGCCTTTGCTCAGTATCTTCAGCAGTGT<br>CCATTTGAAGATCATGTAAAATTAGTGAATGAAGTAACTGAA<br>TTTGCAAAAACATGTGTTGCTGATGAGTCAGCTGAAAATTGT<br>GACAAATCACTTCATACCCTTTTTGGAGACAAATTATGCACA<br>GTTGCAACTCTTCGTGAAACCTATGGTGAAATGGCTGACTGC<br>TGTGCAAAACAAGAACCTGAGAGAAATGCTTCTTGCAA<br>CACAAAGATGACAACCCAAACCTCCCCCGATTGGTGAGACCA<br>GAGGTTGATGTGATGTGCACTGCTTTTCATGACAATGAAGAG<br>ACATTTTTGAAAAAATACTTATATGAAATTGCCAGAAGACAT<br>CCTTACTTTTATGCCCCGGAACTCCTTTTCTTTGCTAAAAGG<br>TATAAAGCTGCTTTTACAGAATGTTGCCAAGCTGCTGATAAA |

TABLE OF SEQUENCES-continued

| Seq ID No | Sequence Name | Description | Sequence |
|---|---|---|---|
| | | | GCTGCCTGCCTGTTGCCAAAGCTCGATGAACTTCGGGATGAA
GGGAAGGCTTCGTCTGCCAAACAGAGACTCAAGTGTGCCAGT
CTCCAAAAATTTGGAGAAAGAGCTTTCAAAGCATGGGCAGTA
GCTCGCCTGAGCCAGAGATTTCCCAAAGCTGAGTTTGCAGAA
GTTTCCAAGTTAGTGACAGATCTTACCAAAGTCCACACGGAA
TGCTGCCATGGAGATCTGCTTGAATGTGCTGATGACAGGGCG
GACCTTGCCAAGTATATCTGTGAAAATCAAGATTCGATCTCC
AGTAAACTGAAGGAATGCTGTGAAAAACCTCTGTTGGAAAAA
TCCCACTGCATTGCCGAAGTGGAAAATGATGAGATGCCTGCT
GACTTGCCTTCATTAGCTGCTGATTTTGTTGAAAGTAAGGAT
GTTTGCAAAACTATGCTGAGGCAAAGGATGTCTTCCTGGGC
ATGTTTTTGTATGAATATGCAAGAAGGCATCCTGATTACTCT
GTCGTGCTGCTGCTGAGACTTGCCAAGACATATGAAACCACT
CTAGAGAAGTGCTGTGCCGCTGCAGATCCTCATGAATGCTAT
GCCAAAGTGTTCGATGAATTTAAACCTCTTGTGGAAGAGCCT
CAGAATTTAATCAAACAAAATTGTGAGCTTTTTGAGCAGCTT
GGAGAGTACAAATTCCAGAATGCGCTATTAGTTCGTTACACC
AAGAAAGTACCCCAAGTGTCAACTCCAACTCTTGTAGAGGTC
TCAAGAAACCTAGGAAAAGTGGGCAGCAAATGTTGTAAACAT
CCTGAAGCAAAAGAATGCCCTGTGCAGAAGACTATCTATCC
GTGGTCCTGAACCAGTTATGTGTGTTGCATGAGAAAACGCCA
GTAAGTGACAGAGTCACCAAATGCTGCACAGAATCCTTGGTG
AACAGGCGACCATGCTTTTCAGCTCTGGAAGTCGATGAAACA
TACGTTCCCAAAGAGTTTAATGCTGAAACATTCACCTTCCAT
GCAGATATATGCACACTTTCTGAGAAGGAGAGACAAATCAAG
AAACAAACTGCACTTGTTGAGCTCGTGAAACACAAGCCCAAG
GCAACAAAAGAGCAACTGAAAGCTGTTATGGATGATTTCGCA
GCTTTTGTAGAGAAGTGCTGCAAGGCTGACGATAAGGAGACC
TGCTTTGCCGAGGAGGGTAAAAAACTTGTTGCTGCAAGTCAA
GCTGCCTTAGGCTTAGGCGGAGGCGGTAGCGGAGGCGGTGGC
TCCGGTGGCGGAGGGTCTGCTTACCGCCCCAGTGAGACCCTG
TGCGGCGGGGAGCTGGTGGACACCCTCCAGTTCGTCTGTGGG
GACCGCGGCTTCTACTTCAGCAGGCCCGCAAGCCGTGTGAGC
CGTCGCAGCCGTGGCATCGTTGAGGAGTGCTGTTTCCGCAGC
TGTGACCTGGCCCTCCTGGAGACGTACTGTGCTACCCCCGCC
AAGTCCGAG |
| 21 | 6xHis-HSA-linker3-IGF2R61A | His tagged HSA fusion IGF2 R61A mutant with a long linker nucleotide sequence | CACCATCACCATCACCATAGCGGCGATGCACACAAGAGTGAG
GTTGCTCATCGTTTAAAGATTTGGGAGAAGAAAATTTCAAA
GCCTTGGTGTTGATTGCCTTTGCTCAGTATCTTCAGCAGTGT
CCATTTGAAGATCATGTAAATTAGTGAATGAAGTAACTGAA
TTTGCAAAAACATGTGTTGCTGATGAGTCAGCTGAAAATTGT
GACAAATCACTTCATACCCTTTTTGGAGACAAATTATGCACA
GTTGCAACTCTTCGTGAAACCTATGGTGAAATGGCTGACTGC
TGTGCAAAACAAGAACCTGAGAGAAATGAATGCTTCTTGCAA
CACAAAGATGACAACCCAAACCTCCCCCGATTGGTGAGACCA
GAGGTTGATGTGATGTGCACTGCTTTTCATGACAATGAAGAG
ACATTTTTGAAAAAATACTTATATGAAATTGCCAGAAGACAT
CCTTACTTTTATGCCCCGGAACTCCTTTTCTTTGCTAAAAGG
TATAAAGCTGCTTTTACAGAATGTTGCCAAGCTGCTGATAAA
GCTGCCTGCCTGTTGCCAAAGCTCGATGAACTTCGGGATGAA
GGGAAGGCTTCGTCTGCCAAACAGAGACTCAAGTGTGCCAGT
CTCCAAAAATTTGGAGAAAGAGCTTTCAAAGCATGGGCAGTA
GCTCGCCTGAGCCAGAGATTTCCCAAAGCTGAGTTTGCAGAA
GTTTCCAAGTTAGTGACAGATCTTACCAAAGTCCACACGGAA
TGCTGCCATGGAGATCTGCTTGAATGTGCTGATGACAGGGCG
GACCTTGCCAAGTATATCTGTGAAAATCAAGATTCGATCTCC
AGTAAACTGAAGGAATGCTGTGAAAAACCTCTGTTGGAAAAA
TCCCACTGCATTGCCGAAGTGGAAAATGATGAGATGCCTGCT
GACTTGCCTTCATTAGCTGCTGATTTTGTTGAAAGTAAGGAT
GTTTGCAAAACTATGCTGAGGCAAAGGATGTCTTCCTGGGC
ATGTTTTTGTATGAATATGCAAGAAGGCATCCTGATTACTCT
GTCGTGCTGCTGCTGAGACTTGCCAAGACATATGAAACCACT
CTAGAGAAGTGCTGTGCCGCTGCAGATCCTCATGAATGCTAT
GCCAAAGTGTTCGATGAATTTAAACCTCTTGTGGAAGAGCCT
CAGAATTTAATCAAACAAAATTGTGAGCTTTTTGAGCAGCTT
GGAGAGTACAAATTCCAGAATGCGCTATTAGTTCGTTACACC
AAGAAAGTACCCCAAGTGTCAACTCCAACTCTTGTAGAGGTC
TCAAGAAACCTAGGAAAAGTGGGCAGCAAATGTTGTAAACAT
CCTGAAGCAAAAGAATGCCCTGTGCAGAAGACTATCTATCC
GTGGTCCTGAACCAGTTATGTGTGTTGCATGAGAAAACGCCA
GTAAGTGACAGAGTCACCAAATGCTGCACAGAATCCTTGGTG
AACAGGCGACCATGCTTTTCAGCTCTGGAAGTCGATGAAACA
TACGTTCCCAAAGAGTTTAATGCTGAAACATTCACCTTCCAT
GCAGATATATGCACACTTTCTGAGAAGGAGAGACAAATCAAG
AAACAAACTGCACTTGTTGAGCTCGTGAAACACAAGCCCAAG
GCAACAAAAGAGCAACTGAAAGCTGTTATGGATGATTTCGCA |

TABLE OF SEQUENCES-continued

| Seq ID No | Sequence Name | Description | Sequence |
|---|---|---|---|
| | | | GCTTTTGTAGAGAAGTGCTGCAAGGCTGACGATAAGGAGACC TGCTTTGCCGAGGAGGGTAAAAAACTTGTTGCTGCAAGTCAA GCTGCCTTAGGCTTAGGCGGAGGCGGTAGCGGAGGCGGTGGC TCCGGTGGCGGAGGGTCTGCTTACCGCCCCAGTGAGACCCTG TGCGGCGGGGAGCTGGTGGACACCCTCCAGTTCGTCTGTGGG GACCGCGGCTTCTACTTCAGCAGGCCCGCAAGCCGTGTGAGC GcTCGCAGCCGTGGCATCGTTGAGGAGTGCTGTTTCCGCAGC TGTGACCTGGCCCTCCTGGAGACGTACTGTGCTACCCCCGCC AAGTCCGAG |
| 22 | 6xHis-HSA-linker3-IGF2R61Q | His tagged HSA fusion IGF2 R61Q mutant with a long linker nucleotide sequence | CACCATCACCATCACCATAGCGGCGATGCACACAAGAGTGAG GTTGCTCATCGGTTTAAAGATTTGGGAGAAGAAAATTTCAAA GCCTTGGTGTTGATTGCCTTTGCTCAGTATCTTCAGCAGTGT CCATTTGAAGATCATGTAAAATTAGTGAATGAAGTAACTGAA TTTGCAAAAACATGTGTTGCTGATGAGTCAGCTGAAAATTGT GACAAATCACTTCATACCCTTTTTGGAGACAAATTATGCACA GTTGCAACTCTTCGTGAAACCTATGGTGAAATGGCTGACTGC TGTGCAAAACAAGAACCTGAGAGAAATGAATGCTTCTTGCAA CACAAAGATGACAACCCAAACCTCCCCCGATTGGTGAGACCA GAGGTTGATGTGATGTGCACTGCTTTTCATGACAATGAAGAG ACATTTTTGAAAAAATACTTATATGAAATTGCCAGAAGACAT CCTTACTTTTATGCCCCGGAACTCCTTTTCTTTGCTAAAAGG TATAAAGCTGCTTTTACAGAATGTTGCCAAGCTGCTGATAAA GCTGCCTGCCTGTTGCCAAAGCTCGATGAACTTCGGGATGAA GGGAAGGCTTCGTCTGCCAAACAGAGACTCAAGTGTGCCAGT CTCCAAAAATTTGGAGAAAGAGCTTTCAAAGCATGGGCAGTA GCTCGCCTGAGCCAGAGATTTCCCAAAGCTGAGTTTGCAGAA GTTTCCAAGTTAGTGACAGATCTTACCAAAGTCCACACGGAA TGCTGCCATGGAGATCTGCTTGAATGTGCTGATGACAGGGCG GACCTTGCCAAGTATATCTGTGAAAATCAAGATTCGATCTCC AGTAAACTGAAGGAATGCTGTGAAAAACCTCTGTTGGAAAAA TCCCACTGCATTGCCGAAGTGGAAAATGATGAGATGCCTGCT GACTTGCCTTCATTAGCTGCTGATTTTGTTGAAAGTAAGGAT GTTTGCAAAAACTATGCTGAGGCAAAGGATGTCTTCCTGGGC ATGTTTTTGTATGAATATGCAAGAAGGCATCCTGATTACTCT GTCGTGCTGCTGCTGAGACTTGCCAAGACATATGAAACCACT CTAGAGAAGTGCTGTGCCGCTGCAGATCCTCATGAATGCTAT GCCAAAGTGTTCGATGAATTTAAACCTCTTGTGGAAGAGCCT CAGAATTTAATCAAACAAAATTGTGAGCTTTTTGAGCAGCTT GGAGAGTACAAATTCCAGAATGCGCTATTAGTTCGTTACACC AAGAAAGTACCCCAAGTGTCAACTCCAACTCTTGTAGAGGTC TCAAGAAACCTAGGAAAAGTGGGCAGCAAATGTTGTAAACAT CCTGAAGCAAAAAGAATGCCCTGTGCAGAAGACTATCTATCC GTGGTCCTGAACCAGTTATGTGTGTTGCATGAGAAAACGCCA GTAAGTGACAGAGTCACCAAATGCTGCACAGAATCCTTGGTG AACAGGCGACCATGCTTTTCAGCTCTGGAAGTCGATGAAACA TACGTTCCCAAAGAGTTTAATGCTGAAACATTCACCTTCCAT GCAGATATATGCACACTTTCTGAGAAGGAGAGACAAATCAAG AAACAAACTGCACTTGTTGAGCTCGTGAAACACAAGCCCAAG GCAACAAAAGAGCAACTGAAAGCTGTTATGGATGATTTCGCA GCTTTTGTAGAGAAGTGCTGCAAGGCTGACGATAAGGAGACC TGCTTTGCCGAGGAGGGTAAAAAACTTGTTGCTGCAAGTCAA GCTGCCTTAGGCTTAGGCGGAGGCGGTAGCGGAGGCGGTGGC TCCGGTGGCGGAGGGTCTGCTTACCGCCCCAGTGAGACCCTG TGCGGCGGGGAGCTGGTGGACACCCTCCAGTTCGTCTGTGGG GACCGCGGCTTCTACTTCAGCAGGCCCGCAAGCCGTGTGAGC CaGCGCAGCCGTGGCATCGTTGAGGAGTGCTGTTTCCGCAGC TGTGACCTGGCCCTCCTGGAGACGTACTGTGCTACCCCCGCC AAGTCCGAG |
| 23 | 6xHis-HSA-linker3-IGF2R64A | His tagged HSA fusion IGF2 R64A mutant with a long linker nucleotide sequence | CACCATCACCATCACCATAGCGGCGATGCACACAAGAGTGAG GTTGCTCATCGGTTTAAAGATTTGGGAGAAGAAAATTTCAAA GCCTTGGTGTTGATTGCCTTTGCTCAGTATCTTCAGCAGTGT CCATTTGAAGATCATGTAAAATTAGTGAATGAAGTAACTGAA TTTGCAAAAACATGTGTTGCTGATGAGTCAGCTGAAAATTGT GACAAATCACTTCATACCCTTTTTGGAGACAAATTATGCACA GTTGCAACTCTTCGTGAAACCTATGGTGAAATGGCTGACTGC TGTGCAAAACAAGAACCTGAGAGAAATGAATGCTTCTTGCAA CACAAAGATGACAACCCAAACCTCCCCCGATTGGTGAGACCA GAGGTTGATGTGATGTGCACTGCTTTTCATGACAATGAAGAG ACATTTTTGAAAAAATACTTATATGAAATTGCCAGAAGACAT CCTTACTTTTATGCCCCGGAACTCCTTTTCTTTGCTAAAAGG TATAAAGCTGCTTTTACAGAATGTTGCCAAGCTGCTGATAAA GCTGCCTGCCTGTTGCCAAAGCTCGATGAACTTCGGGATGAA GGGAAGGCTTCGTCTGCCAAACAGAGACTCAAGTGTGCCAGT CTCCAAAAATTTGGAGAAAGAGCTTTCAAAGCATGGGCAGTA GCTCGCCTGAGCCAGAGATTTCCCAAAGCTGAGTTTGCAGAA |

TABLE OF SEQUENCES-continued

| Seq ID No | Sequence Name | Description | Sequence |
|---|---|---|---|
| | | | GTTTCCAAGTTAGTGACAGATCTTACCAAAGTCCACACGGAA
TGCTGCCATGGAGATCTGCTTGAATGTGCTGATGACAGGGCG
GACCTTGCCAAGTATATCTGTGAAAATCAAGATTCGATCTCC
AGTAAACTGAAGGAATGCTGTGAAAAACCTCTGTTGGAAAAA
TCCCACTGCATTGCCGAAGTGGAAAATGATGAGATGCCTGCT
GACTTGCCTTCATTAGCTGCTGATTTTGTTGAAAGTAAGGAT
GTTTGCAAAAACTATGCTGAGGCAAAGGATGTCTTCCTGGGC
ATGTTTTTGTATGAATATGCAAGAAGGCATCCTGATTACTCT
GTCGTGCTGCTGCTGAGACTTGCCAAGACATATGAAACCACT
CTAGAGAAGTGCTGTGCCGCTGCAGATCCTCATGAATGCTAT
GCCAAAGTGTTCGATGAATTTAAACCTCTTGTGGAAGAGCCT
CAGAATTTAATCAAACAAAATTGTGAGCTTTTTGAGCAGCTT
GGAGAGTACAAATTCCAGAATGCGCTATTAGTTCGTTACACC
AAGAAAGTACCCCAAGTGTCAACTCCAACTCTTGTAGAGGTC
TCAAGAAACCTAGGAAAAGTGGGCAGCAAATGTTGTAAACAT
CCTGAAGCAAAAGAATGCCCTGTGCAGAAGACTATCTATCC
GTGGTCCTGAACCAGTTATGTGTGTTGCATGAGAAAACGCCA
GTAAGTGACAGAGTCACCAAATGCTGCACAGAATCCTTGGTG
AACAGGCGACCATGCTTTTCAGCTCTGGAAGTCGATGAAACA
TACGTTCCCAAAGAGTTTAATGCTGAAACATTCACCTTCCAT
GCAGATATATGCACACTTTCTGAGAAGGAGAGACAAATCAAG
AAACAAACTGCACTTGTTGAGCTCGTGAAACACAAGCCCAAG
GCAACAAAAGAGCAACTGAAAGCTGTTATGGATGATTTCGCA
GCTTTTGTAGAGAAGTGCTGCAAGGCTGACGATAAGGAGACC
TGCTTTGCCGAGGAGGGTAAAAAACTTGTTGCTGCAAGTCAA
GCTGCCTTAGGCTTAGGCGGAGGCGGTAGCGGAGGCGGTGGC
TCCGGTGGCGGAGGGTCTGCTTACCGCCCCAGTGAGACCCTG
TGCGGCGGGGAGCTGGTGGACACCCTCCAGTTCGTCTGTGGG
GACCGCGGCTTCTACTTCAGCAGGCCCGCAAGCCGTGTGAGC
CGTCGCAGCGCTGGCATCGTTGAGGAGTGCTGTTTCCGCAGC
TGTGACCTGGCCCTCCTGGAGACGTACTGTGCTACCCCCGCC
AAGTCCGAG |
| 24 | 6xHis-HSA-linker3-IGF2R64Q | His tagged HSA fusion IGF2 R64Q mutant with a long linker nucleotide sequence | CACCATCACCATCACCATAGCGGCGATGCACACAAGAGTGAG
GTTGCTCATCGGTTTAAAGATTTGGGAGAAGAAAATTTCAAA
GCCTTGGTGTTGATTGCCTTTGCTCAGTATCTTCAGCAGTGT
CCATTTGAAGATCATGTAAAATTAGTGAATGAAGTAACTGAA
TTTGCAAAAACATGTGTTGCTGATGAGTCAGCTGAAAATTGT
GACAAATCACTTCATACCCTTTTTGGAGACAAATTATGCACA
GTTGCAACTCTTCGTGAAACCTATGGTGAAATGGCTGACTGC
TGTGCAAAACAAGAACCTGAGAGAAATGAATGCTTCTTGCAA
CACAAAGATGACAACCCAAACCTCCCCCGATTGGTGAGACCA
GAGGTTGATGTGATGTGCACTGCTTTTCATGACAATGAAGAG
ACATTTTTGAAAAAATACTTATATGAAATTGCCAGAAGACAT
CCTTACTTTTATGCCCCGGAACTCCTTTTCTTTGCTAAAAGG
TATAAAGCTGCTTTTACAGAATGTTGCCAAGCTGCTGATAAA
GCTGCCTGCCTGTTGCCAAAGCTCGATGAACTTCGGGATGAA
GGGAAGGCTTCGTCTGCCAAACAGAGACTCAAGTGTGCCAGT
CTCCAAAAATTTGGAGAAAGAGCTTTCAAAGCATGGGCAGTA
GCTCGCCTGAGCCAGAGATTTCCCAAAGCTGAGTTTGCAGAA
GTTTCCAAGTTAGTGACAGATCTTACCAAAGTCCACACGGAA
TGCTGCCATGGAGATCTGCTTGAATGTGCTGATGACAGGGCG
GACCTTGCCAAGTATATCTGTGAAAATCAAGATTCGATCTCC
AGTAAACTGAAGGAATGCTGTGAAAAACCTCTGTTGGAAAAA
TCCCACTGCATTGCCGAAGTGGAAAATGATGAGATGCCTGCT
GACTTGCCTTCATTAGCTGCTGATTTTGTTGAAAGTAAGGAT
GTTTGCAAAAACTATGCTGAGGCAAAGGATGTCTTCCTGGGC
ATGTTTTTGTATGAATATGCAAGAAGGCATCCTGATTACTCT
GTCGTGCTGCTGCTGAGACTTGCCAAGACATATGAAACCACT
CTAGAGAAGTGCTGTGCCGCTGCAGATCCTCATGAATGCTAT
GCCAAAGTGTTCGATGAATTTAAACCTCTTGTGGAAGAGCCT
CAGAATTTAATCAAACAAAATTGTGAGCTTTTTGAGCAGCTT
GGAGAGTACAAATTCCAGAATGCGCTATTAGTTCGTTACACC
AAGAAAGTACCCCAAGTGTCAACTCCAACTCTTGTAGAGGTC
TCAAGAAACCTAGGAAAAGTGGGCAGCAAATGTTGTAAACAT
CCTGAAGCAAAAGAATGCCCTGTGCAGAAGACTATCTATCC
GTGGTCCTGAACCAGTTATGTGTGTTGCATGAGAAAACGCCA
GTAAGTGACAGAGTCACCAAATGCTGCACAGAATCCTTGGTG
AACAGGCGACCATGCTTTTCAGCTCTGGAAGTCGATGAAACA
TACGTTCCCAAAGAGTTTAATGCTGAAACATTCACCTTCCAT
GCAGATATATGCACACTTTCTGAGAAGGAGAGACAAATCAAG
AAACAAACTGCACTTGTTGAGCTCGTGAAACACAAGCCCAAG
GCAACAAAAGAGCAACTGAAAGCTGTTATGGATGATTTCGCA
GCTTTTGTAGAGAAGTGCTGCAAGGCTGACGATAAGGAGACC
TGCTTTGCCGAGGAGGGTAAAAAACTTGTTGCTGCAAGTCAA
GCTGCCTTAGGCTTAGGCGGAGGCGGTAGCGGAGGCGGTGGC
TCCGGTGGCGGAGGGTCTGCTTACCGCCCCAGTGAGACCCTG |

TABLE OF SEQUENCES-continued

| Seq ID No | Sequence Name | Description | Sequence |
|---|---|---|---|
| | | | TGCGGCGGGGAGCTGGTGGACACCCTCCAGTTCGTCTGTGGG<br>GACCGCGGCTTCTACTTCAGCAGGCCCGCAAGCCGTGTGAGC<br>CGTCGCAGCCaGGGCATCGTTGAGGAGTGCTGTTTCCGCAGC<br>TGTGACCTGGCCCTCCTGGAGACGTACTGTGCTACCCCCGCC<br>AAGTCCGAG |
| 25 | IGF2-linker3-hFc4 | Human IGF2-linker3-hFc4 nucleotide sequence | GCTTACCGCCCCAGTGAGACCCTGTGCGGCGGGGAGCTGGTG<br>GACACCCTCCAGTTCGTCTGTGGGGACCGCGGCTTCTACTTC<br>AGCAGGCCCGCAAGCCGTGTGAGCCGTCGCAGCCGTGGCATC<br>GTTGAGGAGTGCTGTTTCCGCAGCTGTGACCTGGCCCTCCTG<br>GAGACGTACTGTGCTACCCCCGCCAAGTCCGAGGGCGGAGGC<br>GGTAGCGGAGGCGGTGGCTCCGGTGGCGGAGGGTCTGAGTCC<br>AAATATGGTCCCCCATGCCCACCCTGCCCAGCACCTGAGTTC<br>CTGGGGGGACCATCAGTCTTCCTGTTCCCCCCAAAACCCAAG<br>GACACTCTCATGATCTCCCGGACCCCTGAGGTCACGTGCGTG<br>GTGGTGGACGTGAGCCAGGAAGACCCCGAGGTCCAGTTCAAC<br>TGGTACGTGGATGGCGTGGAGGTGCATAATGCCAAGACAAAG<br>CCGCGGGAGGAGCAGTTCAACAGCACGTACCGTGTGGTCAGC<br>GTCCTCACCGTCCTGCACCAGGACTGGCTGAACGGCAAGGAG<br>TACAAGTGCAAGGTCTCCAACAAAGGCCTCCCGTCCTCCATC<br>GAGAAAACCATCTCCAAAGCCAAAGGGCAGCCCCGAGAGCCA<br>CAGGTGTACACCCTGCCCCCATCCCAGGAGGAGATGACCAAG<br>AACCAGGTCAGCCTGACCTGCCTGGTCAAAGGCTTCTACCCC<br>AGCGACATCGCCGTGGAGTGGGAGAGCAATGGGCAGCCGGAG<br>AACAACTACAAGACCACGCCTCCCGTGCTGGACTCCGACGGC<br>TCCTTCTTCCTCTACAGCAGGCTCACCGTGGACAAGAGCAGG<br>TGGCAGGAGGGGAATGTCTTCTCATGCTCCGTGATGCATGAG<br>GCTCTGCACAACCACTACACACAGAAGAGCCTCTCCCTGTCT<br>CTGGGTAAA |
| 26 | IGF2-hFc4 | Human IGF2-hFc4 nucleotide sequence | GCTTACCGCCCCAGTGAGACCCTGTGCGGCGGGGAGCTGGTG<br>GACACCCTCCAGTTCGTCTGTGGGGACCGCGGCTTCTACTTC<br>AGCAGGCCCGCAAGCCGTGTGAGCCGTCGCAGCCGTGGCATC<br>GTTGAGGAGTGCTGTTTCCGCAGCTGTGACCTGGCCCTCCTG<br>GAGACGTACTGTGCTACCCCCGCCAAGTCCGAGGAGTCCAAA<br>TATGGTCCCCCATGCCCACCCTGCCCAGCACCTGAGTTCCTG<br>GGGGGACCATCAGTCTTCCTGTTCCCCCCAAAACCCAAGGAC<br>ACTCTCATGATCTCCCGGACCCCTGAGGTCACGTGCGTGGTG<br>GTGGACGTGAGCCAGGAAGACCCCGAGGTCCAGTTCAACTGG<br>TACGTGGATGGCGTGGAGGTGCATAATGCCAAGACAAAGCCG<br>CGGGAGGAGCAGTTCAACAGCACGTACCGTGTGGTCAGCGTC<br>CTCACCGTCCTGCACCAGGACTGGCTGAACGGCAAGGAGTAC<br>AAGTGCAAGGTCTCCAACAAAGGCCTCCCGTCCTCCATCGAG<br>AAAACCATCTCCAAAGCCAAAGGGCAGCCCCGAGAGCCACAG<br>GTGTACACCCTGCCCCCATCCCAGGAGGAGATGACCAAGAAC<br>CAGGTCAGCCTGACCTGCCTGGTCAAAGGCTTCTACCCCAGC<br>GACATCGCCGTGGAGTGGGAGAGCAATGGGCAGCCGGAGAAC<br>AACTACAAGACCACGCCTCCCGTGCTGGACTCCGACGGCTCC<br>TTCTTCCTCTACAGCAGGCTCACCGTGGACAAGAGCAGGTGG<br>CAGGAGGGGAATGTCTTCTCATGCTCCGTGATGCATGAGGCT<br>CTGCACAACCACTACACACAGAAGAGCCTCTCCCTGTCTCTG<br>GGTAAA |
| 27 | hFc4-linker3-IGF2 | hFc4-linker3-human IGF2 nucleotide sequence | GAGTCCAAATATGGTCCCCCATGCCCACCCTGCCCAGCACCT<br>GAGTTCCTGGGGGGACCATCAGTCTTCCTGTTCCCCCCAAAA<br>CCCAAGGACACTCTCATGATCTCCCGGACCCCTGAGGTCACG<br>TGCGTGGTGGTGGACGTGAGCCAGGAAGACCCCGAGGTCCAG<br>TTCAACTGGTACGTGGATGGCGTGGAGGTGCATAATGCCAAG<br>ACAAAGCCGCGGGAGGAGCAGTTCAACAGCACGTACCGTGTG<br>GTCAGCGTCCTCACCGTCCTGCACCAGGACTGGCTGAACGGC<br>AAGGAGTACAAGTGCAAGGTCTCCAACAAAGGCCTCCCGTCC<br>TCCATCGAGAAAACCATCTCCAAAGCCAAAGGGCAGCCCCGA<br>GAGCCACAGGTGTACACCCTGCCCCCATCCCAGGAGGAGATG<br>ACCAAGAACCAGGTCAGCCTGACCTGCCTGGTCAAAGGCTTC<br>TACCCCAGCGACATCGCCGTGGAGTGGGAGAGCAATGGGCAG<br>CCGGAGAACAACTACAAGACCACGCCTCCCGTGCTGGACTCC<br>GACGGCTCCTTCTTCCTCTACAGCAGGCTCACCGTGGACAAG<br>AGCAGGTGGCAGGAGGGGAATGTCTTCTCATGCTCCGTGATG<br>CATGAGGCTCTGCACAACCACTACACACAGAAGAGCCTCTCC<br>CTGTCTCTGGGTAAAGGCGGAGGCGGTAGCGGAGGCGGTGGC<br>TCCGGTGGCGGAGGGTCTGCTTACCGCCCCAGTGAGACCCTG<br>TGCGGCGGGGAGCTGGTGGACACCCTCCAGTTCGTCTGTGGG<br>GACCGCGGCTTCTACTTCAGCAGGCCCGCAAGCCGTGTGAGC<br>CGTCGCAGCCGTGGCATCGTTGAGGAGTGCTGTTTCCGCAGC<br>TGTGACCTGGCCCTCCTGGAGACGTACTGTGCTACCCCCGCC<br>AAGTCCGAG |

TABLE OF SEQUENCES-continued

| Seq ID No | Sequence Name | Description | Sequence |
|---|---|---|---|
| 28 | IGF2R61A-linker3-hFc4 | Human IGF2 R61A point mutant-linker3-hFc4 nucleotide sequence | GCTTACCGCCCCAGTGAGACCCTGTGCGGCGGGGAGCTGGTG GACACCCTCCAGTTCGTCTGTGGGGACCGCGGCTTCTACTTC AGCAGGCCCGCAAGCCGTGTGAGCGcTCGCAGCCGTGGCATC GTTGAGGAGTGCTGTTTCCGCAGCTGTGACCTGGCCCTCCTG GAGACGTACTGTGCTACCCCCGCCAAGTCCGAGGGCGGAGGC GGTAGCGGAGGCGGTGGCTCCGGTGGCGGAGGGTCTGAGTCC AAATATGGTCCCCCATGCCCACCCTGCCCAGCACCTGAGTTC CTGGGGGGACCATCAGTCTTCCTGTTCCCCCCAAAACCCAAG GACACTCTCATGATCTCCCGGACCCCTGAGGTCACGTGCGTG GTGGTGGACGTGAGCCAGGAAGACCCCGAGGTCCAGTTCAAC TGGTACGTGGATGGCGTGGAGGTGCATAATGCCAAGACAAAG CCGCGGGAGGAGCAGTTCAACAGCACGTACCGTGTGGTCAGC GTCCTCACCGTCCTGCACCAGGACTGGCTGAACGGCAAGGAG TACAAGTGCAAGGTCTCCAACAAAGGCCTCCCGTCCTCCATC GAGAAAACCATCTCCAAAGCCAAAGGGCAGCCCCGAGAGCCA CAGGTGTACACCCTGCCCCCATCCCAGGAGGAGATGACCAAG AACCAGGTCAGCCTGACCTGCCTGGTCAAAGGCTTCTACCCC AGCGACATCGCCGTGGAGTGGGAGAGCAATGGGCAGCCGGAG AACAACTACAAGACCACGCCTCCCGTGCTGGACTCCGACGGC TCCTTCTTCCTCTACAGCAGGCTCACCGTGGACAAGAGCAGG TGGCAGGAGGGGAATGTCTTCTCATGCTCCGTGATGCATGAG GCTCTGCACAACCACTACACACAGAAGAGCCTCTCCCTGTCT CTGGGTAAA |
| 29 | IGF2 | Human IGF2 amino acid sequence | AYRPSETLCGGELVDTLQFVCGDRGFYFSRPASRVSRRSRGI VEECCFRSCDLALLETYCATPAKSE |
| 30 | IGF2-linker1-hFcm | | AYRPSETLCGGELVDTLQFVCGDRGFYFSRPASRVSRRSRGI VEECCFRSCDLALLETYCATPAKSEGSGSGSDKTHTCPPCPAPE AAGGPSVFLFPPKPKDTLMISRTPEVTCVVVDVSHEDPEVKF NWYVDGVEVHNAKTKPREEQYNSTYRVVSVLTVLHQDWLNGK EYKCKVSNKALGAPIEKTISKAKGQPREPQVYTLPPSRDELT KNQVSLTCLVKGFYPSDIAVEWESNGQPENNYKTTPPVLDSD GSFFLYSKLTVDKSRWQQGNVFSCSVMHEALHNHYTQKSLSL SPGK |
| 31 | IGF2-linker2-hFcm | | AYRPSETLCGGELVDTLQFVCGDRGFYFSRPASRVSRRSRGI VEECCFRSCDLALLETYCATPAKSEGSGSGSADKTHTCPPCPAP EAAGGPSVFLFPPKPKDTLMISRTPEVTCVVVDVSHEDPEVK FNWYVDGVEVHNAKTKPREEQYNSTYRVVSVLTVLHQDWLNG KEYKCKVSNKALGAPIEKTISKAKGQPREPQVYTLPPSRDEL TKNQVSLTCLVKGFYPSDIAVEWESNGQPENNYKTTPPVLDS DGSFFLYSKLTVDKSRWQQGNVFSCSVMHEALHNHYTQKSLS LSPGK |
| 32 | IGF2 Big | Full-length human IGF2 | MGIPMGKSMLVLLTFLAFASCCIAAYRPSETLCGGELVDTLQ FVCGDRGFYFSRPASRVSRRSRGIVEECCFRSCDLALLETYC ATPAKSERDVSTPPTVLPDNFPRYPVGKFFQYDTWKQSTQRL RRGLPALLRARRGHVLAKELEAFREAKRHRPLIALPTQDPAH GGAPPEMASNRK |
| 33 | 6xHis-HSA-linker3-IGF2 | His tagged HSA fusion IGF2 with a long linker | HHHHHHSGDAHKSEVAHRFKDLGEENFKALVLIAFAQYLQQC PFEDHVKLVNEVTEFAKTCVADESAENCDKSLHTLFGDKLCT VATLRETYGEMADCCAKQEPERNECFLQHKDDNPNLPRLVRP EVDVMCTAFHDNEETFLKKYLYEIARRHPYFYAPELLFFAKR YKAAFTECCQAADKAACLLPKLDELRDEGKASSAKQRLKCAS LQKFGERAFKAWAVARLSQRFPKAEFAEVSKLVTDLTKVHTE CCHGDLLECADDRADLAKYICENQDSISSKLKECCEKPLLEK SHCIAEVENDEMPADLPSLAADFVESKDVCKNYAEAKDVFLG MFLYEYARRHPDYSVVLLLRLAKTYETTLEKCCAAADPHECY AKVFDEFKPLVEEPQNLIKQNCELFEQLGEYKFQNALLVRYT KKVPQVSTPTLVEVSRNLGKVGSKCCKHPEAKRMPCAEDYLS VVLNQLCVLHEKTPVSDRVTKCCTESLVNRRPCFSALEVDET YVPKEFNAETFTFHADICTLSEKERQIKKQTALVELVKHKPK ATKEQLKAVMDDFAAFVEKCCKADDKETCFAEEGKKLVAASQ AALGLGGGGSGGGGSGGGGSAYRPSETLCGGELVDTLQFVCG DRGFYFSRPASRVSRRSRGIVEECCFRSCDLALLETYCATPA KSE |
| 34 | 6xHis-HSA-linker3-IGF2R61A | His tagged HSA fusion IGF2 R61A mutant with a long linker | HHHHHHSGDAHKSEVAHRFKDLGEENFKALVLIAFAQYLQQC PFEDHVKLVNEVTEFAKTCVADESAENCDKSLHTLFGDKLCT VATLRETYGEMADCCAKQEPERNECFLQHKDDNPNLPRLVRP EVDVMCTAFHDNEETFLKKYLYEIARRHPYFYAPELLFFAKR YKAAFTECCQAADKAACLLPKLDELRDEGKASSAKQRLKCAS LQKFGERAFKAWAVARLSQRFPKAEFAEVSKLVTDLTKVHTE CCHGDLLECADDRADLAKYICENQDSISSKLKECCEKPLLEK |

TABLE OF SEQUENCES-continued

| Seq ID No | Sequence Name | Description | Sequence |
|---|---|---|---|
| | | | SHCIAEVENDEMPADLPSLAADFVESKDVCKNYAEAKDVFLG MFLYEYARRHPDYSVVLLLRLAKTYETTLEKCCAAADPHECY AKVFDEFKPLVEEPQNLIKQNCELFEQLGEYKFQNALLVRYT KKVPQVSTPTLVEVSRNLGKVGSKCCKHPEAKRMPCAEDYLS VVLNQLCVLHEKTPVSDRVTKCCTESLVNRRPCFSALEVDET YVPKEFNAETFTFHADICTLSEKERQIKKQTALVELVKHKPK ATKEQLKAVMDDFAAFVEKCCKADDKETCFAEEGKKLVAASQ AALGLGGGGSGGGGSGGGGSAYRPSETLCGGELVDTLQFVCG DRGFYFSRPASRVSARSRGIVEECCFRSCDLALLETYCATPA KSE |
| 35 | 6xHis-HSA-linker3-IGF2R61Q | His tagged HSA fusion IGF2 R61Q mutant with a long linker | HHHHHHSGDAHKSEVAHRFKDLGEENFKALVLIAFAQYLQQC PFEDHVKLVNEVTEFAKTCVADESAENCDKSLHTLFGDKLCT VATLRETYGEMADCCAKQEPERNECFLQHKDDNPNLPRLVRP EVDVMCTAFHDNEETFLKKYLYEIARRHPYFYAPELLFFAKR YKAAFTECCQAADKAACLLPKLDELRDEGKASSAKQRLKCAS LQKFGERAFKAWAVARLSQRFPKAEFAEVSKLVTDLTKVHTE CCHGDLLECADDRADLAKYICENQDSISSKLKECCEKPLLEK SHCIAEVENDEMPADLPSLAADFVESKDVCKNYAEAKDVFLG MFLYEYARRHPDYSVVLLLRLAKTYETTLEKCCAAADPHECY AKVFDEFKPLVEEPQNLIKQNCELFEQLGEYKFQNALLVRYT KKVPQVSTPTLVEVSRNLGKVGSKCCKHPEAKRMPCAEDYLS VVLNQLCVLHEKTPVSDRVTKCCTESLVNRRPCFSALEVDET YVPKEFNAETFTFHADICTLSEKERQIKKQTALVELVKHKPK ATKEQLKAVMDDFAAFVEKCCKADDKETCFAEEGKKLVAASQ AALGLGGGGSGGGGSGGGGSAYRPSETLCGGELVDTLQFVCG DRGFYFSRPASRVSQRSRGIVEECCFRSCDLALLETYCATPA KSE |
| 36 | 6xHis-HSA-linker3-IGF2R64A | His tagged HSA fusion IGF2 R64A mutant with a long linker | HHHHHHSGDAHKSEVAHRFKDLGEENFKALVLIAFAQYLQQC PFEDHVKLVNEVTEFAKTCVADESAENCDKSLHTLFGDKLCT VATLRETYGEMADCCAKQEPERNECFLQHKDDNPNLPRLVRP EVDVMCTAFHDNEETFLKKYLYEIARRHPYFYAPELLFFAKR YKAAFTECCQAADKAACLLPKLDELRDEGKASSAKQRLKCAS LQKFGERAFKAWAVARLSQRFPKAEFAEVSKLVTDLTKVHTE CCHGDLLECADDRADLAKYICENQDSISSKLKECCEKPLLEK SHCIAEVENDEMPADLPSLAADFVESKDVCKNYAEAKDVFLG MFLYEYARRHPDYSVVLLLRLAKTYETTLEKCCAAADPHECY AKVFDEFKPLVEEPQNLIKQNCELFEQLGEYKFQNALLVRYT KKVPQVSTPTLVEVSRNLGKVGSKCCKHPEAKRMPCAEDYLS VVLNQLCVLHEKTPVSDRVTKCCTESLVNRRPCFSALEVDET YVPKEFNAETFTFHADICTLSEKERQIKKQTALVELVKHKPK ATKEQLKAVMDDFAAFVEKCCKADDKETCFAEEGKKLVAASQ AALGLGGGGSGGGGSGGGGSAYRPSETLQGGELVDTLQFVCG DRGFYFSRPASRVSRRSAGIVEECCFRSCDLALLETYCATPA KSE |
| 37 | 6xHis-HSA-linker3-IGF2R64Q | His tagged HSA fusion IGF2 R64Q mutant with a long linker | HHHHHHSGDAHKSEVAHRFKDLGEENFKALVLIAFAQYLQQC PFEDHVKLVNEVTEFAKTCVADESAENCDKSLHTLFGDKLCT VATLRETYGEMADCCAKQEPERNECFLQHKDDNPNLPRLVRP EVDVMCTAFHDNEETFLKKYLYEIARRHPYFYAPELLFFAKR YKAAFTECCQAADKAACLLPKLDELRDEGKASSAKQRLKCAS LQKFGERAFKAWAVARLSQRFPKAEFAEVSKLVTDLTKVHTE CCHGDLLECADDRADLAKYICENQDSISSKLKECCEKPLLEK SHCIAEVENDEMPADLPSLAADFVESKDVCKNYAEAKDVFLG MFLYEYARRHPDYSVVLLLRLAKTYETTLEKCCAAADPHECY AKVFDEFKPLVEEPQNLIKQNCELFEQLGEYKFQNALLVRYT KKVPQVSTPTLVEVSRNLGKVGSKCCKHPEAKRMPCAEDYLS VVLNQLCVLHEKTPVSDRVTKCCTESLVNRRPCFSALEVDET YVPKEFNAETFTFHADICTLSEKERQIKKQTALVELVKHKPK ATKEQLKAVMDDFAAFVEKCCKADDKETCFAEEGKKLVAASQ AALGLGGGGSGGGGSGGGGSAYRPSETLCGGELVDTLQFVCG DRGFYFSRPASRVSRRSQGIVEECCFRSCDLALLETYCATPA KSE |
| 38 | IGF2-linker3-hFc4 | Human IGF2-linker3-hFc4 | AYRPSETLCGGELVDTLQFVCGDRGFYFSRPASRVSRRSRGI VEECCFRSCDLALLETYCATPAKSEGGGGGGGGSGGGGSESK YGPPCPPCPAPEFLGGPSVFLFPPKPKDTLMISRTPEVTCVV VDVSQEDPEVQFNWYVDGVEVHNAKTKPREEQFNSTYRVVSV LTVLHQDWLNGKEYKCKVSNKGLPSSIEKTISKAKGQPREPQ VYTLPPSQEEMTKNQVSLTCLVKGFYPSDIAVEWESNGQPEN NYKTTPPVLDSDGSFFLYSRLTVDKSRWQEGNVFSCSVMHEA LHNHYTQKSLSLSLGK |
| 39 | IGF2-hFc4 | Human IGF2-hFc4 | AYRPSETLCGGELVDTLQFVCGDRGFYFSRPASRVSRRSRGI VEECCFRSCDLALLETYCATPAKSEESKYGPPCPPCPAPEFL GGPSVFLFPPKPKDTLMISRTPEVTCVVVDVSQEDPEVQFNW |

TABLE OF SEQUENCES-continued

| Seq ID No | Sequence Name | Description | Sequence |
|---|---|---|---|
| | | | YVDGVEVHNAKTKPREEQFNSTYRVVSVLTVLHQDWLNGKEY KCKVSNKGLPSSIEKTISKAKGQPREPQVYTLPPSQEEMTKN QVSLTCLVKGFYPSDIAVEWESNGQPENNYKTTPPVLDSDGS FFLYSRLTVDKSRWQEGNVFSCSVMHEALHNHYTQKSLSLSL GK |
| 40 | hFc4-linker3-IGF2 | hFc4-linker3-human IGF2 | ESKYGPPCPPCPAPEFLGGPSVFLFPPKPKDTLMISRTPEVT CVVVDVSQEDPEVQFNWYVDGVEVHNAKTKPREEQFNSTYRV VSVLTVLHQDWLNGKEYKCKVSNKGLPSSIEKTISKAKGQPR EPQVYTLPPSQEEMTKNQVSLTCLVKGFYPSDIAVEWESNGQ PENNYKTTPPVLDSDGSFFLYSRLTVDKSRWQEGNVFSCSVM HEALHNHYTQKSLSLSLGKGGGGSGGGGSGGGGSAYRPSETL CGGELVDTLQFVCGDRGFYFSRPASRVSRRSRGIVEECCFRS CDLALLETYCATPAKSE |
| 41 | IGF2R61A-linker3-hFc4 | Human IGF2 R61A point mutant-linker3-hFc4 | AYRPSETLCGGELVDTLQFVCGDRGFYFSRPASRVSARSRGI VEECCFRSCDLALLETYCATPAKSEGGGGSGGGGSGGGGSES KYGPPCPPCPAPEFLGGPSVFLFPPKPKDTLMISRTPEVTCV VVVDVSQEDPEVQFNWYVDGVEVHNAKTKPREEQFNSTYRVVS VLTVLHQDWLNGKEYKCKVSNKGLPSSIEKTISKAKGQPREP QVYTLPPSQEEMTKNQVSLTCLVKGFYPSDIAVEWESNGQPE NNYKTTPPVLDSDGSFFLYSRLTVDKSRWQEGNVFSCSVMHE ALHNHYTQKSLSLSLGK |
| 42 | IGF2-mutant region | IGF2 region for mutations to reduce cleavage | RGFYFSRPASRVSRRSR |
| 43 | Linker 1 | A short flexible linker nucleotide sequence | GGATCGGGATCG |
| 44 | Linker 2 | A short flexible linker nucleotide sequence | GGATCTGGGAGCGCT |
| 45 | Linker 3 | A long flexible linker nucleotide sequence | GGCGGAGGCGGTAGCGGAGGCGGTGGCTCCGGTGGCGGAGGG TCT |
| 46 | hFcm IgG1 | Human IgG1 Fc mutant (L234A L235A P329G) nucleotide sequence | GACAAAACTCACACATGCCCACCGTGCCCAGCACCTGAAGCT GCCGGGGGACCGTCAGTCTTCCTCTTCCCCCCAAAACCCAAG GACACCCTCATGATCTCCCGGACCCCTGAGGTCACATGCGTG GTGGTGGACGTGAGCCACGAAGACCCTGAGGTCAAGTTCAAC TGGTACGTGGACGGCGTGGAGGTGCATAATGCCAAGACAAAG CCGCGGGAGGAGCAGTACAACAGCACGTACCGTGTGGTCAGC GTCCTCACCGTCCTGCACCAGGACTGGCTGAATGGCAAGGAG TACAAGTGCAAGGTCTCCAACAAAGCCCTCGGCGCCCCCATC GAGAAAACCATCTCCAAAGCCAAAGGGCAGCCCCGAGAACCA CAGGTGTACACCCTGCCCCCATCCCGGGATGAGCTGACCAAG AACCAGGTCAGCCTGACCTGCCTGGTCAAAGGCTTCTATCCC AGCGACATCGCCGTGGAGTGGGAGAGCAATGGGCAGCCGGAG AACAACTACAAGACCACGCCTCCCGTGCTGGACTCCGACGGC TCCTTCTTCCTCTACAGCAAGCTCACCGTGGACAAGAGCAGG TGGCAGCAGGGGAACGTCTTCTCATGCTCCGTGATGCATGAG GCTCTGCACAACCACTACACGCAGAAaAGCCTCTCCCTGTCT CCGGGTAAA |
| 47 | hFc4 | Human lgG4 Fc with S228P point mutation nucleotide sequence | GAGTCCAAATATGGTCCCCCATGCCCACCCTGCCCAGCACCT GAGTTCCTGGGGGGACCATCAGTCTTCCTGTTCCCCCCAAAA CCCAAGGACACTCTCATGATCTCCCGGACCCCTGAGGTCACG TGCGTGGTGGTGGACGTGAGCCAGGAAGACCCCGAGGTCCAG TTCAACTGGTACGTGGATGGCGTGGAGGTGCATAATGCCAAG ACAAAGCCGCGGGAGGAGCAGTTCAACAGCACGTACCGTGTG GTCAGCGTCCTCACCGTCCTGCACCAGGACTGGCTGAACGGC AAGGAGTACAAGTGCAAGGTCTCCAACAAAGGCCTCCCGTCC TCCATCGAGAAAACCATCTCCAAAGCCAAAGGGCAGCCCCGA GAGCCACAGGTGTACACCCTGCCCCCATCCCAGGAGGAGATG ACCAAGAACCAGGTCAGCCTGACCTGCCTGGTCAAAGGCTTC TACCCCAGCGACATCGCCGTGGAGTGGGAGAGCAATGGGCAG CCGGAGAACAACTACAAGACCACGCCTCCCGTGCTGGACTCC GACGGCTCCTTCTTCCTCTACAGCAGGCTCACCGTGGACAAG AGCAGGTGGCAGGAGGGGAATGTCTTCTCATGCTCCGTGATG CATGAGGCTCTGCACAACCACTACACACAGAAGAGCCTCTCC CTGTCTCTGGGTAAA |

TABLE OF SEQUENCES-continued

| Seq ID No | Sequence Name | Description | Sequence |
|---|---|---|---|
| 48 | 6xHis | Six Histidine short peptide nucleotide sequence | CACCATCACCATCACCAT |
| 49 | Strep11 | Strep-Tactin binding peptide nucleotide sequence | TGGAGCCACCCGCAGTTCGAAAAA |
| 50 | HSA | Full length of Human Serum Albumin nucleotide sequence | GATGCACACAAGAGTGAGGTTGCTCATCGGTTTAAAGATTTG GGAGAAGAAAATTTCAAAGCCTTGGTGTTGATTGCCTTTGCT CAGTATCTTCAGCAGTGTCCATTTGAAGATCATGTAAAATTA GTGAATGAAGTAACTGAATTTGCAAAAACATGTGTTGCTGAT GAGTCAGCTGAAAATTGTGACAAATCACTTCATACCCTTTTT GGAGACAAATTATGCACAGTTGCAACTCTTCGTGAAACCTAT GGTGAAATGGCTGACTGCTGTGCAAAACAAGAACCTGAGAGA AATGAATGCTTCTTGCAACACAAAGATGACAACCCAAACCTC CCCCGATTGGTGAGACCAGAGGTTGATGTGATGTGCACTGCT TTTCATGACAATGAAGAGACATTTTTGAAAAAATACTTATAT GAAATTGCCAGAAGACATCCTTACTTTTATGCCCCGGAACTC CTTTTCTTTGCTAAAAGGTATAAAGCTGCTTTTACAGAATGT TGCCAAGCTGCTGATAAAGCTGCCTGCCTGTTGCCAAAGCTC GATGAACTTCGGGATGAAGGGAAGGCTTCGTCTGCCAAACAG AGACTCAAGTGTGCCAGTCTCCAAAAATTTGGAGAAAGAGCT TTCAAAGCATGGGCAGTAGCTCGCCTGAGCCAGAGATTTCCC AAAGCTGAGTTTGCAGAAGTTTCCAAGTTAGTGACAGATCTT ACCAAAGTCCACACGGAATGCTGCCATGGAGATCTGCTTGAA TGTGCTGATGACAGGGCGGACCTTGCCAAGTATATCTGTGAA AATCAAGATTCGATCTCCAGTAAACTGAAGGAATGCTGTGAA AAACCTCTGTTGGAAAAATCCCACTGCATTGCCGAAGTGGAA AATGATGAGATGCCTGCTGACTTGCCTTCATTAGCTGCTGAT TTTGTTGAAAGTAAGGATGTTTGCAAAAACTATGCTGAGGCA AAGGATGTCTTCCTGGGCATGTTTTTGTATGAATATGCAAGA AGGCATCCTGATTACTCTGTCGTGCTGCTGCTGAGACTTGCC AAGACATATGAAACCACTCTAGAGAAGTGCTGTGCCGCTGCA GATCCTCATGAATGCTATGCCAAAGTGTTCGATGAATTTAAA CCTCTTGTGGAAGAGCCTCAGAATTTAATCAAACAAAATTGT GAGCTTTTTGAGCAGCTTGGAGAGTACAAATTCCAGAATGCG CTATTAGTTCGTTACACCAAGAAAGTACCCCAAGTGTCAACT CCAACTCTTGTAGAGGTCTCAAGAAACCTAGGAAAAGTGGGC AGCAAATGTTGTAAACATCCTGAAGCAAAAAGAATGCCCTGT GCAGAAGACTATCTATCCGTGGTCCTGAACCAGTTATGTGTG TTGCATGAGAAAACGCCAGTAAGTGACAGAGTCACCAAATGC TGCACAGAATCCTTGGTGAACAGGCGACCATGCTTTTCAGCT CTGGAAGTCGATGAAACATACGTTCCCAAAGAGTTTAATGCT GAAACATTCACCTTCCATGCAGATATATGCACACTTTCTGAG AAGGAGAGACAAATCAAGAAACAAACTGCACTTGTTGAGCTC GTGAAACACAAGCCCAAGGCAACAAAAGAGCAACTGAAAGCT GTTATGGATGATTTCGCAGCTTTTGTAGAGAAGTGCTGCAAG GCTGACGATAAGGAGACCTGCTTTGCCGAGGAGGGTAAAAAA CTTGTTGCTGCAAGTCAAGCTGCCTTAGGCTTA |
| 51 | Linker 1 | A short flexible linker amino acid sequence | GSGS |
| 52 | Linker 2 | A short flexible linker amino acid sequence | GSGSA |
| 53 | Linker 3 | A long flexible linker amino acid sequence | GGGGSGGGGSGGGGS |
| 54 | hFcm IgG1 | Human IgG1 Fc mutant (L234A L235A P329G) amino acid sequence | DKTHTCPPCPAPEAAGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALGAPIEKTISKAKGQPREP QVYTLPPSRDELTKNQVSLTCLVKGFYPSDIAVEWESNGQPE NNYKTTPPVLDSDGSFFLYSKLTVDKSRWQQGNVFSCSVMHE ALHNHYTQKSLSLSPGK |

TABLE OF SEQUENCES-continued

| Seq ID No | Sequence Name | Description | Sequence |
|---|---|---|---|
| 55 | hFc4 | Human IgG4 Fc with S228P point mutation amino acid sequence | ESKYGPPCPPCPAPEFLGGPSVFLFPPKPKDTLMISRTPEVT CVVVDVSQEDPEVQFNWYVDGVEVHNAKTKPREEQFNSTYRV VSVLTVLHQDWLNGKEYKCKVSNKGLPSSIEKTISKAKGQPR EPQVYTLPPSQEEMTKNQVSLTCLVKGFYPSDIAVEWESNGQ PENNYKTTPPVLDSDGSFFLYSRLTVDKSRWQEGNVFSCSVM HEALHNHYTQKSLSLSLGK |
| 56 | 6xHis | Six Histidine short peptide amino acid sequence | HHHHHH |
| 57 | StrepII | Strep-Tactin binding peptide amino acid sequence | WSHPQFEK |
| 58 | HSA | Full length of Human Serum Albumin amino acid sequence | DAHKSEVAHRFKDLGEENFKALVLIAFAQYLQQCPFEDHVKL VNEVTEFAKTCVADESAENCDKSLHTLFGDKLCTVATLRETY GEMADCCAKQEPERNECFLQHKDDNPNLPRLVRPEVDVMCTA FHDNEETFLKKYLYEIARRHPYFYAPELLFFAKRYKAAFTEC CQAADKAACLLPKLDELRDEGKASSAKQRLKCASLQKFGERA FKAWAVARLSQRFPKAEFAEVSKLVTDLTKVHTECCHGDLLE CADDRADLAKYICENQDSISSKLKECCEKPLLEKSHCIAEVE NDEMPADLPSLAADFVESKDVCKNYAEAKDVFLGMFLYEYAR RHPDYSVVLLLRLAKTYETTLEKCCAAADPHECYAKVFDEFK PLVEEPQNLIKQNCELFEQLGEYKFQNALLVRYTKKVPQVST PTLVEVSRNLGKVGSKCCKHPEAKRMPCAEDYLSVVLNQLCV LHEKTPVSDRVTKCCTESLVNRRPCFSALEVDETYVPKEFNA ETFTFHADICTLSEKERQIKKQTALVELVKHKPKATKEQLKA VMDDFAAFVEKCCKADDKETCFAEEGKKLVAASQAALGL |
| 59 | HSA-IGF2R61A | HSA fusion IGF2 R61A | SGDAHKSEVAHRFKDLGEENFKALVLIAFAQYLQQCPFEDHV KLVNEVTEFAKTCVADESAENCDKSLHTLFGDKLCTVATLRE TYGEMADCCAKQEPERNECFLQHKDDNPNLPRLVRPEVDVMC TAFHDNEETFLKKYLYEIARRHPYFYAPELLFFAKRYKAAFT ECCQAADKAACLLPKLDELRDEGKASSAKQRLKCASLQKFGE RAFKAWAVARLSQRFPKAEFAEVSKLVTDLTKVHTECCHGDL LECADDRADLAKYICENQDSISSKLKECCEKPLLEKSHCIAE VENDEMPADLPSLAADFVESKDVCKNYAEAKDVFLGMFLYEY ARRHPDYSVVLLLRLAKTYETTLEKCCAAADPHECYAKVFDE FKPLVEEPQNLIKQNCELFEQLGEYKFQNALLVRYTKKVPQV STPTLVEVSRNLGKVGSKCCKHPEAKRMPCAEDYLSVVLNQL CVLHEKTPVSDRVTKCCTESLVNRRPCFSALEVDETYVPKEF NAETFTFHADICTLSEKERQIKKQTALVELVKHKPKATKEQL KAVMDDFAAFVEKCCKADDKETCFAEEGKKLVAASQAALGLG GGSGGGGSGGGGSAYRPSETLCGGELVDTLQFVCGDRGFYF SRPASRVSARSRGIVEECCFRSCDLALLETYCATPAKSE |
| 60 | pro-HSA-IGF2R61A | pro-HSA fusion IGF2 R61A | RGVFRRSGDAHKSEVAHRFKDLGEENFKALVLIAFAQYLQQC PFEDHVKLVNEVTEFAKTCVADESAENCDKSLHTLFGDKLCT VATLRETYGEMADCCAKQEPERNECFLQHKDDNPNLPRLVRP EVDVMCTAFHDNEETFLKKYLYEIARRHPYFYAPELLFFAKR YKAAFTECCQAADKAACLLPKLDELRDEGKASSAKQRLKCAS LQKFGERAFKAWAVARLSQRFPKAEFAEVSKLVTDLTKVHTE CCHGDLLECADDRADLAKYICENQDSISSKLKECCEKPLLEK SHCIAEVENDEMPADLPSLAADFVESKDVCKNYAEAKDVFLG MFLYEYARRHPDYSVVLLLRLAKTYETTLEKCCAAADPHECY AKVFDEFKPLVEEPQNLIKQNCELFEQLGEYKFQNALLVRYT KKVPQVSTPTLVEVSRNLGKVGSKCCKHPEAKRMPCAEDYLS VVLNQLCVLHEKTPVSDRVTKCCTESLVNRRPCFSALEVDET YVPKEFNAETFTFHADICTLSEKERQIKKQTALVELVKHKPK ATKEQLKAVMDDFAAFVEKCCKADDKETCFAEEGKKLVAASQ AALGLGGGGSGGGGSGGGGSAYRPSETLQGGELVDTLQFVCG DRGFYFSRPASRVSARSRGIVEECCFRSCDLALLETYCATPA KSE |

SEQUENCE LISTING

```
Sequence total quantity: 63
SEQ ID NO: 1                    moltype = DNA   length = 66
FEATURE                         Location/Qualifiers
misc_feature                    1..66
                                note = Signal peptide
source                          1..66
                                mol_type = other DNA
                                organism = synthetic construct
SEQUENCE: 1
atgggagccg cccgcctgct gcccaacctc actctgtgct tacagctgct gattctctgc   60
tgtcaa                                                              66

SEQ ID NO: 2                    moltype = DNA   length = 54
FEATURE                         Location/Qualifiers
misc_feature                    1..54
                                note = Signal peptide
source                          1..54
                                mol_type = other DNA
                                organism = synthetic construct
SEQUENCE: 2
atggggctgg cctggggact aggcgtcctg ttcctgatgc atgtgtgtgg cacc          54

SEQ ID NO: 3                    moltype = DNA   length = 72
FEATURE                         Location/Qualifiers
misc_feature                    1..72
                                note = Signal peptide
source                          1..72
                                mol_type = other DNA
                                organism = synthetic construct
SEQUENCE: 3
atgggaatcc caatggggaa gtcgatgctg gtgcttctca ccttcttggc cttcgcctcg   60
tgctgcattg ct                                                       72

SEQ ID NO: 4                    moltype = DNA   length = 87
FEATURE                         Location/Qualifiers
misc_feature                    1..87
                                note = Signal peptide
source                          1..87
                                mol_type = other DNA
                                organism = synthetic construct
SEQUENCE: 4
atgcacgtgc gctcactgcg agctgcggcg ccgcacagct tcgtggcgct ctgggcaccc   60
ctgttcctgc tgcgctccgc cctggcc                                       87

SEQ ID NO: 5                    moltype = DNA   length = 54
FEATURE                         Location/Qualifiers
misc_feature                    1..54
                                note = Signal peptide
source                          1..54
                                mol_type = other DNA
                                organism = synthetic construct
SEQUENCE: 5
atgaagtggg taacctttat ttcccttctt tttctctttta gctcggctta ttcc         54

SEQ ID NO: 6                    moltype = DNA   length = 57
FEATURE                         Location/Qualifiers
misc_feature                    1..57
                                note = Signal peptide
source                          1..57
                                mol_type = other DNA
                                organism = synthetic construct
SEQUENCE: 6
atgacccggc tgacagtcct ggccctgctg gctggtctgc tggcgtcctc gagggcc       57

SEQ ID NO: 7                    moltype = DNA   length = 54
FEATURE                         Location/Qualifiers
misc_feature                    1..54
                                note = Signal peptide
source                          1..54
                                mol_type = other DNA
                                organism = synthetic construct
SEQUENCE: 7
atgagggcct ggatcttctt tctcctttgc ctggccggga gggctctggc agca          54

SEQ ID NO: 8                    moltype = DNA   length = 51
FEATURE                         Location/Qualifiers
misc_feature                    1..51
                                note = Signal peptide
```

```
                        source              1..51
                                            mol_type = other DNA
                                            organism = synthetic construct
SEQUENCE: 8
atgggagtca aagttctgtt tgccctgatc tgcatcgctg tggccgaggc c          51

SEQ ID NO: 9            moltype = AA   length = 22
FEATURE                 Location/Qualifiers
REGION                  1..22
                        note = Signal peptide
source                  1..22
                        mol_type = protein
                        organism = synthetic construct
SEQUENCE: 9
MGAARLLPNL TLCLQLLILC CQ                                          22

SEQ ID NO: 10           moltype = AA   length = 18
FEATURE                 Location/Qualifiers
REGION                  1..18
                        note = Signal peptide
source                  1..18
                        mol_type = protein
                        organism = synthetic construct
SEQUENCE: 10
MGLAWGLGVL FLMHVCGT                                               18

SEQ ID NO: 11           moltype = AA   length = 24
FEATURE                 Location/Qualifiers
REGION                  1..24
                        note = Signal peptide
source                  1..24
                        mol_type = protein
                        organism = synthetic construct
SEQUENCE: 11
MGIPMGKSML VLLTFLAFAS CCIA                                        24

SEQ ID NO: 12           moltype = AA   length = 29
FEATURE                 Location/Qualifiers
REGION                  1..29
                        note = Signal peptide
source                  1..29
                        mol_type = protein
                        organism = synthetic construct
SEQUENCE: 12
MHVRSLRAAA PHSFVALWAP LFLLRSALA                                   29

SEQ ID NO: 13           moltype = AA   length = 18
FEATURE                 Location/Qualifiers
REGION                  1..18
                        note = Signal peptide
source                  1..18
                        mol_type = protein
                        organism = synthetic construct
SEQUENCE: 13
MKWVTFISLL FLFSSAYS                                               18

SEQ ID NO: 14           moltype = AA   length = 19
FEATURE                 Location/Qualifiers
REGION                  1..19
                        note = Signal peptide
source                  1..19
                        mol_type = protein
                        organism = synthetic construct
SEQUENCE: 14
MTRLTVLALL AGLLASSRA                                              19

SEQ ID NO: 15           moltype = AA   length = 18
FEATURE                 Location/Qualifiers
REGION                  1..18
                        note = Signal peptide
source                  1..18
                        mol_type = protein
                        organism = synthetic construct
SEQUENCE: 15
MRAWIFFLLC LAGRALAA                                               18

SEQ ID NO: 16           moltype = AA   length = 17
FEATURE                 Location/Qualifiers
REGION                  1..17
```

```
                        note = Signal peptide
source                  1..17
                        mol_type = protein
                        organism = synthetic construct
SEQUENCE: 16
MGVKVLFALI CIAVAEA                                                      17

SEQ ID NO: 17           moltype = DNA   length = 201
FEATURE                 Location/Qualifiers
source                  1..201
                        mol_type = other DNA
                        organism = Homo sapiens
SEQUENCE: 17
gcttaccgcc ccagtgagac cctgtgcggc ggggagctgg tggacaccct ccagttcgtc        60
tgtggggacc gcggcttcta cttcagcagg cccgcaagcc gtgtgagccg tcgcagccgt       120
ggcatcgttg aggagtgctg tttccgcagc tgtgacctgg ccctcctgga gacgtactgt       180
gctacccccg ccaagtccga g                                                 201

SEQ ID NO: 18           moltype = DNA   length = 894
FEATURE                 Location/Qualifiers
misc_feature            1..894
                        note = Fusion protein
source                  1..894
                        mol_type = other DNA
                        organism = synthetic construct
SEQUENCE: 18
gcttaccgcc ccagtgagac cctgtgcggc ggggagctgg tggacaccct ccagttcgtc        60
tgtggggacc gcggcttcta cttcagcagg cccgcaagcc gtgtgagccg tcgcagccgt       120
ggcatcgttg aggagtgctg tttccgcagc tgtgacctgg ccctcctgga gacgtactgt       180
gctacccccg ccaagtccga gggatcggga tcggacaaaa ctcacacatg cccaccgtgc       240
ccagcacctg aagctgccgg ggaccgtca gtcttcctct tccccccaaa acccaaggac        300
accctcatga tctcccggac ccctgaggtc acatgcgtgg tggtggacgt gagccacgaa       360
gaccctgagg tcaagttcaa ctggtacgtg gacggcgtgg aggtgcataa tgccaagaca       420
aagccgcggg aggagcagta caacagcacg taccgtgtgt tcagcgtcct caccgtcctg       480
caccaggact ggctgaatgg caaggagtac aagtgcaagg tctccaacaa agccctcccg       540
gcccccatcg agaaaaccat ctccaaagcc aaagggcagc cccgagaacc acaggtgtac       600
accctgcccc catcccggga tgagctgacc aagaaccagg tcagcctgac ctgcctggtc       660
aaaggcttct atcccagcga catcgccgtg gagtgggaga gcaatgggca gccggagaac       720
aactacaaga ccacgcctcc cgtgctggac tccgacggct ccttcttcct ctacagcaag       780
ctcaccgtgg acaagagcag gtggcagcag gggaacgtct tctcatgctc cgtgatgcat       840
gaggctctgc acaaccacta cacgcagaaa agcctctccc tgtctccggg taaa             894

SEQ ID NO: 19           moltype = DNA   length = 897
FEATURE                 Location/Qualifiers
misc_feature            1..897
                        note = Fusion protein
source                  1..897
                        mol_type = other DNA
                        organism = synthetic construct
SEQUENCE: 19
gcttaccgcc ccagtgagac cctgtgcggc ggggagctgg tggacaccct ccagttcgtc        60
tgtggggacc gcggcttcta cttcagcagg cccgcaagcc gtgtgagccg tcgcagccgt       120
ggcatcgttg aggagtgctg tttccgcagc tgtgacctgg ccctcctgga gacgtactgt       180
gctacccccg ccaagtccga gggatctggg agcgctgaca aaactcacac atgcccaccg       240
tgcccagcac ctgaagctgc gggggaccg tcagtcttcc tcttccccc aaaacccaag         300
gacaccctca tgatctcccg gacccctgag gtcacatgcg tggtggtgga cgtgagccac       360
gaagaccctg aggtcaagtt caactggtac gtggacggcg tggaggtgca taatgccaag       420
acaaagccgc gggaggagca gtacaacagc acgtaccgtg tggtcagcgt cctcaccgtc       480
ctgcaccagg actggctgaa tggcaaggag tacaagtgca aggtctccaa caaagccctc       540
ccggcgcccc catcgagaaa accatctcca aa gccaaaggg cagccccgaga accacaggt    600
tacaccctgc cccatcccg ggatgagctg accaagaacc aggtcagcct gacctgcctg       660
gtcaaaggct ctatcccag cgacatcgcc gtggagtggg agcaatgg gcagccggag          720
aacaactaca gaccacgcc tccgtgctg gactccgacg gctccttctt cctctacagc        780
aagctcaccg tggacaagag caggtggcag caggggaacg tcttctcatg ctccgtgatg       840
catgaggctc tgcacaacca ctacacgcag aaaagcctct ccctgtctcc gggtaaa          897

SEQ ID NO: 20           moltype = DNA   length = 2025
FEATURE                 Location/Qualifiers
misc_feature            1..2025
                        note = Fusion protein
source                  1..2025
                        mol_type = other DNA
                        organism = synthetic construct
SEQUENCE: 20
caccatcacc atcaccatag cggcgatgca cacaagagtg aggttgctca tcggtttaaa        60
gatttgggag aagaaaattt caaagccttg tgttgattg cctttgctca gtatcttcag       120
cagtgtccat tgaagatca tgtaaaatta gtgaatgaag taactgaatt tgcaaaaaca       180
tgtgttgctg atgagtcagc tgaaaattgt gacaaatcac ttcataccct tttggggac       240
aaattatgca cagttgcaac tcttcgtgaa acctatggtg aaatggctga ctgctgtgca       300
```

```
aaacaagaac ctgagagaaa tgaatgcttc ttgcaacaca agatgacaa ccccaaacctc   360
ccccgattgg tgagaccaga ggttgatgtg atgtgcactg cttttcatga caatgaagag   420
acattttga aaaaatactt atatgaaatt gccagaagac atccttactt ttatgccccg    480
gaactccttt tctttgctaa aaggtataaa gctgctttta cagaatgttg ccaagctgct   540
gataaagctg cctgcctgtt gccaaagctc gatgaacttc gggatgaagg gaaggcttcg   600
tctgccaaac agagactcaa gtgtgccagt ctccaaaaat ttggagaaag agctttcaaa   660
gcatgggcag tagctcgcct gagccagaga tttcccaaag ctgagtttgc agaagtttcc   720
aagttagtga cagatcttac caaagtccac acggaatgct gccatggaga tctgcttgaa   780
tgtgctgatg acagggcgga ccttgccaag tatatctgtg aaaatcaaga ttcgatctcc   840
agtaaactga aggaatgctg tgaaaaacct ctgttggaaa atcccactg cattgccgaa     900
gtggaaaatg atgagatgcc tgctgacttg ccttcattag ctgctgattt tgttgaaagt   960
aaggatgttt gcaaaaacta tgctgaggca aaggatgtct tcctgggcat gttttttgtat 1020
gaatatgcaa gaaggcatcc tgattactct gtcgtgctgc tgctgagact tgccaagaca  1080
tatgaaacca ctctagagaa gtgctgtgcc gctgcagatc ctcatgaatg ctatgccaaa  1140
gtgttcgatg aatttaaacc tcttgtggaa gagcctcaga atttaatcaa acaaaattgt  1200
gagctttttg agcagcttgg agagtacaaa ttccagaatg cgctattagt tcgttacacc  1260
aagaaagtac cccaagtgtc aactccaact cttgtagagg tctcaagaaa cctaggaaaa  1320
gtgggcagca aatgttgtaa acatcctgaa gcaaaaagaa tgccctgtgc agaagactat  1380
ctatccgtgg tcctgaacca gttatgtgtg ttgcatgaga aaacgccagt aagtgacaga  1440
gtcaccaaat gctgcacaga atccttggtg aacaggcgac catgcttttc agctctggaa  1500
gtcgatgaaa catacgttcc caaagagttt aatgctgaaa cattcacctt ccatgcagat  1560
atatgcacac tttctgagaa ggagagacaa atcaagaaac aaactgcact tgttgagctc  1620
gtgaaacaca gcccaaggc aacaaaagag caactgaaag ctgttatgga tgatttcgca  1680
gcttttgtag agaagtgctg caaggctgac gataaggaga cctgctttgc cgaggagggt  1740
aaaaaacttg ttgctgcaag tcaagctgcc ttaggcttag gcggaggcgg tagcggaggc  1800
ggtggctccg gtggcggagg gtctgcttac cgccccagtg agaccctgg cggcggggag  1860
ctggtggaca ccctccagtt cgtctgtggg gaccgcggct tctacttcag caggcccgca  1920
agccgtgtga gccgtcgcag ccgtggcatc gttgaggagt gctgtttccg cagctgtgac  1980
ctggccctcc tggagacgta ctgtgctacc cccgccaagt ccgag                   2025

SEQ ID NO: 21          moltype = DNA  length = 2025
FEATURE                Location/Qualifiers
misc_feature           1..2025
                       note = Fusion protein
source                 1..2025
                       mol_type = other DNA
                       organism = synthetic construct
SEQUENCE: 21
caccatcacc atcaccatag cggcgatgca cacaagagtg aggttgctca tcggtttaaa     60
gatttgggag aagaaaattt caaagccttg tgttgattg cctttgctca gtatcttcag    120
cagtgtccat ttgaagatca tgtaaaatta gtgaatgaag taactgaatt tgcaaaaaca   180
tgtgttgctg atgagtcagc tgaaaattgt gacaaatcac ttcatacccct ttttggagac  240
aaattatgca cagttgcaac tcttcgtgaa acctatgtg aaatggctga ctgctgtgca   300
aaacaagaac ctgagagaaa tgaatgcttc ttgcaacaca agatgacaa cccaaaacctc  360
ccccgattgg tgagaccaga ggttgatgtg atgtgcactg cttttcatga caatgaagag  420
acattttga aaaaatactt atatgaaatt gccagaagac atccttactt ttatgccccg   480
gaactccttt tctttgctaa aaggtataaa gctgctttta cagaatgttg ccaagctgct  540
gataaagctg cctgcctgtt gccaaagctc gatgaacttc gggatgaagg gaaggcttcg  600
tctgccaaac agagactcaa gtgtgccagt ctccaaaaat ttggagaaag agctttcaaa  660
gcatgggcag tagctcgcct gagccagaga tttcccaaag ctgagtttgc agaagtttcc  720
aagttagtga cagatcttac caaagtccac acggaatgct gccatggaga tctgcttgaa  780
tgtgctgatg acagggcgga ccttgccaag tatatctgtg aaaatcaaga ttcgatctcc  840
agtaaactga aggaatgctg tgaaaaacct ctgttggaaa atcccactg cattgccgaa    900
gtggaaaatg atgagatgcc tgctgacttg ccttcattag ctgctgattt tgttgaaagt  960
aaggatgttt gcaaaaacta tgctgaggca aaggatgtct tcctgggcat gttttttgtat 1020
gaatatgcaa gaaggcatcc tgattactct gtcgtgctgc tgctgagact tgccaagaca 1080
tatgaaacca ctctagagaa gtgctgtgcc gctgcagatc ctcatgaatg ctatgccaaa 1140
gtgttcgatg aatttaaacc tcttgtggaa gagcctcaga atttaatcaa acaaaattgt 1200
gagctttttg agcagcttgg agagtacaaa ttccagaatg cgctattagt tcgttacacc 1260
aagaaagtac cccaagtgtc aactccaact cttgtagagg tctcaagaaa cctaggaaaa 1320
gtgggcagca aatgttgtaa acatcctgaa gcaaaaagaa tgccctgtgc agaagactat 1380
ctatccgtgg tcctgaacca gttatgtgtg ttgcatgaga aaacgccagt aagtgacaga 1440
gtcaccaaat gctgcacaga atccttggtg aacaggcgac catgcttttc agctctggaa 1500
gtcgatgaaa catacgttcc caaagagttt aatgctgaaa cattcacctt ccatgcagat 1560
atatgcacac tttctgagaa ggagagacaa atcaagaaac aaactgcact tgttgagctc 1620
gtgaaacaca gcccaaggc aacaaaagag caactgaaag ctgttatgga tgatttcgca  1680
gcttttgtag agaagtgctg caaggctgac gataaggaga cctgctttgc cgaggagggt 1740
aaaaaacttg ttgctgcaag tcaagctgcc ttaggcttag gcggaggcgg tagcggaggc 1800
ggtggctccg gtggcggagg gtctgcttac cgccccagtg agaccctgg cggcggggag   1860
ctggtggaca ccctccagtt cgtctgtggg gaccgcggct tctacttcag caggcccgca 1920
agccgtgtga gcgctcgcag ccgtggcatc gttgaggagt gctgtttccg cagctgtgac 1980
ctggccctcc tggagacgta ctgtgctacc cccgccaagt ccgag                  2025

SEQ ID NO: 22          moltype = DNA  length = 2025
FEATURE                Location/Qualifiers
misc_feature           1..2025
                       note = Fusion protein
source                 1..2025
                       mol_type = other DNA
```

```
                organism = synthetic construct
SEQUENCE: 22
caccatcacc atcaccatag cggcgatgca cacaagagtg aggttgctca tcggtttaaa    60
gatttgggag aagaaaattt caaagccttg gtgttgattg cctttgctca gtatcttcag   120
cagtgtccat ttgaagatca tgtaaaatta gtgaatgaatt taactgaatt tgcaaaaaca   180
tgtgttgctg atgagtcagc tgaaaattgt gacaaatcac ttcatacccct ttttggagac   240
aaattatgca cagttgcaac tcttcgtgaa acctatggtg aaatggctga ctgctgtgca   300
aaacaagaac ctgagagaaa tgaatgcttc ttgcaacaca aagatgacaa cccaaacctc   360
ccccgattgg tgagaccaga ggttgatgtg atgtgcactg cttttcatga caatgaagag   420
acattttga aaaaatactt atatgaaatt gccagaagac atccttactt ttatgccccg    480
gaactccttt tctttgctaa aaggtataaa gctgctttta cagaatgttg ccaagctgct   540
gataaagctg cctgcctgtt gccaaagctc gatgaacttc gggatgaagg gaaggcttcg   600
tctgccaaac agagactcaa gtgtgccagt ctccaaaaat ttggagaaag agcttttcaaa   660
gcatgggcag tagctcgcct gagccagaga tttcccaaag ctgagtttgc agaagtttcc   720
aagttagtga cagatcttac caaagtccac acggaatgct gccatggaga tctgcttgaa   780
tgtgctgatg acagggcgga ccttgccaag tatatctgtg aaaatcaaga ttcgatctcc   840
agtaaactga aggaatgctg tgaaaaacct ctgttgaaa aatcccactg cattgccgaa   900
gtggaaaatg atgagatgcc tgctgacttg ccttcattag ctgctgattt tgttgaaagt   960
aaggatgttt gcaaaaacta tgctgaggca aaggatgtct tcctgggcat gttttttgtat  1020
gaatatgcaa gaaggcatcc tgattactct gtcgtgctgc tgctgagact tgccaagaca  1080
tatgaaacca ctctagagaa gtgctgtgcc gctgcagatc ctcatgaatg ctatgccaaa  1140
gtgttcgatg aattttaacc tctttgtgaa gagcctcaga atttaatcaa acaaaattgt  1200
gagcttttttg agcagcttgg agagtacaaa ttccagaatg cgctattagt tcgttacacc  1260
aagaaagtac cccaagtgtc aactccaact cttgtagagg tctcaagaaa cctaggaaaa  1320
gtgggcagca aatgttgtaa acatcctgaa gcaaaaagaa tgccctgtgc agaagactat  1380
ctatccgtgg tcctgaacca gttatgtgtg ttgcatgaaa aaacgccagt aagtgacaga  1440
gtcaccaaat gctgcacaga atccttggtg aacaggcgac catgctttttc agctctggaa  1500
gtcgatgaaa catacgttcc caaagagttt aatgctgaaa cattcacctt ccatgcagat  1560
atatgcacac tttctgagaa ggagagacaa atcaagaaac aaactgcact tgttgagctc  1620
gtgaaacaca agcccaaggc aacaaaagag caactgaaag ctgttatgga tgatttcgca  1680
gcttttgtag agaagtgctg caaggctgac gataaggaga cctgctttgc cgaggagggt  1740
aaaaaacttg ttgctgcaag tcaagctgcc ttaggcttag gcggaggcgg tagcggaggc  1800
ggtggctccg gtggcggagg gtctgcttac cgccccagtg agaccctgtg cggcggggag  1860
ctggtggaca ccctccagtt cgtctgtggg gaccgcggct tctacttcag caggcccgca  1920
agccgtgtga gccagcgcag ccgtggcatc gttgaggagt gctgtttccg cagctgtgac  1980
ctggccctcc tggagacgta ctgtgctacc cccgccaagt ccgag              2025

SEQ ID NO: 23         moltype = DNA  length = 2025
FEATURE               Location/Qualifiers
misc_feature          1..2025
                      note = Fusion protein
source                1..2025
                      mol_type = other DNA
                      organism = synthetic construct
SEQUENCE: 23
caccatcacc atcaccatag cggcgatgca cacaagagtg aggttgctca tcggtttaaa    60
gatttgggag aagaaaattt caaagccttg gtgttgattg cctttgctca gtatcttcag   120
cagtgtccat ttgaagatca tgtaaaatta gtgaatgaag taactgaatt tgcaaaaaca   180
tgtgttgctg atgagtcagc tgaaaattgt gacaaatcac ttcatacccct ttttggagac   240
aaattatgca cagttgcaac tcttcgtgaa acctatggtg aaatggctga ctgctgtgca   300
aaacaagaac ctgagagaaa tgaatgcttc ttgcaacaca aagatgacaa cccaaacctc   360
ccccgattgg tgagaccaga ggttgatgtg atgtgcactg cttttcatga caatgaagag   420
acattttga aaaaatactt atatgaaatt gccagaagac atccttactt ttatgccccg    480
gaactccttt tctttgctaa aaggtataaa gctgctttta cagaatgttg ccaagctgct   540
gataaagctg cctgcctgtt gccaaagctc gatgaacttc gggatgaagg gaaggcttcg   600
tctgccaaac agagactcaa gtgtgccagt ctccaaaaat ttggagaaag agcttttcaaa   660
gcatgggcag tagctcgcct gagccagaga tttcccaaag ctgagtttgc agaagtttcc   720
aagttagtga cagatcttac caaagtccac acggaatgct gccatggaga tctgcttgaa   780
tgtgctgatg acagggcgga ccttgccaag tatatctgtg aaaatcaaga ttcgatctcc   840
agtaaactga aggaatgctg tgaaaaacct ctgttgaaa aatcccactg cattgccgaa   900
gtggaaaatg atgagatgcc tgctgacttg ccttcattag ctgctgattt tgttgaaagt   960
aaggatgttt gcaaaaacta tgctgaggca aaggatgtct tcctgggcat gttttttgtat  1020
gaatatgcaa gaaggcatcc tgattactct gtcgtgctgc tgctgagact tgccaagaca  1080
tatgaaacca ctctagagaa gtgctgtgcc gctgcagatc ctcatgaatg ctatgccaaa  1140
gtgttcgatg aattttaacc tctttgtgaa gagcctcaga atttaatcaa acaaaattgt  1200
gagcttttttg agcagcttgg agagtacaaa ttccagaatg cgctattagt tcgttacacc  1260
aagaaagtac cccaagtgtc aactccaact cttgtagagg tctcaagaaa cctaggaaaa  1320
gtgggcagca aatgttgtaa acatcctgaa gcaaaaagaa tgccctgtgc agaagactat  1380
ctatccgtgg tcctgaacca gttatgtgtg ttgcatgaaa aaacgccagt aagtgacaga  1440
gtcaccaaat gctgcacaga atccttggtg aacaggcgac catgctttttc agctctggaa  1500
gtcgatgaaa catacgttcc caaagagttt aatgctgaaa cattcacctt ccatgcagat  1560
atatgcacac tttctgagaa ggagagacaa atcaagaaac aaactgcact tgttgagctc  1620
gtgaaacaca agcccaaggc aacaaaagag caactgaaag ctgttatgga tgatttcgca  1680
gcttttgtag agaagtgctg caaggctgac gataaggaga cctgctttgc cgaggagggt  1740
aaaaaacttg ttgctgcaag tcaagctgcc ttaggcttag gcggaggcgg tagcggaggc  1800
ggtggctccg gtggcggagg gtctgcttac cgccccagtg agaccctgtg cggcggggag  1860
ctggtggaca ccctccagtt cgtctgtggg gaccgcggct tctacttcag caggcccgca  1920
agccgtgtga gccgtcgcag cgctggcatc gttgaggagt gctgtttccg cagctgtgac  1980
ctggccctcc tggagacgta ctgtgctacc cccgccaagt ccgag              2025
```

-continued

```
SEQ ID NO: 24           moltype = DNA  length = 2025
FEATURE                 Location/Qualifiers
misc_feature            1..2025
                        note = Fusion protein
source                  1..2025
                        mol_type = other DNA
                        organism = synthetic construct
SEQUENCE: 24
caccatcacc atcaccatag cggcgatgca cacaagagtg aggttgctca tcggtttaaa    60
gatttgggag aagaaaattt caaagccttg gtgttgattg cctttgctca gtatcttcag   120
cagtgtccat ttgaagatca tgtaaaatta gtgaatgaag taactgaatt tgcaaaaaca   180
tgtgttgctg atgagtcagc tgaaaattgt gacaaatcac ttcatacccc ttttggagac   240
aaattatgca cagttgcaac tcttcgtgaa acctatggtg aaatggctga ctgctgtgca   300
aaacaagaac ctgagagaaa tgaatgcttc ttgcaacaca aagatgacaa cccaaacctc   360
ccccgattgg tgagaccaga ggttgatgtg atgtgcactg cttttcatga caatgaagag   420
acatttttga aaaaatactt atatgaaatt gccagaagac atccttactt ttatgccccg   480
gaactccttt tctttgctaa aaggtataaa gctgcttttta cagaatgttg ccaagctgct   540
gataaagctg cctgcctgtt gccaaagctc gatgaacttc gggatgaagg gaaggcttcg   600
tctgccaaac agagactcaa gtgtgccagt ctccaaaaat ttggagaaag agctttcaaa   660
gcatgggcag tagctcgcct gagccagaga tttcccaaag ctgagtttgc agaagtttcc   720
aagttagtga cagatcttac caaagtccac acggaatgct gccatggaga tctgcttgaa   780
tgtgctgatg acagggcgga ccttgccaag tatatctgtg aaaatcaaga ttcgatctcc   840
agtaaactga aggaatgctg tgaaaaacct ctgttggaaa atcccactg cattgccgaa    900
gtggaaaatg atgagatgcc tgctgacttg ccttcattag ctgctgattt tgttgaaagt   960
aaggatgttt gcaaaaacta tgctgaggca aaggatgtct tcctgggcat gttttttgtat  1020
gaatatgcaa gaaggcatcc tgattactct gtcgtgctgc tgctgagact tgccaagaca  1080
tatgaaacca ctctagagaa gtgctgtgcc gctgcagatc ctcatgaatg ctatgccaaa  1140
gtgttcgatg aatttaaacc tcttgtggaa gagcctcaga atttaatcaa acaaaattgt  1200
gagcttttt g agcagcttgg agagtacaaa ttccagaatg cgctattagt tcgttacacc  1260
aagaaagtac cccaagtgtc aactccaact cttgtagagg tctcaagaaa cctaggaaaa  1320
gtgggcagca aatgttgtaa acatcctgaa gcaaaaagaa tgccctgtgc agaagactat  1380
ctatccgtgg tcctgaacca gttatgtgtg ttgcatgaga aaacgccagt aagtgacaga  1440
gtcaccaaat gctgcacaga atccttggtg aacaggcgac catgcttttc agctctggaa  1500
gtcgatgaaa catacgttcc caaagagttt aatgctgaaa cattcacctt ccatgcagat  1560
atatgcacac tttctgagaa ggagagacaa atcaagaaac aaactgcact tgttgagctc  1620
gtgaaacaca agcccaaggc aacaaaagag caactgaaag ctgttatgga tgatttcgca  1680
gcttttgtag agaagtgctg caaggctgac gataaggaga cctgctttgc cgaggagggt  1740
aaaaaacttg ttgctgcaag tcaagctgcc ttaggcttag gcggaggcgg tagcggaggc  1800
ggtggctccg gtggcggagg gtctgcttac cgccccagtg agaccctgtg cggcggggag  1860
ctggtggaca ccctccagtt cgtcgtgggg accgcggct tctacttcag caggcccgca   1920
agccgtgtga gccgtcgcag ccagggcatc gttgaggagt gctgtttccg cagctgtgac  1980
ctggccctcc tggagacgta ctgtgctacc cccgccaagt ccgag                  2025

SEQ ID NO: 25           moltype = DNA  length = 933
FEATURE                 Location/Qualifiers
misc_feature            1..933
                        note = Fusion protein
source                  1..933
                        mol_type = other DNA
                        organism = synthetic construct
SEQUENCE: 25
gcttaccgcc ccagtgagac cctgtgcggc ggggagctgg tggacaccct ccagttcgtc    60
tgtggggacc gcggcttcta cttcagcagg cccgcaagcc gtgtgagccg tcgcagccgt   120
ggcatcgttg aggagtgctg tttccgcagc tgtgacctgc ccctcctgga cacgtactgt   180
gctaccccg ccaagtccga gggcggagc ggtagcggag gcggtggctc cggtggcgga   240
gggtctgagt ccaaatatgg tcccccatgc ccaccctgcc cagcacctga gttcctgggg   300
ggaccatcag tcttcctgtt ccccccaaaa cccaaggaca ctctcatgat ctcccggacc   360
cctgaggtca cgtgcgtggt ggtggacgtg agccaggaag accccgaggt ccagttcaac   420
tggtacgtgg atggcgtgga ggtgcataat gccaagacaa agccgcggga ggagcagttc   480
aacagcacgt accgtgtggt cagcgtcctc accgtcctgc accaggactg gctgaacggc   540
aaggagtaca agtgcaaggt ctccaacaaa ggcctcccgt cctccatcga aaaccatc    600
tccaaagcca aagggcagcc ccgagagcca caggtgtaca ccctgccccc atcccaggag   660
gagatgacca agaaccaggt cagcctgacc tgcctggtca aaggcttcta cccccagcgac  720
atcgccgtgg agtgggagag caatgggcag ccggagaaca actacaagac cacgcctcc   780
gtgctggact ccgacggctc cttcttcctc tacagcaggc tcaccgtgga caagagcagg   840
tggcaggagg ggaatgtctt ctcatgctcc gtgatgcatg aggctctgca caaccactac   900
acacagaaga gcctctccct gtctctgggt aaa                                933

SEQ ID NO: 26           moltype = DNA  length = 888
FEATURE                 Location/Qualifiers
misc_feature            1..888
                        note = Fusion protein
source                  1..888
                        mol_type = other DNA
                        organism = synthetic construct
SEQUENCE: 26
gcttaccgcc ccagtgagac cctgtgcggc ggggagctgg tggacaccct ccagttcgtc    60
tgtggggacc gcggcttcta cttcagcagg cccgcaagcc gtgtgagccg tcgcagccgt   120
```

```
ggcatcgttg aggagtgctg tttccgcagc tgtgacctgg ccctcctgga gacgtactgt  180
gctaccccg  ccaagtccga ggagtccaaa tatggtcccc catgcccacc ctgcccagca  240
cctgagttcc tggggggacc atcagtcttc ctgttccccc caaaacccaa ggacactctc  300
atgatctccc ggacccctga ggtcacgtgc gtggtggtgg acgtgagcca ggaagacccc  360
gaggtccagt tcaactggta cgtggatggc gtggaggtgc ataatgccaa gacaaagccg  420
cgggaggagc agttcaacag cacgtaccgt gtggtcagcg tcctcaccgt cctgcaccag  480
gactggctga acggcaagga gtacaagtgc aaggtctcca acaaaggcct cccgtcctcc  540
atcgagaaaa ccatctccaa agccaaaggg cagccccgag agccacaggt gtacaccctg  600
cccccatccc aggaggagat gaccaagaac caggtcagcc tgacctgcct ggtcaaaggc  660
ttctacccca gcgacatcgc cgtggagtgg gagagcaatg ggcagccgga gaacaactac  720
aagaccacgc ctcccgtgct ggactccgac ggctccttct tcctctacag caggctcacc  780
gtggacaaga gcaggtggca ggaggggaat gtcttctcat gctccgtgat gcatgaggct  840
ctgcacaacc actacacaca gaagagcctc tccctgtctc tgggtaaa            888

SEQ ID NO: 27          moltype = DNA  length = 933
FEATURE                Location/Qualifiers
misc_feature           1..933
                       note = Fusion protein
source                 1..933
                       mol_type = other DNA
                       organism = synthetic construct
SEQUENCE: 27
gagtccaaat atggtccccc atgcccaccc tgcccagcac ctgagttcct ggggggacca  60
tcagtcttcc tgttcccccc aaaacccaag gacactctca tgatctcccg gacccctgag  120
gtcacgtgcg tggtggtgga cgtgagccag gaagaccccg aggtccagtt caactggtac  180
gtggatggcg tggaggtgca taatgccaag acaaagccgc gggaggagca gttcaacagc  240
acgtaccgtg tggtcagcgt cctcaccgtc ctgcaccagg actggctgaa cggcaaggag  300
tacaagtgca aggtctccaa caaaggcctc ccgtcctcca tcgagaaaac catctccaaa  360
gccaaagggc agccccgaga gccacaggtg tacaccctgc ccccatccca ggaggagatg  420
accaagaacc aggtcagcct gacctgcctg gtcaaaggct tctaccccag cgacatcgcc  480
gtggagtggg agagcaatgg gcagccggag aacaactaca agaccacgcc tcccgtgctg  540
gactccgacg gctccttctt cctctacagc aggctcaccg tggacaagag caggtggcag  600
gaggggaatg tcttctcatg ctccgtgatg catgaggctc tgcacaacca ctacacacag  660
aagagcctct ccctgtctct gggtaaaggc ggaggcggta gcgaggcgg tggctccggt  720
ggcggagggt ctgcttaccg ccccagtgag accctgtgcg gcggggagct ggtggacacc  780
ctccagttcg tctgtgggga ccgcggcttc tacttcagca ggcccgcaag ccgtgtgagc  840
cgtcgcagcc gtggcatcgt tgaggagtgc tgtttccgca gctgtgacct ggcccctcctg  900
gagacgtact gtgctacccc cgccaagtcc gag                              933

SEQ ID NO: 28          moltype = DNA  length = 933
FEATURE                Location/Qualifiers
misc_feature           1..933
                       note = Fusion protein
source                 1..933
                       mol_type = other DNA
                       organism = synthetic construct
SEQUENCE: 28
gcttaccgcc ccagtgagac cctgtgcggc ggggagctgg tggacaccct ccagttcgtc  60
tgtggggacc gcggcttcta cttcagcagg cccgcaagcc gtgtgagcgc tcgcagccgt  120
ggcatcgttg aggagtgctg tttccgcagc tgtgacctgg ccctcctgga gacgtactgt  180
gctaccccg  ccaagtccga gggcggaggc ggtagcgcgg cggttggctcc cggtggccgt  240
gggtctgagt ccaaatatgg tcccccatgc ccaccctgcc cagcacctga gttcctgggg  300
ggaccatcag tcttcctgtt cccccaaaac ccaaggaca  ctctcatgat ctcccggacc  360
cctgaggtca cgtgcgtggt ggtggacgtg agccaggaag accccgaggt ccagttcaac  420
tggtacgtgg atggcgtgga ggtgcataat gccaagacaa agccgcggga ggagcagttc  480
aacagcacgt accgtgtggt cagcgtcctc accgtcctgc accaggactg gctgaacggc  540
aaggagtaca agtgcaaggt ctccaacaaa ggcctcccgt cctccatcga gaaaaccatc  600
tccaaagcca agggcagcc ccgagagcca caggtgtaca ccctgccccc atcccaggag  660
gagatgacca agaaccaggt cagcctgacc tgcctggtca aaggcttcta ccccagcgac  720
atcgccgtgg agtgggagag caatgggcag ccggagaaca actacaagac cacgcctccc  780
gtgctggact ccgacggctc cttcttcctc tacagcaggc tcaccgtgga caagagcagg  840
tggcaggagg ggaatgtctt ctcatgctcc gtgatgcatg aggctctgca caaccactac  900
acacagaaga gcctctccct gtctctgggt aaa                              933

SEQ ID NO: 29          moltype = AA  length = 67
FEATURE                Location/Qualifiers
source                 1..67
                       mol_type = protein
                       organism = Homo sapiens
SEQUENCE: 29
AYRPSETLCG GELVDTLQFV CGDRGFYFSR PASRVSRRSR GIVEECCFRS CDLALLETYC  60
ATPAKSE                                                            67

SEQ ID NO: 30          moltype = AA  length = 298
FEATURE                Location/Qualifiers
REGION                 1..298
                       note = Fusion protein
source                 1..298
                       mol_type = protein
```

```
                              organism = synthetic construct
SEQUENCE: 30
AYRPSETLCG  GELVDTLQFV  CGDRGFYFSR  PASRVSRRSR  GIVEECCFRS  CDLALLETYC   60
ATPAKSEGSG  SDKTHTCPPC  PAPEAAGGPS  VFLFPPKPKD  TLMISRTPEV  TCVVVDVSHE  120
DPEVKFNWYV  DGVEVHNAKT  KPREEQYNST  YRVVSVLTVL  HQDWLNGKEY  KCKVSNKALG  180
APIEKTISKA  KGQPREPQVY  TLPPSRDELT  KNQVSLTCLV  KGFYPSDIAV  EWESNGQPEN  240
NYKTTPPVLD  SDGSFFLYSK  LTVDKSRWQQ  GNVFSCSVMH  EALHNHYTQK  SLSLSPGK    298

SEQ ID NO: 31           moltype = AA  length = 299
FEATURE                 Location/Qualifiers
REGION                  1..299
                        note = Fusion protein
source                  1..299
                        mol_type = protein
                        organism = synthetic construct
SEQUENCE: 31
AYRPSETLCG  GELVDTLQFV  CGDRGFYFSR  PASRVSRRSR  GIVEECCFRS  CDLALLETYC   60
ATPAKSEGSG  SADKTHTCPP  CPAPEAAGGP  SVFLFPPKPK  DTLMISRTPE  VTCVVVDVSH  120
EDPEVKFNWY  VDGVEVHNAK  TKPREEQYNS  TYRVVSVLTV  LHQDWLNGKE  YKCKVSNKAL  180
GAPIEKTISK  AKGQPREPQV  YTLPPSRDEL  TKNQVSLTCL  VKGFYPSDIA  VEWESNGQPE  240
NNYKTTPPVL  DSDGSFFLYS  KLTVDKSRWQ  QGNVFSCSVM  HEALHNHYTQ  KSLSLSPGK   299

SEQ ID NO: 32           moltype = AA  length = 180
FEATURE                 Location/Qualifiers
REGION                  1..180
                        note = Fusion protein
source                  1..180
                        mol_type = protein
                        organism = synthetic construct
SEQUENCE: 32
MGIPMGKSML  VLLTFLAFAS  CCIAAYRPSE  TLCGGELVDT  LQFVCGDRGF  YFSRPASRVS   60
RRSRGIVEEC  CFRSCDLALL  ETYCATPAKS  ERDVSTPPTV  LPDNFPRYPV  GKFFQYDTWK  120
QSTQRLRRGL  PALLRARRGH  VLAKELEAFR  EAKRHRPLIA  LPTQDPAHGG  APPEMASNRK  180

SEQ ID NO: 33           moltype = AA  length = 675
FEATURE                 Location/Qualifiers
REGION                  1..675
                        note = Fusion protein
source                  1..675
                        mol_type = protein
                        organism = synthetic construct
SEQUENCE: 33
HHHHHHSGDA  HKSEVAHRFK  DLGEENFKAL  VLIAFAQYLQ  QCPFEDHVKL  VNEVTEFAKT   60
CVADESAENC  DKSLHTLFGD  KLCTVATLRE  TYGEMADCCA  KQEPERNECF  LQHKDDNPNL  120
PRLVRPEVDV  MCTAFHDNEE  TFLKKYLYEI  ARRHPYFYAP  ELLFFAKRYK  AAFTECCQAA  180
DKAACLLPKL  DELRDEGKAS  SAKQRLKCAS  LQKFGERAFK  AWAVARLSQR  FPKAEFAEVS  240
KLVTDLTKVH  TECCHGDLLE  CADDRADLAK  YICENQDSIS  SKLKECCEKP  LLEKSHCIAE  300
VENDEMPADL  PSLAADFVES  KDVCKNYAEA  KDVFLGMFLY  EYARRHPDYS  VVLLLRLAKT  360
YETTLEKCCA  AADPHECYAK  VFDEFKPLVE  EPQNLIKQNC  ELFEQLGEYK  FQNALLVRYT  420
KKVPQVSTPT  LVEVSRNLGK  VGSKCCKHPE  AKRMPCAEDY  LSVVLNQLCV  LHEKTPVSDR  480
VTKCCTESLV  NRRPCFSALE  VDETYVPKEF  NAETFTFHAD  ICTLSEKERQ  IKKQTALVEL  540
VKHKPKATKE  QLKAVMDDFA  AFVEKCCKAD  DKETCFAEEG  KKLVAASQAA  LGLGGGGSGG  600
GGSGGGGSAY  RPSETLCGGE  LVDTLQFVCG  DRGFYFSRPA  SRVSRRSRGI  VEECCFRSCD  660
LALLETYCAT  PAKSE                                                      675

SEQ ID NO: 34           moltype = AA  length = 675
FEATURE                 Location/Qualifiers
REGION                  1..675
                        note = Fusion protein
source                  1..675
                        mol_type = protein
                        organism = synthetic construct
SEQUENCE: 34
HHHHHHSGDA  HKSEVAHRFK  DLGEENFKAL  VLIAFAQYLQ  QCPFEDHVKL  VNEVTEFAKT   60
CVADESAENC  DKSLHTLFGD  KLCTVATLRE  TYGEMADCCA  KQEPERNECF  LQHKDDNPNL  120
PRLVRPEVDV  MCTAFHDNEE  TFLKKYLYEI  ARRHPYFYAP  ELLFFAKRYK  AAFTECCQAA  180
DKAACLLPKL  DELRDEGKAS  SAKQRLKCAS  LQKFGERAFK  AWAVARLSQR  FPKAEFAEVS  240
KLVTDLTKVH  TECCHGDLLE  CADDRADLAK  YICENQDSIS  SKLKECCEKP  LLEKSHCIAE  300
VENDEMPADL  PSLAADFVES  KDVCKNYAEA  KDVFLGMFLY  EYARRHPDYS  VVLLLRLAKT  360
YETTLEKCCA  AADPHECYAK  VFDEFKPLVE  EPQNLIKQNC  ELFEQLGEYK  FQNALLVRYT  420
KKVPQVSTPT  LVEVSRNLGK  VGSKCCKHPE  AKRMPCAEDY  LSVVLNQLCV  LHEKTPVSDR  480
VTKCCTESLV  NRRPCFSALE  VDETYVPKEF  NAETFTFHAD  ICTLSEKERQ  IKKQTALVEL  540
VKHKPKATKE  QLKAVMDDFA  AFVEKCCKAD  DKETCFAEEG  KKLVAASQAA  LGLGGGGSGG  600
GGSGGGGSAY  RPSETLCGGE  LVDTLQFVCG  DRGFYFSRPA  SRVSARSRGI  VEECCFRSCD  660
LALLETYCAT  PAKSE                                                      675

SEQ ID NO: 35           moltype = AA  length = 675
FEATURE                 Location/Qualifiers
REGION                  1..675
```

```
                         note = Fusion protein
source                   1..675
                         mol_type = protein
                         organism = synthetic construct
SEQUENCE: 35
HHHHHHSGDA HKSEVAHRFK DLGEENFKAL VLIAFAQYLQ QCPFEDHVKL VNEVTEFAKT  60
CVADESAENC DKSLHTLFGD KLCTVATLRE TYGEMADCCA KQEPERNECF LQHKDDNPNL 120
PRLVRPEVDV MCTAFHDNEE TFLKKYLYEI ARRHPYFYAP ELLFFAKRYK AAFTECCQAA 180
DKAACLLPKL DELRDEGKAS SAKQRLKCAS LQKFGERAFK AWAVARLSQR FPKAEFAEVS 240
KLVTDLTKVH TECCHGDLLE CADDRADLAK YICENQDSIS SKLKECCEKP LLEKSHCIAE 300
VENDEMPADL PSLAADFVES KDVCKNYAEA KDVFLGMFLY EYARRHPDYS VVLLLRLAKT 360
YETTLEKCCA AADPHECYAK VFDEFKPLVE EPQNLIKQNC ELFEQLGEYK FQNALLVRYT 420
KKVPQVSTPT LVEVSRNLGK VGSKCCKHPE AKRMPCAEDY LSVVLNQLCV LHEKTPVSDR 480
VTKCCTESLV NRRPCFSALE VDETYVPKEF NAETFTFHAD ICTLSEKERQ IKKQTALVEL 540
VKHKPKATKE QLKAVMDDFA AFVEKCCKAD DKETCFAEEG KKLVAASQAA LGLGGGGSGG 600
GGSGGGGSAY RPSETLCGGE LVDTLQFVCG DRGFYFSRPA SRVSQRSRGI VEECCFRSCD 660
LALLETYCAT PAKSE                                                675

SEQ ID NO: 36            moltype = AA  length = 675
FEATURE                  Location/Qualifiers
REGION                   1..675
                         note = Fusion protein
source                   1..675
                         mol_type = protein
                         organism = synthetic construct
SEQUENCE: 36
HHHHHHSGDA HKSEVAHRFK DLGEENFKAL VLIAFAQYLQ QCPFEDHVKL VNEVTEFAKT  60
CVADESAENC DKSLHTLFGD KLCTVATLRE TYGEMADCCA KQEPERNECF LQHKDDNPNL 120
PRLVRPEVDV MCTAFHDNEE TFLKKYLYEI ARRHPYFYAP ELLFFAKRYK AAFTECCQAA 180
DKAACLLPKL DELRDEGKAS SAKQRLKCAS LQKFGERAFK AWAVARLSQR FPKAEFAEVS 240
KLVTDLTKVH TECCHGDLLE CADDRADLAK YICENQDSIS SKLKECCEKP LLEKSHCIAE 300
VENDEMPADL PSLAADFVES KDVCKNYAEA KDVFLGMFLY EYARRHPDYS VVLLLRLAKT 360
YETTLEKCCA AADPHECYAK VFDEFKPLVE EPQNLIKQNC ELFEQLGEYK FQNALLVRYT 420
KKVPQVSTPT LVEVSRNLGK VGSKCCKHPE AKRMPCAEDY LSVVLNQLCV LHEKTPVSDR 480
VTKCCTESLV NRRPCFSALE VDETYVPKEF NAETFTFHAD ICTLSEKERQ IKKQTALVEL 540
VKHKPKATKE QLKAVMDDFA AFVEKCCKAD DKETCFAEEG KKLVAASQAA LGLGGGGSGG 600
GGSGGGGSAY RPSETLCGGE LVDTLQFVCG DRGFYFSRPA SRVSRRSAGI VEECCFRSCD 660
LALLETYCAT PAKSE                                                675

SEQ ID NO: 37            moltype = AA  length = 675
FEATURE                  Location/Qualifiers
REGION                   1..675
                         note = Fusion protein
source                   1..675
                         mol_type = protein
                         organism = synthetic construct
SEQUENCE: 37
HHHHHHSGDA HKSEVAHRFK DLGEENFKAL VLIAFAQYLQ QCPFEDHVKL VNEVTEFAKT  60
CVADESAENC DKSLHTLFGD KLCTVATLRE TYGEMADCCA KQEPERNECF LQHKDDNPNL 120
PRLVRPEVDV MCTAFHDNEE TFLKKYLYEI ARRHPYFYAP ELLFFAKRYK AAFTECCQAA 180
DKAACLLPKL DELRDEGKAS SAKQRLKCAS LQKFGERAFK AWAVARLSQR FPKAEFAEVS 240
KLVTDLTKVH TECCHGDLLE CADDRADLAK YICENQDSIS SKLKECCEKP LLEKSHCIAE 300
VENDEMPADL PSLAADFVES KDVCKNYAEA KDVFLGMFLY EYARRHPDYS VVLLLRLAKT 360
YETTLEKCCA AADPHECYAK VFDEFKPLVE EPQNLIKQNC ELFEQLGEYK FQNALLVRYT 420
KKVPQVSTPT LVEVSRNLGK VGSKCCKHPE AKRMPCAEDY LSVVLNQLCV LHEKTPVSDR 480
VTKCCTESLV NRRPCFSALE VDETYVPKEF NAETFTFHAD ICTLSEKERQ IKKQTALVEL 540
VKHKPKATKE QLKAVMDDFA AFVEKCCKAD DKETCFAEEG KKLVAASQAA LGLGGGGSGG 600
GGSGGGGSAY RPSETLCGGE LVDTLQFVCG DRGFYFSRPA SRVSRRSQGI VEECCFRSCD 660
LALLETYCAT PAKSE                                                675

SEQ ID NO: 38            moltype = AA  length = 311
FEATURE                  Location/Qualifiers
REGION                   1..311
                         note = Fusion protein
source                   1..311
                         mol_type = protein
                         organism = synthetic construct
SEQUENCE: 38
AYRPSETLCG GELVDTLQFV CGDRGFYFSR PASRVSRRSR GIVEECCFRS CDLALLETYC  60
ATPAKSEGGG GSGGGGSGGG GSESKYGPPC PPCPAPEFLG GPSVFLFPPK PKDTLMISRT 120
PEVTCVVVDV SQEDPEVQFN WYVDGVEVHN AKTKPREEQF NSTYRVVSVL TVLHQDWLNG 180
KEYKCKVSNK GLPSSIEKTI SKAKGQPREP QVYTLPPSQE EMTKNQVSLT CLVKGFYPSD 240
IAVEWESNGQ PENNYKTTPP VLDSDGSFFL YSRLTVDKSR WQEGNVFSCS VMHEALHNHY 300
TQKSLSLSLG K                                                    311

SEQ ID NO: 39            moltype = AA  length = 296
FEATURE                  Location/Qualifiers
REGION                   1..296
                         note = Fusion protein
```

```
source                  1..296
                        mol_type = protein
                        organism = synthetic construct
SEQUENCE: 39
AYRPSETLCG GELVDTLQFV CGDRGFYFSR PASRVSRRSR GIVEECCFRS CDLALLETYC    60
ATPAKSEESK YGPPCPPCPA PEFLGGPSVF LFPPKPKDTL MISRTPEVTC VVVDVSQEDP   120
EVQFNWYVDG VEVHNAKTKP REEQFNSTYR VVSVLTVLHQ DWLNGKEYKC KVSNKGLPSS   180
IEKTISKAKG QPREPQVYTL PPSQEEMTKN QVSLTCLVKG FYPSDIAVEW ESNGQPENNY   240
KTTPPVLDSD GSFFLYSRLT VDKSRWQEGN VFSCSVMHEA LHNHYTQKSL SLSLGK       296

SEQ ID NO: 40           moltype = AA   length = 311
FEATURE                 Location/Qualifiers
REGION                  1..311
                        note = Fusion protein
source                  1..311
                        mol_type = protein
                        organism = synthetic construct
SEQUENCE: 40
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKG GGSGGGGSG    240
GGGSAYRPSE TLCGGELVDT LQFVCGDRGF YFSRPASRVS RRSRGIVEEC CFRSCDLALL   300
ETYCATPAKS E                                                        311

SEQ ID NO: 41           moltype = AA   length = 311
FEATURE                 Location/Qualifiers
REGION                  1..311
                        note = Fusion protein
source                  1..311
                        mol_type = protein
                        organism = synthetic construct
SEQUENCE: 41
AYRPSETLCG GELVDTLQFV CGDRGFYFSR PASRVSARSR GIVEECCFRS CDLALLETYC    60
ATPAKSEGGG GSGGGGSGGG GSESKYGPPC PPCPAPEFLG GPSVFLFPPK PKDTLMISRT   120
PEVTCVVVDV SQEDPEVQFN WYVDGVEVHN AKTKPREEQF NSTYRVVSVL TVLHQDWLNG   180
KEYKCKVSNK GLPSSIEKTI SKAKGQPREP QVYTLPPSQE EMTKNQVSLT CLVKGFYPSD   240
IAVEWESNGQ PENNYKTTPP VLDSDGSFFL YSRLTVDKSR WQEGNVFSCS VMHEALHNHY   300
TQKSLSLSLG K                                                        311

SEQ ID NO: 42           moltype = AA   length = 17
FEATURE                 Location/Qualifiers
REGION                  1..17
                        note = Portion of IGF2
source                  1..17
                        mol_type = protein
                        organism = synthetic construct
SEQUENCE: 42
RGFYFSRPAS RVSRRSR                                                   17

SEQ ID NO: 43           moltype = DNA   length = 12
FEATURE                 Location/Qualifiers
misc_feature            1..12
                        note = Short flexible linker
source                  1..12
                        mol_type = other DNA
                        organism = synthetic construct
SEQUENCE: 43
ggatcgggat cg                                                        12

SEQ ID NO: 44           moltype = DNA   length = 15
FEATURE                 Location/Qualifiers
misc_feature            1..15
                        note = Short flexible linker
source                  1..15
                        mol_type = other DNA
                        organism = synthetic construct
SEQUENCE: 44
ggatctggga gcgct                                                     15

SEQ ID NO: 45           moltype = DNA   length = 45
FEATURE                 Location/Qualifiers
misc_feature            1..45
                        note = Long flexible linker
source                  1..45
                        mol_type = other DNA
                        organism = synthetic construct
SEQUENCE: 45
ggcggaggcg gtagcggagg cggtggctcc ggtggcggag ggtct                    45
```

```
SEQ ID NO: 46            moltype = DNA  length = 681
FEATURE                  Location/Qualifiers
misc_feature             1..681
                         note = Fusion protein
source                   1..681
                         mol_type = other DNA
                         organism = synthetic construct
SEQUENCE: 46
gacaaaactc acacatgccc accgtgccca gcacctgaag ctgccggggg accgtcagtc    60
ttcctcttcc ccccaaaacc caaggacacc ctcatgatct cccggacccc tgaggtcaca   120
tgcgtggtgg tggacgtgag ccacgaagac cctgaggtca agttcaactg gtacgtggac   180
ggcgtggagg tgcataatgc caagacaaag ccgcgggagg agcagtacaa cagcacgtac   240
cgtgtggtca gcgtcctcac cgtcctgcac caggactggc tgaatggcaa ggagtacaag   300
tgcaaggtct ccaacaaagc cctcggcgcc cccatcgaga aaaccatctc caaagccaaa   360
gggcagcccc gagaaccaca ggtgtacacc ctgcccccat cccgggatga gctgaccaag   420
aaccaggtca gcctgacctg cctggtcaaa ggcttctatc ccagcgacat cgccgtggag   480
tgggagagca atgggcagcc ggagaacaac tacaagacca cgcctcccgt gctggactcc   540
gacggctcct tcttcctcta cagcaagctc accgtggaca agagcaggtg gcagcagggg   600
aacgtcttct catgctccgt gatgcatgag gctctgcaca accactacac gcagaaaagc   660
ctctccctgt ctccgggtaa a                                             681

SEQ ID NO: 47            moltype = DNA  length = 687
FEATURE                  Location/Qualifiers
misc_feature             1..687
                         note = Fusion protein
source                   1..687
                         mol_type = other DNA
                         organism = synthetic construct
SEQUENCE: 47
gagtccaaat atggtccccc atgcccaccc tgcccagcac ctgagttcct ggggggacca    60
tcagtcttcc tgttcccccc aaaacccaag gacactctca tgatctcccg gacccctgag   120
gtcacgtgcg tggtggtgga cgtgagccag gaagaccccg aggtccagtt caactggtac   180
gtggatggcg tggaggtgca taatgccaag acaaagccgc gggaggagca gttcaacagc   240
acgtaccgtg tggtcagcgt cctcaccgtc ctgcaccagg actggctgaa cggcaaggag   300
tacaagtgca aggtctccaa caaaggcctc ccgtcctcca tcgagaaaac catctccaaa   360
gccaaagggc agccccgaga gccacaggtg tacaccctgc ccccatccca ggaggagatg   420
accaagaacc aggtcagcct gacctgcctg gtcaaaggct tctaccccag cgacatcgcc   480
gtggagtggg agagcaatgg gcagccggag aacaactaca agaccacgcc tcccgtgctg   540
gactccgacg gctccttctt cctctacagc aggctcaccg tggacaagag caggtggcag   600
gaggggaatg tcttctcatg ctccgtgatg catgaggctc tgcacaacca ctacacacag   660
aagagcctct ccctgtctct gggtaaa                                       687

SEQ ID NO: 48            moltype = DNA  length = 18
FEATURE                  Location/Qualifiers
misc_feature             1..18
                         note = Six His peptide
source                   1..18
                         mol_type = other DNA
                         organism = synthetic construct
SEQUENCE: 48
caccatcacc atcaccat                                                  18

SEQ ID NO: 49            moltype = DNA  length = 24
FEATURE                  Location/Qualifiers
misc_feature             1..24
                         note = Strep-Tactin binding peptide
source                   1..24
                         mol_type = other DNA
                         organism = synthetic construct
SEQUENCE: 49
tggagccacc cgcagttcga aaaa                                           24

SEQ ID NO: 50            moltype = DNA  length = 1755
FEATURE                  Location/Qualifiers
source                   1..1755
                         mol_type = other DNA
                         organism = Homo sapiens
SEQUENCE: 50
gatgcacaca agagtgaggt tgctcatcgg tttaaagatt tgggagaaga aaatttcaaa    60
gccttggtgt tgattgcctt tgctcagtat cttcagcagt gtccatttga agatcatgta   120
aaattagtga atgaagtaac tgaatttgca aaaacatgtg ttgctgatga gtcagctgaa   180
aattgtgaca atcacttca tacccttttt ggagacaaat atgcacagt tgcaactctt   240
cgtgaaacct atggtgaaat ggctgactgc tgtgcaaaac aagaacctga gaaaatgaa   300
tgcttcttgc aacacaaaga tgacaaccca aacctccccc gattggtgag accagaggtt   360
gatgtgatgt gcactgcttt tcatgacaat gaagagacat tttgaaaaa atacttttat   420
gaaattgcca aagacatcc ttactttat gccccggaac tccttttctt tgctaaaagg   480
tataaagctg cttttacaga atgttgccaa gctgctgata agctgcctg cctgttgcca   540
aagctcgatg aacttcggga tgaagggaag gcttcgtctg ccaaacagag actcaagtgt   600
```

```
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg cttgaatgtg ctgatgacag ggcggacctt    780
gccaagtata tctgtgaaaa tcaagattcg atctccagta aactgaagga atgctgtgaa    840
aaacctctgt tggaaaaatc ccactgcatt gccgaagtga aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag catcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc ctcagaattt aatcaaacaa aattgtgagc ttttgagca gcttggagag   1200
tacaaattcc agaatgcgct attagttcgt tacaccaaga aagtacccca agtgtcaact   1260
ccaactcttg tagaggtctc aagaaaccta ggaaagtgg gcagcaaatg ttgtaaacat   1320
cctgaagcaa aaagaatgcc ctgtgcagaa gactatctat ccgtggtcct gaaccagtca   1380
tgtgtgttgc atgagaaaac gccagtaagt gacagagtca ccaaatgctg cacagaatcc   1440
ttggtgaaca ggcgaccatg cttttcagct ctggaagtcg atgaaacata cgttcccaaa   1500
gagtttaatg ctgaaacatt caccttccat gcagatatat gcacactttc tgagaaggag   1560
agacaaatca agaaacaaac tgcacttgtt gagctcgtga acacaagcc caaggcaaca   1620
aaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
gctgccttag gctta                                                    1755

SEQ ID NO: 51          moltype = AA   length = 4
FEATURE                Location/Qualifiers
REGION                 1..4
                       note = Short flexible linker
source                 1..4
                       mol_type = protein
                       organism = synthetic construct
SEQUENCE: 51
GSGS                                                                    4

SEQ ID NO: 52          moltype = AA   length = 5
FEATURE                Location/Qualifiers
REGION                 1..5
                       note = Short flexible linker
source                 1..5
                       mol_type = protein
                       organism = synthetic construct
SEQUENCE: 52
GSGSA                                                                   5

SEQ ID NO: 53          moltype = AA   length = 15
FEATURE                Location/Qualifiers
REGION                 1..15
                       note = Long flexible linker
source                 1..15
                       mol_type = protein
                       organism = synthetic construct
SEQUENCE: 53
GGGGSGGGGS GGGGS                                                       15

SEQ ID NO: 54          moltype = AA   length = 227
FEATURE                Location/Qualifiers
REGION                 1..227
                       note = Fusion protein
source                 1..227
                       mol_type = protein
                       organism = synthetic construct
SEQUENCE: 54
DKTHTCPPCP APEAAGGPSV FLFPPKPKDT LMISRTPEVT CVVVDVSHED PEVKFNWYVD       60
GVEVHNAKTK PREEQYNSTY RVVSVLTVLH QDWLNGKEYK CKVSNKALGA PIEKTISKAK      120
GQPREPQVYT LPPSRDELTK NQVSLTCLVK GFYPSDIAVE WESNGQPENN YKTTPPVLDS      180
DGSFFLYSKL TVDKSRWQQG NVFSCSVMHE ALHNHYTQKS LSLSPGK                    227

SEQ ID NO: 55          moltype = AA   length = 229
FEATURE                Location/Qualifiers
REGION                 1..229
                       note = Fusion protein
source                 1..229
                       mol_type = protein
                       organism = synthetic construct
SEQUENCE: 55
ESKYGPPCPP CPAPEFLGGP SVFLFPPKPK DTLMISRTPE VTCVVVDVSQ EDPEVQFNWY       60
VDGVEVHNAK TKPREEQFNS TYRVVSVLTV LHQDWLNGKE YKCKVSNKGL PSSIEKTISK      120
AKGQPREPQV YTLPPSQEEM TKNQVSLTCL VKGFYPSDIA VEWESNGQPE NNYKTTPPVL      180
DSDGSFFLYS RLTVDKSRWQ EGNVFSCSVM HEALHNHYTQ KSLSLSLGK                  229

SEQ ID NO: 56          moltype = AA   length = 6
FEATURE                Location/Qualifiers
```

| | | |
|---|---|---|
| REGION | 1..6 | |
| | note = Six His peptide | |
| source | 1..6 | |
| | mol_type = protein | |
| | organism = synthetic construct | |

SEQUENCE: 56
HHHHHH                                                                6

| | | |
|---|---|---|
| SEQ ID NO: 57 | moltype = AA   length = 8 | |
| FEATURE | Location/Qualifiers | |
| REGION | 1..8 | |
| | note = Strp-Tactin binding peptide | |
| source | 1..8 | |
| | mol_type = protein | |
| | organism = synthetic construct | |

SEQUENCE: 57
WSHPQFEK                                                              8

| | | |
|---|---|---|
| SEQ ID NO: 58 | moltype = AA   length = 585 | |
| FEATURE | Location/Qualifiers | |
| source | 1..585 | |
| | mol_type = protein | |
| | organism = Homo sapiens | |

SEQUENCE: 58
```
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV 120
DVMCTAFHDN EETFLKKYLY EIARRHPYFY APELLFFAKR YKAAFTECCQ AADKAACLLP 180
KLDELRDEGK ASSAKQRLKC ASLQKFGERA FKAWAVARLS QRFPKAEFAE VSKLVTDLTK 240
VHTECCHGDL LECADDRADL AKYICENQDS ISSKLKECCE KPLLEKSHCI AEVENDEMPA 300
DLPSLAADFV ESKDVCKNYA EAKDVFLGMF LYEYARRHPD YSVVLLLRLA KTYETTLEKC 360
CAAADPHECY AKVFDEFKPL VEEPQNLIKQ NCELFEQLGE YKFQNALLVR YTKKVPQVST 420
PTLVEVSRNL GKVGSKCCKH PEAKRMPCAE DYLSVVLNQL CVLHEKTPVS DRVTKCCTES 480
LVNRRPCFSA LEVDETYVPK EFNAETFTFH ADICTLSEKE RQIKKQTALV ELVKHKPKAT 540
KEQLKAVMDD FAAFVEKCCK ADDKETCFAE EGKKLVAASQ AALGL                  585
```

| | | |
|---|---|---|
| SEQ ID NO: 59 | moltype = AA   length = 669 | |
| FEATURE | Location/Qualifiers | |
| REGION | 1..669 | |
| | note = Fusion protein | |
| source | 1..669 | |
| | mol_type = protein | |
| | organism = synthetic construct | |

SEQUENCE: 59
```
SGDAHKSEVA HRFKDLGEEN FKALVLIAFA QYLQQCPFED HVKLVNEVTE FAKTCVADES  60
AENCDKSLHT LFGDKLCTVA TLRETYGEMA DCCAKQEPER NECFLQHKDD NPNLPRLVRP 120
EVDVMCTAFH DNEETFLKKY LYEIARRHPY FYAPELLFFA KRYKAAFTEC CQAADKAACL 180
LPKLDELRDE GKASSAKQRL KCASLQKFGE RAFKAWAVAR LSQRFPKAEF AEVSKLVTDL 240
TKVHTECCHG DLLECADDRA DLAKYICENQ DSISSKLKEC CEKPLLEKSH CIAEVENDEM 300
PADLPSLAAD FVESKDVCKN YAEAKDVFLG MFLYEYARRH PDYSVVLLLR LAKTYETTLE 360
KCCAAADPHE CYAKVFDEFK PLVEEPQNLI KQNCELFEQL GEYKFQNALL VRYTKKVPQV 420
STPTLVEVSR NLGKVGSKCC KHPEAKRMPC AEDYLSVVLN QLCVLHEKTP VSDRVTKCCT 480
ESLVNRRPCF SALEVDETYV PKEFNAETFT FHADICTLSE KERQIKKQTA LVELVKHKPK 540
ATKEQLKAVM DDFAAFVEKC CKADDKETCF AEEGKKLVAA SQAALGLGGG GSGGGGSGGG 600
GSAYRPSETL CGGELVDTLQ FVCGDRGFYF SRPASRVSAR SRGIVEECCF RSCDLALLET 660
YCATPAKSE                                                         669
```

| | | |
|---|---|---|
| SEQ ID NO: 60 | moltype = AA   length = 675 | |
| FEATURE | Location/Qualifiers | |
| REGION | 1..675 | |
| | note = Fusion protein | |
| source | 1..675 | |
| | mol_type = protein | |
| | organism = synthetic construct | |

SEQUENCE: 60
```
RGVFRRSGDA HKSEVAHRFK DLGEENFKAL VLIAFAQYLQ QCPFEDHVKL VNEVTEFAKT  60
CVADESAENC DKSLHTLFGD KLCTVATLRE TYGEMADCCA KQEPERNECF LQHKDDNPNL 120
PRLVRPEVDV MCTAFHDNEE TFLKKYLYEI ARRHPYFYAP ELLFFAKRYK AAFTECCQAA 180
DKAACLLPKL DELRDEGKAS SAKQRLKCAS LQKFGERAFK AWAVARLSQR FPKAEFAEVS 240
KLVTDLTKVH TECCHGDLLE CADDRADLAK YICENQDSIS SKLKECCEKP LLEKSHCIAE 300
VENDEMPADL PSLAADFVES KDVCKNYAEA KDVFLGMFLY EYARRHPDYS VVLLLRLAKT 360
YETTLEKCCA AADPHECYAK VFDEFKPLVE EPQNLIKQNC ELFEQLGEYK FQNALLVRYT 420
KKVPQVSTPT LVEVSRNLGK VGSKCCKHPE AKRMPCAEDY LSVVLNQLCV LHEKTPVSDR 480
VTKCCTESLV NRRPCFSALE VDETYVPKEF NAETFTFHAD ICTLSEKERQ IKKQTALVEL 540
VKHKPKATKE QLKAVMDDFA AFVEKCCKAD DKETCFAEEG KKLVAASQAA LGLGGGGSGG 600
GGSGGGGSAY RPSETLCGGE LVDTLQFVCG DRGFYFSRPA SRVSARSRGI VEECCFRSCD 660
LALLETYCAT PAKSE                                                  675
```

| | | |
|---|---|---|
| SEQ ID NO: 61 | moltype = AA   length = 4 | |
| FEATURE | Location/Qualifiers | |

```
REGION                  1..4
                        note = Glycine-rich sequence
source                  1..4
                        mol_type = protein
                        organism = synthetic construct
SEQUENCE: 61
GGGS                                                                        4

SEQ ID NO: 62           moltype = AA  length = 5
FEATURE                 Location/Qualifiers
MOD_RES                 1..5
                        note = Any amino acid except Pro
source                  1..5
                        mol_type = protein
                        organism = synthetic construct
SEQUENCE: 62
VPGXG                                                                       5

SEQ ID NO: 63           moltype = AA  length = 5
FEATURE                 Location/Qualifiers
REGION                  1..5
                        note = 4GS linker
source                  1..5
                        mol_type = protein
                        organism = synthetic construct
SEQUENCE: 63
GGGGS                                                                       5
```

What is claimed is:

1. A fusion protein comprising an insulin-like growth factor 2 (IGF2) polypeptide fused to an N-terminal human serum albumin (HSA) polypeptide, wherein the IGF2 polypeptide comprises the amino acid sequence of SEQ ID NO: 29 and an R61A mutation in the amino acid sequence of SEQ ID NO: 32, wherein the R61A mutation resides within an IGF2 C-domain, and wherein the fusion protein exhibits reduced cleavage within the IGF2 C-domain.

2. The fusion protein of claim 1, wherein the HSA polypeptide of the fusion protein comprises the amino acid sequence of SEQ ID NO: 58.

3. The fusion protein of claim 1, further comprising a glycine-rich linker that couples the N-terminal HSA polypeptide to the IGF2 polypeptide.

4. The fusion protein of claim 3, wherein the glycine-rich linker is a glycine-serine linker.

5. The fusion protein of claim 4, wherein the glycine-serine linker comprises the amino acid sequence of SEQ ID NO: 63.

6. The fusion protein of claim 4, wherein the glycine-serine linker comprises a multimer of the 4GS linker of SEQ ID NO: 63, with repeats of 2, 3, 4, or 5 4GS linkers.

7. The fusion protein of claim 4, wherein the glycine-serine linker comprises the amino acid sequence of SEQ ID NO: 53.

8. The fusion protein of claim 7, comprising an amino acid sequence at least 98% identical to SEQ ID NO: 59.

9. The fusion protein of claim 7, comprising an amino acid sequence at least 99% identical to SEQ ID NO: 59.

10. The fusion protein of claim 7, comprising the amino acid sequence of SEQ ID NO: 59.

11. The fusion protein of claim 7, consisting essentially of the amino acid sequence of SEQ ID NO: 59.

12. A pharmaceutical composition comprising:
a fusion protein comprising an insulin-like growth factor 2 (IGF2) polypeptide fused to an N-terminal human serum albumin (HSA) polypeptide, wherein the IGF2 polypeptide comprises the amino acid sequence of SEQ ID NO: 29 and an R61A mutation in the amino acid sequence of SEQ ID NO: 32, wherein the R61A mutation resides within an IGF2 C-domain, and wherein the fusion protein exhibits reduced cleavage within the IGF2 C-domain; and
a pharmaceutically acceptable excipient, carrier, or diluent.

* * * * *